(12) United States Patent
Hayama et al.

(10) Patent No.: US 6,958,333 B1
(45) Date of Patent: Oct. 25, 2005

(54) BIARYLUREA DERIVATIVES

(75) Inventors: Takashi Hayama, Tsukuba (JP); Kyoko Hayashi, Tsukuba (JP); Teruki Honma, Tsukuba (JP); Ikuko Takahashi, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 23 days.

(21) Appl. No.: 10/031,795

(22) PCT Filed: Jul. 26, 2000

(86) PCT No.: PCT/JP00/04991

§ 371 (c)(1),
(2), (4) Date: Apr. 2, 2002

(87) PCT Pub. No.: WO01/07411

PCT Pub. Date: Feb. 1, 2001

(30) Foreign Application Priority Data

Jul. 26, 1999 (JP) .......................................... 11-211384

(51) Int. Cl.⁷ ................... C07D 498/04; A61K 31/5365
(52) U.S. Cl. .................................... 514/230.2; 544/101
(58) Field of Search ........................ 544/101; 514/230.2

(56) References Cited

U.S. PATENT DOCUMENTS 5,696,138 A 12/1997 Olesen et al. ............... 514/349

FOREIGN PATENT DOCUMENTS

| JP | 2-115176 | 4/1990 |
|----|----------|--------|
| WO | 96/25157 | 8/1996 |
| WO | 97/29743 | 8/1997 |
| WO | 99/24416 | 5/1999 |
| WO | 99/31086 | 6/1999 |
| WO | 99/54308 | 10/1999 |
| WO | 99/65884 | 12/1999 |
| WO | 00/26203 | 5/2000 |
| WO | 00/47577 | 8/2000 |

OTHER PUBLICATIONS

March, J., "Advanced Organic Chemistry, Third Edition", John Wiley & Sons, p. 786, 984–985 (1985).
Pines, J. "The Cell Cycle Kinases", Semin. Cancer Biol., vol. 5, No. 4, p. 305–313, (1994).

*Primary Examiner*—Richard L. Raymond
*Assistant Examiner*—Kahsay Habte
(74) *Attorney, Agent, or Firm*—Wenderoth, Lind & Ponack, L.L.P.

(57) ABSTRACT

The present invention relates to a compound of Formula (I) and the manufacturing method(s) thereof and the use thereof:

Formula (I)

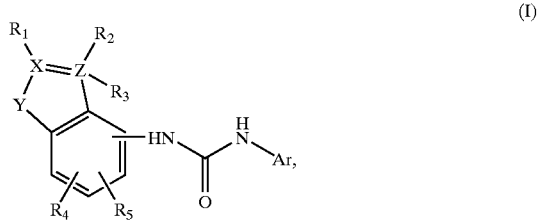

wherein: Ar is a nitrogen-containing heteroaromatic ring group; X and Z are each a carbon atom, and so on; Y is CO, and so on; $R_1$ is a hydrogen atom, and so on; $R_2$ and $R_3$ are each a hydrogen atom, and so on; $R_4$ and $R_5$ are each a hydrogen atom, and so on; and the formula === is a single bond or a double bond.

According to the present invention, the compound of the present invention can provide Cdk4 and/or Cdk6 inhibitors for treating malignant tumors, because the compounds of the present invention exhibit a prominent growth inhibitory activity against tumor cells.

8 Claims, No Drawings

```
                              SEQUENCE LISTING

<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: Description of Artificial Sequence: Synthetic
      Peptide

<400> SEQUENCE: 1

Arg Pro Pro Thr Leu Ser Pro Ile Pro His Ile Pro Arg
  1               5                  10

<210> SEQ ID NO 2
<211> LENGTH: 10
<212> TYPE: PRT
<213> ORGANISM: Artificial sequence
<220> FEATURE:
<223> OTHER INFORMATION: Description of Artificial Sequence: Synthetic
      Peptide

<400> SEQUENCE: 2

Lys Ala Pro Leu Ser Pro Lys Lys Ala Lys
  1               5                  10

<210> SEQ ID NO 3
<211> LENGTH: 13
<212> TYPE: PRT
<213> ORGANISM: Artificial sequence
<220> FEATURE:
<223> OTHER INFORMATION: Description of Artificial Sequence: Synthetic
      Peptide

<400> SEQUENCE: 3

Arg Pro Pro Thr Leu Ser Pro Ile Pro His Ile Pro Arg
  1               5                  10
```

BIARYLUREA DERIVATIVES

This is a divisional of Ser. No. 10/031,795, filed Apr. 2, 2002, which is a U.S. national stage of International Application No. PCT/JP00/04991 filed Jul. 26, 2000.

TECHNICAL FIELD

The present invention relates to biarylurea derivatives di-substituted with aromatic ring or heteroaromatic ring, which are useful as pharmaceutical composition, and to the production method and use thereof.

BACKGROUND ART

In the growth of the normal cells, cell division and its pause occur orderly according to the cell cycle, on the contrary, the growth of cancer cells is characterized by its disorderedness, thus the abnormality in the cell-cycle regulating system is presumed to be directly related to the oncogenesis and malignunant degeneration of cancer. The cell cycle of mammalian cells is controlled by a group of serine/threonine kinase called as cyclin dependent kinase (hereinafter denoted as "Cdk") family. Cdk needs to form a complex with a regulatory subunit called cyclin, in order to exhibit its enzyme activity. Cyclins also have a family. Each Cdk molecule of which is considered to regulate progression at a specific stage of the cell cycle by forming a complex with the specific cyclin molecule which is expressed at the corresponding stage of the cell cycle. For example, D-type cyclin regulates the progression of G1 phase by binding to Cdk4 or Cdk6, and cyclin E-Cdk2 regulates the progression of G1/S boundary, cyclin A-Cdk2 regulates the progression of S stage, and furthermore, cyclin B-cdc2 regulates the progression of G2/M, respectively. In addition, there are three subtypes D1, D2 and D3 in D type cyclin. Furthermore, Cdk activity is considered to be regulated not only by the binding with cyclins, but also by phosphorylation/dephosphorylation of Cdk molecule, degradation of the cyclin molecule and binding with Cdk-inhibitor proteins. [Advances in Cancer Research (Advance Cancer Res.), Vol.66, pp. 181–212(1995); Current Opinion in Cell Biology (Current Opin. Cell Biol.). Vol. 7, pp. 773–780 (1995); Nature (Nature), Vol. 374, pp. 131–134 (1995)].

The Cdk-inhibitor proteins of mammalian cells can be divided broadly into two categories, Cip/Kip family and INK4 family according to their structures and properties. The former inhibits a variety of cyclin-Cdk complexes broadly, whereas the latter inhibits Cdk4 and Cdk6 specifically [Nature (Nature), Vol.366, pp. 704–707 (1993); Molecular and Cellular Biology (Mol. Cell. Biol.), Vol. 15, pp. 2627–2681 (1995); Genes and Development (Genes Dev.), Vol. 9, pp. 1149–1163 (1995)].

Cip/Kip family can be represented by p21 (Sdi1/Cip1/Waf1), and its expression induced by the tumor suppressor gene product p53 [Genes and Development (Genes Dev.), Vol.9, pp.935–944 (1995)]

On the other hand, p16 (INK4a/MTS1/CDK4I/CDKN2), for example, is one of the Cdk inhibitor proteins which belong to INK family. Human p16 gene is encoded on the chromosome 9p21. Abnormalities of this locus are detected with a high frequency in human cancer cells. Actually, a lot of cases of deletion and mutation of the p16 gene have been reported. Also, a high frequency of tumorigenesis in the p16 knockout mice has been reported [Nature Genetics (Nature Genet.), Vol. 8, pp. 27–32 (1994); Trends in Genetics (Trends Genet.), Vol. 11, pp. 136–140 (1995): Cell (Cell), Vol. 85, pp. 27–37 (1996)].

Each Cdk regulates the progression of cell cycle by phosphorylating the target protein at the specific phase of cell cycle, and retinoblastoma (RB) protein is considered to be one of the most important target proteins. RB protein is the key protein that regulates the progression from G1 phase to S phase. It is phosphorylated rapidly in the period from late G1 phase through early S phase. The phosphorylation is considered to be carried out by the cyclin D-Cdk4/Cdk6 complex, followed by the cyclin E-Cdk2 complex, leading the progression of cell cycle. The complex composed of hypophosphorylated RB and transcription factor E2F at dissociates when RB protein becomes hyperphosphorylated. As a result, E2F will become the transcriptional activator, and at the same time, the suppression of the promoter activity due to the RB-E2F complex will be removed, thus leading to the activation of the E2F-dependent transcription. At present, the Cdk-RB pathway, which consists of E2F and its suppressor RB protein, Cdk4/Cdk6 which repressively regulates the function of RB protein, Cdk inhibitor protein which controls the kinase activity of Cdk4/Cdk6, and D-type cyclin is thought to be the important mechanism to regulate the progression of G1 phase to S phase [Cell (Cell), Vol. 58, pp.1097–1105 (1989); Cell (Cell), Vol. 65, 1053–1061 (1991); Oncogene (Oncogene). Vol. 7, pp. 1067–1074 (1992); Current Opinion in Cell Biology (Curren Opin. Cell Biol.), Vol. 8, pp. 805–814 (1996); Molecular and Cellular Biology (Mol. Cell. Biol.), Vol. 18, pp. 753–761 (1998)].

In fact, the DNA binding sequence of E2F is, for example, in the promoter region of many genes related to cell proliferation and are important during S phase. The transcription of more than one of them has been reported to be activated in an E2F-dependent manner during the period from late G1 phase to early S phase [The EMBO Journal (EMBO J.), Vol. 9, pp.2179–2184 (1990); Molecular and Cellular Biology (Mol. Cell. Biol), Vol. 13, pp. 1610–1618 (1993)].

Abnormalities of any factors composing Cdk-RB pathway such as deletion of functional p16, high expressions of cyclin D1 and Cdk4, and deletion of functional RB protein have been detected with a high frequency in human cancers [Science (Science), Vol. 254, pp. 1138–1146 (1991); Cancer Research (Cancer Res.), Vol. 53, pp.5535–5541 (1993); Current Opinion in Cell Biology (Current Opin. Cell Biol.), Vol. 8, pp.805–814 (1996)]. As all of them lead to abnormalities of promoting the progression from G1 to S phase, it is clear that this pathway plays a crucial role in tumorigenesis of cells or the neoplasia of cancer cells.

As for the known compounds having Cdk family inhibitory activity, a series of chromone derivatives represented by, for example, flavopiridol. (WO97/16447, 98/13344) are already known.

As the prior art structurally similar to the compounds of the present invention, there may be cited, for example, WO96/25157 (reference A), WO97/29743 (reference B), U.S. Pat. No. 5,696,138 (reference C) and Japanese Patent Publication for Laid-Open 115176/1989 (reference D).

References A and B disclose ureas or thioureas derivatives, both of which are substituted with the aryl groups on both N- and N'-positions. But, the aryl groups in the references A and B are completely different from nitrogen-containing heteroaromatic ring groups of the present invention in view of the chemical structure, thus it can be safely said that the compounds disclosed in the references A and B have no direct relationship with the compounds of the present invention. Furthermore, the use of the compounds disclosed in the references A and B is related to chemokine receptor antagonists, intended for producing a therapeutic agent for treating, for example, psoriasis, atopic dermatitis, asthma, chronic occlusive pulmonary disease and Alzheimer's disease, and so on, thus, having no relationship with the use of compounds of the present invention.

In the reference C, urea or thiourea derivatives are disclosed, having aromatic cyclic groups which may contain one nitrogen atom and benzene rings which may be condensed. The main compounds of the invention in the reference C are, however, urea derivatives substituted with two phenyl groups on the N- and N'-positions, and three urea derivatives substituted with a pyridyl group on the N'-position are disclosed only in the third column (on lines 11, 13 and 26), in the fifth column (on lines 17 and 19), in the seventh column (on lines 13 and 15), in the seventeenth column (on lines 24 and 42) and in the twentieth column (on the 14th line from the bottom of the column) of the specification. Descriptions in these columns are common. In addition, all the substituents, which exsist on the N-position of the urea compounds, are phenyl groups, thus the compounds are completely different from those of the present invention. Furthermore, in the case where the compounds of the reference C may have a fused benzene ring as the N-substituent, although it is defined that the ring structures which are fused with the benzene ring may be saturated or unsaturated, there is no description about the substituents on the fused ring, thus, said fused ring is interpreted to be non-substituted on the fused ring (in contrast, the compounds of the present invention have an oxo-group there). And, in addition, judging from the description in the reference C, the examples of the fused benzene ring are limited to naphthyl groups. Thus, the compounds in the reference C and those in the present invention differ in their chemical structures, and it can be said that the two inventions have no direct relationship with each other.

Furthermore, the use of the compounds described in the reference C is related to the potassium channel activators, as described in the sixteenth column, aiming at a therapeutic agent for treating, for example, potassium channel dependent convulsion, asthma, ischemia, and so on, so there is no relations of it with the use of the present invention.

In the Example 7 in the reference D, a urea compound wherein the N-position is substituted with a triazinyl group and the N'-position is substituted with a 9-fluorenone group.

The invention of the reference D is the one which relates to radiosensitive compositions, namely, photosensitive agents, and differs from the present invention in term of the technical fields they belong to, and also no other compound similar to the compound of the present invention is mentioned, except for that in the Example 7 described above. Because the compounds in the reference D are the compounds having various types of structure, that is, a triazine nucleus is used as the core structure, more than ten substituents containing a fluorenone group are applied at a photo-initiation part of the triazine nucleus, and more than ten combinations of connecting groups including urea, which connect a photo-initiation part and a triazine nucleus, are exemplified. Therefore, it is safely stated that the compounds of the present invention and the use thereof cannot be reached from the descriptions in the reference D including the compound in the Example 7, and the reference D is an invention which has no direct relation to the present invention.

Thus, since the present invention relates to the novel compounds which have not been described in the literatures yet and the novel use thereof, also the present invention can not be attained easily based on the above-mentioned reference A to D.

Furthermore, up to date, no Cdk6 inhibitor is exemplified.

As stated above, some chromone derivatives can be exemplified as the compounds with Cdk family inhibitory activity, however, their inhibitory activity against Cdk4 is not strong enough, and compounds with a higher activity are still desired. More specifically, novel compounds which will simultaneously show heterogenous inhibitory activities, for example, against Cdk6 and so on, different from the known inhibitors, are desired.

DISCLOSURE OF THE INVENTION

The present inventors have assiduously studied so as to provide novel compounds having an excellent Cdk4- or Cdk6-inhibitory activity, and as a result, found that a series of novel compounds having biarylurea structure show Cdk4- and/or Cdk6-inhibitory activity, and thus completed the present invention.

The present invention relates to a compound represented by Formula (I) or pharmaceutically acceptable salts thereof, preparation methods thereof and the use thereof:

Formula (I)

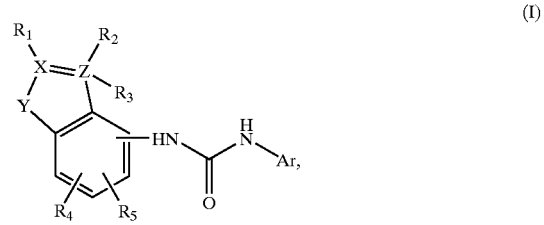

(I)

wherein: Ar is a nitrogen-containing heteroaromatic ring group selected from a set of groups of a pyridyl group, a pyrimidinyl group, a pyradinyl group, a pyridazinyl group, a thiazolyl group, an isothiazolyl group, an oxazolyl group, an isoxazolyl group, a pyrazolyl group, a pyrrolyl group, an imidazolyl group, an indolyl group, an isoindolyl group, an isoquinolyl group, a benzothiazolyl group, and a benzoxazolyl group, which:

(1) may be substituted with one to three of the same or different substituent(s) selected from either a set of groups consisting of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a set of groups represented by a formula $Y_1-W_1-Y_2-R_p$ (wherein: $R_p$ is any of a hydrogen atom, or a lower alkyl group, a lower alkenyl group or a lower alkynyl group which may be substituted with one to three of said substituent(s), or a cyclo lower alkyl group, an aryl group, a heteroaromatic ring group selected from a set of groups consisting of an imidazolyl group, an isoxazolyl group, an isoquinolyl group, an isoindolyl group, an indazolyl group, an indolyl group, an indolizinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group selected from a set of groups of an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, pyrrolinyl group, a morpholino group, a tetrahydroquinolinyl group and a tetrahydroisoquinolinyl group, each of which cyclic group may be substituted with one to three of said substituent(s) or, furthermore, may have a bicyclic or tricyclic fused ring of a partial structure selected from a set of groups consisting of:

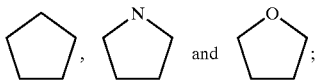

$W_1$ is a single bond, an oxygen atom, a sulfur atom, SO, $SO_2$, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, C≡C, CO, CS, OC(O), $OC(O)NR_q$, $OC(S)NR_q$, SC(O), $SC(O)NR_q$ and C(O)O (wherein: $R_q$ and $R_r$ are respectively a substituent selected from a set of groups of (i) a hydrogen atom, (ii) a substituent selected from a set of groups consisting of a lower alkyl group, a cyclo lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or (iii) a lower alkyl group, an aryl group or an aralkyl group which may be substituted with one to three of said substituent(s).); $Y_1$ and $Y_2$ are each, the same or different, a single bond or a straight-chain or branched lower alkylene group which may have a said bicyclic or tricyclic fused ring);

(2) may have a five- to seven-membered fused ring selected from a set of groups consisting of:

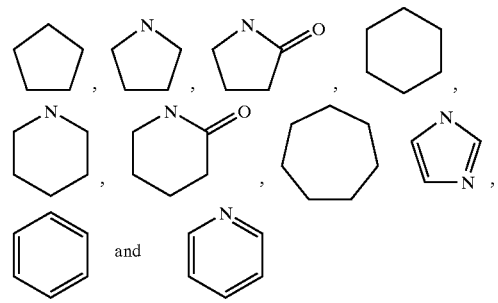

which may be formed together with the carbon atom of said nitrogen-containing heteroaromatic ring group, on which the substituent, which is selected from a set of groups consisting of a lower alkyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkylsulfinyl group, a lower alkylsulfonyl group, a lower alkylsulfonylamino group, and a lower alkanoylamidino lower alkyl group (hereinafter indicated as ring-substituent) stands, the carbon atom next to said carbon atom, and a carbon atom, an oxygen atom and/or a nitrogen atom on said ring-substituent; or, (3) may have a five- to seven-membered ring selected from a set of groups consisting of:

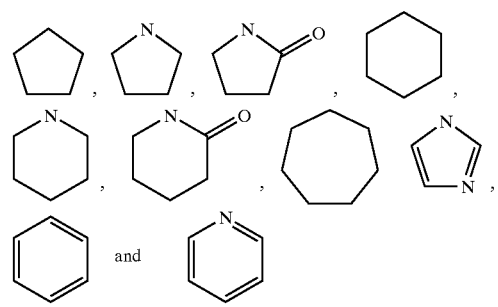

which may be formed together with the carbon atom of said nitrogen-containing heteroaromatic ring group on which a substituent represented by the formula $Y_1—W_1—Y_2—R_p$ (wherein: $Y_1$, $W_1$, $Y_2$ and $R_p$ have the same meanings as stated above) stands, the carbon atom next to said carbon atom, and a carbon atom, an oxygen atom and/or a nitrogen atom on said ring-substituent.

; X and Z are each, the same or different, a carbon atom or a nitrogen atom, or being taken together with $R_1$ or $R_2$ and/or $R_3$ which may exist on X or Z, form a CH or a nitrogen atom; Y is CO, SO or $SO_2$; $R_1$ is any of a hydrogen atom or a substituent represented by a formula $Y_3$—$W_2$—$Y_4$—$R_s$ (wherein: $R_s$ is any of a hydrogen atom or a lower alkyl group, a lower alkenyl group, a lower alkynyl group, a cyclo lower alkyl group, an aryl group, and a heteroaromatic ring group selected from a set of groups consisting of an imidazolyl group, an isoxazolyl group, an isoquinolyl group, an isoindolyl group, an indazolyl group, an indolyl group, an indolizinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group selected from a set of groups comprising an isoxazolinyl group, an isoxazolidinyl group, a tetrahydropyridyl group, an imidazolidinyl group, a tetrahydrofuranyl group, a piperazinyl group, a piperidinyl group, a pyrrolidinyl group, pyrrolinyl group, a morpholino group, a tetrahydroquinolinyl group and a tetrahydroisoquinolinyl group, all of which may be substituted with one to three of said substituent(s); $W_2$ is a single bond, an oxygen atom, a sulfur atom, SO, $SO_2$, $NR_t$, $SO_2NR_t$, $N(R_t)SO_2NR_u$, $N(R_t)SO_2$, $CH(OR_t)$, $CONR_t$, $N(R_t)CO$, $N(R_t)CONR_u$, $N(R_t)COO$, $N(R_t)CSO$, $N(R_t)COS$, $C(R_v)=CR_t$, C≡C, CO, CS, OC(O), $OC(O)NR_t$, $OC(S)NR_t$, SC(O), $SC(O)NR_t$ and C(O)O (wherein: $R_t$ and $R_u$ are each a hydrogen atom or a substituent selected from a set of groups consisting of a lower alkyl group, a hydroxy group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group a halo lower alkyl group, a carboxy lower alkyl group, a carbamoyl lower alkyl group, lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a lower alkyl group, an aryl group or an aralkyl group which may be substituted with one to three of said substituent(s)); $Y_3$ and $Y_4$ are each, the same or different, a single bond or a straight-chain or branched lower alkylene group), or an lower alkyl group which may be substituted with one to three of the same or different substituent(s) selected from a set of groups consisting of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a substituent selected from a set of groups represented by the formula $Y_3$—$W_2$—$Y_4$—$R_s$ (wherein: $R_s$, $W_2$, $Y_3$ and $Y_4$ have the same meanings as stated above), or forms a nitrogen atom, together with X.); $R_2$ and $R_3$ are each independently, the same or different, a hydrogen atom, a hydroxy group, a lower alkyl group, a lower alkoxy group, or a substituent represented by the formula $Y_3$—$W_2$—$Y_4$—$R_s$ (wherein: $R_s$, $W_2$, $Y_3$ and $Y_4$ have the same meanings as stated above), or either $R_2$ or $R_3$ forms, together with $R_1$ and X, a saturated five- to eight-membered cyclic group selected from sets of groups of (a) and (b):

(a)

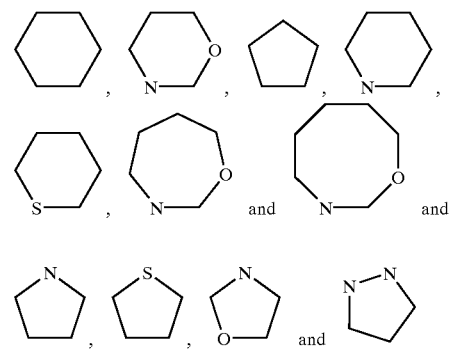

(b)

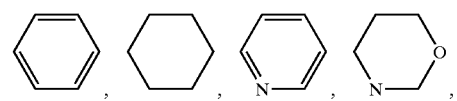

and the other one of $R_2$ or $R_3$ binds to a carbon atom or a nitrogen atom on the ring, or to a carbon atom, an oxygen atom and/or a nitrogen atom on said ring-substituent of said ring to form a five- to seven-membered ring, or $R_2$ and $R_3$ are combined to form a spiro cyclo lower alkyl group, or are combined with Z on which they exist to form an oxo (keto, or carbonyl) group, or they ($R_2$ and $R_3$) form, together with Z, $R_1$ and X to which they bind, a saturated or an unsaturated five- to eight membered cyclic group which may be selected from sets of groups of (a) and (b):

(a)

9

-continued

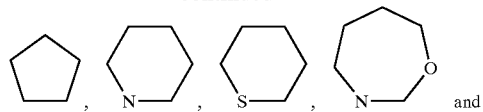 and

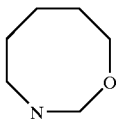 and (b)

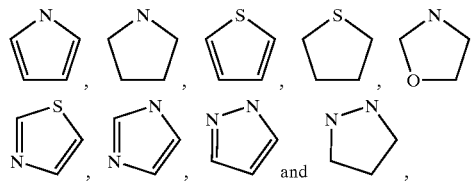 and which may contain one or more kinds of hetero atom(s) selected from the group of a nitrogen atom, an oxygen atom and a sulfur atom, or may be condensed with any of a cyclo lower alkyl group, an aryl group, a heteroaromatic ring group selected from a set of groups consisting of an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group(s) selected from a set of groups comprising an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, pyrrolinyl group, a morpholino group, a tetrahydroquinolinyl group and a tetrahydroisoquinolinyl group, which may be substituted with one to three of the same or different substituent(s) selected from a set of groups consisting of a lower alkyl group, a spiro cyclo lower alkyl group which may be substituted, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and a substituent selected from a set of groups represented by the formula $Y_1—W_1—Y_2—R_p$ (wherein: $R_p$, $W_1$, $Y_1$ and $Y_2$ have the same meanings as stated above); $R_4$ and $R_5$ are each, the same or different, a hydrogen atom, halogen atoms, a hydroxy group, an amino group, or a substituent represented by the formula $Y_3—W_2—Y_4—R_s$ (wherein: $R_s$, $W_2$, $Y_3$ and $Y_4$ have the same meanings as stated above), or any of a lower alkyl group, an aryl group or an aralkyl group which may be substituted with one to three of the same or different substituent(s) selected from both a set of groups consisting of a lower alkyl group, a cyano group, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and a set of groups represented by the formula $Y_3—W_2—Y_4—R_s$ (wherein: $R_s$, $W_2$, $Y_3$ and $Y_4$ have the same meanings as stated above); and the formula $=\!=\!=$ represents either a single bond or a double bond.

Symbols and terms described in this specification are to be explained as follows.

"Nitrogen-containing heteroaromatic ring group" is an aromatic ring group which has at least one nitrogen atom, and also an aromatic ring group which has one or more hetero atoms selected from a group consisting of an oxygen atom and a sulfur atom other than the above-mentioned nitrogen atom. As specific examples of such groups, there may be mentioned, for example, a pyridyl group, a pyrimidinyl group, a pyradinyl group, a pyridazinyl group, a thiazolyl, a isothiazolyl, a oxazolyl, a isoxazolyl, a pyrazolyl group, a pyrrolyl group, an imidazolyl, a indolyl, a isoindolyl, a quinolyl group, a isoquinolyl, a benzothiazolyl group or a benzoxazolyl group. Among them, a pyridyl group, a pyrimidinyl group, a pyradinyl group, a pyridazinyl group, a thiazolyl, a pyrazolyl group, or an imidazolyl group are more preferable, and a pyridyl group and a pyrazolyl group are especially preferable.

As a lower alkyl group, a straight-chain or branched chain alkyl group with one to six carbon atoms such as a methyl group, an ethyl group, a propyl group, an isopropyl group, a butyl group, an isobutyl group, a sec-butyl group, a tert-butyl group, a pentyl group and a hexyl group is preferable. Among them, a methyl group, an ethyl group and a butyl group are more preferably employed.

As halogen atoms, there may be mentioned, for example, a fluorine atom, a chlorine atom, a bromine atom and an iodine atom, more preferably, among them, a fluorine atom and a chlorine atom, and so on.

As a lower alkanoyl group, preferable is a group which may be formed by substituting a carbonyl group with an alkyl group which consists of one to five carbon atoms. As specific examples of such groups, there may be mentioned an acetyl group, a propionyl group, a butyryl group, an isobutyryl group, a valeryl group, and an isovaleryl group, a pivaloyl group and a pentanoyl group. Among them, for example, an acetyl group and a propionyl group and a pivaloyl group are more preferable.

A lower alkanoyloxy group is a group where an oxygen atom is substituted with the lower alkanoyl group stated above. As specific examples of such groups, there may be mentioned an acetoxy group, a propionyloxy group, a butyryloxy group, an isobutyryloxy group, a valeryloxy group, and an isovaleryloxy group, a pivaloyloxy group and a pentanoyloxy group, and so on. Among them, for example, an acetoxy group and a propionyloxy group and a pivaloyloxy group are more preferable.

As a hydroxy lower alkyl group, preferable is an alkyl group with one to six carbon atoms substituted with hydroxyl group. Specific examples are, for example, a hydroxymethyl group, a dihydroxymethyl group, a trihydroxymethyl group, a 1-hydroxyethyl group, a 2-hydroxyethyl group, a 1-hydroxypropyl group, a 2-hydroxypropyl group, a 3-hydroxypropyl group, a 1-hydroxy-2-methylethyl group, a 1-hydroxy-2,2-dimethylethyl group, a 1-hydroxypentyl group, a 1-hydroxy-2-methylbutyl group, a 1-hydroxyhexyl group, a 1-hydroxy-2-methylpentyl group, and so on. Among them, for example, a hydroxymethyl group, a 1-hydroxyethyl group, a 2-hydroxyethyl group and a 1-hydroxy-2-methylethyl group, and so on are more preferable.

As a cyano lower alkyl group, preferable is an alkyl group with one to six carbon atoms having cyano group. Specific examples are, for example, a cyanomethyl group, a 1-cyanoethyl group, a 2-cyanoethyl group, a 1-cyanopropyl group, a 2-cyanopropyl group, a 3-cyanopropyl group, a 1-cyano-2-methylethyl group, a 1-cyanobutyl group, a 1-cyano-2-methylpropyl group, a 1-cyano-2,2-dimethylethyl group, a 1-cyanopentyl group, a 1-cyano-2-methylbutyl group, a 1-cyanohexyl group and 1-cyano-2-methylpentyl group, and so on. Among them, for example, a cyanomethyl group, a 1-cyanoethyl group, a 2-cyanoethyl group and a 1-cyano-2-methylethyl group, and so on are more preferable.

As a halo lower alkyl group, preferable is an alkyl group with one to six carbon atoms having halo group. Specific examples are, for example, a fluoromethyl group, a chloromethyl group, a bromomethyl group, a iodomethyl group, a difluoromethyl group, a dichloromethyl group, a trifluoromethyl group, 1-fluoroethyl group, a 2-fluoroethyl group, a 1-chloroethyl group, a 2-chloroethyl group, 1-chloropropyl group, a 2-chloropropyl group, a 1-fluoro-2-methylethyl group, a 1-chloro-2-methylethyl group, a 1-chlorobutyl group, a 1-chloro-2-methylpropyl group, 1-chloro-2,2-dimethylethyl group, a 1-chloropentyl group, a 1-chloro-2-methylbutyl group, a 1-chlorohexyl group, a 1-chloro-2-methylpentyl group, and so on. Among them, for example, a chloromethyl group, a trifluoromethyl group, a 1-fluoroethyl group, a 1-chloroethyl group, and a 1-chloro-2-methylethyl group, and so on are more preferable.

As a carboxy lower alkyl group, preferable is an alkyl group with one to six carbon atoms having carboxy group. Specific examples are, for example, a carboxymethyl group, a 1-carboxyethyl group, a 1-carboxypropyl group, a 2-carboxypropyl group, a 3-carboxypropyl group, a 1-carboxy-2-methylethyl group, a 1-carboxybutyl group, 1-carboxy-2-methylpropyl group, a 1-carboxy-2,2-dimethylethyl group, a 1-carboxypentyl group, a 1-carboxy-2-methylbutyl group, 1-carboxyhexyl group, a 1-carboxy-2-methylpentyl group, and so on. Among them, for example, a carboxymethyl group, a 1-carboxyethyl group, a 2-carboxyethyl group, and a 1-carboxy-2-methylethyl group, and so on are more preferable.

As a carbamoyl lower alkyl group, preferable is an alkyl group with one to six carbon atoms having carbamoyl group. Specific examples are, for example, a carbamoylmethyl group, a 1-carbamoylethyl group, a 1-carbamoylpropyl group, a 2-carbamoylpropyl group, a 3-carbamoylpropyl group, a 1-carbamoyl-2-methylethyl group, a 1-carbamoylbutyl group, 1-carbamoyl-2-methylpropyl group, a 1-carbamoyl-2,2-dimethylethyl group, a 1-carbamoylpentyl group, a 1-carbamoyl-2-methylbutyl group, 1-carbamoylhexyl group, a 1-carbamoyl-2-methylpentyl group, and so on. Among them, for example, a carbamoylmethyl group, a 1-carbamoylethyl group, 2-carbamoylethyl group, and a 1-carbamoyl-2-methylethyl group, and so on are more preferable.

As a lower alkoxy group, preferable is the one constructed by substituting an oxygen atom with an alkyl group of one to six carbon atoms. As the specific examples, there may be mentioned a methoxy group, an ethoxy group, a propoxy group, an isopropoxy group, a butoxy group, an isobutoxy group, a sec-butoxy group, a tert-butoxy group, a pentyloxy group, a neeopentyloxy, a hexyloxy group and an isohexyloxy group. Among them, a methoxy group, an ethoxy group, a isopropyloxy group and a tert-butoxy group are more preferable.

A lower alkoxycarbonyl group is a group constructed by substituting an carbonyl group with an alkyl group of one to six carbon atoms. As the specific examples, there may be mentioned a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a neopentyloxycarbonyl, a hexyloxycarbonyl group and an isohexyloxycarbonyl group. Among them, a methoxycarbonyl group, an ethoxycarbonyl group, a isopropyloxycarbonyl group and a tert-butoxycarbonyl group are more preferable.

A lower alkylcarbamoyl group is a group constructed by substituting the nitrogen atom of a carbamoyl group with an alkyl group mentioned above. As the specific examples, there may be mentioned, for example, a N-methylcarbamoyl group, a N-ethylcarbamoyl group, a N-propylcarbamoyl group, a N-isopropylcarbamoyl group, a N-butylcarbamoyl group, a N-isobutylcarbamoyl group, a N-tert-butylcarbamoyl group, a N-pentylcarbamoyl group, a N-hexylcarbamoyl group. Among them, a N-methylcarbamoyl group, a N-ethylcarbamoyl group and a N-butylcarbamoyl group are more preferable.

A di-lower alkylcarbamoyl group is a group constructed by di-substituting the nitrogen atom of a carbamoyl group with two lower alkyl groups stated above. As the specific examples, there may be mentioned, for example, a N,N-dimethylcarbamoyl group, a N,N-diethylcarbamoyl group, a N,N-dipropylcarbamoyl group, a N,N-diisopropylcarbamoyl group, a N,N-dibutylcarbamoyl group, a N,N-diisobutylcarbamoyl group, a N,N-di-tert-butylcarbamoyl group, a N,N-dipentylcarbamoyl group, a N,N-dihexylcarbamoyl, a N-ethyl-N-methylcarbamoyl group and a N-methyl-N-propylcarbamoyl group, and so on. Among them, for example, N,N-dimethylcarbamoyl group, a N,N-diethylcarbamoyl group, a N,N-dibutylcarbamoyl group, a N-ethyl-N-methylcarbamoyl group and a N-methyl-N-propylcarbamoyl group, and so on are more preferable.

A lower alkylcarbamoyloxy group is a group constructed by substituting an oxygen atom with a lower alkylcarbamoyl group mentioned above. As the specific examples, there may be mentioned, for example, a N-methylcarbamoyloxy group, a N-ethylcarbamoyloxy group, a N-propylcarbamoyloxy group, a N-isopropylcarbamoyloxy group, a N-butylcarbamoyloxy group, a N-isobutylcarbamoyloxy group, a N-tert-butylcarbamoyloxy group, a N-pentylcarbamoyloxy group and a N-hexylcarbamoyloxy group. Among them, for example, a N-methylcarbamoyloxy group, an N-ethylcarbamoyloxy group and a N-butylcarbamoyloxy group are more preferable.

A di-lower alkylcarbamoyloxy group is a group constructed by substituting an oxygen atom with a di-lower alkylcarbamoyl group mentioned above. As the specific examples, there may be mentioned, for example, a N,N-dimethylcarbamoyloxy group, a N,N-diethylcarbamoyloxy group, a N-dipropylcarbamoyloxy group, a N,N-diisopropylcarbamoyloxy group, a N,N-butylcarbamoyloxy group, a N,N-diisobutylcarbamoyloxy group and a N,N-di-tert-butylcarbamoyloxy group, a N,N-dipentylcarbamoyloxy group, a N,N-dihexylcarbamoyloxy group and a N-ethyl-N-methylcarbamoyloxy group and a N-methyl-N-propylcarbamoyloxy, and so on. Among them, a N,N-dimethylcarbamoyloxy group, a N,N-diethylcarbamoyloxy group, a N,N-dibutylcarbamoyloxy group, a N-ethyl-N-methylcarbamoyloxy group and a N-methyl-N-propylcarbamoyloxy group, and so on are more preferable.

A lower alkylamino group is a group constructed by substituting an amino group with an lower alkyl group stated above. As the specific examples, there may be mentioned, for example, a N-methylamino group, a N-ethylamino group, a N-propylamino group, a N-isopropylamino group, a N-butylamino group, a N-isobutylamino group, a N-tert-butylamino group, a N-pentylamino group and a N-hexylamino group. Among them, for example, a N-methylamino group, a N-ethylamino group and a N-butylamino group are more preferable.

A di-lower alkylamino group is a group constructed by N,N-di-substituting an amino group with the lower alkyl groups. As the specific examples, there may be mentioned, for example, a N,N-dimethylammino group, a N,N-diethylamino group, a N,N-dipropylamino group, a N,N-diisopropylamino group, a N,N-dibutylamino group, a N,N-diisobutylamino group, a N,N-di-tert-butylamino group, a N,N-dipentylamino group, a N,N-dihexylamino, a N-ethyl-N-methylamino group and a N-methyl-N-propylamino group, and so on. Among them, for example, a N,N-dimethylamino group, a N,N-diethylamino group, a N,N-dibutylamino group, a N-ethyl-N-methylamino group and a N-methyl-N-propylamino group, and so on are more preferable.

A tri-lower alkylammonio group is a group which is constructed by N,N,N-tri-substituting an amino group with lower alkyl groups. As the specific example, there may be C3 mentioned, for example, a N,N,N-trimethylammonio group, a N,N,N-triethylammonio group, a N,N,N-tripropylammonio group, a N,N,N-triisopropylammonio group, a N,N,N-tributylammonio group, a N,N,N-triisobutylammonio group, a N,N,N-tri-tert-butylammonio group, a N,N,N-tripentylammonio group, a N,N,N-trihexylammonio group and a N-ethyl-N,N-dimethylammonio group and, N,N-dimethyl-N-propylammonio group, and so on. Among them, for example, a N,N,N-trimethylammonio group, a N,N,N-triethylammonio group, a N,N,N-tributylammonio group, a N-ethyl-N,N-dimethylammonio group and a N,N-dimethyl-N-propylammonio group, and so on are more preferable.

As an amino lower alkyl group, an alkyl group of one to six carbon atoms substituted with an amino group(s) is preferable. As the specific example, for example, there may be mentioned an aminomethyl group, a diaminomethyl group, a triaminomethyl group group, a 1-aminoethyl group, a 2-aminoethyl group, a 1-amino-propyl group, a 2-aminopropyl group, a 3-aminopropyl group, a 1-amino-2-methylethyl group, a 1-aminobutyl group, a 1-amino-2-methylpropyl group, a 1-amino-2,2-dimethyethyl group, a 1-aminopentyl group and a 1-amino-2-methylbutyl group, a 1-aminohexyl group and a 1-amino-2-methylpentyl group, and so on. Among them, for example, an aminomethyl group, a 1-aminoethyl group, a 2-aminoethyl group and 1-amino-2-methylethyl group, and so on, are more preferable.

A lower alkylamino lower alkyl group is a lower alkyl group substituted with a lower alkylamino group mentioned above. As the specific examples, there may be mentioned, for example, a N-methylaminomethyl group, a N-ethylaminomethyl group, a N-propylaminomethyl group, a N-isopropylaminomethyl group, a N-butylaminomethyl group, a N-isobutylaminomethyl group, a N-tert-butylaminomethyl group, a N-pentylaminomethyl group and a N-hexylaminomethyl group, and so on. Among them, for example, a N-methylaminomethyl group, a N-ethylaminomethyl group and a N-butylaminomethyl group, and so on, are more preferable.

A di-lower alkylamino lower alkyl group is a substituent in which a lower alkyl group is substituted with a di-lower alkylamino group mentioned above. As the specific example, there may be mentioned, for example, a N,N-dimethylaminomethyl group, a N,N-diethylaminomethyl group, a N,N-dipropylaminomethyl group, a N,N-diisopropylaminomethyl group, a N,N-dibutylaminomethyl group, a N,N-diisobutylaminomethyl group, a N,N-di-tert-butylaminomethyl group, a N,N-dipentylamlnomethyl group, a N,N-di-hexylaminomethyl group and a N-ethyl-N-methylaminomethyl group and N-methyl-N-propylaminomethyl group, and so on. Among them, for example, a N,N-dimethylaminomethyl group, a N,N-diethylaminomethyl group, a N,N-dibutylaminomethyl group, N-ethyl-N-methylaminomethyl group and a N-methyl-N-propylaminomethyl group, and so on are more preferable.

A tri-lower alkylammonio lower alkyl group is a substituent in which a lower alkyl group is substituted with a tri-lower alkylammonio group stated above. As the specific example, there may be mentioned, for example, a N,N,N-trimethylammoniomethyl group, a N,N,N-triethylammoniomethyl group, a N,N,N-tripropylammoniomethyl group, a N,N,N-triisopropylammoniomethyl group, a N,N,N-tributylammoniomethyl group, a N,N,N-triisobutylammoniomethyl group, a N,N,N-tri-tert-butylammoniomethyl group, a N,N,N-tripentylammoniomethyl group, a N,N,N-trihexylammoniomethyl group and a N,N-dimethyl-N-propylammoniomethyl group, and so on. Among them, for example, a N,N,N-trimethylammoniomethyl group, a N,N,N-triethylammoniomethyl group, a N,N,N-tributylammoniomethyl group, N-ethyl-N,N-dimethylammoniomethyl group and a N,N-dimethyl-N-propylammoniomethyl group, and so on are more preferable.

A lower alkanoylamino group is a substituent in which an amino group is substituted with a lower alkanoyl group mentioned above, being exemplified, for example, with a N-acetylamino group, a N-propionylamino group and a N-butylylamino group, and so on. Among them, for example, N-acetylamino and N-propionylamino groups are preferable.

A lower aroylamino group is a substituent in which an amino group is substituted with an aroyl group, being exemplified, for example, with a N-benzoylamino group and N-naphthylamino group, and so on. Among them, for example, a N-benzoylamino group, and so on are preferable.

A lower alkanoylamidino lower alkyl group is a substituent in which an amidino lower alkyl group is substituted with a lower alkanoyl group stated above, being exemplified with, for example, a N-acetylamidinomethyl group, N-propionylamidinomethyl group, and N-butyrylamidinomethyl group, and so on. Among them, for example, N-acetylaminodimethyl and N-propionylamidinomethyl groups are preferable.

A lower alkyl sulfinyl group is a substituent in which a sulfinyl group is substituted with a lower alkyl group stated above, exemplified with, for example, a N-methyl sulfinyl group, a N-ethylsulfinyl group, and a N-butylsulfinyl group, and so on. Among them, for example, N-methylsulfinyl and N-ethylsulfinyl groups are preferable.

A lower alkyl sulfonyl group is a substituent in which a sulfonyl group is substituted with a lower alkyl group stated above, exemplified with, for example, a N-methyl sulfonyl group, a N-ethylsulfonyl group, and a N-butylsulfonyl group, and so on. Among them, for example, N-methylsulfonyl and N-ethylsulfonyl groups are preferable.

A lower alkyl sulfonylamino group is a substituent in which an amino group is N-substituted with a lower alkyl sulfonyl group stated above, exemplified with, for example, a N-methyl sulfonylamino group, a N-ethylsulfonylamino group, and a N-butylsulfonylamino group, and so on. Among them, for example, N-methylsulfonylamino and N-ethylsulfonylamino groups are preferable.

A lower alkoxyimino group is a substituent in which is substituted an imino group with a lower alkoxy group stated above, being exemplified with a methoxyimino group, an ethoxyimino group, and a propoxyimino group. Among them, for example, methoxyimino and ethoxyimino groups, and so on are preferable.

As a lower alkenyl group, a straight-chain or branched alkenyl group with two to six carbons, and so on is preferable. As such groups, there may be mentioned, for example, a vinyl group, an allyl group, an isopropenyl group, a 1-butenyl group, a 3-butenyl group, al, 3-butanedienyl group, a 2-pentenyl group, a 4-pentenyl group, a 1-hexenyl group, a 3-hexenyl group, a 5-hexenyl group, and so on. Among them, 1-propenyl, allyl, isopropenyl and 1-butenyl groups are preferable.

As a lower alkynyl group, for example, a straight-chain or branched alkynyl group with two to six carbons is preferable. As such alkynyl groups, there may be mentioned a 2-propynyl, 2-butynyl, 3-butynyl, 2-pentynyl, and so on. Among them, 2-propynyl and a 2-butynyl are more preferable.

As a cyclo lower alkyl group, a monocyclic or bicyclic alkyl group with three to ten carbon atoms, and so on is preferable. As the specific examples, there may be mentioned, for example, a cyclopropyl group, a cyclobutyl group, a cyclopentyl group, a cyclohexyl group, a cycloheptyl group, a cyclooctyl group, and so on. Among them, for example, cyclopentyl, cyclohexyl, cycloheptyl and cyclooctyl groups, and so on are preferable.

As an aryl group, the one aryl comprising six to fifteen carbon atoms are preferable, being exemplified with a phenyl group and a naphthyl group, and so on. Among them, for example, a phenyl group, and so on is preferable.

As a heteroaromatic ring group, preferable is an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, and so on. Among them, for example, an imidazolyl group, an isoxazolyl group, an isoquinolyl group, an indolyl group, an ethylenedioxyphenyl group, a pyridyl group, a pyrimidinyl group, a pyridazinyl group, a pyrazolyl group, a quinolyl group, a benzoimidazolyl group, a thiazolyl group and a thienyl group are more preferable, and a pyridyl group and a pyrazolyl group are especially preferable.

An aliphatic heterocyclic group is an aliphatic mono-, bi- or tricyclic heterocyclic group, which may be saturated aliphatic heterocyclic group and an unsaturated aliphatic heterocyclic group. Specifically, for example, there may be mentioned an isoxazolinyl group, an isoxazolidinyl group, a tetrahydropyridyl group, an imidazolidinyl group, a tetrahydrofuranyl group, a tetrahydropyranyl group, a piperadinyl group, a piperidinyl group, a pyrrolydinyl group, a pyrrolinyl group, a morpholino group, a tetrahydroquinolinyl group and a tetrahydroisoquinolinyl group, and so on are preferable. Among them, for example, an isoxazolinyl group, an isoxazolidinyl group, a tetrahydropyridyl group, a tetrahydrofuranyl group, tetrahydropyranyl group, a piperadinyl group, a piperidinyl group, a pyrrolidinyl group, a morpholino group, a tetrahydroisoquinolinyl groups, and so on are more preferable, and, furthermore, an isoxazolinyl group, a tetrahydropyridyl group, a piperadinyl group, a piperidinyl group, a pyrrolidinyl group, a morpholino group and a tetrahydroisoquinolinyl group, and so on are especially preferable.

As an aralkyl group, the one aralkyl comprising seven to fifteen carbons are preferable. As specific examples, there may be mentioned, for example, a benzyl group, an alpha-methylbenzyl group, a phenethyl group, a 3-phenylpropyl group, 1-naphthylmethyl group, 2-naphthylmethyl group, an alpha-methyl(1-naphthyl)methyl group, an alpha-methyl(2-naphthyl)methyl group, an alpha-ethyl(1-naphthyl)methyl group, an alpha-ethyl(2-naphthyl)methyl group, diphenylmethyl group and a dinaphthylmethy group, and so on, and a benzyl group, an alpha-methylbenzyl group and a phenethyl group, and so on are especially preferable.

As a straight-chain or branched lower alkylene group, an alkylene group comprising one to six carbon atoms is preferable. As the specific examples, there may be mentioned a methylene group, an ethylene group, a propylene group, a tetramethylene group, a dimethylmethylene group, a diethylmethylene group, and so on. Among them, for example, a methylene group, an ethylene group, a propylene group and a dimethylmethylene group, and so on are preferable.

As a spiro cyclo lower alkyl group, an alkyl group which forms a spiro ring of three to six carbon atoms is preferable.

As the specific examples, there may be mentioned a spiro cyclopropyl group, a spiro cyclobutyl group, a Spiro cyclopentyl group and a spiro cyclohexyl group, and so on. Among them, a spiro cyclopentyl group and a spiro cyclohexyl group, and so on are more preferable.

Ar represents a nitrogen-containing heteroaromatic ring group selected from a group consisting of a pyridyl group, a pyrimidinyl group, a pyradinyl group, a pyridazinyl group, a thiazolyl group, an isothiazolyl group, an oxazolyl group, an isoxazolyl group, a pyrazolyl group, a pyrrolyl group, an imidazolyl group, an indolyl group, an isoindolyl group, an isoquinolyl group, a benzothiazolyl group and a benzoxazolyl group. Among them, for example, a pyridyl group, a pyrimidinyl group, a pyradinyl group, a pyridazinyl group, a thiazolyl group, a pyrazolyl group, an imidazolyl group, and so on are more preferable, and, for example, a pyridyl group and a pyrazolyl group, and so on are especially preferable.

Said nitrogen-containing heteroaromatic ring group (1) may be substituted, the same or different, with one to three substitutent(s) selected from a group consisting of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and the substituent represented by a formula $Y_1$—$W_1$—$Y_2$—$R_p$ (wherein: $R_p$ is a hydrogen atom or a lower alkyl group, a lower alkenyl group or a lower alkynyl group optionally having one to three of said substituent(s); or a cyclo lower alkyl group, an aryl group, a heteroaromatic ring group selected from a group consisting of an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or, an aliphatic heterocyclic group selected from a set of groups of an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, pyrrolinyl group, a morpholino group, a tetrahydroquinolinyl group and a tetrahydroisoquinolinyl group, each of which cyclic groups may be substituted with one to three of said substituent(s) or, furthermore, may has a bicyclic- or tricyclic-fused ring containing the partial structure selected from a set of groups consisting of:

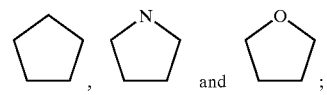

$W_1$ is a single bond, an oxygen atom, a sulfur atom, SO, $SO_2$, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, $C\equiv C$, CO, CS, OC(O), OC(O)$NR_q$, OC(S)$NR_q$, SC(O), SC(O)$NR_q$ and C(O)O (wherein: $R_q$ and $R_r$ are a hydrogen atom or a substituent selected from a set of groups of a lower alkyl group, a cyclo lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a lower alkyl group, an aryl group or an aralkyl group which may be substituted with one to three of said substitutent(s).); $Y_1$ and $Y_2$ are each the same or different, a single bond or a straight-chain or branched lower alkylene group which may have a said bicyclic or tricyclic fused ring.), (2) may form a five- to seven-membered ring selected from a set of groups of:

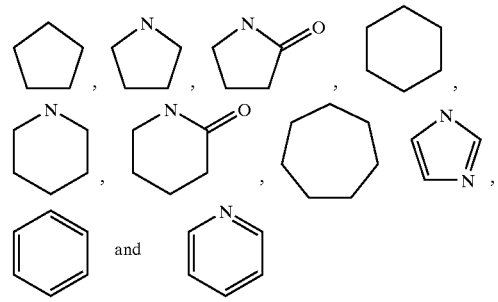

which may be formed together with the carbon atom of said nitrogen-containing heteroaromatic cyclic group, on which the substituent, which is selected from a set of groups consisting of a lower alkyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkylsulfinyl group, a lower alkylsulfonyl group, a lower alkylsulfonylamino group, and a lower alkanoylamidino lower alkyl group (hereinafter indicated as ring-substituent) stands, the carbon atom next to said carbon atom, and a carbon atom, an oxygen atom and/or a nitrogen atom on said ring-substituent;

(3) may form a fifth- to seven-membered ring selected from a set of groups consisting of:

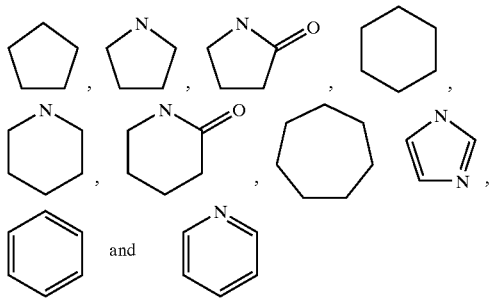

which may be formed together with the carbon atom of said nitrogen-containing heteroaromatic group on which a substituent represented by the formula $Y_1-W_1-Y_2-R_p$ (wherein: $Y_1$, $W_1$, $Y_2$ and $R_p$ have the same meanings as stated above) stands, the carbon atom next to said carbon atom, and a carbon atom, an oxygen atom and/or a nitrogen atom on said ring-substituent.

Next, the forms of substituents in the category (1) will be explained in detail. As specific examples of the substituents, there may be mentioned (1-1) a substituent selected from a set of groups of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group; and (1-2) a substituent selected from a set of groups represented by a formula of $Y_1-W_1-Y_2-R_p$ (wherein: $R_p$ is a hydrogen atom or a lower alkyl group, a lower alkenyl group or a lower alkynyl group or a cyclo lower alkyl group, an aryl group, a heteroaromatic ring group or an aliphatic heterocyclic group; $W_1$ is a single bond, an oxygen atom, a sulfur atom, SO, $SO_2$, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, CC, CO, CS, OC(O), $OC(O)NR_q$, OC(S)$NR_q$, SC(O), $SC(O)NR_q$ and C(O)O (wherein: $R_q$ and $R_r$ are each a hydrogen atom, a lower alkyl group, an aryl group or an aralkyl group which may be substituted with one to three of said substituents); $Y_1$ and $Y_2$ are the same or different, a straight-chain or branched lower alkylene which may have said bicyclic or tricyclic fused ring.), and said nitrogen-containing heteroaromatic group may be substituted with one to three of the same or different of said substituents.

In (1-1), the more preferable substituents are, for example, a lower alkyl group, a hydroxyl group, halogen atoms, a nitro group, a carboxyl group, a carbamoyl group, a formyl group, a lower alkanoyloxy group, a hydroxy lower alkyl group, a halo lower alkyl group, a carbamoyl lower alkyl group, lower alkoxy group, a lower alkoxycarbonyl group, a lower alkylcarbamoyl group, a lower alkylcarbamoyloxy group, an amino group, a lower alkylamino group, a di-lower alkylamino group, an amino lower alkyl group, a lower alkylamino lower alkyl group, a di-lower alkylamino lower alkyl group, a lower alkanoylamino group, an aroylamino group, a lower alkylsulfonylamino group, and so on, and especially preferable are, for example, a hydroxy group, halogen atoms, a lower alkanoyloxy group, a hydroxy lower alkyl group, a lower alkoxy group, a lower alkoxycarbonyl group, an amino group and a lower alkylamino lower alkyl groups, and so on.

In the formula $Y_1-W_1-Y_2-R_p$ in (1-2), when $R_p$ is any of a lower alkyl group, a lower alkenyl group, a lower alkynyl group, a cyclo lower alkyl group, an aryl group, a heteroaromatic ring group or an aliphatic heterocyclic group, each of these substituents ($=R_p$) may be substituted to form said nitrogen-containing heteroaromatic ring substituted with one to three of the same or different substituent(s) selected from a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, fan aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group.

In cases where $R_p$ is a cyclo lower alkyl group, an aryl group, a heteroaromatic ring group or an aliphatic heterocyclic group, each of these groups may have, in addition to the substituents described above, a bicyclic or tricyclic fused ring having a partial structure selected from a set of groups of:

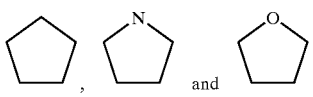

In the formula $Y_1-W_1-Y_2-R_p$, $W_1$ is a single bond, an oxygen atom, a sulfur atom, SO, $SO_2$, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, C—C, CO, CS, OC(O), $OC(O)NR_q$, $OC(S)NR_q$, SC(O), $SC(O)NR_q$ and C(O)O (wherein: $R_q$ and $R_r$ are hydrogen atom or a substituent selected from a set of groups of a lower alkyl group, a cyclo lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a lower alkyl group, an aryl group or an aralkyl group which may be substituted with one to three of said substituents.). Among them, an oxygen atom, a sulfur atom, $NR_q$, $SO_2NR_q$, $N(R_q)SO_2$, $CONR_q$, $N(R_q)CO$, $N(R_q)COO$, $C(R_q)=CR_r$, OC(O), $OC(O)NR_q$, C(O)O, and so on, are more preferable and $NR_q$, $N(R_q)SO_2$, $CONR_q$, $N(R_q)CO$, $N(R_q)COO$, OC(O). C(O)O, and so on are especially preferable.

Furthermore, $R_q$ and $R_r$ in $W_1$ are each a hydrogen atom or a substituent selected from a set of groups, namely, a lower alkyl group, a cyclo lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a lower alkyl group, an aryl group or an aralkyl group, which may be substituted with one to three of said substituent(s). Said lower alkyl group, said aryl group, or said aralkyl group may be substituted with one to three substituent(s) selected from a set of groups of, a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group.

In the formula $Y_1-W_1-Y_2-R_p$, $Y_1$ and $Y_2$ are each of same or different, a single bond or a straight-chain or branched lower alkylene. Said straight-chain or branched lower alkylene may have a bicyclic or tricyclic fused ring containing a partial structure selected from the set of groups;

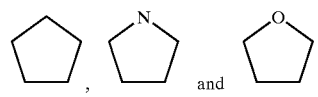

Next, the forms of the substituent in (2) will be explained in detail. This substituent is a five- to seven-membered ring selected from a set of groups:

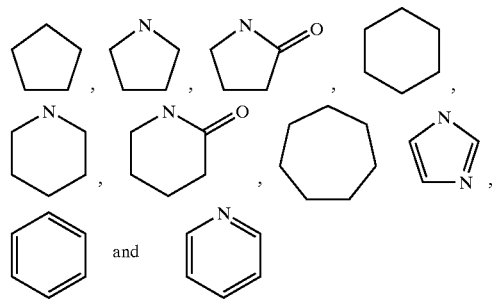

which may be formed together with the carbon atom of said nitrogen-containing heteroaromatic cyclic group, on which the substituent, which is selected from a set of groups consisting of a lower alkyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkylsulfinyl group, a lower alkylsulfonyl group, a lower alkylsulfonylamino group, and a lower alkanoylamidino lower alkyl group stands, the carbon atom next to said carbon atom, and a carbon atom, an oxygen atom and/or a nitrogen atom on said ring-substituent.

Furthermore, among said ring-substituents, more preferable are a lower alkyl group, a lower alkanoyloxy group, a hydroxy lower alkyl group, a halo lower alkyl group, a carbamoyl lower alkyl group, a lower alkoxy group, a lower alkoxycarbonyl group, a lower alkylcarbamoyl group, a lower alkylcarbamoyloxy group, a lower alkylamino group, a di-lower alkylamino group, an amino lower alkyl group, a lower alkylamino lower alkyl group, a di-lower alkylamino lower alkyl group, a lower alkanoylamino group, an aroylamino group, and so on. Among them, especially preferable are a lower alkanoyloxy group, a hydroxy lower alkyl group, a lower alkoxy group, a lower alkoxycarbonyl group, a lower alkylamino lower alkyl group, and so on.

Next the forms of the substituents (3) will be explained in detail. This substituent is a five- to seven-membered ring, and so on, which may be selected from a set of groups:

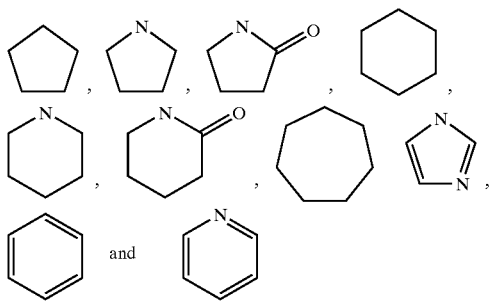

which may be formed by the participation of the ring-carbon atom on a ring which the substituent of the formula $Y_1$—$W_1$—$Y_2$—$R_p$ (wherein: $Y_1$, $W_1$, $Y_2$ and $R_p$ have the same meanings as mentioned above) bind to, the carbon atom next to said carbon atom, and a carbon atom, an oxygen atom and/or a nitrogen atom on said ring-substituent.

Although all said substituents and groups constructed on said nitrogen-containing heteroaromatic ring groups of (1), (2) and (3) are preferable, more preferable forms of them are:

(1') a substituent selected from both the set of groups consisting of a lower alkyl group, a hydroxyl group, halogen atoms, a formyl group, a lower alkanoyloxy group, a hydroxy lower alkyl group, a halo lower alkyl group, a carbamoyl lower alkyl group, lower alkoxy group, a lower alkoxycarbonyl group, a lower alkylcarbamoyl group, a lower alkylcarbamoyloxy group, an amino group, a lower alkylamino group, a di-lower alkylamino group, an amino lower alkyl group, a lower alkylamino lower alkyl group, a di-lower alkylamino lower alkyl group, a lower alkanoylamino group, an aroylamino group and a lower alkylsulfonyl group, a lower alkylsulfonylamino group, a hydroxyimino group and a lower alkoxyimino group, and a substituent represented by a formula $Y_{1a}$—$W_{1a}$—$Y_{2a}$—$R_{pa}$ (wherein: $R_{pa}$ is a hydrogen atom or a lower alkyl group, a lower alkenyl group or a lower alkynyl group which may be substituted with one to three of said substituents or a cyclo lower alkyl group, an aryl group, a heteroaromatic ring group selected from a set of groups of an imidazolyl group, an isoxazolyl group, an isoquinolyl group, an indolyl group, an ethylenedioxyphenyl group, a pyridyl group, a pyrimidinyl group, a pyridazinyl group, a pyrazolyl group, a quinolyl group, a benzoimidazolyl group, a thiazolyl group, a thienyl and a triazolyl group, and an aliphatic heterocyclic group selected from a set of groups of an isoxazolinyl group, an isoxazolidinyl group, a tetrahydropyridyl group, a tetrahydrofuranyl group, a tetrahydropyranyl group, a piperadinyl group, a piperidinyl group, a pyrrolidinyl group, a morpholino group and a tetrahydroisoquinolinyl group, which may be substituted with one to three of said substituent(s) and may, furthermore, have a bicyclic or a tricyclic fused ring of a partial structure selected from a set of structures of:

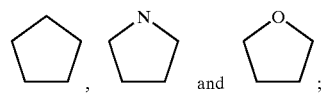

$W_{1a}$ is an oxygen atom, a sulfur atom, $NR_{qa}$, $SO_2NR_{qa}$, $N(R_{qa})SO_2$, $CONR_{qa}$, $N(R_{qa})CO$, $N(R_{qa})COO$, $C(R_{qa})=CR_{ra}$, $OC(O)$, $OC(O)NR_{qa}$, and $C(O)O$ (wherein $R_{qa}$ and $R_{ra}$ are each either a substituent selected from a set of groups of a hydrogen atom, a lower alkyl group, a cyclo lower alkyl group, a hydroxyl group, halogen atoms, a formyl group, a lower alkanoyloxy group, a hydroxy lower alkyl group, a halo lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a lower alkylcarbamoyloxy group, an amino group, a lower alkylamino group, a di-lower alkylamino group, an amino lower alkyl group, a lower alkylamino lower alkyl group, a di-lower alkylamino lower alkyl group, a lower alkanoylamino group, an aroylamino group, and a lower alkylsulfonylamino group or a lower alkyl group, an aryl group or an aralkyl group which may be substituted with said substituent(s)): $Y_{1a}$ and $Y_{2a}$, are the same or different, a single bond or a straight-chain or branched lower alkylene group which may have a said bicyclic or tricyclic fused ring;

(2') a nitrogen-containing heteroaromatic ring group which has a condensed five- or six-membered ring selected from the group of rings:

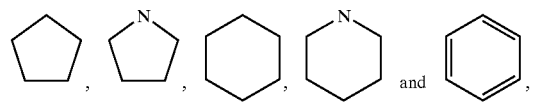

which are formed together with the ring-carbon atom on said heterocyclic ring on which the ring-substituent selected from a set of groups of a lower alkyl group, a lower alkanoyloxy group, a hydroxy lower alkyl group, a halo lower alkyl group, a carbamoyl ower alkyl group, a lower alkoxy group, a lower alkoxycarbaonyl group, a lower alkylcarbamoyl group a lower alkylcarbamoyloxy group, a lower alkylamino group, a di-loser alkylamino group, an amino lower alkyl group, a lower alkylamino lower alkyl group, a di-lower alkylamino lower alkyl group, a lower alkanoylamino group and an aroylamino group stands, the carbon atom next to said carbon atom, and a carbon atom, an oxygen atom and/or a nitrogen atom on said ring-substituent; or, (3') a fused five- or six-membered ring selected from a group of rings:

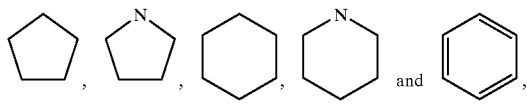

which are formed together with the ring-carbon atom which the substituent represented by the formula of $Y_{1a}$—$W_{1a}$—$Y_{2a}$—$R_{pa}$ (wherein: $Y_{1a}$, $W_{1a}$, $Y_{2a}$ and $R_{pa}$ have the same meanings as stated above) binds to, the carbon atom next to said carbon atom, and a carbon atom, an oxygen atom and/or a nitrogen atom on said substituent.

Furthermore, the more preferable substituent groups are:
(1") a substituent selected from the group consisting from a hydroxy group, halogen atoms, a lower alkanoyloxy group, a hydroxy lower alkyl group, a lower alkoxy group, a lower alkoxycarbonyl group, an amino group and a lower alkylamino lower alkyl group, and a group represented by a formula $Y_{1b}$—$W_{1b}$—$Y_{2b}$—$R_{pb}$ (wherein: $R_{pb}$ is a hydrogen atom or a lower alkyl group, a lower alkenyl group or a lower alkynyl group which are optionally substituted with one to three of said substituent(s), or a cyclo lower alkyl group, an aryl group, a heteroaromatic ring group selected from a set of groups of a pyridyl group and a pyrazolyl group or an aliphatic heterocyclic group selected from a set of groups of an isoxazolinyl group, a tetrahydropyridyl group, a piperadinyl group, a piperidinyl group, a pyrrolidinyl group, and amino group and a tetrahydroisoquinolinyl group, which may be substituted with one to three said substituent and which may have bicyclic or tricyclic fused ring containing partial structure selected from a group of;

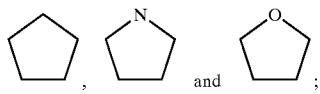

$W_{1b}$ is a $NR_{qb}$, $N(R_{qb})SO_2$, $CONR_{qb}$, $N(R_{qb})CO$, $N(R_{qb})COO$, $OC(O)$ or $C(O)O$ (wherein: $R_{qb}$ and $R_{rb}$ are each a hydrogen atom or a substituent selected from a set of groups which consists of a hydroxyl group, halogen atoms, a lower alkanoyloxy group, a hydroxy lower alkyl group, a lower alkoxy group, a lower alkoxycarbonyl group, an amino group and a lower alkylamino lower alkyl group, or a lower alkyl group, an aryl group or an aralkyl group which may be substiuented with one to three of said substituent(s)); $Y_{1b}$ and $Y_{2b}$ are each, the same or different, a single bond or a straight-chain or branched lower alkylene group which may have a said bicyclic or tricyclic fused ring.)

(2") a five- or six-membered ring selected from a group of:

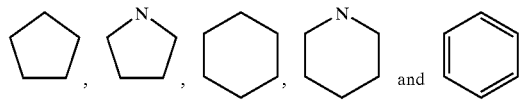

which is formed together with a ring-carbon atom to which a substituent selected from a set of groups of a lower alkanoyloxy group, a hydroxy lower alkyl group, a lower alkoxy group, a lower alkoxycarbonyl group and a lower alkylamino lower alkyl group binds, the carbon atom next to said carbon atom, and a carbon atom, an oxygen atom and/or a nitrogen atom on said substituent; or (3") a five- or six-membered ring selected from a group of:

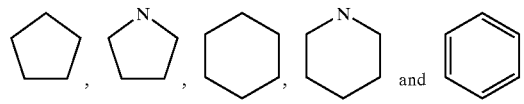

which is formed together with a ring-carbon atom to which a substituent represented by the formula $Y_{1b}$—$W_{1b}$—$Y_{2b}$—$R_{pb}$ (wherein: $Y_{1b}$, $W_{1b}$, $Y_{2b}$ and $R_{pb}$ have the same meanings as stated above) binds, the carbon atom next to said carbon atom and a carbon atom, an oxygen atom and/or a nitrogen atom of said substituent.

X and Z are each, the same or different, either a carbon atom or a nitrogen atom, or, if approproate, a CH or a nitrogen atom together with the $R_1$, $R_2$ and/or $R_3$ which they bind to.

Y is CO, SO or $SO_2$.

$R_1$ is a hydrogen atom or a substituent represented by a formula $Y_3$—$W_2$—$Y_4$—$R_s$ (wherein: $R_s$ is a hydrogen atom or a lower alkyl group, a lower alkenyl group, a lower alkynyl group, a cyclo lower alkyl group, an aryl group, or a heteroaromatic ring group selected from a set of groups of an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group selected from a set of groups of an isoxazolinyl group, an isoxazolidinyl group, a tetrahydropyridyl group, an imidazolidinyl group, a tetrahydrofuranyl group, a piperazinyl group, a piperidinyl group, a pyrrolidinyl group, pyrrolinyl group, a morpholino group, a tetrahydroquinolinyl group and a tetrahydroisoquinolinyl group, which may be substituted with one to three of said substituent(s); $W_2$ is a single bond, an oxygen atom, a sulfur atom, SO, $SO_2$, $NR_t$, $SO_2NR_t$, $N(R_t)SO_2NR_u$, $N(R_t)SO_2$, $CH(OR_t)$, $CONR_t$, $N(R_t)CO$, $N(R_t)CONR_u$, $N(R_t)COO$, $N(R_t)CSO$, $N(R_t)COS$, $C(R_v)=CR_t$, $C\equiv C$, Co, CS, OC(O), OC(O)$NR_t$, OC(S)$NR_t$, SC(O), SC(O)$NR_t$ or C(O)O (wherein: each of $R_t$ and $R_u$ is a hydrogen atom or a substituent selected from a set of groups of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a lower alkyl group, an aryl group or an aralkyl group, which may be substituted with one to three of said substituent(s)); $Y_3$ and $Y_4$ are each, the same or different, a single bond or a straight-chain or branched lower alkylene), or a lower alkyl group which may be substituted with one to three of the same or different substituent(s) selected from both a set of groups of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkylcarbamoyl group, a di-lower alkylcarbamoyl group, a carbamoyloxy group, a lower alkylcarbamoyloxy group, a di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and a set of groups represented by the formula $Y_3$—$W_2$—$Y_4$—R, (wherein: $R_s$, $W_2$, $Y_3$ and $Y_4$ have the same meanings as stated above); or forms a nitrogen atom together with X.

Here comes a detailed explanation of the various forms of $R_1$. Thus, $R_1$ is a hydrogen atom or a substituent represented by the formula $Y_3$—$W_2$—$Y_4$—$R_s$ (wherein: $R_s$, $W_2$, $Y_3$ and $Y_4$ have the same meanings as stated above), or a lower alkyl group which may be substituted with one to three of the same or different substituent(s), or forms a nitrogen atom together with X.

Regarding the formula $Y_3$—$W_2$—$Y_4$—$R_s$, $R_s$ is a lower alkyl group, a lower alkenyl group, a lower alkynyl group, a cyclo lower alkyl group, an aryl group, a heteroaromatic ring group, or an aliphatic heterocyclic group, and so on, and each of these substituents may, optionally, be substituted with one to three substituent(s) selected from a set of groups of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group. As more preferable substituents, there may be mentioned the same ones as those mentioned as the substituents on Ar.

With the formula $Y_3$—$W_2$—$Y_4$—$R_s$, $W_2$ is a single bond, an oxygen atom, a sulfur atom, SO, $SO_2$, $NR_t$, $SO_2NR_t$, $N(R_t)SO_2NR_u$, $N(R_t)SO_2$, CH(OR$_t$), CONR$_t$, $N(R_t)CO$, $N(R_t)CONR_u$, $N(R_t)COO$, $N(R_t)CSO$, $N(R_t)COS$, $C(R_v)=CR_r$, C≡C, CO, CS, OC(O), OC(O)NR$_t$, OC(S)NR$_t$, SC(O), SC(O)NR$_t$ and C(O)O, wherein $R_t$ and $R_u$ are each a hydrogen atom or a substituent selected from a set of groups of a lower alkyl group, a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or a lower alkyl group, an aryl group or an aralkyl group which may be substituted with one to three of said substituent(s). Furthermore, each of said lower alkyl group, said aryl group and said aralkyl group may be substituted with one to three of said substituent(s) as $R_s$ may be.

With the formula $Y_3$—$W_2$—$Y_4$—$R_s$, $Y_3$ and $Y_4$ are each, the same or different, a single bond or a straight-chain or branched lower alkylene group.

As more preferable examples of $R_1$, there may be mentioned, for example, a hydrogen or a lower alkyl which may be substituted with one to three of same or different substituent(s) selected from a substituent represented by a formula $Y_{3a}$—$W_{2a}$—$Y_{4a}$—$R_{sa}$ (wherein: $R_{sa}$ is a hydrogen atom or a lower alkyl group, a lower alkenyl group, a cyclo lower alkyl group, an aryl group, a heteroaromatic ring group selected from an indolyl group, or an aliphatic heterocyclic group selected from a set of groups of a tetrahydropyridyl group, a piperadinyl group, a piperidinyl group, a pyrrolidinyl group and a morpholino group, all of which groups may be substituted with one to three of said substituent(s); $W_{2a}$ is a single bond. $NR_{ta}$, CH(OR$_{ta}$), CONR$_{ta}$, $N(R_{ta})CO$, $N(R_{ta})COO$, OC(O)NR$_{ta}$ or C(O)O (wherein: $R_{ta}$ and $R_{ua}$ are each a hydrogen atom or a lower alkyl group, an aryl group or an aralkyl group which may be substituted with one to three of said substituent(s)); $Y_{3a}$ and $Y_{4a}$ are each, the same or different, a single bond, or a straight-chain or branched lower alkylene group), or a lower alkyl group which may be substituted with one to three of the same or different substituent(s) selected from both a set of groups of a lower alkyl group, a hydroxyl group, a carbamoyl group, a lower alkanoyloxy group, a hydroxy lower alkyl group, a lower alkoxy group, a lower alkoxycarbonyl group, a lower alkylcarbamoyl group, a di-lower alkylcarbamoyl group, a carbamoyloxy group, a lower alkylcarbamoyloxy group, a lower alkylamino group, a di-lower alkylamino group, an amino lower alkyl group, a lower alkylamino lower alkyl group, a di-lower alkylamino lower alkyl group, a lower alkanoylamino group and an aroylamino group), and a substituent represented by the formula $Y_{3a}-W_{2a}-Y_{4a}-R_{sa}$ (wherein: $R_{sa}$, $W_{2a}$, $Y_{3a}$ and $Y_{4a}$ have the same meanings as stated above). $R_1$ may also preferably form a nitrogen atom together with X. And, as the especially preferable examples of $R_1$, there may be mentioned a hydrogen or a lower alkyl group which may be substituted with one to three of the same or different substituent(s) selected from a substituent represented by a formula $Y_{3b}-W_{2b}-Y_{4b}-R_{sb}$ (wherein: $R_{2b}$ is a hydrogen atom or a lower alkyl group, a cyclo lower alkyl group and an aryl group which may be substituted with one to three of said substituent(s); $W_{2b}$ is a single bond, $N(R_{tb})COO$ or $C(O)O$ (wherein $R_{tb}$ is a hydrogen atom, a lower alkyl group, an aryl group or an aralkyl group which may be substituted with one to three of said substituent(s)); $Y_{3b}$ and $Y_{4b}$ are respectively, the same or different, a single bond, a straight-chain or branched lower alkylene or a hydroxy lower alkyl group) and a substituent represented by the formula $Y_{3b}-W_{2b}-Y_{4b}-R_{sb}$ (wherein: $R_{sb}$, $W_{2b}$, $Y_{3b}$ and $Y_{4b}$ have the same meanings as stated above)). $R_1$ also forms, very preferably, a nitrogen atom together with X.

$R_2$ and $R_3$ are each independently, the same or different:
(i) a hydrogen, a hydroxy group, a lower alkyl group, a lower alkoxy group, or a substituent represented by the formula $Y_3-W_2-Y_4-R_s$ (wherein: $R_s$, $W_2$, $Y_3$ and $Y_4$ have the same meanings as stated above), or
(ii) either $R_2$ or $R_3$ forms, together with $R_1$ and X, a saturated five- to eight-membered cyclic group selected from groups of (a) and (b):

(a)

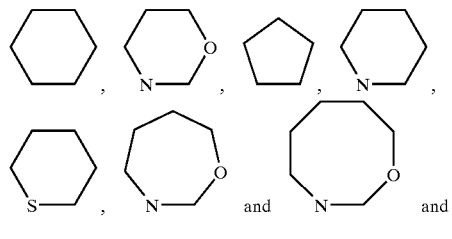

(b)

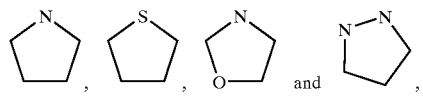

the other (remaining) one forming a five- to seven-membered ring together with a ring carbon atom or a ring nitrogen atom, and a carbon atom, an oxygen atom and/or a nitrogen atom in the ring-substituent on said ring, or
(iii) $R_2$ and $R_3$, being taken together, form a spiro cyclo lower alkyl group, and also form an oxo group together with Z to which they bind, or form, together with Z to which they bind, $R_1$ and X, either a saturated or an unsaturated five- to eight-membered cyclic group selected from sets of groups of (a) and (b)

(a)

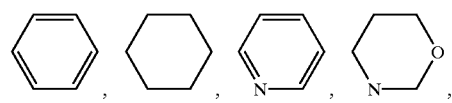

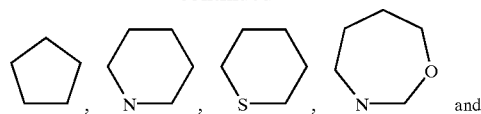 and

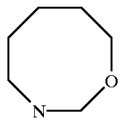

(b)

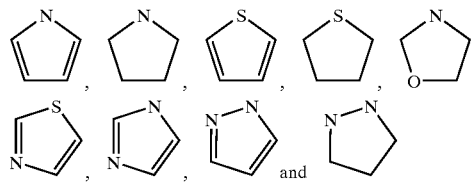 and which may both contain one or more kinds of heteroatoms selected from a group of a nitrogen atom, an oxygen atom and a sulfur atom and which may be substituted with one to three of the same or different substituent(s) selected from both a set of groups of a lower alkyl group, a spiro cyclo lower alkyl group which may be substituted, a hydroxy group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, carbamoyl lower alkyl group, a lower alkoxy group, a lower alkoxycarbonyl group, a lower alkoxycarbonylamino group, a lower alkoxycarbonylamino lower alkyl group, a lower alkyl carbamoyl group, di-lower alkyl carbamoyl group, a carbamoyloxy group, a lower alkylcarbamoyloxy group, di-lower alkyl carbamoyloxy group, and amino group, a lower alkylamino group, di-lower alkylamino group, tri-lower alkylammonio group, an amino lower alkyl group, a lower alkylamino lower alkyl group, di-lower alkylamino lower alkyl group, tri-lower alkylammonio lower alkyl group, a lower alkanoylamino group, an aroylamino group, a lower alkanoylamidino lower alkyl group, a lower alkyl sulfinyl group, a lower alkylsulfonyl group, a lower alkylsulfonylamino group, a hydroxyimino group and a lower alkoxyimino group, and a set of substituents represented by the formula $Y_1-W_1-Y_2-R_p$ (wherein: $R_p$, $W_1$, $Y_1$ and $Y_2$ have the same meanings as stated above), and furthermore may be fused with a cyclo alkyl group, an aryl group, a heteroaromatic ring group selected from a set of groups of an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, and an aliphatic heterocyclic group(s) selected from an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, pyrrolinyl group, a morpholino group, a tetrahydroquinolinyl group and a tetrahydroisoquinolinyl group, which may be substituted with one to three of the same or different substituent(s).

Here, $R_2$ and $R_3$ are explained more specifically as follows. The present invention includes all of the three cases where (i) each of the $R_2$ and $R_3$ has, the same or different, a substituent, independently; (ii) either $R_2$ or $R_3$ forms a substituent together with other substituent(s), followed by the formation of a second substituent between the substituent formed and the remaining $R_2$ or $R_3$ group; and (iii) both $R_2$ and $R_3$ work together or further collaborate with other substituent(s) and so on, to form a substituent.

Next each form of the substituents $R_2$ and $R_3$ is explained.

(i) $R_2$ and $R_3$ are each, the same or different and independently, a hydrogen atom, a hydroxy group, a lower alkyl group, a lower alkoxy group, or a substituent which is represented by the formula $Y_3$—$W_2$—$Y_4$—$R_s$ (wherein: $R_9$, $W_2$, $Y_3$ and $Y_4$ have the meanings stated above);

(ii) either $R_2$ or $R_3$ forms, together with $R_1$ and X, a saturated five- to eight-membered ring selected from sets of groups (a) and (b):

(a)

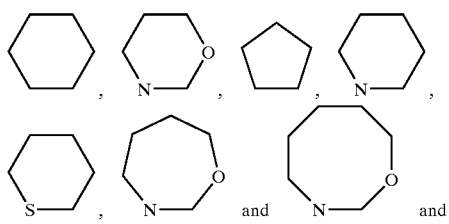

(b)

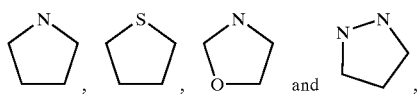

and the remaining group, $R_2$ or $R_3$, may form a five- to seven-membered ring, together with said five- to eight-membered ring, by collaborating with a carbon atom or a nitrogen atom on said ring, and a carbon atom, an oxygen atom and/or a nitrogen atom in the ring-substituent on said ring.

(iii) $R_2$ and $R_3$ may (iii-1) work together to form a Spiro cyclo lower alkyl group, or (iii-2) form an oxo (keto or carbonyl) group together with Z which they bind to, or (iii-3) form, together with Z which they bind to, $R_1$ and X, a saturated or an unsaturated five- to eight-membered ring selected from sets of groups of (a) and (b):

(a)

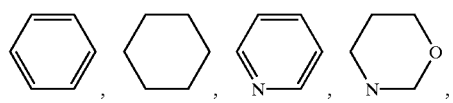

-continued

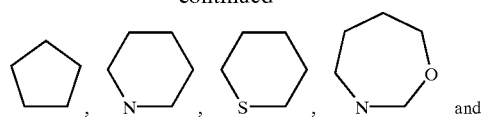

(b)

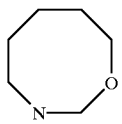

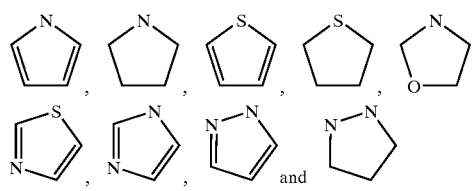

which may contain one or more kinds of hetero atoms selected from a nitrogen atom, an oxygen atom and a sulfur atom, Said saturated or unsaturated five- to eight-membered rings may be substituted with one to three of the same or different substituent(s) selected from both a set of groups of a lower alkyl group, a spiro cyclo lower alkyl group which may have a substituent(s), a hydroxyl group, a cyano group, halogen atoms, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and a set of groups of substituent represented by a formula $Y_1$—$W_1$—$Y_2$—$R_p$ (wherein: $R_p$, $W_1$, $Y_1$ and $Y_2$ have the same meanings as stated above).

In addition, as the substituents on the spiro cyclo lower alkyl groups, there may be mentioned, for example, a lower alkyl group, a lower alkoxy group, a hydroxy lower alkyl group, an aryl group, and so on, and, among them, a lower alkyl group and a lower alkoxy group, and so on, are more preferable.

Said saturated or unsaturated five- to eight-membered rings may be further fused with any of a cyclic lower alkyl group, a heteroaromatic ring group selected from a set of groups of an aryl group, an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group(s) selected from an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, pyrrolinyl group, a morpholino group, a tetrahydroquinolinyl group and a tetrahydroisoquinolinyl group.

Said fused rings may be substituted with one to three of the same or different substituents. As the specific examples of such substituents, there may be mentioned the same ones as the substituents on Ar.

More preferably, $R_2$ and $R_3$ are each, common in all of (i), (ii) and (iii), the same or different and independently, a hydrogen atom, a hydroxy group, a lower alkyl group, a lower alkoxy group, or a substituent represented by the formula $Y_{3a}$—$W_{2a}$—$Y_{4a}$—$R_a$ (wherein: $R_{sa}$, $W_{2a}$, $Y_{3a}$ and $Y_{4a}$ have the same meanings as stated above), or either $R_{2a}$ or $R_{3a}$ forms, together with $R_{1a}$ and $X_a$, a saturated five- to eight-membered ring selected from sets of groups of (a-1) and (b-1):

(a-1)
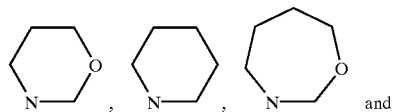

(b-1)
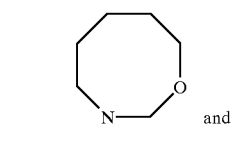
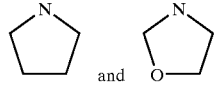

and the remaining one combines with a carbon atom or a nitrogen atom on said ring, and with a carbon atom, an oxygen atom and/or a nitrogen atom on said ring-substituent to form a five- to seven-membered ring, or $R_2$ and $R_3$ work together to form a spiro cyclo lower alkyl group, or an oxo (keto, carbonyl) group together with Z to which they bind, or form, together with $Z_a$ to which they bind, $R_{1a}$ and $X_a$, a saturated or an unsaturated five- to eight-membered cyclic group which is selected from a set of groups of (a-1) and (a-2):

(a-1)
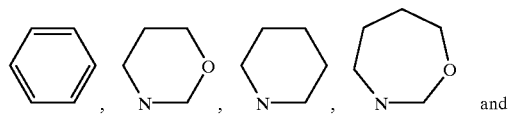

(a-2)
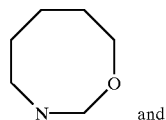

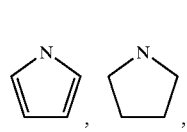 

which may have one or more kinds of hetero atoms selected from a nitrogen atom, an oxygen atom and a sulfur atom, and which may be substituted with one to three of the same or different substituent(s) selected from both a set of groups of a lower alkyl group, a spiro cyclo lower alkyl group which may be substituted, a hydroxy group, a hydroxy lower alkyl group, a lower alkoxy group, a lower alkyl group, a lower alkanoyloxy group, a hydroxy lower alkyl group, a halo lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a lower alkylcarbamoyloxy group, a lower alkylamino group, a di-lower alkylamino group, an amino lower alkyl group, a lower alkylamino lower alkyl group, a di-lower alkylamino lower alkyl group, a lower alkanoylamino group and an aroylamino group, and a substituent represented by the formula $Y_{1a}$—$W_{1a}$—$Y_{2a}$—$R_{pa}$ (wherein: $R_{pa}$, $W_{1a}$, $Y_{1a}$ and $Y_{2a}$ have the same meanings as stated above), and further which may be fused with a ring selected from a cyclo lower alkyl group, an aryl group, a heteroaromatic ring group selected from a pyridyl group and a pyrazolyl group or an aliphatic heterocyclic group selected from a piperidinyl group and a pyrrolidinyl group, all of these cyclic groups may be substituted with one to three of the same or different substituent(s) selected from the substituents mentioned above.

Among those cases, $R_{2b}$ and $R_{3b}$ are each, preferably, the same or different and independently, a hydrogen atom, a hydroxyl group, a lower alkyl group, a lower alkoxy group or a substituent represented by the formula $Y_{3b}$—$W_{2b}$—$Y_{4b}$—$R_{sb}$ (wherein: $R_{1b}$, $W_{2b}$, $Y_{3b}$ and $Y_{4b}$ have the same meanings as stated above), or either $R_{2b}$ or $R_{3b}$ forms, together with $R_{1b}$ and $X_b$, a saturated five- to seven-membered cyclic group selected from a group of (b-1) and (b-2), (b-1)
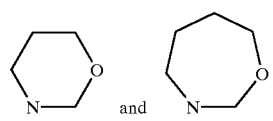

(b-2)
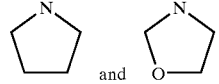

and the remaining one of $R_{2b}$ or $R_{3b}$ forms a five- to seven membered ring by combining with a carbon atom or a nitrogen atom on said ring, and with a carbon atom, an oxygen atom and/or a nitrogen atom in a ring-substituent on said ring, or $R_{2b}$ and $R_{3b}$ work together to form a spiro cyclo lower alkyl group, or to form an oxo (keto, carbonyl) group together with Z to which they bind, or they ($R_{2b}$ and $R_{3b}$) work together with $Z_b$, $R_{1b}$ and $X_b$ to form a saturated or an unsaturated five- to seven-membered cyclic group selected from a set of groups of (b-1) and (b-2)

(b-1)

(b-2)

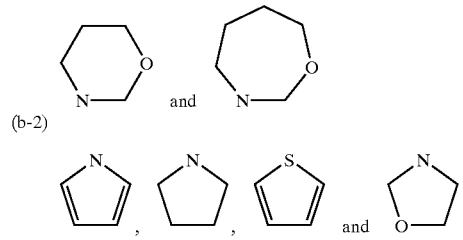

which may have one or more kinds of hetero atoms selected from a nitrogen atom, an oxygen atom and a sulfur atom, and which may be substituted with one to three of the same or different substituent(s) selected from both a set of groups of a lower alkyl group, a Spiro cyclo lower alkyl group which may be substituted, a hydroxy lower alkyl group and a lower alkoxycarbonyl, and a set of groups represented by a formula $Y_{1b}$—$W_{1b}$—$Y_{2b}$—$R_{pb}$ (wherein: $R_{pb}$, $W_{1b}$, $Y_{1b}$ and $Y_{2b}$ have the same meanings as stated above), which may be fused with a ring selected from a set of groups of a cyclic lower alkyl group, an aryl group and an aliphatic heterocyclic group selected from a group comprising a piperidinyl group and a pyrrolidinyl group, all of these cyclic groups may be substituted with one to three substituent(s) selected from both a set of groups of a lower alkyl group, a spiro cyclo lower alkyl group, a hydroxy lower alkyl group and a lower alkoxycarbonyl group, and a set of groups represented by the formula $Y_{1b}$—$W_{1b}$—$Y_{2b}$—$R_{pb}$ (wherein: $R_{pb}$, $W_{1b}$, $Y_{1b}$ and $Y_{2b}$ have the same meanings as stated above).

$R_4$ and $R_5$ are each, the same or different, a hydrogen atom, a halogen atoms, a hydroxyl group, an amino group, or a substituent represented by the formula $Y_3$—$W_2$—$Y_4$—$R_s$ (wherein: $R_s$, $W_2$, $Y_3$ and $Y_4$ have the same meanings as stated above), or a lower alkyl group, an aryl group or an aralkyl group which may be substituted with one to three of the same or different substituent(s) selected from both a set of groups consisting of a lower alkyl group, a cyano group, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group and a set of groups represented by the formula $Y_3$—$W_2$—$Y_4$—$R_s$ (wherein: $R_s$, $W_2$, $Y_3$ and $Y_4$ have the same meanings as stated above).

Here is a more detailed explanation about the forms of $R_4$ and $R_5$. Thus, $R_4$ and $R_5$ are each a hydrogen atom, halogen atoms, a hydroxy group, an amino group or a substituent represented by the formula $Y_3$—$W_2$—$Y_4$—$R_s$ (wherein: $R_s$, $W_2$, $Y_3$ and $Y_4$ have the same meanings as stated above), or a lower alkyl group, an aryl group or an aralkyl group which may be substituted. Said lower alkyl group, aryl group and aralkyl group may be substituted with one to three of the same or different substituent(s).

As specific examples of the substituents, there may be mentioned, for example, a substituent which may be selected either from both a set of groups of a lower alkyl group, a cyano group, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group and a set of groups represented by the formula $Y_3$—$W_2$—$Y_4$—$R_s$ (wherein: $R_s$, $W_2$, $Y_3$ and $Y_4$ have the same meanings as stated above).

The formula ═══ is a single bond or a double bond, depending on the nature of the Z, $R_1$, $R_2$, $R_3$ and X, which relate to the formulae.

What follows is the explanation about the compounds of the general formula (I) of the present invention.

Formula (I)

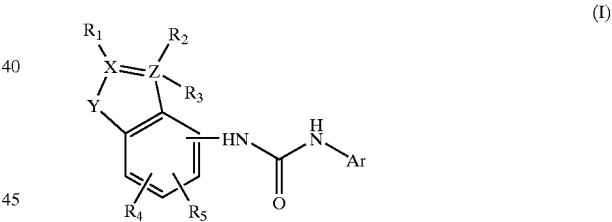

(I)

[wherein: Ar, X, Y, Z, $R_1$, $R_2$, $R_3$, $R_4$, $R_5$ and the formula ═══ have the same meanings as stated above.]

Compounds of the general formula (I) have a good Cdk4 and/or Cdk6 inhibitory activity, and among them, compounds of the general formula (I-a)

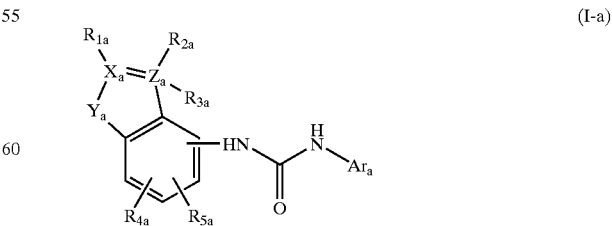

(I-a)

[wherein: $Ar_a$, $X_a$, $Y_a$, $Z_a$, $R_{1a}$, $R_{2a}$, $R_{3a}$, $R_{4a}$, $R_{5a}$ and the formula ═══ have the same meanings as stated above.] are more preferable, and especially the compounds of the general formula (I-b)

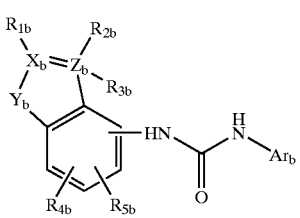

(I-b)

[wherein: $Ar_b$, $X_b$, $Y_b$, $Z_b$, $R_{1b}$, $R_{2b}$, $R_{3b}$, $R_{4b}$, $R_{5b}$ and the formula ≡≡≡ have the same meanings as stated above.] are especially preferable.

Furthermore, the compounds represented by the general formula (I-p)

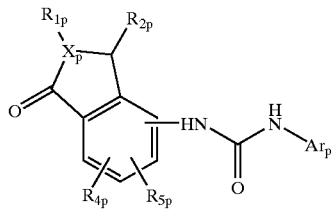

(I-p)

[wherein: $Ar_p$ is a nitrogen-containing heteroaromatic ring group which may be substituted; $X_p$ is a carbon atom (CH) or a nitrogen atom; $R_{1p}$ is a hydrogen or a lower alkyl group which may be substituted; $R_{2p}$ is a hydrogen atom or an oxo group (forms a carbonyl group together with the carbon atom to which it binds), or forms, together with the carbon atom to which it binds, $R_{1p}$ and $X_p$, a saturated or an unsaturated five- or six-membered cyclic group which may contain one or more kinds of hetero atom(s) selected from a group of a nitrogen atom and a sulfur atom, which may be substituted; $R_{4p}$ and $R_{5p}$ are each, the same or different, a hydrogen atom, halogen atoms, a hydroxy group, an amino group and a lower alkyl group, an aryl group, or an aralkyl group which may be substituted] are included in the compounds of general formula (I) and show a good Cdk4 and/or Cdk6 inhibitory activity.

A further explanation about the compounds of the general formula (I-p) is as follows. $Ar_p$ is, for example, a nitrogen-containing heteroaromatic ring group selected from a set of groups of a pyridyl group, a pyrimidinyl group, a pyradinyl group, a pyridazinyl group, a thiazolyl group, an isothiazolyl group, an oxazolyl group, an isoxazolyl group, a pyrazolyl group, a pyrrolyl group, an imidazolyl group, an indolyl group, an isoindolyl group, a quinolyl group, an isoquinolyl group, a benzothiazolyl group and a benzoxazolyl group, and, among them, for example, a nitrogen-containing heteroaromatic ring group selected from a set of groups of a pyridyl group, a pyrimidinyl group, pyrazinyl group, a pyridazinyl group, a thiazolyl group, a pyrazolyl group and an imidazolyl group is more preferable, and a nitrogen-containing heteroaromatic ring group selected from a set of groups of, for example, a pyridyl group and a pyrazolyl group is especially preferable.

As specific examples of the saturated or unsaturated five- or six-membered cyclic groups which $R_{2b}$ forms, together with the carbon atom to which it bind, $R_{1b}$ and $X_p$, there may be mentioned those in (a) or in (b), and so on.

(a)

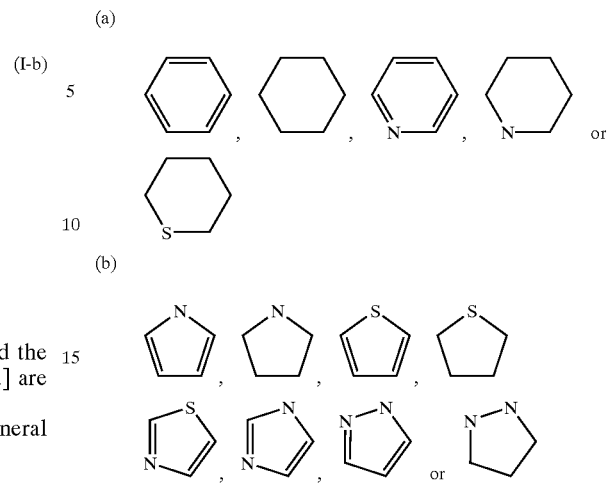

(b)

Among the compounds of the general formula (I-p), preferable compounds are, for example, those which are optionally substituted on $Ar_p$ or on the saturated or unsaturated five- or six-membered cyclic groups which forms together with the carbon atom binding to $R_{2p}$, $R_{1p}$ and $X_p$, with one to three substituent(s) selected from either a set of groups consisting of a lower alkyl group, a hydroxyl group, a cyano group, halogen atoms, a nitro group, a carboxyl group, a carbamoyl group, a formyl group, a lower alkanoyl group, a hydroxy lower alkyl group, a cyano lower alkyl group, a halo lower alkyl group, a carboxy lower alkyl group, a carbamoyl lower alkyl group, lower alkoxy group, a lower alkoxycarbonyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfonylamino group, a hydroxyimino group and a lower alkoxyimino group, or those represented by a formula $Y_{1p}$—W—$Y_{2p}$—$R_{pp}$ [wherein: $R_{pp}$ is a hydrogen atom or a lower alkyl group, a cyclo lower alkyl group, a lower alkenyl group, a lower alkynyl group, an aryl group, a heteroaromatic ring group or an aliphatic heterocyclic group, each of which may be substituted; W is a single bond, an oxygen atom, a sulfur atom, a sulfinyl group, a sulfonyl group. $NR_{qp}$, $SO_2NR_{qp}$, $N(R_{qp})SO_2NR_{rp}$, $N(R_{qp})SO_2$, $CH(OR_{qp})$, $CONR_{qp}$, $N(R_{qp})CO$, $N(R_{qp})CONR_{rp}$, $N(R_{qp})COO$, $N(R_{qp})CSO$, $N(R_{qp})COS$, $C(R_{gp})$=$CR_{rp}$, C=—C, CO, CS, OC(O), OC(O)$NR_{qp}$, OC(S)$NR_{qp}$, SC(O), SC(O)$NR_{rp}$ or C(O)O (wherein: $R_{qp}$ and $R_{rp}$ are each a hydrogen, a lower alkyl group, an aryl group or an aralkyl group which may be substituted); $Y_{1p}$ and $Y_{2p}$ are each, the same or different, a single bond or a straight-chain or branched lower alkylene group].

Furthermore, in the compounds of the general formula (I):

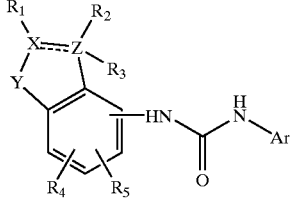
(I)

[wherein: Ar, X, Y, Z, $R_1$, $R_2$, $R_3$, $R_4$, $R_5$ and the formula ═══ have the same meanings as stated above.]
substitution with $R_4$, $R_5$ and —HNCONH—Ar may occur at any positions of the benzene ring. Therefore, the compounds of the general formula (I) are composite of the compounds of the general formula (1-1),

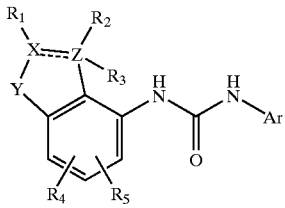
(I-1)

[wherein: Ar, X, Y, Z, $R_1$, $R_2$, $R_3$, $R_4$, $R_5$ and the formula ═══ have the same meanings as stated above.]
and the compounds of the general formula (1-2)

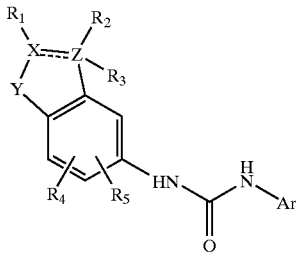
(I-2)

[wherein: Ar, X, Y, Z, $R_1$, $R_2$, $R_3$, $R_4$, $R_5$ and the formula ═══ have the same meanings as stated above.]
and the compounds of the general formula (1-3),

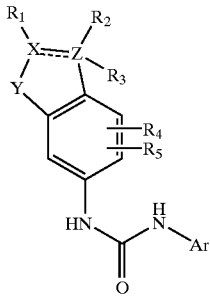
(I-3)

[wherein: Ar, X, Y, Z, $R_1$, $R_2$, $R_3$, $R_4$, $R_5$ and the formula ═══ have the same meanings as stated above.]
and the compounds of the general formula (1-4).

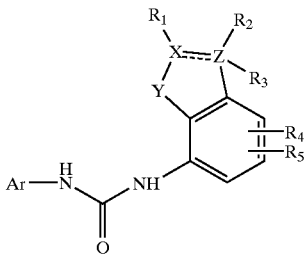
(I-4)

[wherein: Ar, X, Y, Z, $R_1$, $R_2$, $R_3$, $R_4$, $R_5$ and the formula ═══ have the same meanings as stated above.].

Among these compounds, the compounds of the general formula (I-1) are the most preferable.

As the pharmaceutically acceptable salts of the compounds of the general formula (I), there may be mentioned those ordinally ones usually acceptable as medicines, namely, salts of the carboxyl group which may exist as the ring-substituent, and those of the basic or acidic residue(s) in the side chain(s).

As the basic additive salt of said carboxyl group or other acidic residue, there may be mentioned, for example, in addition to the alkali metal salts such as, for example, a sodium salt or potassium salt; the alkaline earth metal salts, such as calcium salt and magnesium salt, the ammonium salts, such as trimethylamine salt, triethylamine salt; aliphatic amine salts, such as dicyclohexylamine salt, ethanolamine salt, diethanolamine salt, triethanolamine salt, procaine salt, and so on; aralkylamine salts, such as dibenzylethylenediamine salt, and so on; herero aromatic amine salt, such as pyridine sale, picoline salt, quinoline salt, isoquinoline salt, and so on; the quaternary ammonium salts, such as tetramethylammonium salt, tetraethylammonium salt, benzyltrimethylammonium salt, benzyltriethylammonium salt, benzyltributylammonium salts, methyltrioctylammonium salt, tetrabutylammonium salt, and so on; the basic aminoacid salts, such as arginine salt and lysine salt, and so on.

As acid additive salt of the basic group(s) on the side chain(s), there may be mentioned, for example, the inorganic salts, such as hydrochloride, sulfate, nitrate, phosphate, carbonate, bicarbonate, perchlorate, and so on; the organic salts, such as acetate, propionate, lactate, maleate, fumarate, tartrate, malate, citrate, ascorbate, and so on; the sulfonic acid salts, such as methanesulfonate, isethionic acid salt, benzenesulfonate, toluenesulfonate, and so on; the acidic aminoacid salts, such as aspartate, glutamate, and so on.

As pharmaceutically acceptable nontoxic esters of the compounds of the general formula (I), there may be mentioned ordinally esters of said carboxyl group.

What follows are the examples of the most preferable compounds among the compounds of the general formula (I) of the present invention. Those are, in addition to the compounds in the Examples described below, N'-(pyrrolidino[2,1-b]isoindolin-4-on-8-yl)-N-(5-(2-octylaminomethyl)pyrazol-3-yl)urea (compound 563), N'-(pyrrolidino[2,1-b]isoindolin-4-on-8-yl)-N-(5-(2-methyl-4,4-dimethylpentylaminomethyl)pyrazol-3-yl)urea (compound 564), N'-(pyrrolidino[2,1-b]isoindolin-4-on-8-yl)-N-(5-(2-methoxyindan-2-ylaminomethyl)pyrazol-3-yl)urea (compound 581), N'-(pyrrolidino[2,1-b]isoindolin-4-on-8-yl)-N-(5-(2-methylindan-2-ylaminomethyl)pyrazol-3-yl)urea (compound 589), N'-(pyrrolidino[2,1-b]isoindolin- 4-on-8-yl)-N-(5-(5-chloroindan-2-ylaminomethyl)pyrazol-3-yl)urea (compound 595), N'-(pyrrolidino[2,1-b]isoindolin-4-on-8-yl)-N-(5-(6-methylpyridin-2-yl)pyrazol-3-yl)urea (compound 605), N'-(pyrrolidino[2,1-b]isoindolin-4-on-8-yl)-N-(5-(pyrrolidin-2-yl)pyrazol-3-yl)urea (compound 611), N'-(pyrrolidino[2,1-b]isoindolin-4-on-8-yl)-N-(5-(t-butylaminomethyl)pyrazol-3-yl)urea (compound 662), N'-(pyrrolidino[2,1-b]isoindolin-4-on-8-yl)-N-(5-(pyrazolo[5,4-b]pyridin-3-yl)urea (compound 613), N'-(pyrrolidino[2,1-b]isoindolin-4-on-8-yl)-N-(5-(1-hydroxymethylcyclopentylaminomethyl)pyrazol-3-yl)urea (compound 572), N'-(pyrrolidino[2,1-b]-4-oxoisoindolin-8-yl)-N-(5-(N-t-butyl-N-methyl-aminomethyl)pyrazol-3-yl)urea (compound 596), N'-(pyrrolidino[2,1-b]isoindolin-4-on-8-yl)-N-(4-(N-benzyl-1,2,5,6-tetrahydropyridin-4-yl)pyridin-2-yl)urea (compound 254), N'-(pyrrolidino[2,1-b]isoindolin-4-on-8-yl)-N-(4-(N-benzyl-4-piperidyl)pyridin-2-yl)urea (compound 255), N'-(pyrrolidino[2,1-b]isoindolin-4-on-8-yl)-N-(4-(N-benzyl-1,2,5,6-tetrahydropyridin-3-yl)pyridin-2-yl)urea (compound 256), N'-(pyrrolidino[2,1-b]isoindolin-4-on-8-yl)-N-(4-(N-benzyl-3-piperidyl)pyridin-2-yl)urea (compound 257), N'-(pyrrolidino[2,1-b]-4-oxoisoindolin-8-yl)-N-(4-(1,2,5,6-tetrahydropyridin-3-yl)pyridin-2-yl)urea, N'-(pyrrolidino[2,1-b]isoindolin-4-on-8-yl)-N-(4-(N-acetyl-3-piperidyl)pyridin-2-yl)urea, N'-(pyrrolidino[2,1-b]isoindolin-4-on-8-yl)-N-(piperidino[3,4-c]pyridin-5-yl)urea (compound 317), N'-(pyrrolidino[2,1-b]isoindolin-4-on-8-yl)-N-(pyrrolidino[3,4-c]pyridin-5-yl)urea, N'-(pyrrolidino[2,1-b]isoindolin-4-on-8-yl)-N-(4-(cyclohexylaminoethyl)pyridin-2-yl)urea, N'-(pyrrolidino[2,1-b]isoindolin-4-on-8-yl)-N-(4-(N-cyclohexylpyrrolidin-3-yl)pyridin-2-yl)urea (compound 180), N'-(pyrrolidino[2,1-b]isoindolin-4-on-8-yl)-N-(4-(N-benzylpyrrolidin-3-yl)pyridin-2-yl)urea (compound 165), N'-(N-cyclopentyl-3-methylisoindolin-1-on-4-yl)-N-(pyridin-2-yl)urea (compound 428), N'-(3-t-butylisoindolino[3,2-b]oxazolidin-4-on-8-yl)-N-(4-(N-benzylpyrrolidin-3-yl)pyridin-2-yl)urea (compound 526), N'-(2-methylisoindolino[3,2-b]perhydro-1,3-oxazin-5-on-9-yl)-N-(4-(N-benzylpyrrolidin-3-yl)pyridin-2-yl)urea (compound 541), and N'-(isoindolino[2,3-b]perhydro-1,4-methano-6,11a-benzoxazin-11-on-7-yl)-N-(pyridin-2-yl)urea (compound 476), and so on.

Among them, those compounds which follow, for example, are especially preferable:

N'-(pyrrolidino[2,1-b]isoindolin-4-on-8-yl)-N-(5-(2-octylaminomethyl)pyrazol-3-yl)urea, N'-(pyrrolidino[2,1-b]isoindolin-4-on-8-yl)-N-(5-(2-methyl-4,4-dimethylpentylaminomethyl)pyrazol-3-yl)urea, N'-(pyrrolidino[2,1-b]isoindolin-4-on-8-yl)-N-(5-(2-methoxyindan-2-ylaminomethyl)pyrazol-3-yl)urea, N'-(pyrrolidino[2,1-b]isoindolin-4-on-8-yl)-N-(5-(2-methylindan-2-ylaminomethyl)pyrazol-3-yl)urea, N'-(pyrrolidino[2,1-b]isoindolin-4-on-8-yl)-N-(5-(5-chloroindan-2-ylaminomethyl)pyrazol-3-yl)urea, N'-(pyrrolidino[2,1-b]isoindolin-4-on-8-yl)-N-(4-(N-benzyl-1,2,5,6-tetrahydropyridin-4-yl)pyridin-2-yl)urea, N'-(pyrrolidino[2,1-b]isoindolin-4-on-8-yl)-N-(4-(N-benzyl-4-piperidyl)pyridin-2-yl)urea, N'-(pyrrolidino[2.1-b]isoindolin-4-on-8-yl)-N-(4-(N-benzyl-N'-(pyrrolidino[2,1-b]isoindolin-4-on-8-yl)-N-(piperidino[3,4-c]pyridin-5-yl)urea, N'-(pyrrolidino[2,1-b]isoindolin-4-on-8-yl)-N-(4-(N-cyclohexylpyrrolidin-3-yl)pyridin-2-yl)urea, N'-(pyrrolidino[2,1-b]isoindolin-4-on-8-yl)-N-(4-(N-benzylpyrrolidin-3-yl)pyridin-2-yl)urea, N'-(3-t-butylisoindolino[3,2-b]oxazolidin-4-on-8-yl)-N-(4-(N-benzylpyrrolidin-3-yl)pyridin-2-yl)urea, N'-(2-methylisoindolino[3,2-b]perhydro-1,3-oxazin-5-on-9-yl)-N-(4-(N-benzylpyrrolidin-3-yl)pyridin-2-yl)urea, and N'-(isoindolino[2,3-b]perhydro-1,4-methano-6,11a-benzoxazin-11-on-7-yl)-N-(pyridin-2-yl)urea, and so on.

Preparation Methods of the Compound of Formula (I)

Next, the preparation methods of the compound of formula (I) of the present invention are illustrated.

The compound of the general formula (I) can be prepared by the following preparation method A, B and C, respectively.

Preparation Method A

The compound of formula (I) can be prepared by reacting the compound of formula (III)

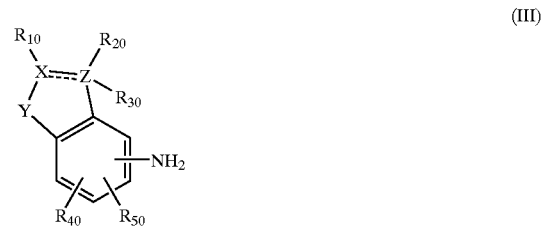

[in the formula. X and Z independently represent carbon atom or nitrogen atom, or, if appropriate, form CH or nitrogen, together with $R_{10}$ or $R_{20}$ and/or $R_{30}$ to which they bind, Y is CO, SO or $SO_2$, $R_{10}$ is (1) hydrogen or (2) a substituent represented by $Y_{30}$—$W_{20}$—$Y_{40}$—$R_{s0}$ (wherein, $R_{s0}$ is hydrogen or lower alkyl group, lower alkenyl group, lower alkynyl group, cyclo-lower alkyl group, aryl group, heteroaromatic ring group selected form the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidinyl group, pyridazinyl group, pyrazolyl group, quinoxalinyl group, quinolyl group, dihydroisoindolyl group, dihydroindolyl group, thionaphthyl group, naphthidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or aliphatic heterocyclic group selected form the group consisting of isoxazolyl group, isoxazolidinyl group, tetrahydropyridyl group, imidazoldinyl group, tetrahydrofuryl group, piperazinyl group, piperidinyl group, pyrrolidinyl group, pyrrolinyl group, morpholino group, tetrahydroquinolyl group and tetrahydroisoquinolyl group, each of which may have 1 to 3 substituents, $W_{20}$ is a single bond, oxygen, sulfur, SO, $SO_2$, $NR_{t0}$, $SO_2NR_{t0}$, $N(R_{t0})SO_2NR_{u0}$, $N(R_{t0})SO_2$, $CH(OR_{t0})$, $CONR_{t0}$, $N(R_{t0})CO$, $N(R_{t0})CONR_{u0}$, $N(R_{t0})COO$, $N(R_{t0})CSO$, $N(R_{t0})COS$, $C(R_{v0})=CR_{t0}$, C=C, CO, CS, OC(O), OC(O)NR$_{t0}$, OC(S)NR$_{t0}$, SC(O), SC(O)NR$_{t0}$ or C(O)O (wherein, $R_{t0}$ and $R_{u0}$ are (i) hydrogen or (ii) a substituent selected from the group consisting of lower alkyl group, optionally protected hydroxyl group, cyano, halogen atom, nitro group, carboxyl group which may be protected, carbamoyl group, formyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, optionally protected amino group, lower alkylamino group, di-lower alkylamino group, tri-lower alkylammonio, optionally protected amino lower alkyl group, lower alkyl amino-lower alkyl group, di-lower alkyl amino-lower alkyl group, tri-lower alkyl amino-lower alkyl group, lower alkanoylamino group, aroylamino group, lower alknoylammonio-lower alkyl group, lower alkylsulfinyl group, lower alkylsulfonyl group, lower alkylsulfonylamino group, optionally protected hydroxyimino and lower alkoxyimino group or (iii) lower alkyl group, aryl group or aralkyl group, each of which may have 1 to 3 substituents defined above in (ii)), $Y_{30}$ and $Y_{40}$ are independently single bond or straight-chain or branched lower alkylene), (3) lower alkyl group, which may have independently 1 to 3 substituents selected from the group (A) consisting of lower alkyl group, optionally protected hydroxyl group group, cyano group, halogen atom, nitro group, carboxyl group which may be protected, carbamoyl group, formyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl, lower alkylcarbamoyl, di-lower alkylcarbamoyl, carbamoyloxy group, lower alkylcarbamoyloxy group, di-lower alkylcarbamoyloxy group, optionally protected amino group, lower alkyl amino group, di-lower alkyl amino group, tri-lower alkylammonio group, amino lower alkyl group, lower alkyl amino-lower alkyl group, di-lower alkyl amino-lower alkyl group, tri-lower alkyl amino-lower alkyl group, lower alknoylamino group, aroylamino group, lower alknoylammonio-lower alkyl group, lower alkylsulfinyl group, lower alkylsulfonyl group, lower alkylsulfonylamino group, optionally protected hydroxyimino and lower alkoxyimino group, and the group (B) represented by the formula of $Y_{30}$—$W_{20}$—$Y_{40}$—$R_{s0}$ (wherein, $R_{s0}$, $W_{20}$, $Y_{30}$ and $Y_{40}$ have the same meanings as described above), or $R_{10}$ is taken together with X to form nitrogen atom, $R_{20}$ and $R_{30}$ are, the same or different, independently hydrogen or optionally protected hydroxyl group, lower alkyl group, lower alkoxy or the substituent represented by the formula of $Y_{30}$—$W_{20}$—$Y_{40}$—$R_{s0}$ (wherein, $R_{s0}$, $W_{20}$, $Y_{30}$ and $Y_{40}$ have the same meanings as described above), either $R_{20}$ or $R_{30}$ is taken together with $R_{10}$ and X to form saturated five to eight-membered rings selected from the group consisting of (a)

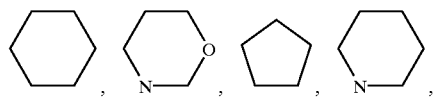

-continued

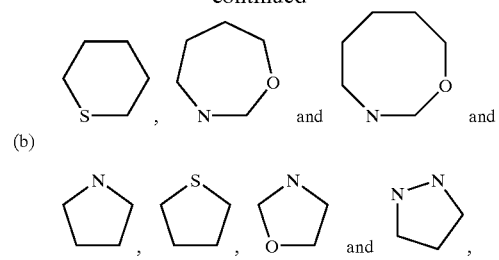

(b)

and the other may form the five- to seven-membered rings by binding to the carbon atom or nitrogen atom of the ring, the carbon atom, oxygen atom and/or nitrogen atom in the substituent of the ring, or $R_{20}$ and $R_{30}$ are taken together to form spirocyclic lower alkyl, oxo group together with Z to which they bind, or $R_{20}$ and $R_{30}$ form together Z, $R_1$, X, to which they bind or saturated or unsaturated five- to eight-membered rings selected from sets of the groups of (a) and (b):

(a)

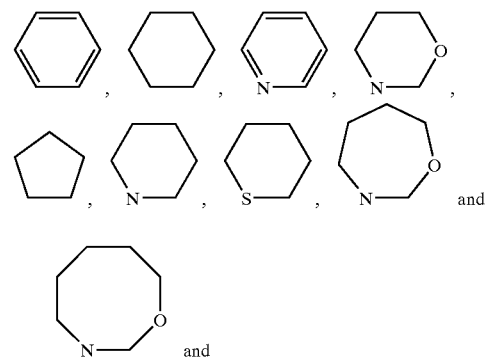

(b)

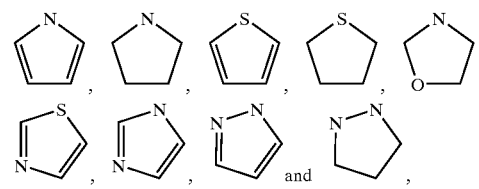

which may contain one or more kinds of hetero atom(s) selected from a group of a nitrogen atom, an oxygen atom and a sulfur atom, and which may be fused with the group selected from (i) cyclo-lower alkyl group, (ii) aryl group, (iii) heteroaromatic ring group selected from the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidinyl group, pyridazinyl group, pyrazolyl group, quinoxalinyl group, quinolyl group, dihydroisoindolyl group, dihydroindolyl group, thionaphthyl group, naphthidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or
(iv) aliphatic heterocyclic group selected from the group consisting of isoxazolyl group, isoxazolidinyl group, tetrahydropyridyl group, imidazoldinyl group, tetrahydrofuryl group, piperazinyl group, piperidinyl group, pyrrolidinyl group, pyrrolinyl group, morpholino group, tetrahydroquinolyl group and tetrahydroisoquinolyl group, which may have the same or diffent 1 to 3 substituent(s) selected from
(1) a substituent selected from the group consisting of lower alkyl, optionally substituted spirocyclic lower alkyl, optionally protected hydroxyl group, cyano, halogen atom, nitro, carboxyl group which may be protected, carbamoyl group, formyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, optionally protected amino group, lower alkyl amino group, di-lower alkylamino group, tri-lower alkylammonio group, optionally protected amino lower alkyl group, lower alkylamino-lower alkyl group, di-lower alkylamino-lower alkyl group, tri-lower alkylamino-lower alkyl group, lower alknoylamino group, aroylamino group, lower alknoylammonio-lower alkyl group, lower alkylsulfinyl group, lower alkylsulfonyl group, lower alkylsulfonylamino group, optionally protected hydroxyimino group and lower alkoxyimino group, and
(2) the group represented by formula of $Y_{10}$—$W_{10}$—$Y_{20}$—$R_{p0}$ (wherein, $R_{p0}$ is hydrogen atom or lower alkyl, lower alkenyl, or lower alkynyl, each of which may have 1 to 3 of said substituents, or
(i) cyclo-lower alkyl group,
(ii) aryl group,
(iii) heteroaromatic ring group selected form the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidinyl group, pyridazinyl group, pyrazolyl group, quinoxalinyl group, quinolyl group, dihydroisoindolyl group, dihydroindolyl group, thionaphthyl group, naphthidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or
(iv) aliphatic heterocyclic group selected form the group consisting of isoxazolyl group, isoxazolidinyl group, tetrahydropyridyl group, imidazolidinyl group, tetrahydrofuryl group, piperazinyl group, piperidinyl group, pyrrolidinyl group, pyrrolinyl group, morpholino group, tetrahydroquinolyl group and tetrahydroisoquinolyl group, each of which in (i) to (iv) may have bicyclic or tricyclic fused rings containing the partial structure selected from

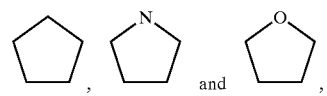

$W_{10}$ is single bond, oxygen, and sulfur,
SO, $SO_2$, $NR_{q0}$, $SO_2NR_{q0}$, $N(R_{q0})SO_2NR_{r0}$, $N(R_{q0})SO_2$, $CH(OR_{q0})$, $CONR_{q0}$, $N(R_{q0})CO$, $N(R_{q0})CONR_{r0}$, $N(R_{q0})COO$, $N(R_{q0})CSO$, $N(R_{q0})COS$, $C(R_{q0})=CR_{r0}$, C=C, CO, CS, OC(O), OC(O)$NR_{q0}$, OC(S)$NR_{q0}$, SC(O), SC(O)$NR_{q0}$ or C(O)O
(wherein, $R_{q0}$ and $R_{r0}$ are
(i) hydrogen or
(ii) a substituent selected from the group consisting of lower alkyl group, cyclo-lower alkyl group, optionally protected hydroxyl group, cyano group, halogen atom, nitro, carboxyl group which may be protected, carbamoyl group, formyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, optionally protected amino group, lower alkylamino group, di-lower alkylamino group, tri-lower alkylammonio, optionally protected amino lower alkyl group, lower alkylamino-lower alkyl group, di-lower alkylamino-lower alkyl group, trilower alkylammonio-lower alkyl group, lower alknoylamino group, aroylamino group, lower alknoylammoniolower alkyl group, lower alkylsulfinyl group, lower alkylsulfonyl group, lower alkylsulfonylamino group, optionally protected hydroxyimino and lower alkoxyimino group, or (iii) lower alkyl group, aryl or aralkyl group, each of which may have 1 to 3 substituent described above in (ii)) $Y_{10}$ and $Y_{20}$ independently represent single bond or straight-chain or branched lower alkyl group, each of which may have one of said bicyclic ring or tricyclic ring), and moreover, a saturated or unsaturated five- to eight-membered rings selected from the following group;

(a)

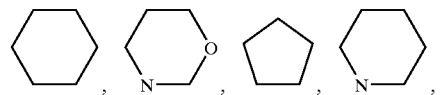

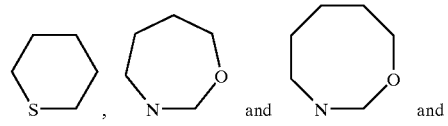

(b)

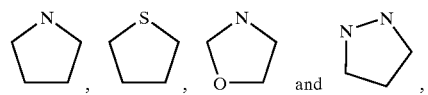

which may be fused with the ring selected from the groups consisting of
(i) cyclo-lower alkyl group,
(ii) aryl group, or (iii) heteroaromatic ring group selected form the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidinyl group, pyridazinyl group, pyrazolyl group, quinoxalinyl group, quinolyl group, dihydroisoindolyl group, dihydroindolyl group, thionaphthyl group, naphthidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or (iv) aliphatic heterocyclic group selected form the group consisting of isoxazolyl group, isoxazolidinyl group, tetrahydropyridyl group, imidazolidinyl group, tetrahydrofuryl group, piperazinyl group, piperidinyl group, pyrrolidinyl group, pyrrolinyl group, morpholino group, tetrahydroquinolyl group and tetrahydroisoquinolyl group, $R_{40}$ and $R_{5c}$ are independently hydrogen, halogen atom, optionally protected hydroxyl group, optionally protected amino or the substituent represented by the formula of $Y_{30}$—$W_{20}$—$Y_{40}$—$R_{s0}$ (wherein, $R_{s0}$, $W_{20}$, $Y_{30}$ and $Y_{40}$ have the same meanings as described above), or lower alkyl group, aryl group, or aralkyl group, each of which may have the same or diffent 1 to 3 substituent(s) selected from the substituent group consisting of lower alkyl group, cyano group, nitro group, carboxyl group which may be protected, carbamoyl group, formyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, optionally protected amino group, lower alkylamino group, di-lower alkylamino group, tri-lower alkylammonio group, optionally protected amino lower alkyl group, lower alkylamino-lower alkyl group, di-lower alkylamino-lower alkyl group, tri-lower alkylammonio-lower alkyl group, lower alknoylamino, aroylamino group, lower alknoylammonio-lower alkyl group, lower alkylsulfinyl group, lower alkylsulfonyl group, lower alkylsulfonylamino group, optionally protected hydroxyimino and lower alkoxyimino group, and the substituent group represented by the formula of $Y_{30}$—$W_{20}$—$Y_{40}$—$R_{s0}$ (wherein, $R_{s0}$, $W_{20}$, $Y_{30}$ and $Y_{40}$ have the same meanings as described above), the formula === represents a single bond or double bond] with the compound of formula (IV)

(IV)

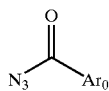

[in the formula, $Ar_0$ is nitrogen containing heteroaromatic ring group selected from the group consisting of pyridyl group, pyrimidinyl group, pyrazinyl group, pyridazinyl group, thiazolyl group, isothiazolyl group, oxazolyl group, isoxazolyl group, pyrazolyl group, pyrrolinyl group, imidazolyl group, indolyl group, isoindolyl group, isoquinolyl group, benzothiazolyl group and benzoxazolyl group:(1) heteroaromatic ring group, which may have the same or diffent 1 to 3 substituent(s) selected from the substituents consisting of lower alkyl group, optionally protected hydroxyl group, cyano group, halogen atom, nitro group, carboxyl group which may be protected, carbamoyl group, formyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, optionally protected amino group, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, optionally protected hydroxyimino and lower alkoxyimino group, and the substituent represented by the formula $Y_{10}$—$W_{10}$—$Y_{20}$—$R_{p0}$ (wherein, $R_{p0}$, $W_{10}$, $Y_{10}$ and $Y_{20}$ have the same meanings as described above), (2) which heteroaromatic ring group forms optionally protected 5 to 7 membered rings selected from

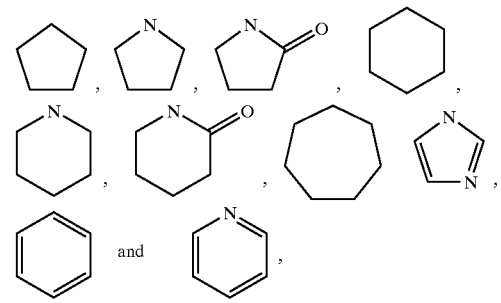

in which, the substituent (abbreviated as optionally protected substituent of the ring below) selected from the group consisting of lower alkyl group, lower alkynoyl group, lower alkynoyloxy group, optionally protected hydroxyl lower alkyl group, cyano lower alkyl group, halogenated lower alkyl group, optionally protected carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, lower alkylamino group, di-lower alkylamino group, tri-lower alkylammonio group, optionally protected amino lower alkyl group, lower alkylamino-lower alkyl group, di-lower alkylamino-lower alkyl group, tri-lower alkylammonio-lower alkyl group, lower alknoylamino group, aroylamino group, lower alkylsulfinyl group, lower alkylsulfonyl group, lower alkylsulfonylamino group, lower alknoylamidino-lower alkyl group, together with carbon atom of the ring, or the neighouring carbon atom and carbon atom, oxygen atom and/or nitrogen atom in the optionally protected substituent of the ring, or (3) which form optionally protected 5 to 7 membered rings selected from

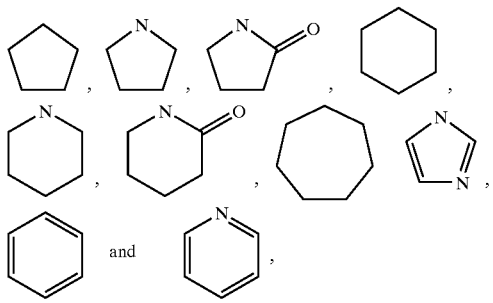

in which, the substituent represented by formula: $Y_{10}$—$W_{10}$—$Y_{20}$—$R_{p0}$(wherein, $Y_{10}$, $W_{10}$, $Y_{20}$ and $R_{p0}$ have the meanings given above) is taken together with the carbon atom of the ring, and the neighbouring carbon atom, carbon atom, oxygen atom and/or nitrogen atom in said substituent] to give the compound of formula (II)

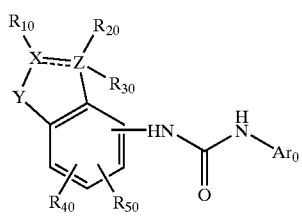

(II)

[in the formula, wherein, $Ar_0$, X, Y, Z, $R_{10}$, $R_{20}$, $R_{30}$, $R_{40}$, $R_{50}$ and the formula === have the same meanings as described above], followed by the elimination of appropriate pretective group to obtain the compound of formula (I)

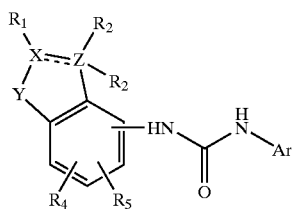

(I)

[in the formula,
Ar is nitrogen containing heteroaromatic ring group selected form the group consisting of pyridyl group, pyrimidinyl group, pyrazinyl group, pyridazinyl group, thiazolyl group, isothiazolyl group, oxazolyl group, isoxazolyl group, pyrazolyl group, pyrrolinyl group, imidazolyl group, indolyl group, isoindolyl group, isoquinolyl group, benzothiazolyl group and benzoxazolyl group,
(1) heteroaromatic ring group, which may have the same or different 1 to 3 substituent(s) selected from
(i) substituent consisting of lower alkyl group, hydroxyl group, cyano group, halogen atom, nitro group, carboxyl group, carbamoyl group, formyl group, lower alkynoyl group, lower alkynoyloxy group, optionally protected hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, amino group, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, hydroxyimino group and lower alkoxyimino group, and
(ii) the substituent represented by formula $Y_1$—$W_1$—$Y_2$—$R_p$ (in the formula, $R_p$ is hydrogen or lower alkyl, lower alkenyl, or lower alkynyl, each of which may have 1 to 3 said substituents, or
(a) cyclo-lower alkyl group,
(b) aryl group,
(iii) heteroaromatic ring group selected from the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidiyl group, pyridazinyl group, pyrazolyl group, quinoxalinyl group, quinolyl group, dihydroisoindolyl group, dihydroindolyl group, thionaphthyl group, naphthidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or
(iv) aliphatic heterocyclic group selected form the group consisting of isoxazolinyl group, isoxazolidinyl group, tetrahydropyridnyl group, imidazolidinyl group, tetrahydrofuryl group, tetrahydropyrayl group, piperazinyl group, piperidinyl group, pyrrolidinyl group, pyrrolinyl group, morpholino group, tetrahydroquinolyl group and tetrahydroisoquinolyl group,
each of which may contain bicyclic or tricyclic fused ring selected from the partial structure consisting of

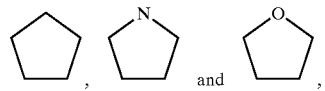

and which may have 1 to 3 said substituents,
$W_1$ is single bond, oxygen atom, sulfur atom,
SO, $SO_2$, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, C≡C, CO, Cs, OC(O), $OC(O)NR_q$, $OC(S)NR_q$, SC(O), $SC(O)NR_q$ or C(O)O
(wherein, $R_q$ and $R_r$ are
(i) hydrogen or
(ii) the substituent selected from the group consisting of lower alkyl group, cyclo-lower alkyl group, hydroxyl group, cyano group, halogen atom, nitro group, carboxyl group, carbamoyl group, formyl group, lower alkynoyl group, lower alkynoyloxy group, hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, amino, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, hydroxyimino and lower alkoxyimino group, or (iii) lower alkyl, aryl or aralkyl, each of which may have 1 to 3 substituents given in (ii)), $Y_1$ and $Y_2$ are independently single bond or straight-chain or branched lower alkylene, which may have one of said bicyclic or tricyclic condesed ring), (2) which heteroaromatic ring group form 5 to 7 membered rings selected from

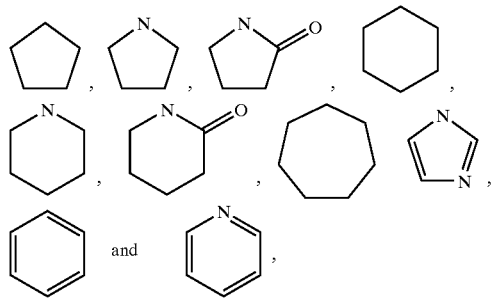

in which, the substituent (abbreviated as the substituent of the ring) selected from the group consisting of lower alkyl group, lower alkynoyl group, lower alkynoyloxy group, hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alkylsulfinyl group, lower alkylsulfonyl group, lower alkylsulfonylamino and lower alkynoylamidino lower alkyl group, together with carbon atom of the ring, the substutent or the neighouring carbon atom and carbon atom, oxygen atom and/or nitrogen atom in the substituent of the ring, or (3) which heteroaromatic ring group forms 5 to 7 membered rings selected from

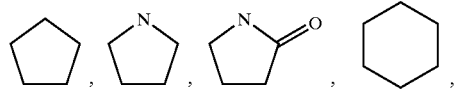

-continued

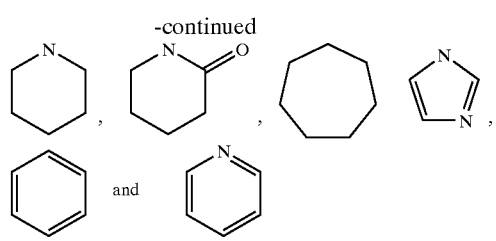

the substituent represented by formula $Y_1-W_1-Y_2-R_p$ (in the formula, $Y_1$, $W_1$, $Y_2$ and $R_p$ have the same meanings given above) together with carbon atom of the ring, or the neighouring carbon atom, carbon atom, oxygen atom and/or nitrogen atom in said substituent, $R_1$ is (1) hydrogen or (2) the substituent represented by formula $Y_3-W_2-Y_4-R_s$ (in the formula, $R_s$ is (i) hydrogen or (ii) lower alkyl group, lower alkenyl group, lower alkynyl group, cyclo-lower alkyl group, aryl group, (iii) heteroaromatic ring group selected form the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidinyl group, pyridazinyl group, pyrazolyl group, quinoxaliyl group, quinolyl group, dihydroisoindolyl group, dihydroindolyl group, thionaphthyl group, naphtidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or (iv) aliphatic heterocyclic group selected form the group consisting of isoxazolyl group, isoxazolidinyl group, tetrahydropyridyl group, imidazolidinyl group, tetrahydrofuryl group, piperazinyl group, piperidinyl group, pyrrolidinyl group, pyrrolinyl group, morpholino group, tetrahydroquinolyl group and tetrahydroisoxaquinolyl group, each of which in (ii) to (iv) may have 1 to 3 said substituents.

$W_2$ is single bond, oxygen, sulfur, SO, $SO_2$, $NR_t$, $SO_2NR_t$, $N(R_t)SO_2NR_u$, $N(R_t)SO_2$, $CH(OR_t)$, $CONR_t$, $N(R_t)CO$, $N(R_t)CONR_u$, $N(R_t)COO$, $N(R_t)CSO$, $N(R_t)COS$, $C(R_v)=CR_t$, $C\equiv C$, CO, CS, OC(O), OC(O)$NR_t$, OC(S)$NR_t$, SC(O), SC(O)$NR_t$ or C(O)O (wherein, $R_t$ and $R_u$ are (i) hydrogen or (ii) the substituent selected from lower alkyl group, hydroxyl group, cyano group, halogen atom, nitro, carboxyl group, group carbamoyl group, formyl group, lower alkynoyl group, lower alkynoyloxy group, hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, amino, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, hydroxyimino and lower alkoxyimino group, or (iii) lower alkyl group, aryl or aralkyl group, each of which may have 1 to 3 said substituents given in (ii)), $Y_3$ and $Y_4$ are independently single bond or straight-chain or branched lower alkylene group), (3) lower alkyl group, which may have the same or diffent 1 to 3 substituent(s) selected from (i) the substituent selected from lower alkyl group, hydroxyl group, cyano group, halogen atom, nitro group, carboxyl group, carbamoyl group, formyl group, lower alkynoyl group, lower alkynoyloxy group, hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, amino group, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, hydroxyimino and lower alkoxyimino group, and (ii) the substituent represented by formula $Y_3$—$W_2$—$Y_4$—$R_s$ (in the formula, $R_s$, $W_2$, $Y_3$ and $Y_4$ have the same meanings given above), or form nitrogen atom together with X, $R_2$ and $R_3$ are independently hydrogen atom, hydroxyl group, lower alkyl group, lower alkoxy group or a substituent represented by the formula: $Y_3$—$W_2$—$Y_4$—$R_s$ (in the formula, $R_s$, $W_2$, $Y_3$ and $Y_4$ have the same meanings given above), or one of $R_2$ or $R_3$ forms, together with $R_1$ and X, saturated 5 to 8 membered rings selected from (a)

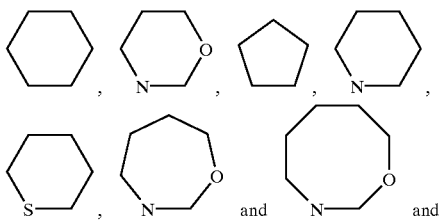

(b)

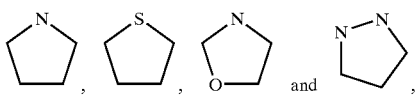

the other of $R_2$ or $R_3$ forms 5 to 7 membered rings by taking together with the carbon atom or nitrogen atom of the ring, carbon atom, oxygen atom and/or nitrogen atom, each of which is comprised in the substituent of the ring, or $R_2$ and $R_3$ are taken together with to form Spiro lower alkyl, oxo together with Z, or form saturated or unsaturated 5 to 8 membered rings selected from (a)

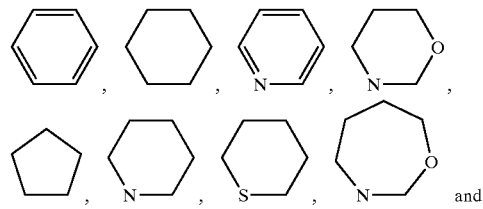

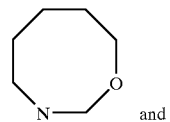 and (b)

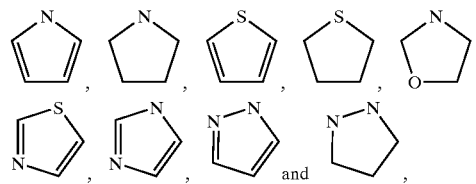

which may be fused together with the ring selected from (1) cyclo-lower alkyl group, each of which may contain 1 or more hetero atoms selected from nitrogen atom, oxygen atom and sulfur atom, which is taken together with binding (2) aryl group, (3) heteroaromatic ring group selected from the group consisting of imidazolyl group, isoxazolyl group, isoquinolyl group, isoindolyl group, indanzolyl group, indolyl group, indolizinyl group, isothiazolyl group, ethylenedioxophenyl group, oxazolyl group, pyridyl group, pyrazinyl group, pyrimidiyl group, pyridazinyl group, pyrazolyl group, quinoxalinyl group, quinolyl group, dihydroisoindolyl group, dihydroindolyl group, thionaphthyl group, naphtidinyl group, phenazinyl group, benzoimidazolyl group, benzoxazolyl group, benzothiazolyl group, benzotriazolyl group, benzofuranyl group, thiazolyl group, thiadiazolyl group, thienyl group, pyrrolinyl group, furyl group, furazanyl group, triazolyl group, benzodioxanyl group and methylenedioxyphenyl group, or (4) aliphalic heterocyclic group selected from the group consisting of isoxazolinyl group, isoxazolidinyl group, tetrahydropyridyl group, imidazolidinyl group, tetrahydrofuryl group, tetrahydropyranyl group, piperazinyl group, piperidinyl group, pyrrolidinyl group, pyrrolinyl group, morpholino group, tetrahydroquinolyl group and tetrahydroisoquinolyl group each of which may have the same or diffent 1 to 3 substituent(s) selected from (i) a substituent selected from the group consisting of lower alkyl, optionally substituted spirocyclo-lower alkyl group, hydroxyl group, cyano group, halogen atom, nitro group, carboxyl group, carbamoyl group, formyl group, lower alkynoyl group, lower alkynoyloxy group, hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, amino, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, hydroxyimino and lower alkoxyimino group, $R_1$ and X, and (ii) a substituent represented by the formula: $Y_1$—$W_1$—$Y_2$—$R_p$ (in the formula, $R_p$, $W_1$, $Y_1$ and $Y_2$ have the same meanings given above), $R_4$ and $R_5$ are same or independently hydrogen atom, halogen atom, hydroxyl, amino or the substituent represented by formula: $Y_3$—$W_2$—$Y_4$—$R_s$ (in the formula, $R_s$, $W_2$, $Y_3$ and $Y_4$ have the meanings given above), or lower alkyl, aryl or aralkyl, each of which may have 1 to 3 substituents selected from (i) the substituent selected from the group consisting of lower alkyl group, cyano group, nitro group, carboxyl group, carbamoyl group, formyl group, lower alkynoyl group, lower alkynoyloxy group, hydroxyl lower alkyl group, cyano lower alkyl group, halogenated lower alkyl group, carboxyl lower alkyl group, carbamoyl lower alkyl group, lower alkoxy group, lower alkoxycarbonyl group, lower alkoxycarbonylamino group, lower alkoxycarbonylamino-lower alkyl group, lower alkylcarbamoyl group, di-lower alkylcarbamoyl group, carbamoyloxy group, lower alkylcarbamoyloxy group, di-lower alkylcarbamoyloxy group, amino group, lower alkylamino group, di-lower alkylamino group, tri-lower alkylammonio group, amino lower alkyl group, lower alkylamino-lower alkyl group, di-lower alkylamino-lower alkyl group, tri-lower alkylammonio-lower alkyl group, lower alknoylamino group, aroylamino group, lower alknoylamidino-lower alkyl group, lower alkylsulfinyl group, lower alkylsulfonyl group, lower alkylsulfonylamino group, hydroxyimino group and lower alkoxyimino group, and (ii) the substituent represented by formual: $Y_3$—$W_2$—$Y_4$—$R_s$ (in the formula, $R_s$, $W_2$, $Y_3$ and $Y_4$ have the same meanings given above), X, Y. Z and the formula have the same meanings given above].

The compound of the formula (I) can be prepared by subjecting the compound of the formula (III) to trichloroacetylation or p-nitorphenoxycarbonylation followed by reacting with the compound of the formula (VI).

The reaction of the compound the formula (III) with the compound of the formula (IV) is usually carried out using 1 mole of the compound the formula (III) together with preferably about 1 mol of the compound of the formula (IV).

In the reaction of trichloroacetylation or p-nitorphenoxycarbonylation of the compound of the formula (III), to 1 mole of the compound of the formula (III), the halogenated compound is used in usually 1 to 5 moles, preferably 1 mol. To 1 mole of the trichloroacetylated or p-nitorphenoxycarbonylated compound of the compound in formula (III), the compound in formula (VI) is used in usually 1 to 5 mol, preferably 1 mol.

The reaction may be carried out in the inactive solvents including the ether such as tetrahydrofuran, dioxane, and the like, aromatic hydrocarbon such as benzene, toluene, and the like, or the mixture thereof.

The reaction temperature depends on the type of the starting material, usually between 0° C. and the boiling point of the solvent used, preferably, within the range from 20 to 100° C.

The reaction time is usually within the range from 20 minutes to 24 hours, preferably, from 1 to 4 hours, and can be reduced or increased appropriately.

In the case of the compounds of the formula (III) and formula (IV), which contain functional group such as hydroxyl, amino, carboxyl or the like or the substituent including such a functional group, such as hydroxyl lower alkyl group, amino lower alkyl group, carboxyl lower alkyl group and the like, said hydroxyl group, amino group, carboxyl group, hydroxyl lower alkyl group, amino lower alkyl group, carboxyl lower alkyl group and the like are preferably protected by the appropriate protective group for hydroxyl, amino, carboxyl in advance. After the reaction, said protective group for the compound of the formula (II) is removed to obtain the compound of the formula (I).

The protecting group of hydroxyl includes lower alkylsilyl such as tert-butyldimethylsilyl group, tert-butyldiphenylsilyl group, and the like, lower alkoxymethyl such as methoxymethyl group, 2-methoxyethoxymethyl group, and the like group, aralkyl such as benzyl group, p-methoxybenzyl group, and the like, acyl such as formyl group, acetyl group, and the like. Preferably, tert-butyldimethylsilyl, acetyl and the like are used.

The amino-protecting group includes arylalkyl group such as benzyl group, p-nitrobenzyl group, and the like, acyl such as formyl group, acetyl, and the like, lower alkoxycarbonyl group such as ethoxycarbonyl group, tert-butoxycarbonyl group, and the like, arylkyloxycarbonyl group such benzyloxycarbonyl group, p-nitorbenzyloxycarbonyl group, and the like. Preferably, p-nitorbenzyl, tert-butoxycarbonyl group, benzyloxycarbonyl group and the like are used.

The carboxyl-protecting group includes tri-substituted silyl such as methyl, ethyl, tert-butyl and the like, arylalkyl such as benzyl, p-methoxybenzyl and the like. Preferably, methyl, ethyl, benzyl and the like are used.

The method for removing the protecting group depends on the type and stability of the compound. Usually, it is carried out according to the method disclosed in [Protective Groups in Organic Synthesis by T. W. Greene, published by John Wiley & Sons Co.(1981)] or a similar method thereof. Specifically, it includes solvolysis using acid or base, chemical reduction using metal hydride or catalytic hydrogenation using palladium carbon catalyst, Raney-nickle catalyst.

One example of the compound of formula (I), which forms a bicyclic fused ring is illustrated as follows.

The compound of formula (I')

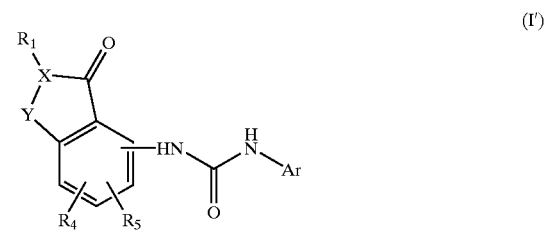

(I')

(wherein, Ar, X, Y, $R_1$, $R_4$ and $R_5$ have the meanings given above), which is the compound in which $R_2$ and $R_3$ are combined, together with Z, to form oxo radical, can be prepared by reacting the compound represented by formula (IV)

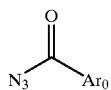

(wherein $Ar_0$ has the meaning given above) with the compound represented by formula (III')

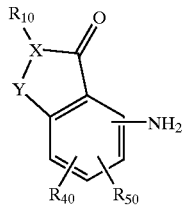

(III')

(wherein X, Y, $R_{10}$, $R_{40}$ and $R_{50}$ have the meaning given above) to afford the compound represented by formula (II'-a)

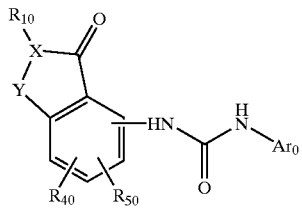

(II'-a)

(wherein, Aro, X, Y, $R_{10}$, $R_{40}$ and $R_{50}$ have the meaning given above) followed by the removal of the appropriate protective group. The reaction condition of each steps follows the similar condition to the preparation method A.

Preparation method B

The compound of formula (I) can be prepared by reacting the compound represented by formula (V)

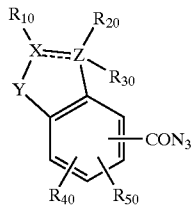

(V)

(wherein, X, Y, Z, $R_{10}$, $R_{20}$, $R_{30}$, $R_{40}$, $R_{50}$ and the formula === have the meanings given above) with the compound represented by formula (VI)

(VI)

(wherein, $Ar_0$ has the meaning given above) to afford the compound represented by formula (II)

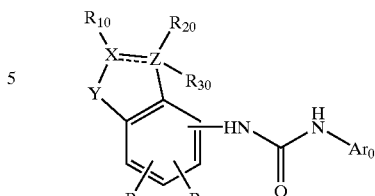

(II)

(wherein, Aro, X, Y, Z, $R_{10}$, $R_{20}$, $R_{30}$, $R_{40}$, $R_{50}$ and the formula === have the meanings given above) followed by the removal of the appropriate protective group to afford the compound represented by formula (I)

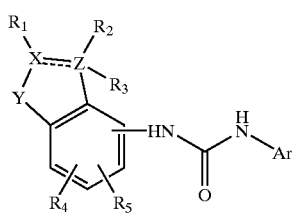

(I)

(wherein, Ar, X, Y, Z, $R_1$, $R_2$, $R_3$, $R_4$, $R_5$ and the formula === have the meanings given above).

Each step of said preparation method follows the method described in preparation method A for preparing the compound of formula (I) and formula (II).

Preparation method C

This method illustrates the preparation of the compound represented by formula (I), in which Ar is pyrrazolyl group.

Reacting the compound represented by formula (VII)

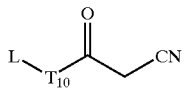

(VII)

(wherein, L is an optionally protected reactive group, which has the functional group converted to other functional group, $T_{10}$ is single bond or $Ar_0$, which has the convertible functional group including straight-chain or branched lower alkylene group, aryl group, heteroaromatic group, aliphatic heterocyclic group, or arylalkyl group, each of the above group may be protected) with the compound represented by formula (VIII)

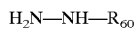

(VIII)

(wherein, $R_{60}$ is hydrogen or the protective group of amino group) affords the compound represented by formula (IX)

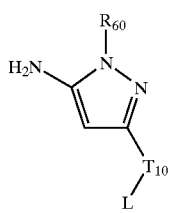

(IX)

(wherein, $T_{10}$, $R_{60}$ and L have the meanings given above), which is allowed to be reacted with the compound of formula (III)

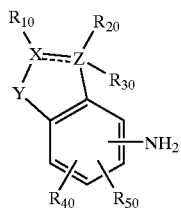

(III)

(wherein, X, Y, Z, $R_{10}$, $R_{20}$, $R_{30}$, $R_{40}$, $R_{50}$ and the formula === have the meanings given above) and the reactive formic ester derivative at the presence of desired base to afford the compound of formula (X)

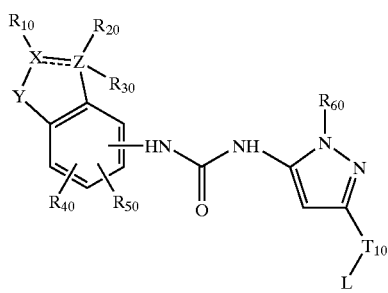

(X)

(wherein, X, Y, Z, $T_{10}$, $R_{10}$, $R_{20}$, $R_{30}$, $R_{40}$, $R_{50}$, the formula === and L have the meanings given above) followed by transformation of substituent L and/or the removal of the protective group to provide the compound of formula (I″)

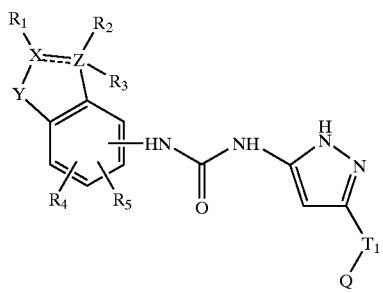

(I″)

(wherein, $T_1$ is single bond or Ar, which has the convertible functional group including straight-chain or branched lower alkylene group, aryl group, heteroaromatic, aliphatic heterocyclic, or arylalkyl group, Q represents $W_1$—$Y_2$—$R_p$ (wherein, $W_1$, $Y_2$ and $R_p$ have the meanings given above), X, Y, Z, $R_1$, $R_2$, $R_3$, $R_4$, $R_5$ and the formula have the meanings given above).

In case of the preparation of the compound of formula (IX), which was prepared by the condensation of the compound of formula (VII) and the compound of formula (VIII), corresponding to 1 mole of the compound of formula (VII), 1 or more mole, preferably, 2 to 3 moles of the compound of formula (VIII) is used. The reaction can be carried out in the alcohol such as ethanol, butanol. In case where the compound of formula (VIII) form a salt with an acid, the base such as triethylamine is preferably used in 2 to 5 moles, preferably 2 to 3 moles corresponding to 1 mole of the compound of formula (VIII) to give the compound of formula (VIII) presence in free form.

The reaction temperature is, usually between 20° C. and the boiling point of the solvent used, preferably, within the range from 50° C. to 150° C.

The reaction time is usually within the range from 1 to 48 hours, preferably, from 2 to 24 hours.

In the reaction, where the compund of formula (X) is prepared by the reaction of the compound of formula (IX), the compound of formula (III) and the reactive formic ester derivative under the presence of an appropriate base, 1 mole or more, preferably, 1 to 3 mole of the compound of formula (III) is used corresponding to 1 mole of the compound of formula (IX). 1 mole or more, preferably. 1 to 3 mole of the reactive formic ester derivative is used corresponding to 1 mole of the compound of formula (IX), and the base is used in 1 mole or more, preferably, 1 to 3 moles corresponding to the reactive derivative of formic ester.

Said reactive formic ester derivative includes the compound, which may form amide carboxylic ester and is not limited but represented by p-nitrophenyl chloro formate, methyl chloroformate.

The reaction is usually carried out in an inactive solvent. Said solvent includes haloalkane such as dichloromethane, chloroform, ether such as ethylether, tetrahydrofuran, aromatic hydrocarbon such as benzene, toluene, aprotic polar solvent such as dimethylformamide, acetone, ethyl acetate, or the mixed solvent thereof.

The reaction temperature in the reaction of the compound of formula (IX) with reactive formic ester derivative, is usually between 20° C. and the boiling point of the solvent used, preferably, within the range from 20° C. to 50° C. The reaction time is usually within the range from 30 minutes to 24 hours, preferably, from 1 to 24 hours. The reaction temperature is, usually between 20° C. and the boiling point of the solvent used, preferably, within the range from 50 to 100° C. in the step reacting with the compound of formula (III) after the reaction has been completed.

The compound of formula (I″) can be prepared by introducing a carboxyl group into the compound of formula (X) using metal complex as a catalyst, followed by converting the compound to the amide, ester, and so on according to the ordinary method and, if necessary, optional combination with the deprotecting of protective group for hydroxyl, amino and carboxyl, and so on.

Alternatives to the preparation method using the compound of formula (IX), the compound of formula (III) and reactive formic ester derivative, the compound of formula (X) can also be prepared by reacting the compound of formula (III) with diphosgene in the presence of activated carbon to afford isocyanate, followed by the reaction with the compound of formula (IX).

The reaction is usually carried out in an inactive solvent such as tetrahydrofuran.

The compound of formula (III) and diphosgene are used in a ratio of 1:1 mole or more, preferably, 1:1. To 5 grams of activated carbon, the compound of formula (IX) is used in 1 or more moles, preferably 1 mole.

The reaction temperature is usually between 20° C. and the boiling point of the solvent used, preferably, within the range from 30° C. to 100° C.

The reaction time is usually from 30 minutes to 24 hours, preferably, within the range from 30 minute to 6 hours.

To the process for converting the reactive substituent L, which has a functional group convertible to the other functional group of the compound of formula (X), for instance, in a case where R represents an aromatic ring and L is a halogen atom, the reaction of the compound of formula (X) with carbon monoxide using palladium as a catalyst in the presence of phosphine ligand and base, in the alcohol solvent such as methanol and ethanol to afford the ester of formula (X) followed by hydrolysis of the ester under the basic condition can be applied.

Said reactive substituent, which has a functional group convertible to the other functional group includes for example, hydroxyl, amino, carboxyl, ester, halogen atom.

In case of that the compound of formula (X) is used in 1 mole, palladium complex such as palladium acetate and phosphine ligand such as 1-bis(diphenylphosphino) ferrocene are each 5 to 50% by weight, preferably, 10 to 20% by weight: and the base such as sodium hydrogen carbonate is 2 to 10 mole, preferably, 2 to 3 moles. The reaction temperature is usually between 20° C. and the boiling point of the solvent used, preferably, within the range from 50 to 100° C. The reaction time is usually from 30 minutes to 24 hours, preferably, within the range from 5 to 24 hours.

The method for further transforming the carboxylic acid prepared above can be carried out as similarly as the method follows a method similar to the method for transforming the substituent of Ar described below. After the completion of the reaction followed by routine method, the compound of formula (I″) can be obtained, if necessary, by deprotecting the protective group of hydroxyl, amino and carboxyl.

The deprotecting method of the protective group depends on the type of the protective group and the stability of the desired compound and so on, and may follows the appropriate method described in literature mentioned above, or a similar method there of.

Next, the transformation methods of the substituent on Ar of the compound of formula (I) are illustrated.

Ar may have various substituents as described above. For example, as described in the preparation method A and B, the desired compound can be prepared by using the compound in which the desired sbustituent is introduced into the starting material. However, for the purpose of improving the reactivity and yield and so on, for example, after the preparation of the compound of formula (II), which has —$T_1$—$OR_7$ (wherein, $R_7$ is the protective group of hydroxyl, $T_1$ has the meaning given above), various transforming reaction described in the transformation methods B to H methioned below can be carried out for further transforming the functional group (Transformation method A) or protecting urea moiety of the compound of formula (II) followed by introducing of the desired substituent.

Transformation method A

This method is a method for transforming the functional group on Ar without protecting the urea moiety. As the various transformation methods, for example, as a starting material, the compound of formula (II-c) was used;

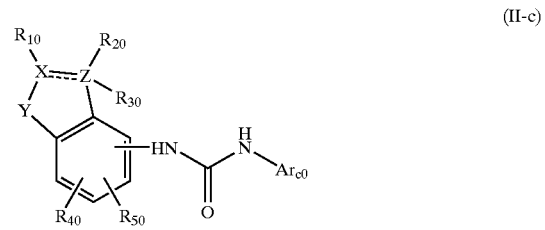
(II-c)

[in the formula, Arco represents $Ar_0$ given above, which comprises a substituent of —$T_1$—$OR_7$(wherein, $R_7$ and $T_1$ have the meanings given above), X, Y, Z, $R_{10}$, $R_{20}$, $R_{30}$, $R_{40}$, $R_{50}$ and the formula === have the same meanings as given above], to give the compound of formula (II-d);

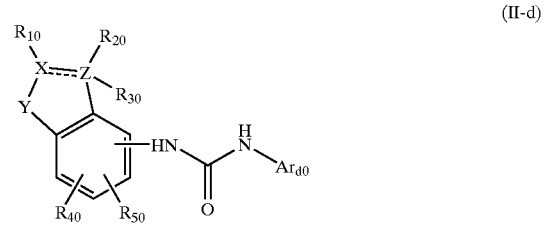
(II-d)

[in the formula. $Ar_{d0}$ represents $Ar_0$ given above, which comprises a substituent of —$T_1$—OH (wherein, $T_1$ has the meaning given above), X, Y, Z, $R_{10}$, $R_{20}$, $R_{30}$, $R_{40}$, $R_{50}$ and the formula === have the saem meanings as given above] can be prepared. And, for example, the compound of formula (II-d) can be transformed to the compound of formula (II-e);

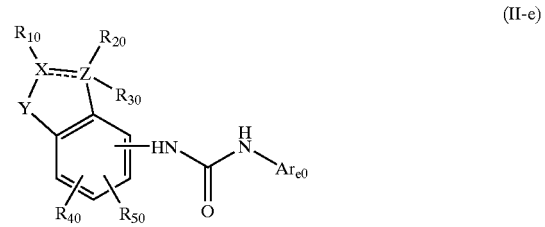
(II-e)

[in the formula, $Ar_{e0}$ represents $Ar_0$ given above, which comprises a substituent of —$T_1$—$NH_2$ (wherein, $T_1$ has the meaning given above), X, Y. Z, $R_{10}$, $R_{20}$, $R_{30}$, $R_{40}$, $R_{50}$ and the formula === have the meanings given above], according to the well known synthetic method in organic synthetic chemistry for transforming alcohol to amine.

The deprotecting method of the protective group of hydroxyl group varies depending on the type of the protective group and the stability of the desired compound, and, if appropriate, may follows for example, the appropriate method in the literature described above or a similar method thereof.

The synthetic method for transforming alcohol to amine and the reaction condition are illustrated as follows. For example, the Mitsunobu reaction using diethylazodicarboxylate, triphenylphosphine and phthalimide (or diazide compound phenylphosphate) can be used, or the method comprising the sulfonation using sulfonating agent such as methanesulfonylchloride in the presence of base such as triethylamine followed by the reaction with phthalimide (or sodium azide compound) and then treatment (or reduction) of the resulting compound with hydrazine is preferable.

The above reaction is usually carried out in an inactive solvent. Said solvent in Mitsunobu reaction, includes for example, tetrahydrofuran, chloroform, dimethoxyethane, benzene, toluene and the like. In the reaction involved in the sulfonation and the amination using phthalimide (or sodium azide compound), the solvent such as dichloromethane, chloroform, tetrahydrofuran, benzene, ethyl acetate, dimethylformamide can be used.

In the cleavage reaction of phthalimide using hydrazine, alcohols such as methanol and ethanol, in the reduction reaction of azide compound compound using hydrogenated metal complex, ether such as ethyl ether and tetrehydrofuran, in the phosphine reduction using triphenylphosphine, tetrahydrofuran containing water, in the hydrogenation reduction, alcohol such as methanol and ethanol are preferable respectively.

In the mitsunobu reaction, to 1 mole of the compound of formula (II-d), diethylazodicarboxylate, triphenylphosphine and phthalimide (or diphenylphosphornylazide compound) are used in 1 mole or more, preferably, 1 to 5 mole, respectively. In the reaction with phthalimide (or sodium azide compound) after sulfonation, to 1 mole of the compound of formula (II-d), the sulfonating agent is used in 1 mole or more, preferably, 1 to 3 mole. And the base used is 1 mole or more, preferably, 1 to 3 mole corresponding to 1 mole of the sulfonating agent. In the next reaction with phthalimide (or sodium azide compound), to 1 mole of the sulfonating reagent, phthalimide and a base or sodium azide compound compound is used in 1 mole or more, preferably, 1 to 5 mole. In the cleavage reaction of a phthalimide group using hydarzine, to 1 mole or more of the phthalimide compound, and the hydrazine is used in 1 mole or more, preferably, 1 to 10 mole. In the reduction of azide compound compund using hydrogenated metal complex or triphenylphosphine, to 1 mole of the azide compound compound, the reducing agent is used in 1 mole or more, preferably, 1 to 2 mole.

The reaction temperature in the Mitsunobu reaction is usually from −70 to 100° C., preferably, within the range from 20 to 50° C. The reaction time is usually from 5 minutes to 48 hours, preferably, from 30 minutes to 24 hours.

The reaction temperature in the cleavage reaction of phthalimide group using hydrazine, is usually from 0° C. to the boiling point of the solvent, preferably, from 20 to 100° C. The reaction time is usually from 5 minutes to 48 hours, preferably, from 30 minutes to 24 hours.

The reaction temperature in the reduction reaction of transforming azide compound compound to amine compound using hydrogenated metal complex, is usually −70 to 150° C., preferably, within the range from 20 to 50° C. The reaction time is usually from 5 minutes to 48 hours, preferably, from 10 minutes to 10 hours. In case of using triphenylphosphine as a reductive agent, the temperature is usually from 20° C. to the boiling point of the solvent, preferably, within the range from 30 to 100° C. The reaction time is usually from 10 minutes to 48 hours, preferably, from 30 minutes to 24 hours. The reaction temperature in the hydrogenation reduction, is usually from 0 to 100° C., preferably, within the range from 20 to 50° C. The reaction time is usually from 10 minutes to 48 hours, preferably, from 10 minutes to 24 hours.

After the completion of the reaction, followed by routine treatment, the compound of formula (II-e) can be obtained, if necessary, by protecting the protective group of hydroxyl group, amino group and carboxyl group.

In the compound of formula (II-d), the compound of formula (II-$d_1$);

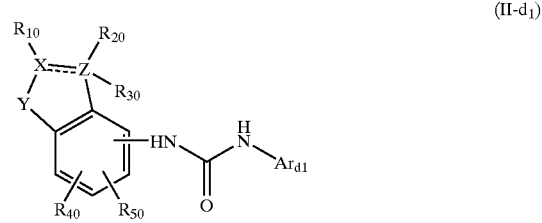

(II-$d_1$)

[in the formula, $Ar_{d1}$ represents $Ar_0$ given above, which comprises the substituent of —$T_1$—CH($R_{d1}$)—OH (wherein, $R_{d1}$ represents hydrogen, or lower alkyl group, arylalkyl group, aromatic ring group beteroaromatic ring group, each of which may have a protected substituents, or a saturated or unsaturated aliphatic cyclic group which may contain one or more hetero atom selected from the group consisting of nitrogen, oxygen and sulfur, $T_1$ has the meaning given above), X, Y, Z, $R_{10}$, $R_{20}$, $R_{30}$, $R_{40}$, $R_{50}$ and the formula === have the meaning given above] is subject to oxidation to afford the compound of formula (II-$d_2$);

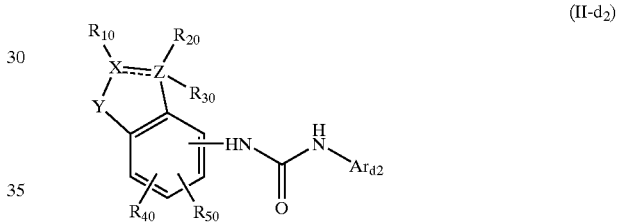

(II-$d_2$)

[in the formula, $Ar_{d2}$ represents $Ar_0$ given above, which comprises the substituent of —$T_1$—C(=O)—$R_{d1}$ (wherein, $R_{d1}$ and $T_1$ have the meanings given above), X, Y, Z, $R_{10}$, $R_{20}$, $R_{30}$, $R_{40}$, $R_{50}$ and the formula have the meaning given above], followed by the reductive amination to give the compound of formula (II-$d_3$);

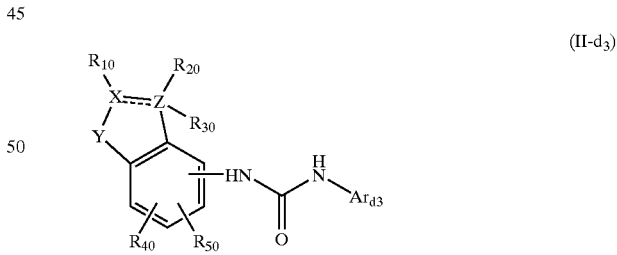

(II-$d_3$)

[in the formula, $Ar_{d3}$ represents $Ar_0$ given above, which comprises the substituent of —$T_1$—CH($R_{d1}$)—$NRd_2Rd_3$ (wherein, $R_{d2}$ and $R_{d3}$ represent, the same or different, hydrogen, or lower alkyl group, arylalkyl group, aromatic ring group, hetero aromatic ring group, which may have an substituent optionally protected, or saturated or unsaturated aliphatic cyclic group which may have one or more hetero atom selected from a group consisting of nitrogen, oxygen and sulfur, $T_1$ has the meaning given above), X, Y, Z, $R_{10}$, $R_{20}$, $R_{30}$, $R_{40}$, $R_{50}$ and the formula === have the meaning given above].

As the reaction wherein the compound of formula (II-d$_2$) can be prepared by oxidizing the compound of formula (II-d$_1$), the well-known oxidization reaction can be used.

In the reductive amination reaction between the compound of formula (II-d$_2$) and Rd$_2$Rd$_3$NH (in the formula, R$_{d2}$ and R$_{d3}$ have the meanings given above), to 1 mole of the compound of formula (II-d$_2$), Rd$_2$Rd$_3$NH is used in 1 mole or more, preferably 3 to 5 mole, and a reducing agent such as sodium borohydride or triacetoxy sodium borohydride is used in 1 mole or more, preferably 3 to 5 mole. In the reaction, if necessary, molecular sieve 3A is used in 3 times of the compound of formula (II-d$_2$) by weight.

The reaction is carried out usually in an inactive solvent such as chloroform and methanol or mixed solvent thereof. The reaction temperature is usually from 20° C. to the boiling point of the solvent, preferably from 20 to 60 Oc.

The process wherein the compound of formula (II-d$_3$) can be prepared by starting from the compound of formula (II-d$_1$) via the compound of formula (II-d$_3$) can be carried out after the moiety of urea is protected according to the transformation method B.

The compound of formula (I) can be prepared by optionally eliminating the protective group of the compounds of formula (II-c), formula (II-d) and formula (II-e) obtained according to the above method. The method of cleavaging the protective group varies depending on the type of the protective group and the stability of the desired compound and usually may follow the general method described in the literature given above, or a similar method thereof.

Transformation Method B

This method is a method of the transformation reaction after the urea moiety is protected.

The compound of formula (XI);

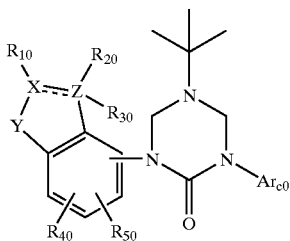

(XI)

[in the formula, Arco. X. Y, Z, R$_{10}$, R$_{20}$, R$_{30}$, R$_{40}$, R$_{50}$ and the formula === have the meanings given above] can be produced by stirring the compound of formula (II-c):

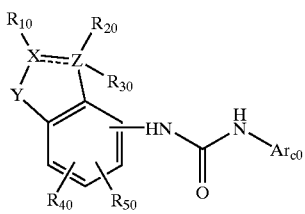

(II-c)

[in the formula, Ar$_{c0}$ represents Ar$_0$ given above, which comprises the substituent of —T$_1$—OR$_6$ (wherein, R$_6$ and T$_1$ have the meanings given above), X, Y, Z, R$_{10}$, R$_{20}$, R$_{30}$, R$_{40}$, R$_{50}$ and the formula === have the meaning given above] in imine prepared from tert-butylamine and paraformaldehyde.

The compound of formula (XI) can be a starting compound of the present transformation method, and the compound of formula (XII);

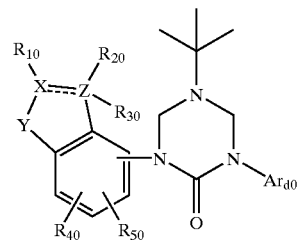

(XII)

[in the formula, Ar$_{d0}$ represents Ar$_0$ given above, which comprises the substituent of —T$_1$—OH (wherein, T$_1$ has the meaning given above), X, Y, Z, R$_{10}$, R$_{20}$, R$_{30}$, R$_{40}$, R$_{50}$ and the formula === have the meanings given above] can be prepared by eliminating the protective group of hydroxyl group of the compound of formula (XI).

In the reaction for preparing the compound of formula (XI), to 1 mole of the compound of formula (II-c), imine prepared from tert-butylamine and paraformaldehyde is used in 3 to 5 mole, preferably 4 mole.

The above reaction can be usually carried out in an inactive solvent such as chloroform, dichloromethane and tetrahydrofuran, and so on.

The reaction temperature is usually from 50° C. to the boiling point of the solvent, from 80 to 150° C. The reaction time is usually from 12 to 72 hours, preferably from 24 to 72 hours. If necessary, one drop of acid such as sulfuric acid may be added to accelerate the reaction.

The compound of formula (XII) can be derived from the compound of formula (XI), by the transformation method for preparing the compound of formula (II-d) from the compound of formula (II-c).

The compound of formula (XII), which is the key intermediate for preparing the compound of formula (I), can be derived from the compound of formula (XII) or its derivative according to, for example, the transformation method C to E described hereinafter.

Transformation Method C

By reacting the compound of formula (XII);

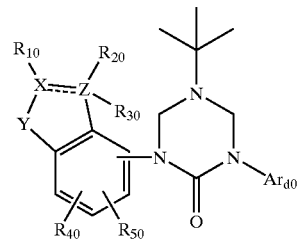

(XII)

[in the formula, Ar$_{d0}$, Y, Z, R$_{10}$, R$_{20}$, R$_{30}$, R$_{40}$, R$_{50}$ and the formula === have the meanings given above], with the compound of formula (XIII);

(XIII)

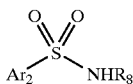

[in the formula, $Ar_2$ represents phenyl substituted with 1 or 2 nitro group, $R_8$ represents benzyl substituted with 1 to 3 methoxy groups] to give the compound of formula (XIV);

(XIV)

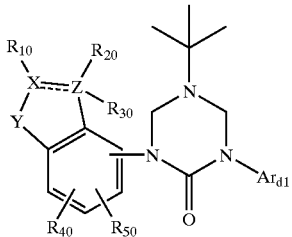

[in the formula, $Ar_{d1}$ represents $Ar_0$ given above, which comprises the substituent of —$T_1$—$N(R_8)SO_2Ar_2$(wherein, $T_1$, $R_8$ and $Ar_2$ have the meanings given above), X, Y, Z, $R_{10}$, $R_{20}$, $R_{30}$, $R_{40}$, $R_{50}$ and the formula === have the meanings given above].

The reaction is carried out by Mitsunobu reaction. To 1 mol of the compound of formula (XII), the compound of formula (XIII) is used 1 mole or excess mole, preferably 1 to 3 mole. For example, the compound of formula (XII) is activated by reacting with azodicarboxylic acid diester such as diethylazadicarboxylate and phosphines such as triphenylphosphine, which is further reacted with the compound of formula (XIII) to obtain the compound of formula (XIV).

The reaction is usually carried out in an inactive solvent such as haloalkenes like dichloromethane and chloroform, ethers such as ethyl ether and tetrahydrofuran or a mixed solvent thereof and so on.

To 1 mole of the compound of formula (XII), azodicarboxylic acid diester such as diethylazadicarboxylate and phosphines such as triphenylphosphine are used 1 mole or more, preferably 1 to 3 mole.

The reaction temperature is usually from 0° C. to the boiling point of the solvent, preferably from 20 to 40° C.

The reaction time is usually from 1 hour to 24 hours, preferably from 2 to 24 hours.

After the completion of the reaction followed by the ordinary treatment, the crude compound of formula (XIV) can be obtained, which is purified according to the conventional method to obtain the compound of formula (XIV).

The compound of formula (XV);

(XV)

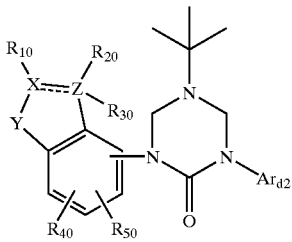

[in the formula, $Ar_{d2}$ represents $Ar_0$ given above, which comprises the substituent of —$T_1$—$NHSO_2Ar_2$ (wherein, $T_1$ and $Ar_2$ have the meanings given above), X, Y, Z, $R_{10}$, $R_{20}$, $R_{30}$, $R_{40}$, $R_{50}$ and the formula === have the meanings given above], is prepared by the ordinary cleavage of aralkyl group as amino-protecting group described in the literature given above.

In the reaction for preparing the compound of formula (XVI);

(XVI)

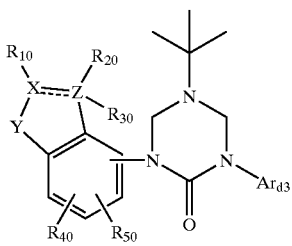

[in the formula, $Ar_{d3}$ represents $Ar_0$ given above, which comprises the substituent of —$T_1$—$N(R_q)SO_2Ar_2$ (wherein, $R_q$, $T_1$ and $Ar_2$ have the meanings given above), X, Y, Z, $R_{10}$, $R_{20}$, $R_{30}$, $R_{40}$, $R_{50}$ and the formula === have the meanings given above], from the compound of formula (XV), to 1 mole of the compound of formula (XV), $R_q$—OH (wherein $R_q$ has the meaning given above) is used in 1 or excess mole, preferably 1 to 3 mole. Said reaction can be carried out according to the similar reaction of the compound of formula (XII) with the compound of formula (XIII). Thus, the reaction condition and so on can apply to said reaction.

The reaction for preparing the compound of formula (XVII);

(XVII)

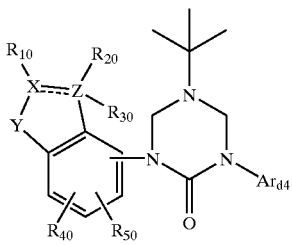

[in the formula, $Ar_{d4}$ represents $Ar_0$ given above, which comprises the substituent of —$T_1$—$NHR_q$(wherein, $R_q$ and $T_1$ have the meanings given above), X, Y, Z, $R_{10}$, $R_{20}$, $R_{30}$, $R_{40}$, $R_{50}$ and the formula === have the meanings given above], from the compound of formula (XVI), can be carried out according to ordinary hydrolysis of arylsulfonamide, in which for example, thiophenol, sodium carbonate are used in an inactive solvent. Said solvent is, for example, preferably dimethylformamide, and so on.

According to the reaction condition similar to that of the reaction of transforming the compound of formula (XVI) into the compound of formula (XVII), the compound, in which $R_q$ has a convertible substituent, can be prepared by introduction of an appropriate substituent on the compound of formula (XVI).

The reaction temperature is usually from 20° C. to the boiling point of the solvent, preferably from 20 to 80° C.

The reaction time is usually 2 to 48 hours, preferably, 2 to 24 hours.

The reaction for preparing the compound of formula (II-f);

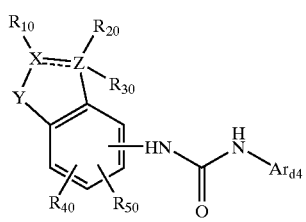

(II-f)

[in the formula, $Ar_{d4}$ represents $Ar_0$ given above, which comprises the substituent of —T1—$NHR_q$(wherein, $R_q$ and $T_1$ have the meanings given above), X, Y, Z, $R_{10}$, $R_{20}$, $R_{30}$, $R_{40}$, $R_{50}$ and the formula === have the meanings given above], from the compound of formula (XVII), can be carried out by reacting the compound of formula (XVII) with an appropriate acid such as hydrochloric acid, trifluoroacetic acid and so on. If necessary, the reaction can be carried out in a mixture of said reagent(s) and an inactive solvent such as tetrahydrofuran and chloroform.

The similar reaction for the compound, in which an appropriate substituent is introduced can be carried out by applying the transformation reaction of the substituent on $R_q$ of the compound of formula (XVI).

The compound of formula (II-f) can be prepared by reductive amination of the compound of formula (XXIII). In said method, the compound of formula (II-f) can be prepared by deprotecting the protective group for urea moiety using for example, hydrochloric acid or trifluroacetic acid, before or after the reductive amination reaction.

The protective group of the intermediate in each step of the preparation method can be removed appropriately at each step and at the final step to obtain the compound of formula (I).

The method of eliminating the protective group depends on the type of the protective group and the stability of the desired compound and usually may follow the method described in the literature given above or a similar method thereof.

Transformation Method D

In the present transformation method, by using the compound of formula (XVII) prepared in the transformation method C, the compound of formula (XIX);

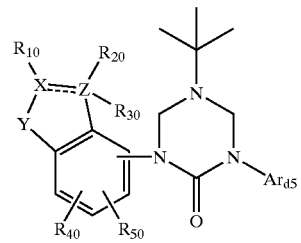

(XIX)

[in the formula, $Ar_{d5}$ represents $Ar_0$ given above, which comprises the substituent of —$T_1$—$NR_q$—$T_2$—$R_p$ (wherein, $T_2$ represents carbonyl group or sulfonyl group, $R_p$, $R_q$, $T_1$, $Ar_2$ have the meaning given above), X, Y, Z, $R_{10}$, $R_{20}$, $R_{30}$, $R_{40}$. $R_{50}$ and the formula === have the meanings given above] is obtained, and then the compound of formula (II-g);

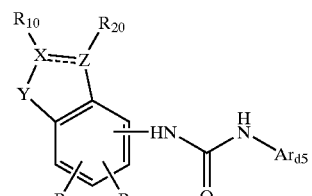

iig

[in the formula, $Ar_{d5}$ represents $Ar_0$ given above, which comprises the substituent of —$T_1$—$NR_q$—$T_2$—$R_p$ (wherein, $T_1$, $Ar_2$ $R_p$, $R_q$ and $T_2$ have the meanings given above), X, Y, Z, $R_{10}$ $R_{20}$, $R_{30}$, $R_{40}$, $R_{50}$ and the formula === have the meanings given above]can be prepared.

The reaction for preparing the compound of formula (XIX) from the compound of formula (XVII) is carried out by reacting the compound of formula (XVII) with the carboxylic acid, sulfonic acid or the reactive derivative thereof represented by compound of formula (XVIII) $R_p$—$T_2$—OH [in the formula, $R_p$ and $T_2$ have the meanings given above]. The examples of reactive derivatives of carboxylic acid or sulfonic acid of formula (XVIII) include, for example, acid halide, mixed anhydride, active ester, active amide, and so on.

In case where carboxylic acid of formula (XVIII) is used, the reaction is carried out preferably in the presence of a condensing agent such as N,N'-dicyclohexylcarbodiimide, 1-ethyl-3-(3-dimethylaminopropyl)carbodiimide, 2-chloro-1,3-dimethylimidazolylchloride, and so on.

In the reaction of the compound of formula (XVII) with the compound of formula (XVIII), to 1 mole of the compound of formula (XVII), the compound of formula (XVIII) is used in 1 mole or more, preferably 1 to 5 mole.

The reaction is usually carried out in an inactive solvent. Said solvent includes haloalkane such as dichloromethane, chloroform and so on, ethers such as ethyl ether, tetrahydrofuran, and so on, aromatic hydrocarbons such as benzene, toluene, and so on, non-proton polar solvents such as dimethylformamide, acetone, ethyl acetate, or a mixed solvent thereof.

The reaction temperature is usually from −20° C. to the boiling point of the solvent, preferably from 0 to 50 Oc.

The reaction time is usually from 10 minutes to 48 hours, preferably from 30 minutes to 24 hours.

The reaction can also be carried out in the presence of a base. Said base includes an inorganic base such as sodium hydroxide, potassium hydroxide, calcium hydroxide, sodium bicarbonate, potassium carbonate, sodium hydrogen carbonate, or an organic base such as triethylamine, N-ethyldiisopropylamine, pyridine, 4-dimethylaminopyridine, N,N-dimethylaniline.

To 1 mole of the compound of the formula (XVIII), the base is used in 1 mole or more, preferably 1 to 5 mole.

The acid halide of formula (XVIII) can be prepared by reacting carboxylic acid or sulfonic acid of formula (XVIII) with halogenating agent, following a conventional method. The halogenating agent includes thionylchloride, phosphorus trichloride, phosphorus pentachloride, phosphorus oxychloride, phosphorus tribromide, oxyzly chloride, phosgene, and so on.

The mixed anhydride of carboxylic acid of formula (XVIII) can be prepared by reacting carboxylic acid of formula (XVIII) with chloroformic ester such as ethyl chloroformate or aliphatic carboxylic acid chloride such as acetyl chloride.

The active ester of carboxylic acid of formula (XVIII) can be prepared by reacting carboxylic acid of formula (XVIII) with, for example, N-hydroxyl compound such as N-hydroxysucuimide, N-hydroxyphthalimide, 1-hydroxybenzotriazole, phenol compound such as 4-nitrophenol, pentanchlorophenol, according to the conventional method in the presence of a condensing agent such as N,N'-dicyclohexylcarbodiimide, 1-ethyl-3-(3-dimethylaminopropyl)carbodiimide, and the like.

The active amide of carboxylic acid of formula (XVIII) can be prepared by reacting carboxylic acid of formula (XVIII) with, for example, 1,1'-carbonyldiimidazole, 1,1'-carbonylbis(2-methylimidazole), according to the conventional method.

The compound of formula (I) can be prepared, if appropriate, by deprotecting the protective group of compound of formula (XIX) prepared above, to afford the compound of formula (II-g), followed by further elimination of the protective group.

The compound of formula (II-g) can be prepared by reacting the compound of formula (XIX) with an appropriate acid such as hydrochloric acid and trifluoroacetic acid, optionally in mixture with the inactive solvent such as tetrahydrofuran and chloroform.

Also, the compound of formula (II-g) can be prepared according to this preparation method using the compound of formula (II-f) in the transformation method A.

Transformation Method E

In this method, using the compound of formula (XII), the compound of formula (XX);

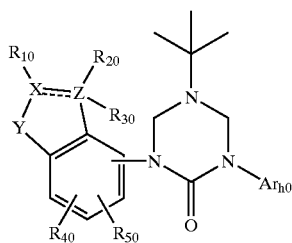

(XX)

[in the formula. $Ar_{h0}$ represents $Ar_0$ given above, which comprises the substituent of —$T_1$—O—$R_p$(wherein, $R_p$ and $T_1$ have the meanings given above), X, Y, Z, $R_{10}$, $R_{20}$, $R_{30}$, $R_{40}$, $R_{50}$ and the formula ═ have the meanings given above], can be obtained and then the compound of formula (II-h);

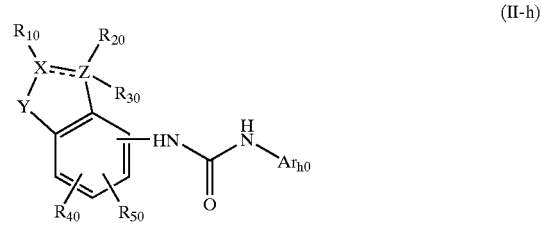

(II-h)

[in the formula, $Ar_{h0}$ represents $Ar_0$ given above, which comprises the substituent of —$T_1$—O—$R_p$(wherein, $R_p$ and $T_1$ have the meanings given above), X, Y, Z, $R_{10}$, $R_{20}$, $R_{30}$, $R_{40}$, $R_{50}$ and the formula ═ have the meanings given above] can be prepared.

The reaction for preparing the compound of formula (XX) from the compound of formula (XII) is carried out by following various synthetic methods and reaction contidions for transforming alcohol into ether. For example, aryl ether can be prepared by reacting aryl alcohol with diethylazodicarboxylate and triphenylphosphine (what is called, Mitsunobu reaction). Alkyl ether can be prepared by reacting halogen compound (some of the compounds are commercially available), or sulfonate ester such as methanesulfonate ester, each of which can be prepared from alcohol represented by formula (XXI)$R_p$—OH (wherein, $R_p$ has the meaning given above) in the presence of a base.

Furthermore, the method for synthesizing alkyl ether and aryl ether is illustrated by for example, transforming the compound of formula (XII) into the corresponding halogen compound or sulfonate ester followed by reacting with an alcohol represented by formula (XXI) $R_p$—OH in the presence of a base. The transformation of said alcohol into said halogen compound is usually carried out by an ordinary method, for example, reacting with carbon tetra-bromide and triphenylphosphine in an inactive solvent such as carbon tetrachloride and the like. Similarly, sulfonate ester such as methanesulfonate ester can be prepared by reacting with methanesulfonyl chloride and a base such as triethylamine in an inactive solvent such as ethyl acetate.

The compound of formula (II-h) can be prepared appropriately in combination with cleavage of the protective group for hydroxyl group, amino group and carboxyl group of the compound of formula (XX) obtained above.

The above reaction is usually carried out in an inactive solvent. As said solvent, tetrahydrofuran, chloroform, dimethoxyethane, benzene, toluene, and the like are preferably used in Mitsunobu reaction; haloalkanes such as carbon tetrachloride, chloroform, and the like are preferably used in the halogenation; dichloromethane, chloroform, tetrahydrofuran, benzene, ethyl acetate, dimethylformamide are preferably used in sulfonation.

In Mitsunobu reaction, to 1 mole of the compound of formula (XII), the amount of diethylazadicarboxylate, phosphine and aryl alcohol are each 1 mole or more, preferably 1 to 5 mole.

In the reaction of the compound of formula (XII) after halogenating the alcohol of formula (XII), to 1 mole of the alcohol of formula (XXI), the halogenating agent is used in 1 mole or more, preferably 1 to 3 mole. In the next reaction of the compound of formula (XII), to 1 mole of the compound of formula (XII), the halogenating agent is used in 1 mole or more, preferably 1 to 5 mole. To 1 mole of the halogenating agent, the base is used in 1 mole or more, preferably 1 to 5 mole. In the reaction of compound of formula (XII) after transforming the alcohol of formula (XXI) to sulfonate ester, to 1 mole of the alcohol of formula (XXI), the sulfonating agent is used in 1 mole or more, preferably 1 to 3 mole. To 1 mole of the sulfonating agent, the base is used in 1 mole or more, preferably 1 to 5 mole. In the next reaction of the compound of formula (XII), to 1 mole of the compound of formula (XII), the sulfonate ester is used in 1 mole or more, preferably 1 to 5 mole. To 1 mole of the sulfonate ester, the base is used in 1 mole or more, preferably 1 to 5 mole.

In case where the compound of formula (XII) is first converted to the corresponding halide or sulfonate ester, which is then reacted with the alcohol of formula (XXI) in the presence of base, the reaction can be carried out according to the procedure described above.

In the Mitsunobu reaction described above, the reaction temperature is usually from −70 to 100° C., preferably from 20 to 50° C. The reaction time is usually from 5 minutes to 48 hours, preferably from 30 minutes to 2 to 24 hours. In the reaction of the compound of formula (XII) after the halogenation of the alcohol of formula (XXI), the reaction temperature is usually from 0° C. to the boiling point of the solvent, preferably from 20 to 100° C. The reaction time is usually from 5 minutes to 48 hours, preferably from 30 minutes to 24 hours. In the reaction of the compound of formula (XII) after the transformation of the alcohol of formula (XXI) to the sulfonate ester, the reaction temperature is usually from 0 to 100° C., preferably from 0 to 30° C. The reaction time is usually from 5 minutes to 48 hours, preferably from 10 minutes to 10 hours. In case where the compound of formula (XII) is first converted to the corresponding halide or sulfonate ester, which is then reacted with the alcohol of formula (XXI) in the presence of base, the reaction can be carried out according to the procedure describe above.

After the completion of the reaction followed by the ordinary treatment, the compound of formula (II-h) is obtained optionally in combination with the deprotecting reaction of the protective group for hydroxyl group, amino group and carboxyl group, and then the compound of formula (I) is obtained by deprotecting of all protective groups.

The deprotecting method of a protective group depends on the type of the protective group and the stability of the desired compound, which can be carried out for example, if appropriate, according to the literature method described above or a similar method thereof.

Transformation Method F

In this method, using the compound of formula (XII), the compound of formula (XXII);

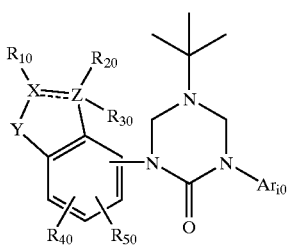

(XXII)

[in the formula, $Ar_{i0}$ represents $Ar_0$ given above, which comprises the substituent of —$T_1$—CHO (wherein, $T_1$ has the meaning given above), X, Y, Z, $R_{10}$, $R_{20}$, $R_{30}$, $R_{40}$, $R_{50}$ and the formula ══ have the meanings given above], can be obtained and then the compound of formula (XXIII);

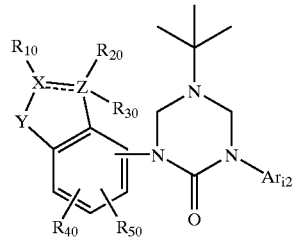

(XXIII)

[in the formula, $Ar_{i2}$ represents $Ar_0$ given above, which comprises the substituent of —$T_1$—CH=$R_v$ (wherein, $T_1$ has the meaning given above, $R_v$ represents an ester group), X, Y, Z, $R_{10}$, $R_{20}$, $R_{30}$, $R_{40}$, $R_{50}$ and the formula ══ have the meanings given above] can be prepared.

In the reaction, to 1 mole of the compound of formula (XII), manganese dioxide is used in 1 mole or more, preferably 20 mole. After the compound of formula (XXII) is obtained, the compound of formula (XXIII) can be prepared by reacting with dialkylphosphonoacetate and an appropriate base such as sodium hydride in 1 mole or more, preferably, 3 to 5 mole, respectively. The reaction is carried out usually in an inactive solvent. Said solvent includes tetrahydrofuran and ethyl ether and the like.

The reaction temperature in synthesizing the compound of formula (XXII) from the compound of formula (XII) is usually from 0° C. to the boiling point of the solvent used, preferably from 20 to 50° C. The reaction temperature in synthesizing the compound of formula (XXIII) from the compound of formula (XXII) is usually from −78 to 20° C., preferably from −78 to 0° C.

By either Diels-Alder reaction or well known 1,3 dipolar addition reaction between the compound of formula (XXIII) and reactive diene compound followed by the treatment with acid, the compound of formula (II-i);

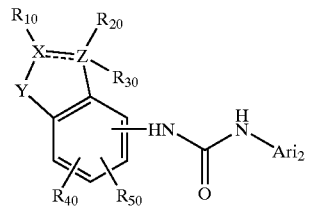

(II-i)

[in the formula, $Ar_{i2}$ represents $Ar_0$ given above, which comprises the substituent of —$T_1$—Cy (wherein, $T_1$ has the meaning given above, Cy represents aliphatic cyclic group which may contain hetero atom and which may be substituted), X, Y, Z, $R_{10}$, $R_{20}$, $R_{30}$, $R_{40}$, $R_{50}$ and the formula ══ have the meanings given above] can be prepared.

To 1 mole of the compound of formula (XXIII), the reactive diene is usually used in 1 mole or more, preferably 10 mole.

The above reaction is usually carried out in an inactive solvent. Said solvent includes preferably, haloalkanes such as dichloromethane and chloroform, or acetonitrile and so on.

The reaction temperature is usually from 0° C. to the boiling point of the solvent used, preferably, within the range from 20 to 120° C.

The compound of formula (II-i) can be prepared from the compound obtained above by following the method similar to the process for preparing the compound of formula (II-f) from the compound of formula (XVII).

Transformation Method G

By reacting the compound of formula (XXIV);

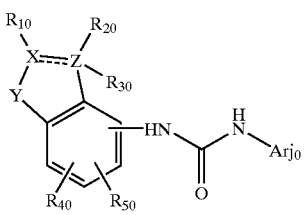

(XXIV)

[in the formula, $Ar_{j0}$ represents $Ar_0$ given above, which comprises the substituent of —Sn—$R_v$3(wherein, $R_v$ represents lower alkyl group), X, Y, Z, $R_{10}$, $R_{20}$, $R_{30}$, $R_{40}$, $R_{50}$ and the formula have the meanings given above] with the compound of formula (XXV):

$$R_x—L_i \quad \text{(XXV)}$$

[in the formula, $R_x$ represents cyclic or non-cyclic aliphatic group, aromatic group, or hetero-aromatic group, each of which may have protected substituent(s) and in which carbon atom which $L_1$ binds to may have an unsaturated bond to which $Ar_{j1}$ binds, $L_1$ represents halogen atom or trifluoromethanesulfonyloxy group], the compound of formula (II-j);

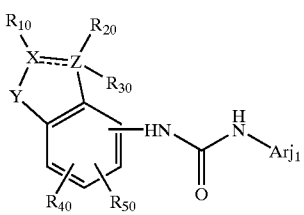

(II-j)

[in the formula, $Ar_1$ represents $Ar_0$ given above, which comprises the substituent of —$R_x$ (wherein, $R_x$ represents cyclic or non-cyclic aliphatic group, aromatic group, or hetero-aromatic ring group, each of which may have protected substitutent(s) and in which carbon atom to which $Ar_{j1}$ binds may have an unsaturated bond), X, Y, Z, $R_{10}$, $R_{20}$, $R_{30}$, $R_{40}$, $R_{50}$ and the formula === have the meanings given above] can be prepared.

In the reaction, to 1 mole of the compound of formula (XXIV), the compound of formula (XXV) is used in 1 mole or more, preferably 1 to 3 mole. Preferably, the reaction can be carried out by adding for example, palladium catalyst such as tris(dibenzelidenacetone) dipalladium(0) (Pd$_2$(dba) 3), phosphine ligand such as triphenylphosphine and if necessary adding lithium chloride, in the presence of inactive gas.

The reaction is usually carried out in an inactive solvent. Said inactive solvent includes preferably, ethers such as dioxane and tetrahydrofuran, aromatic hydrocarbons such as toluene.

The reaction temperature is usually for 20° C. to the boiling point of the inactive solvent used, preferably from 50 to 130° C.

Transformation Method H

From the compound of formula (XII-i);

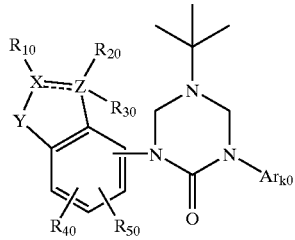

(XII-i)

[in the formula, $Ar_{k0}$ represents $Ar_0$ given above, which comprises the substituent of —(CH$_2$)$_2$—OH, Y, Z, $R_{10}$, $R_{20}$, $R_{30}$, $R_{40}$, $R_{50}$ and the formula === have the meanings given above], the compound of formula (XXVI);

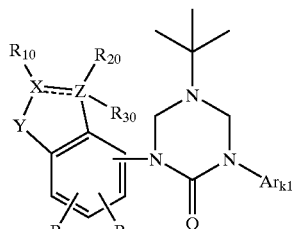

(XXVI)

[in the formula, $Ar_{k1}$ represents $Ar_0$ given above, which comprises the substituent of —CH=CH$_2$, X, Y, Z, $R_{10}$, $R_{20}$, $R_{30}$, $R_{40}$, $R_{50}$ and the formula === have the meanings given above] can be synthesized, and then reacting said compound with the compound of formula (XXVII);

$$Ry—SH \quad \text{(XXVII)}$$

[in the formula, $R_y$ has the aliphatic group or aromatic group, each of which may have protected substituent(s)] to prepare the compound of formula (II-k);

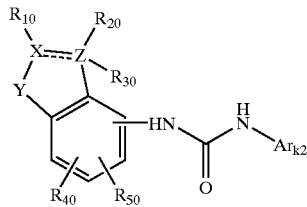

(II-k)

[in the formula, $Ar_{k2}$ represents $Ar_0$ given above, which comprises the substituent of —(CH$_2$)$_2$—$SR_y$ (wherein, $R_y$ has the meanings given above, X, Y, Z, $R_{10}$, $R_{20}$, $R_{30}$, $R_{40}$, $R_{50}$ and the formula === have the meanings given above)].

In the reaction for preparing the compound of formula (XXVI) from the compound of formula (XII-i), to 1 mole of the compound of formula (XII-i), for example, methanesulfonyl chloride is used in 1 mole or more, preferably 1 to 3 mole; an appropriate base, for example, aliphatic tertiary amine such as 1,8-diazabicyclo[5,4,0]undecan-7-ene (DBU) is used in 1 or more mole, preferably 1 to 3 mole.

The reaction is carried out usually in an inactive solvent. Said solvent includes preferably, tetrahydrofuran and ethyl acetate. The reaction temperature is usually from 20° C. to the boiling point of the inactive solvent used, preferably from 20 to 50° C.

In the reaction for preparing the compound of formula (II-k) from the compound of formula (XXVI), to 1 mole of the compound of formula (XXVI), for example, RY—SH is used in 1 mole or more, preferably 1 to 5 mole: and the base such as sodium ethoxide is used in 1 mole or more, preferably 1 to 5 mole. The compound of formula (II-k) is therefore obtained by the completion of the above reaction followed by the treatment with acids such as hydrochloric acid.

The reaction is usually carried out in alcohols such as methanol and ethanol. The reaction temperature is usually from 0° C. to the boiling point of the solvent used, preferably from 0 to 50° C.

Applying the method similar to the method for preparing the compound (II-i) from the compound of (XXIII) to the compound of (XXVI), the compound of formula (II-i');

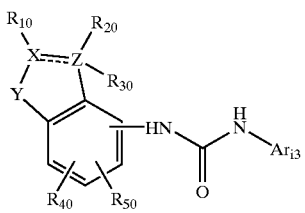

(II-i')

[in the formula, $Ar_{i3}$ represents $Ar_0$ given above, which comprises the substituent of —$T_1$—Cy' (wherein, $T_1$ has the meaning given above, Cy' has an aliphatic cyclic group, which may have protected substituents and which may contain heteroatom), X, Y. Z, $R_{10}$, $R_{20}$, $R_{30}$, $R_{40}$, $R_{50}$ and the formula === have the meanings given above] can be prepared.

The above reaction is carried out under the condition similar to the reaction condition for preparing the compound (II-i) from the compound of (XXIII).

Next, the method for preparing starting materials of the present invention is illustrated as follows.

As described above, the compound of formula (I) can be prepared by using the compound of formula (III), the compound of formula (IV), the compound of formula (V) and the compound of formula (VI) as starting materials. The starting materials can be prepared from the known compounds by per se known general synthetic method. The main synthetic routes are illustrated as follows.

The compound of formula (III) can be prepared by using the synthetic methods A to J; the compound of formula (IV) can be prepared by using the synthetic methods K to M; and the compound of formula (V) can be prepared by using the synthetic method N.

Among the compound (III) used in the preparation method A, the compound wherein X is nitrogen, and Y is c=O, that is, the compound of formula (III-i):

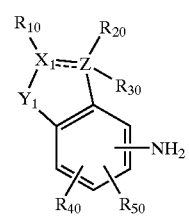

(III-i)

[in the formula, $X_1$ is nitrogen, $Y_1$ is CO, Z, $R_{10}$, $R_{20}$, $R_{30}$, $R_{40}$, $R_{50}$ and the formula === have the meanings given above] can be prepared by using the synthetic method A.

Synthetic Method A

This method comprises converting the carboxylic acid of formula (1);

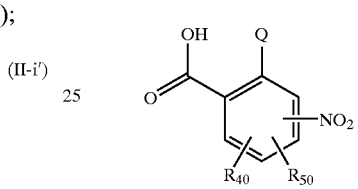

(1)

[in the formula, Q is halogen atom, $R_{40}$ and $R_{50}$ have the meanings given above] to its reactive derivative (1'), reacting the active derivative (1') with the compound of formula (2);

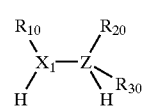

(2)

[in the formula, X, $R_{10}$, $R_{20}$, $R_{30}$ and Z have the meanings given above] to afford the compound of formula (3);

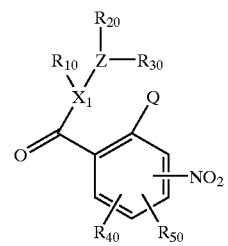

(3)

[in the formula, X, $R_{10}$, $R_{20}$. $R_3$, $R_{40}$, $R_{50}$, Q and Z have the meanings given above], then subjecting the compound of formula (3) to an intramolecular ring closure reaction using palladium as a catalyst to afford the compound of formula (4) [in the formula, X, $R_{10}$, $R_{20}$, $R_{30}$ and Z have the meanings given above] to obtain the compound of formula (4);

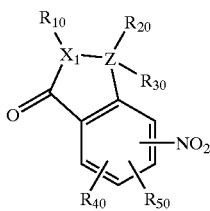

(4)

[in the formula, X, $R_{10}$, $R_{20}$, $R_{30}$, $R_{40}$, $R_{50}$ and Z have the meanings given above], and then reacting with a reducing agent.

The reaction between the active derivative (1') of carboxylic acid of formula (1) and the compound of formula (2) can be carried out by method similar to the process wherein the compound (XIX) is produced from the compound of formula (XVII) in the above-mentioned transformation method, thus the similar reaction condition can be applied.

In the reaction of preparing the compound of formula (4) from the compound of formula (3), to 1 mole of the compound of formula (3), palladium complex such as tetrakistriphenylphosphine palladium is used in 5 to 50% by weight, preferably, 10 to 20% by weight; and the base such as potassium acetate is used in 2 to 10 mole, preferably 2 to 5 mole.

The reaction is carried out usually in an inactive solvent. Said solvent includes halogenated hydrocarbons such as dichloromethane, chloroform, and the like; ethers such as ethyl ether, tetrahydrofuran, dioxane, and the like; aromatic hydrocarbons such as benzene, toluene, and the like; aprotic polar solvent such as dimethylformamide, acetone, ethyl acetate, and the like; or a mixed solvent thereof.

The reaction temperature is usually 20° C. to the boiling point of the solvent used, preferably, within the range from 50 to 100° C. The reaction time is usually 30 minutes to 24 hours, preferably 5 to 24 hours.

Among the compound of formula (III-i), the compound (III-$i_a$), in which the five- or six-membered ring formed by $R_{20}$ with $R_{10}$ and X is unsaturated, and the compound (III-$i_b$), in which the five- or six-membered ring formed by $R_{20}$ with $R_{10}$ and X is saturated can be prepared from the compound of formula (4) under an appropriate condition selected.

The compound (III-$i_a$) which is unsaturated can be obtained in the reaction where, to 1 mole of the compound of formula (4), for example, iron dust used in is 5 to 20 mole, preferably 5 to 10 mole in the presence of hydrochloric acid. The compound (III-$i_b$) which is saturated can be prepared by subjecting the compound of formula (4) to hydrogenation. In the reaction, to 1 mole of the compound (4), for example, 10% palladium carbon catalyst is used 5 to 50% by weight, preferably, 10% to 20% by weight.

The reaction is carried out usually in an inactive solvent. Said solvent includes alcohol such as methanol and ethanol for the reaction using iron dust in the presence of hydrochloric acid, ethers such as ethyl ether and tetrahydrofuran, alcohols such as methanol and ethanol or a mixed solvent thereof for the hydrogenation.

In the reduction reaction using iron dust in the presence of hydrochloric acid, the reaction temperature is usually 0° C. to the boiling point of the solvent used, preferably, within the range from 20 to 50° C.: and the reaction time is 30 minutes to 24 hours, preferably 30 minutes to 2 hours. In the hydrogenation, the reaction temperature is usually 0° C. to the boiling point of the solvent used, preferably, within the range from 20 to 50° C.; and the reaction time is 1 hour to 48 hours, preferably 5 to 24 hours.

After the completion of the reaction followed by routine treatment method optionally in combination with deprotection of the protective group of hydroxyl group, amino group and carboxyl group can be prepared the compound of formula (III).

The deprotecting method of the protective group varies depending on the type of the protective group and the stability of the desired compound, and may follows the appropriate method described above or a similar method thereof.

The compound (wherein, X is nitrogen, Y is CO, Z is carbon atom) of the formula (III-ii);

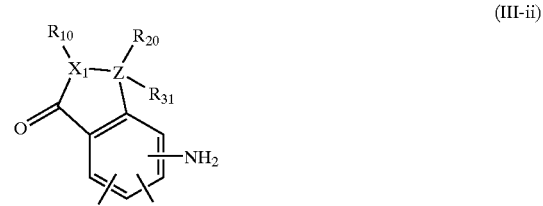

(III-ii)

[in the formula, $R_{21}$ represents hydrogen atom or a hydroxyl group, $R_3$, represents hydrogen atom, $R_{10}$, $R_{40}$, $R_{50}$ and $X_1$ have the meanings given above], which is a starting material in the preparation method A, can be prepared as follows.

Preparation Method B

The compound of (III-ii) can be prepared by subjecting the compound of formula (5);

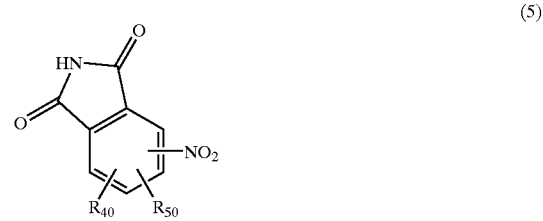

(5)

[in the formula, $R_{40}$ and $R_{50}$ have the meanings given above] to alkylation by Mitsunobu reaction followed by the reduction with sodium borohydride to obtain the compound of formula (6);

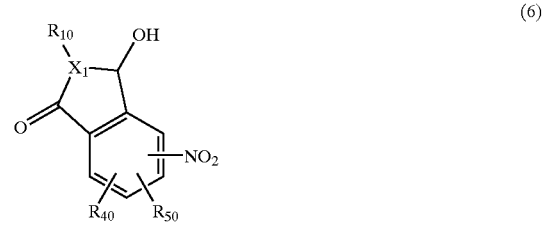

(6)

[in the formula, $X_1$, $R_{10}$, $R_{40}$ and $R_{50}$ have the meanings given above], followed by hydrogenation using palladium catalyst.

The Mitsunobu reaction of the compound of formula (5) can be carried out by a method similar to method for preparing the compound of formula (XX) from the compound of formula (XII). The compound of formula (6) can be prepared by applying the well-known reduction reaction using sodium borohydride after Mitsunobu reaction.

The compound of formula (III-ii) can be prepared from the compound of formula (6) by applying hydrogenation reaction using for example, palladium catalyst such as palladium hydroxide. Said reaction is carried out usually in an inactive solvent. The solvent includes tetrahydrofuran and methanol. The reaction temperature is usually 20° C. to the boiling point of the solvent used, preferably, within the range from 20 to 50° C.

By controlling the reaction condition of the hydrogenation appropriately, the compound of formula (III-ii$_a$) (wherein, $R_{21}$ is hydrogen atom, $X_1$, $R_{10}$, $R_{31}$, $R_{40}$ and $R_{50}$ have the meanings given above) and the compound of formula (III-ii$_b$) (wherein, $R_{21}$ is hydroxyl group, $X_1$, $R_{10}$, $R_{31}$, $R_{40}$ and $R_{50}$ have the meanings given above) can be prepared.

The compound of formula (III-iii);

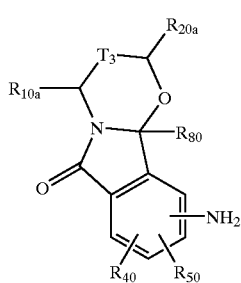

(III-iii)

[in the formula, $T_3$ is single bond, or alkyl group or aralkyl group which may have protected substituent(s) having 1 to 3 carbon atoms, $R_{10a}$ and $R_{20a}$ are, the same or different, and independently optionally substituted saturated or unsaturated hydrocarbon group, $R_{80}$ is a hydrogen atom or a saturated or an unsaturated hydrocarbon group, which may form a ring structure by binding to either $R_{20a}$ or $T_3$, and which may have optionally protected substituent(s), $R_{40}$ and $R_{50}$ have the meanings given above], which is a starting material of the preparation method A, can be prepared as follows.

Synthetic Method C

The compound of formula (III-iii) can be prepared by undertaking the Mitsunobu's reaction of the compound of formula (5) with the compound of formula (7);

$$R_{10a}\text{—CH(OH)—}T_3\text{—CO—}R_{20a} \quad (7)$$

[in the formula, $T_3$, $R_{10a}$, and $R_{20a}$ have the meanings given above] followed by reduction using sodium borohydride and then ring closure under an acidic condition to produce the compound of formula (8);

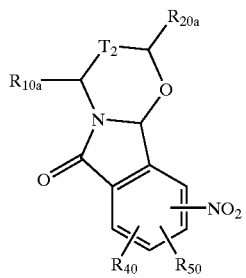

(8)

[in the formula, $T_3$, $R_{10a}$, $R_{20a}$, $R_{40}$ and $R_{50}$ have the meanings given above], which is subjected to hydrogenation to obtain the compound of formula (III-iii');

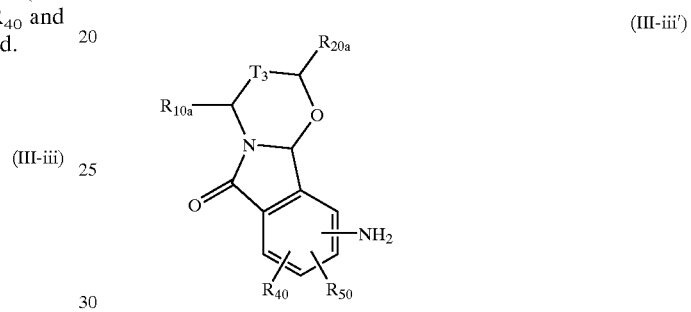

(III-iii')

[in the formula, $T_3$, $R_{10a}$, $R_{20a}$, $R_{40}$ and $R_{50}$ have the meanings given above] followed by introducing a substituent using $R_{80}$—$L_{iii}$ (wherein, $L_{iii}$ is halogen atom).

The Mitsunobu reaction of the compound of formula (5) can be carried out by a method similar to the method for preparing the compound of formula (XX) from the compound of formula (XII). After the Mitsunobu reaction, the reduction reaction is carried out by the well-known reduction method using sodium borohydride. Next, the reaction is carried out in an inactive solvent such as tetrahydrofuran by adding the organic acid such as trifluoroacetic acid, acetic acid and formic acid to afford the compound of formula (8).

The reaction temperature is usually 20° C. to the boiling point of the solvent used, preferably, within the range from 70 to 130° C.

The hydrogenation reduction of the compound of formula (8) can be carried out by the method similar to the method for preparing the compound of formula (III-ii) from the compound of formula (6) to produce the compound of formula (III-iii').

The process wherein the compound of formula (III-iii) can be transformed from the compound of formula (III-iii') is carried out by the protection the amino group using the well-known protective group for amino group such as tert-butoxycarbonyl group followed by the reaction with $R_{80}$—$L_{iii}$ in the presence of an appropriate base such as lithium hexamethylsilazide and the removal of the protective group for amino group.

The protection for amino group can be carried out under ordinary condition.

In the reaction with $R_{80}$—$L_{iii}$, to 1 mole of that the compound of formula (III-iii'), $R_{80}$—$L_{iii}$ is usually used in 1 mole or more, preferably 3 mole; the base such as lithium hexamethylsilazide is usually used in 1 or more moles, preferably 3 mole. The reaction temperature is preferably −78 to 20° C. The protective group of amino group can be removed according to the ordinary method.

The compound of formula (8) can be prepared by reducing the compound of formula (9);

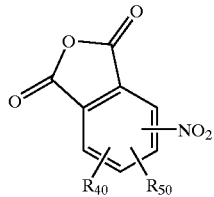

[in the formula, $R_{40}$ and $R_{50}$ have the meanings given above] to produce the compound of formula (10);

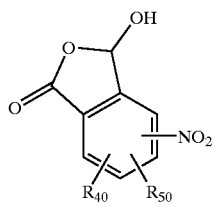

[in the formula, $R_{40}$ and $R_{50}$ have the meanings given above], which is reacted with the compound of formula (11); $R_{10a}$—CH(NH$_2$)—T$_3$—CH(OH)—R$_{20a}$ (11) [in the formula. T$_3$, $R_{20a}$ and $R_{20a}$ have the meanings given above].

In the reduction of the compound of formula (9), to 1 mole of the compound of formula (9), sodium borohydride is used in 0.5 mole preferably in an inactive solvent such as tetrahydrofuran. The reaction temperature is below 0° C., preferably −78° C.

In the reaction between the compound of formula (10) and the compound of formula (11), to 1 mole of the compound of formula (11), the compound of formula (11) is used in 1 mole or more, preferably 1 mole; and molecular sieves 4A can be added in 3 times the weight of the compound of formula (10).

The reaction is usually carried out in inactive solvent. The inactive solvent is preferably tetrahydrofuran and dimethylformamide, and so on.

The reaction temperature is usually 20° C. to the boiling point of the solvent used, preferably, within the range from 100 to 120° C.

The compound of formula (III-iv);

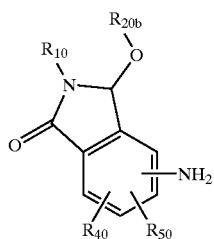

[$R_{20b}$ represents optionally substituted lower alkyl group or aralkyl group, $R_{10}$, $R_{40}$ and $R_{50}$ have the meanings given above], which is a starting material of the synthetic method A, can be prepared by using the compound of formula (6) as a starting material as follows.

Synthetic Method D

The compound of formula (III-iv) can be prepared by reacting the compound of formula (6) with $R_{20b}$—OH (wherein, $R_{20b}$ has the meaning given above) followed by hydrogenation.

The reaction between the compound of formula (6) and $R_{20b}$—OH can be carried out by dissolving the compound of formula (6) into $R_{20b}$—OH, the reaction can be carried out, for example, in case where the compound of formula (6) is used in 1 mole, the catalytic amount of p-toluenesulfonic acid, preferably 0.1 mole is added.

The reaction temperature is usually 20° C. to the boiling point of the $R_{20b}$—OH used (wherein, $R_{20b}$ has the meaning given above), preferably, within the range from 90 to 100° C.

Next, the compound of formula (III-iv) can be prepared by applying hydrogenation under the condition similar to that of the reaction for preparing the compound of formula (III-ii) from the compound of formula (6).

The compound of formula (II) synthesized by the synthetic method A using the compound of formula (III-iv) as a starting material can also be prepared by reacting the compound of formula (III-iv');

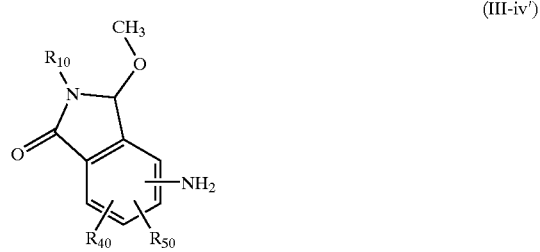

[in the formula, $R_{10}$, $R_{40}$ and $R_{50}$ have the meanings given above] with the compound of formula (II) synthesized from the compound of formula (IV) under condition similar to that of the reaction between the compound of formula (6) and the $R_{20b}$-OH.

The compound of formula (III-v);

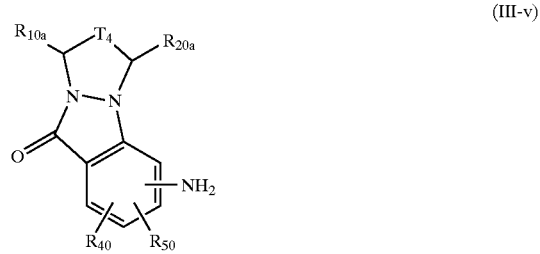

[in the formula. T$_4$ represents optionally substituted C$_{1-2}$ alkylene group. $R_{10a}$, $R_{20a}$, $R_{40}$ and $R_{50}$ have the meanings given above], which is the starting material of the synthetic method A, can be prepared by transforming the compound of formula (1) to hydrazide followed by the ring closure to obtain the compound of formula (12);

(12)

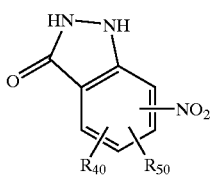

[in the formula, $R_{40}$ and $R_{50}$ have the meanings given above], which is reacted with the compound of formula (13);

$$R_{10a}—CH(L_a)—T_4—CH(La)—R_{20a} \tag{13}$$

[in the formula, La represents halogen atom, $T_4$, $R_{10a}$ and $R_{20a}$ have the meanings given above] followed by hydrogenation.

Synthetic Method E

The hydrazide compound of formula (1) can be prepared by the reaction similar to the reaction between the compound of formula (1) and the compound of formula (2), thus, the hydrazide compound of formula (1) can be synthesized by activating the compound of formula (1) under the similar condition followed by reaction with hydrazine.

To 1 mole of the compound of formula (1), hydrazine is used in 1 or more mole, preferably 1 to 3 mole.

The reaction is usually carried out in an inactive solvent. Said solvent includes preferably tetrahydrofuran, dimethylformamide, and so on.

The reaction temperature is usually 20° C. to the boiling point of the inactive solvent used, preferably, within the range from 20 to 50° C.

The hydrazide obtained above is heated in an inactive solvent such as dimethylformamide to prepare the compound of formula (12).

In the reaction between the compound of formula (12) and the compound of formula (13), to the compound of formula (12) of 1 mole the compound of formula (13) is 1 mole or slightly more, preferably 1 mole. Said reaction can be carried out in an inactive solvent such as dimethylformamide usually without the addition of base. However, the reaction can be carried in the presence of tertiary amine such as triethylamine.

The reaction temperature is usually from room temperature to the boiling point of the inactive solvent used, preferably, within the range from 100 to 120° C.

After the completion of the above reaction followed by applying hydrogenation under condition similar to that of the reaction for preparing the compound of formula (III-ii) from the compound of formula (6), the compound of formula (III-iv) can be obtained.

The compound of formula (III-vi);

(III-vi)

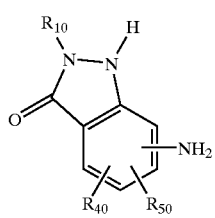

[in the formula, $R_{10}$, $R_{40}$ and $R_{50}$ have the meanings given above], which is the starting material of the synthetic method A, can be prepared by using the compound of formula (12) as a starting material as follows.

Synthetic method F

The compound of formula (III-vi) can be prepared by reacting the compound of formula (12) with the compound of formula (14);

$$R_{10}—L_a \tag{14}$$

[in the formula, La has the meaning given above] followed by hydrogenation.

The reaction for preparing the compound of formula (III-vi) from the compound of formula (12) and the compound of formula (14) can be carried out under condition similar to that of the reaction for preparing the compound of formula (III-v) from the compound of formula (12).

The compound of formula (III-vii);

(III-vii)

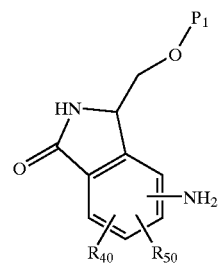

[in the formula, $P_1$ represents a protective group of hydroxyl group, $R_{40}$ and $R_{50}$ have the meanings given above], which is the starting material of the synthetic method A, can be prepared by applying the following method using the compound of formula (1) as a starting material.

Synthetic Method G

The compound of formula (III-vii) can be prepared by synthesizing amide compound from the compound of formula (1) and diethyl amino malonate followed by cyclization and then decarboxylation under a basic condition to obtain ester compound, the ester group of which is subjected to reduction to prepare hydroxyl compound, which is protected by the appropriate protective group and then subjected to hydrogenation.

The reaction between the compound of formula (1) and diethyl aminomalonate can be carried under condition similar to that of the step for preparing the compound of formula (XIX) from the compound of formula (XVII).

The cyclization reaction is carried out by using an appropriate base, for example, sodium hydride. To 1 mole of the amide compound, sodium hydride is usually used in 1 mole or more, preferably 1 to 3 mole.

The reaction is usually carried out in an inactive solvent such as tetrahydrofuran, dimethylformamide and dimethylsulfoxide. The reaction temperature is usually 0° C. to the boiling point of the inactive solvent used, preferably, within the range from 20 to 100° C.

The decarboxylation reaction is carried out in the presence of an appropriate base such as sodium hydroxide. To 1 mole of the cyclized compound, the base such as sodium hydroxide is usually used in 1 mole or more, preferably 3 to 5 mole. The reaction is usually carried out in an inactive solvent. Said solvent includes preferably alcohols such as ethanol. The reaction temperature is usually 20° C. to the boiling point of the inactive solvent used, preferably, within the range from 50 to 100° C.

The reduction of ester can be carried out according to ordinary reduction method by using, for example, sodium borohydride. To 1 mole of the ester compound, sodium borohydrade is usually used in 1 mole or more, preferably 3 to 10 mole. The reaction is usually carried out in inactive solvent. Said solvent includes preferably alcohols such as methanol and ethanol. The reaction temperature is usually 0° C. to 20° C., preferably 0° C.

As to the protective group for newly formed hydroxyl group, the groups described in the synthetic method A can be used. The preferable examples include tert-butyldimethylsilyl group, tert-butyldiphenylsilyl group and so on. As to the reaction condition, the generally well-known condition can be applied.

After the completion of the above reaction followed by applying hydrogenation under the condition similar to that of the reaction for preparing the compound of formula (III-ii) from the compound of formula (6), the compound of ° C. formula (III-vii) can be obtained.

The compound of formula (III-viii);

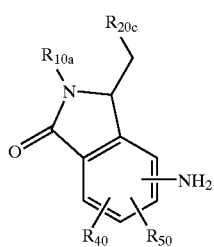

(III-viii)

[in the formula, $R_{10a}$ represents optionally protected saturated or unsaturated hydrocarbon group, $R_{20c}$ represents hydrogen atom or optionally substituted saturated or unsaturated hydrocarbon group, $R_{40}$ and $R_{50}$ have the meanings given above], which is the starting material of the synthetic method A, can be prepared by using the compound of formula (1) as a starting material as follows.

Synthetic Method H

The compound of formula (III-viii) can be prepared by esterification of the compound of formula (1) followed by coupling reaction with the compound of formula (15);

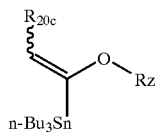

(15)

[in the formula, $R_z$ represents methyl group or ethyl group, $R_{20c}$ has the meaning given above] to afford the compound of formula (16);

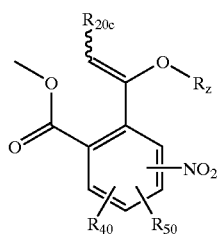

(16)

[in the formula, $R_2$, $R_{20c}$, $R_{40}$ and $R_{50}$ have the meanings given above], which is converted to the amide compound by using $R_{10a}$—$NH_2$ (wherein, $R_{10a}$ has the meaning given above) followed by cyclization under an acidic condition, and then reducing alkoxy group and nitro group respectively.

The methyl-esterification of the compound of formula (1) is carried out in methanol by adding a small amount of concentrated sulfuric acid under heating according to the generally well-known condition in terms of chemical synthesis.

In the reaction between the above methyl ester and the compound of formula (15), to 1 mole of the methyl ester, the compound of formula (15) is usually used in 1 mole or more, preferably 1 to 3 moles and palladium catalyst such as tetrakistriphosphine palladium is used in preferably 3 to 5 mole %.

The reaction is usually carried out in an inactive solvent such as tetrahedrofuran. The reaction temperature is usually 50° C. to the boiling point of the solvent used, preferably 70 to 100° C.

The amidation between the compound of formula (16) and $R_{10a}$—$NH_2$ can be carried out by applying the condition similar to that of the process for preparing the compound of formula (XIX) from the compound of formula (XVII).

The cyclization reaction of the amide compound obtained above can be usually carried out under an acidic condition for example, in mixed solvent such as concentrated sulfuric acid and an inactive solvent like ethanol. The reaction temperature is usually 20° C. to the boiling point of the inactive solvent, preferably 20 to 50

The reduction of alkoxy group can be carried out for example, by using triethylsilane with the addition of an appropriate acid.

To 1 mole of the cyclized compound, triethylsilane is usually used in 1 or more moles, preferably 3 to 5 mole and the acid added such as the complex of boron trifluoride with ether is used in 1 mole or more, preferably 3 to 5 moles. The reaction is usually carried out in an inactive solvent such as chloroform and dichloromethane. The reaction temperature is usually 0 to 50° C. preferably 20° C.

The reduction of nitro group can be carried out by applying hydrogenation in condition similar to that of the process for preparing the compound of formula (III-ii) from the compound of formula (6) to synthesize the compound of formula (III-viii).

According to the synthetic method A, the compound of formula (III-viii');

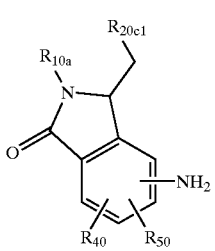

(III-viii')

[in the formula, $R_{20\ 1}$ is hydrogen atom, $R_{10a}$, $R_{40}$ and $R_{50}$ have the meanings given above], which is used as a starting material for preparing the compound of formula (II-viii');

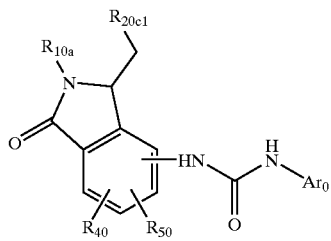

(II-viii')

[in the formula, $Ar_0$, $R_{10a}$, $R_{20c1}$, $R_{40}$ and $R_{50}$ have the meanings given above], which can also be prepared by applying the following method.

The reaction of the compound of formula (III-vii) with the compound of formula (14) followed by using the compound of formula (IV) according to the synthetic method A, affords the compound of formula (II-viii');

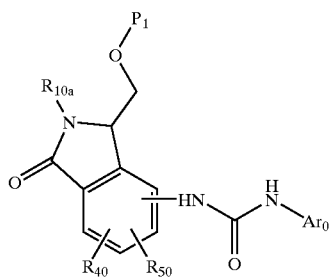

(II-viii'')

[in the formula, Aro, $R_{10a}$, $P_1$, $R_{40}$ and $R_{50}$ have the meanings given above]. Next, the protective group of hydroxyl group is removed to afford the hydroxyl compound, which is converted to methanesulfonate ester and then treated under a basic condition, finally followed by hydrogenation to obtain the compound of formula (II-viii').

The deprotection of the protective group of hydroxyl group in the compound of formula (II-viii') can be carried out according to the genelally well-known method. For example, in case where the protective group is, for example, tert-butyldimethylsilyl, the deprotection can be carried out by using concentrated hydrochloric acid in methanol.

In the methanesulfonation, to 1 mole of the alcohol obtained above, triethylamine is usually used in 1 mole or more, preferably 1 to 3 mole and methanesulfonic chloride is usually 1 mole or more, preferably 1 to 3 mole. The base used in the next step, for example, 1,8-diazabicyclo[5,4,0]undeca-7-ene (DBU) is usually 1 mole or more, preferably 1 to 3 moles. The reaction is usually carried out in an inactive solvent such as dimethylformamide. The reaction temperature is usually 0 to 50° C., preferably 0 to 20° C.

The compound of formula (III-viii') can be prepared by hydrogenation of the compound obtained in the above reaction under the condition similar to the reaction for preparing the compound of formula (III-ii) from the compound of formula (6).

The compound of formula (III-ix'):

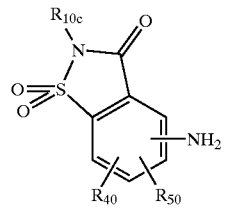

(III-ix')

[in the formula, $R_{10c}$ represents optionally substituted saturated or unsaturated hydrocarbon group, $R_{40}$ and $R_{50}$ have the meanings given above] and the compound of formula (III-ix'');

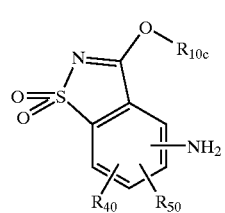

(III-ix'')

[in the formula, $R_{10}$, $R_{40}$ and $R_{50}$ have the meanings given above], which are the starting material(s) in the synthetic method A, can be synthesized according to the following method, using the known compound(s) per se represented by the formula (17);

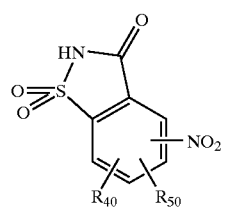

(17)

or the compound(s) prepared from said compound(s) by per se known methods as starting material(s).

Synthetic Method I

The compound of formula (III-ix') and the compound of formula (III-ix'') can be prepared by the Mitsunobu reaction between the compound of formula (17) and $R_{10c}$—OH [in the formula, $R_{10c}$ has the meaning given above] followed by hydrogenation.

The Mitsunobu's reaction of the compound of formula (17) can be carried out by applying the method similar to that for preparing the compound of formula (XX) from the compound of formula (XII).

The hydrogenation of the compound obtained in the above reaction, is carried out by applying the condition similar to that of the method for preparing the compound of formula (III-ii) from the compound of formula (6) to obtain the compound of formula (III-ix') and the compound of formula (III-ix'').

The compound of formula (III-x);

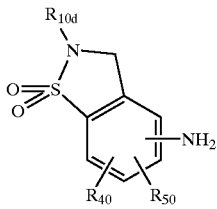

(III-x)

[in the formula, $R_{10d}$ represents optionally substituted saturated or unsaturated hydrocarbon group, $R_{40}$ and $R_{50}$ have the meanings given above], which is the starting material in the synthetic method A, can be prepared by using the compound of formula (18);

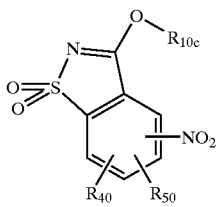

(18)

[in the formula, $R_{10c}$, $R_{40}$ and $R_{50}$ have the meanings given above], which is the intermediate in the synthetic method I, according to the following method.
Synthetic Method J The compound of formula (18) is subjected to the reduction to afford the compound of formula (19);

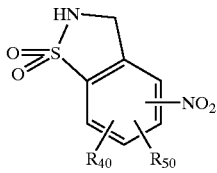

(19)

[in the formula, $R_{40}$ and $R_{50}$ have the meanings given above], which is subjected to the Mitsunobu reaction with $R_{10d}$—OH [in the formula, $R_{10d}$ has the meaning given above] followed by hydrogenation to obtain the compound of formula (III-x).

In the reduction of the compound of formula (18), to 1 mole of the compound of formula (18), sodium borohydride is usually used in 1 mole or more, preferably 3 to 5 mole. The reaction is usually carried out in an inactive solvent such as tetrahydrofuran. The reaction temperature is usually 0 to 50° C., preferably 20° C.

The Mitsunobu reaction of the compound of formula (19) can be carried out by applying a similar method for preparing the compound of formula (XX) from the compound of formula (XII).

The compound of formula (III-x) can be obtained by applying hydrogenation according to a similar method for preparing the compound of formula (III-ii) from the compound of formula (6).

The compound of formula (1), the compound of formula (5) and the compound of formula (15) can be known compounds or can be prepared by using the known compound according to the conventional method.

Next, the synthetic method of the compound of formula (IV), which is another starting material in the synthetic method A, is illustrated. Specifically, the compound of formula (IV) can be prepared according to the following synthetic methods from K to M.

Synthetic Method K

Treating the ester compound of formula (20);

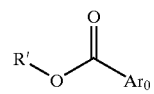

(20)

[in the formula, R' represents lower alkyl group, $Ar_0$ has the meaning given above] with hydrazine followed by reaction with nitrous acid, the compound of formula (IV);

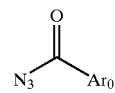

IV

[in the formula, $Ar_0$ has the meaning given above] can be prepared.

In transforming reaction wherein the compound of formula (20) is treated with hydrazine followed by reaction with nitrous acid to obtain the compound of formula (IV), hydrazine is usually used in 1 to 10 mole, preferably 3 to 5 mole to the ester of the compound of formula (20) of 1 mole. In the next reaction with nitrous acid, to 1 mole of the ester of the compound of formula (20), sodium nitrite is usually used in 1 to 5 mole, preferably 3 to 5 mole. In the reaction, to 1 mole of the sodium nitrite acid, 1N hydrochloric acid is usually used in 1 L to 5 L, preferably 1 L to 3 L.

The reaction is usually carried out in an inactive solvent.

Said solvent includes for example, alcohol such as methanol and ethanol in the reaction with hydrazine, and water, ethers such as tetrehydrofuran and dioxane, halogenated hydrocarbons such as dichloromethane and chloroform or the mixed solvent thereof in the reaction with nitrous acid.

The reaction temperature in the reaction with hydrazine is usually 0° C. to the boiling point of the solvent used, preferably 20 to 50° C. and the reaction time is usually 1 to 48 hours, preferably 5 to 24 hours. The reaction temperature in the reaction with nitrous acid is usually 0 to 50° C., preferably 0 to 20° C. and the reaction time is usually 30 minutes to 5 hours, preferably 30 minutes to 2 hours.

The compound of formula (20) is the known compound or can be prepared according to the conventional method for preparing ester.

Synthetic Method L

The compound of formula (IV-i);

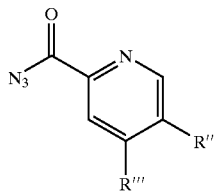

(IV-i)

[in the formula, R" and R'" independently represent optionally substituted saturated or unsaturated 5 or 6 membered rings, which may contain nitrogen atom taken together with carbon atom to which they bind, respectively.] can be prepared from the known compound, that is ethyl 1,2,4-triazin-5-carboxylate as a starting material, after synthesizing the compound of formula (21);

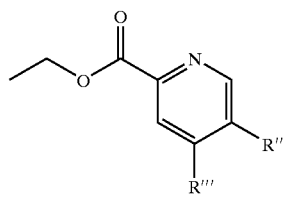

(21)

[in the formula, R" and R'" have the meanings given above] according to the synthetic method K.

The compound of formula (21) can be obtained by reacting ethyl 1,2,4-triazin-5-carboxylate with the compound of formula (22);

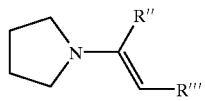

(22)

[in the formula, R" and R'" have the meanings given above].

To 1 mole of ethyl 1,2,4-triazin-5-carboxylate, the compound of formula (22) is usually used in 1 or more moles, preferably 1 to 5 mole. The reaction is usually carried out in an inactive solvent. Said solvent includes for example, chloroform. The reaction temperature is usually 20° C. to the boiling point of the inactive solvent used, preferably 20 to 70° C.

The compound of formula (IV-i) can be prepared from the compound of formula (21) by applying the method similar to the method for preparing the compound of formula (IV) from the compound of formula (20) in the synthetic method K.

Synthetic Method M
The compound of formula (IV-ii);

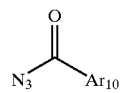

IV-ii

[in the formula, $Ar_{10}$ represents $Ar_0$ which comprises a substituent of $-Sn(n-Bu)_3$] can be prepared by using the compound of formula (23);

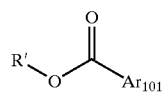

(23)

[in the formula, $Ar_{10i}$ represents $Ar_0$ given above, which comprises a substituent of $-X_{10}$ (wherein, $X_{10}$ is halogen atom). R' has the meaning given above] as a starting material.

The compound of formula (24);

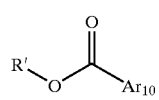

(24)

[in the formula, $Ar_{10i}$ and R' have the meanings given above]can be synthesized by reacting the compound of formula (23) with hexa-n-butylditin using palladium complex such as tetrakistriphenylphosphine palladium as a catalyst according to the synthetic method K.

In the reaction between the compound of formula (23) and hexa-n-butylditin, to 1 mole of the compound of formula (23), hexa-n-butylditin is usually used in 1 or more moles, preferably 1.5 to 3 moles and tetrakistriphenylphosphine palladium is usually used in 0.05 to 0.2, preferably 0.1 mole. The reaction is usually carried out in an inactive solvent. Said solvent includes for example, dioxane. The reaction temperature is usually 50° C. to the boiling point of the inactive solvent used, preferably 70 to 130° C.

The compound of formula (IV-ii) can be prepared from the compound of formula (24) by applying the method similar to the method for preparing the compound of formula (IV) from the compound of formula (20) in the synthetic method K.

Next, the preparation method of the compound of formula (V);

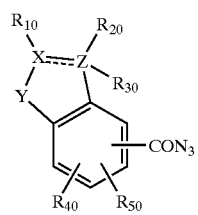

(V)

[in the formula, X, Y, Z. $R_{10}$, $R_{20}$, $R_{30}$, $R_{40}$, $R_{50}$ and—have the meanings given above], which is the starting material in the preparation method B, is illustrated. Specifically, the compound of formula (V) can be prepared according to the following synthetic method N.

Synthetic Method N

The compound of formula (V) can be prepared by converting the compound of formula (25);

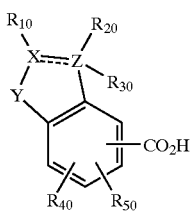

(25)

[in the formula, X, Y, Z, $R_{10}$, $R_{20}$, $R_{30}$, $R_{40}$, $R_{50}$ and—have the meanings given above] to the corresponding chloride followed by reaction with sodium azide.

The reaction for transforming to the chloride of carboxylic acid compound of formula (25) can be carried out by applying the method similar to that for preparing acid halide from the compound of formula (XVIII) under a similar reaction condition. To 1 mole of acid chloride obtained above, sodium azide is usually used in 1 to 5 mole, preferably 1 to 3 mole. The reaction can be carried out in water or, if necessary, a mixed solvent of water and tetrahydrofuran to obtain the compound of (V).

The reaction temperature is usually 0 to 50° C., preferably 0 to 20° C. and the reaction time is usually 30 minutes to 12 hours, preferably 1 to 5 hours.

The compound of formula (VI), which is another starting material in the preparation method B is a known compound or can be prepared by applying the conventional method for synthesizing amino compound.

The $IC_{50}$ values for Cdk4 and Cdk6 activities and cell growth inhibition were determined to show the utility of the compounds in the invention concretely.

Cdk4 Inhibory Activity (1) Preparation of cyclin D1-Cdk4 and cyclin D2-Cdk4 cDNA of Cdk4 and its activator cyclin D1 or D2 was subcloned into a baculovirus-expression vector to make recombinant baculovirus and then, they are co-infected to insect cell Sf9 to express an active complex of cyclin D1-Cdk4 or cyclin D2-Cdk4. The cells were recovered and solubilized and purified by HPLC columnchromatography (The the enzyme are EMBO J. vol.15, p.7060–7069, 1996).

(2) Enzyme assay of cyclin D1-Cdk4 and cyclin D2-Cdk4

Synthetic peptide, which correspond to the amino acids on the positions of No. 775 to 787 of RB protein (Arg-Pro-Pro-Thr-Leu-Ser-Pro-Ile-Pro-His-Ile-Pro-Arg) (SEQ ID No. 1) was used as a substrate. (The EMBO J. vol. 15, p. 7060–7069, 1996)

The reaction was carried out using the modified procedure of Kitagawa's method (Oncogene, vol.7, p.1067–1074, 1992). The volume of the reaction solution was 21.1 μL. The reaction buffer (R buffer) consisted of 20 mM Tri-HCl buffer (pH7.4)/10 mM $MgCl_2$/4.5 mM 2-mercaptoethanol/1 mM ethyleneglycolbis(β-aminoethylether)-N,N,N',N'-tetracetic acid (EGTA). Purified cyclin D1-Cdk4 or D2-Cdk4, 100 μM peptide substrate, 50 μM unlabeled ATP and ATP labeled with 1 μCi γ-33P(2000–4000 Ci/mmole) were added to the reaction mixture. The mixture was incubated at 30° C. for 45 min. 10 μL of phosphate buffer (350 mM) was added to stop the reaction. The peptide substrate was absorbed to P81 paper and its radioactivity was measured by a liquid scintillation counter. ATP labeled with γ-33P was purchased from Daiich Chemicals, Ltd.

1.1 μL of the solution of test compound in DMSO was added to the reaction mixture, while the addition of DMSO (1.1 μL) was used as the control.

As the typical compounds of the present invention, compounds in working examples No.131, 165, 329 and 579 were selected to be tested. The $IC_{50}$ values for cyclin D1-Cdk4 and cyclin D2-Cdk4 were determined and the results were shown in the following table.

TABLE 1

| Compounds | $IC_{50}$(μM) | |
|---|---|---|
| | cyclin D1-Cdk4 | cyclin D1-Cdk4 |
| Working Example No. 131 | 0.061 | 0.019 |
| Working Example No. 329 | — | 0.033 |
| Working Example No. 165 | — | 0.016 |
| Working Example No. 579 | — | 0.011 |
| (±)flavopiridol | 0.36 | 0.056 |

It is clear that compounds of the invention have stronger inhibitory activity against cyclin D1-Cdk4 or cyclin D2-Cdk4 than that of the known Cdk4 inhibitor (±)flavopiridol.

Cdk6 Inhibiting Activity (1) Preparation of cyclin D1-Cdk6 and cyclin D3-Cdk6

As the same method of preparing cyclin D1-Cdk4, cDNA of Cdk6 and its activator cyclin D1 or D3 was recombined with baculovirus-expression vector to make recombinant baculovirus. This was co-infected to insect cell Sf9 to express an active complex of cyclin D1-Cdk6 or cyclin D3-Cdk6. The cells were recovered and solubilized and purified by HPLC columnchromatography.

(2) Enzyme assay of cyclin D1-Cdk6 and cyclin D3-Cdk6.

A peptide substrate used for cyclin D1-Cdk6 was synthetic peptide (Lys-Ala-Pro-Leu-Ser-Pro-Lys-Lys-Ala-Lys) (SEQ ID No. 2) and that used for cyclin D3-Cdk6 was synthetic peptide (Arg-Pro-Pro-Thr-Leu-Ser-Pro-Ile-Pro-His-Ile-Pro-Arg) (SEQ ID No. 3) (The EMBO J. vol. 15, p. 7060–7069, 1996).

The reaction was carried out using the modified procedure of Kitagawa's method (Oncogene, vol.7, p.1067–1074, 1992). The volume of the reaction solution was 21.1 μL. Purified cyclin D1-Cdk6 in R buffer and 400 μM peptide substrate or cyclin D3-Cdk6 and 100 μM pipetide substrate, unlabeled ATP (50 μM) and 1 μCi ATP labeled with γ-33P (2000–4000 Ci/mmole) were added to the reaction mixture. The mixture was incubated at 30° C. for 20 or 45 min. Then, 10 μL of phosphate buffer (350 mM) was added to stop the reaction. The peptide substrate was absorbed to P81 paper and its radioactivity was measured by a liquid scintillation counter.

1.1 μL of the solution of test compound in DMSO was added to the reaction mixture, while the addition of DMSO (1.1 μL) was used as the control.

As the typical compounds of the present invention, compounds in working examples No. 131, 165, 329 and 579 were selected to be tested. The $IC_{50}$ values for cyclin D1-Cdk6 and cyclin D3-Cdk6 were determined and the results were shown in the following table.

TABLE 2

| Compounds | IC$_{50}$($\mu$M) | |
| --- | --- | --- |
| | cyclin D1-Cdk6 | cyclin D3-Cdk6 |
| Working Example No. 131 | 0.013 | — |
| Working Example No. 329 | 0.065 | — |
| Working Example No. 165 | — | 0.013 |
| Working Example No. 579 | — | 0.022 |

This results show that the compounds in this invention have a strong inhibitory activities against cyclin D1-Cdk6 and cyclin D3-Cdk6.

Activity of Inhibiting Cell Growth (1) Method of cell culture

Clinical separative cancer cells HCT116 were cultured in Dulbecco' modified Eagle's medium with 10% Fetal Bovine Serum, and clinical separative cancer cells MKN-1 were cultured in RPMI1640 medium added 10% Fetal Bovine Serum. Both cells were cultured at 37° C., under 5% $CO_2$ and saturated steam.

(2) Determination of activity of inhibiting cell growth

The activity of inhibiting cell growth was measured using the modified method of Skehan's method (J. Natl. Cancer Inst. Vol.82, p.1107–1112, 1990), and so on. One hundred $\mu$L each of the culture medium containing $1 \times 10^3$ HCT116 or MKN-1 as living cells was pipetted to 96-well dish and cultured over night. On the next day, DMSO solution of compounds No.131 and (±)flavopiridol were diluted with DMSO serially. Then, the diluted compounds or DMSO as the control, was added to the medium. One hundred $\mu$L of the medium added with the diluted drug solutions or DMSO was added to the cells cultured in 96-well dish, and was incubated for further 3 days.

To each well, 50 $\mu$L of trichloroacetic acid (50%) was added to fix the cells. The cells were stained using 0.4% sulforhodamine B. Sulforhodamine B was extracted with 10 mM tris buffer, and the optical density at 560 nm was compared with that of control at 450 nm. The results of IC$_{50}$ values of the compound in working example No.131 and (±)flavopiridol were shown in the following table.

TABLE 3

| Compounds | IC$_{50}$($\mu$M) HCT116 Cell | IC$_{50}$($\mu$M) MKN-1 Cell |
| --- | --- | --- |
| Compound in Working Example No. 131 | 0.013 | 0.10 |
| (±)flavopiridol | 0.15 | 0.87 |

This results show that the compounds in the invention have a stronger activity of inhibiting cell growth in compared with that of the known compound, (±)flavopiridol which has an activity of inhibiting Cdk. Therefore, they may be used as antitumor agent.

The compounds in the invention may be used in cancer treatment for example the treatment of human colon cancer.

When used as antitumor agent, the compounds may be used in the form of pharmaceutically acceptable salts like salts with metals such as sodium, potassium, and so on.

The salts, which can be pharmaceutically acceptable, can be synthesized by combining the methods generally used in organic chemistry, for example, the neutralization titration of the free form of the compounds in the present invention using alkaline solution.

When used as an antitumor agent, the compounds in the invention may be administrated in any formulation, for example, oral formulations such as tablets, capsules, powders, granules or sterilized parenteral formulations such as solutions, suspensions, and so on.

In cases of solid formulation, compounds in the invention may be prepared directly as the forms of tablets, capsules, powders, or prepared with proper additives. As the additives, there can be mentioned the additives generally used in preparing the above-mentioned formulations, for example, sugars, like dextrose, lactose, and so on, starches, like maize, wheat, rice, and so on, aliphatic acids like, steric acid, and so on, inorganic salts, like sodium metasilicate, magnasium aluminate, anhydrous calcium phosphate, and so on, synthetic polymer, like polyvinylpyrrolidone, polyalkyleneglycol, and so on, salts of aliphatic acid, like calcium stearate, meganisium stearate, and so on, alcohols, like stearylalcohol, benzyl alcohol, and so on, synthetic cellulose derivatives, like methylcellulose, carboxylmethylcellulose, ethylcellulose, hydroxy propyl methylcellulose, and so on, others, like water, zeratine, tark, plant oil, gum Arabic, and so on.

In the solid pharmaceutical composition of the invention, such as tablets, capsules, granules, powders, and so on, the amount of active ingredient is usually 0.1 to 100% by weight, or preferably 5 to 100% by weight of total weight of the composition. In cases of the liquid pharmaceutical composition of the invention, water, alcohols or plant oil, like soybean oil, peanuts oil, sesame oil, and the like may be used as proper additives to prepare suspensions, syrups, injections, and so on.

When administrated orally as intramuscular injection, intravenous injection or subcutaneous injection, the examples of proper solvents may be the following substances or their mixture; distilled water for injection, lidocaine hydrochloride aq.solution (for intramuscular injection), physiological saline, dextrose, ethanol, liquids for intravenous injection (like solution of citric acid, sodium citrate, and so on), electrolyte solutions (for intravenous drip infusion, intravenous injections), and so on.

When used as injections, the above-mentioned substances or their mixture may be used by dissolving prior to use, or used by dissolving the powder or with proper additives before use. The content of active ingredient in these injections is usually in the range of 0.1 to 10% by weight, or preferably 1 to 5%. When used as solutions such as suspensions or syrups, the content of active ingredient can be 0.5 to 10% by weight.

As a practical matter, the preferable dosage of the present invention can be determined according to the kind of the compounds, the kinds of contents used in formulation, frequency of the use, specific position to be treated and the situation of the patients. For example, oral dosage for an adult may be 10 to 500 mg/day and parenteral dosage like injection may be 10 to 100 mg/day. Single dose or multiple dose of 2 to 5 times a day may be applied, while times of administration may be different depending on administration routs and situation of the patients.

THE BEST MODE FOR CARRYING OUT THE INVENTION

Hereunder, the present invention is illustrated in more detail by the following Reference Examples and Examples. However, the scope of the present invention is not to be considered to be restricted to the present embodiment.

In the Thin Layer chromatography in the Examples and Reference Examples, the Silica gel$_{60}$F$_{254}$ plates manufactured by Merck & Co., were used as the TLC-plate, and as the detection method, the UV-detector was adopted. As silica gel for the column chromatography, Wako gel TM C-300 or C-200 manufactured by Wako Pure Chemicals, Ltd. was used. As HPLC, HP1100 series manufactured by Heulet Packard was used. MS spectrum was measured by JMS-SX102A (JEOL) or QUATTRO II (Micro Mass). NMR (Nuclear Magnetic Resonance) spectrum was measured by a Gemini-200(200 MHz, Varian). Gemini-300(300 MHz, Varian) and VXR-300(300 MHz, Varian), using TMS(tetra methyl silan) for deuterated chloroform solutions, and methanol for deuterated methanol as internal standard. All δ values were in ppm.

Abbreviations used in NMR have the following meanings;

s: singlet
d: doublet
dd: double-doublet
t: triplet
dt: double triplet
q: quartet
m: multiplet
br: broad
J: coupling constant
Hz: Hertz
CDCl$_3$: deuterated chloroform
D$_2$O: deuterium oxide
DMSO-d$_6$: deuterated dimethylsulfoxide
CD$_3$OD: deuterated methanol Abbreviations used in Reaction formulas or the like have the following meanings;

Ac: Acetyl group
Et: Ethyl group
n-Bu: n-Butyl group
Bn: Benzoic group
n-Pr: n-propyl group
i-Pr: iso-propyl group
Me: Methyl group
Ph: Phenyl group
Py: Pyridine group
TEA: Triethylamine Examples of the compounds in the present invention are concretely shown in the following tables.

TABLE 4

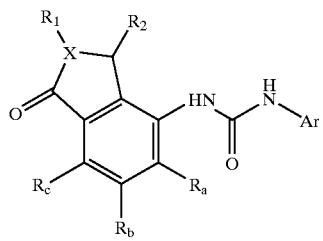

(Ia)

| Example | Ring structure formed by $R_1$, $R_2$ and X taken together | Ar | $R_a$ | $R_b$ | $R_c$ |
|---|---|---|---|---|---|
| 1 | phenyl | 2-pyridyl | H | H | H |
| 2 | phenyl | 3-Na-2-pyridyl | H | H | H |
| 3 | phenyl | 3-HO-2-pyridyl | H | H | H |
| 4 | phenyl | 3-BnO-2-pyridyl | H | H | H |
| 5 | phenyl | 3-HO$_2$C-2-pyridyl | H | H | H |
| 6 | phenyl | 4-Me-2-pyridyl | H | H | H |
| 7 | phenyl | 4-Cl-2-pyridyl | H | H | H |
| 8 | phenyl | 4-HNO$_2$-2-pyridyl | H | H | H |
| 9 | phenyl | 4-HN$_2$-2-pyridyl | H | H | H |

TABLE 5

(Ia)

Structure: Isoindolinone with R1, R2, X ring, C=O, Rc, Rb, Ra substituents on benzene ring, connected via HN-C(=O)-NH-Ar urea linkage.

| Example | Ring structure formed by R₁, R₂ and X taken together | Ar | Rₐ | R_b | R_c |
|---|---|---|---|---|---|
| 10 | benzene | pyridin-2-yl, 4-NHn-Bu | H | H | H |
| 11 | benzene | pyridin-2-yl, 4-CH₂OH | H | H | H |
| 12 | benzene | pyridin-2-yl, 5-Me | H | H | H |
| 13 | benzene | pyridin-2-yl, 5-Cl | H | H | H |
| 14 | benzene | pyridin-2-yl, 5-Br | H | H | H |
| 15 | benzene | pyridin-2-yl, 5-NO₂ | H | H | H |
| 16 | benzene | pyridin-2-yl, 5-CONH₂ | H | H | H |
| 17 | benzene | pyridin-2-yl, 5-CO₂H | H | H | H |
| 18 | benzene | pyridin-2-yl, 5-NHn-Bu | H | H | H |

TABLE 5-continued (Ia)

| Example | Ring structure formed by R₁, R₂ and X taken together | Ar | Rₐ | R_b | R_c |
|---|---|---|---|---|---|
| 19 | benzene | pyridin-2-yl, 5-Ph(4-NHCl) | H | H | H |
| 20 | benzene | 6-Me-pyridin-2-yl, Me | H | H | H |

TABLE 6

(Ia)

| Example | Ring structure formed by R₁, R₂ and X taken together | Ar | Rₐ | R_b | R_c |
|---|---|---|---|---|---|
| 21 | benzene | pyridin-2-yl, 6-NH₂ | H | H | H |
| 22 | benzene | pyridin-2-yl, 6-NHn-Bu | H | H | H |
| 23 | benzene | 6-Me-pyridin-2-yl, 3-Et | H | H | H |
| 24 | benzene | 4,6-diMe-pyridin-2-yl | H | H | H |

TABLE 6-continued

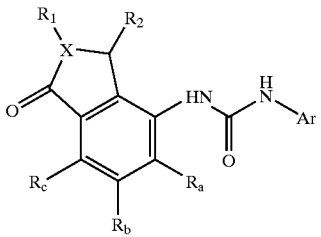

(Ia)

| Example | Ring structure formed by R₁, R₂ and X taken together | Ar | $R_a$ | $R_b$ | $R_c$ |
|---|---|---|---|---|---|
| 25 | benzene | 6-carbamoyl-3,5-dimethylpyridin-2-yl | H | H | H |
| 26 | benzene | pyrimidin-2-yl | H | H | H |
| 27 | benzene | 4-hydroxypyrimidin-2-yl | H | H | H |
| 28 | benzene | 4-methylpyrimidin-2-yl | H | H | H |
| 29 | benzene | 5-acetyl-4-methylpyrimidin-2-yl | H | H | H |
| 30 | benzene | 4,6-dimethylpyrimidin-2-yl | H | H | H |
| 31 | benzene | 4,6-dimethoxypyrimidin-2-yl | H | H | H |

TABLE 7

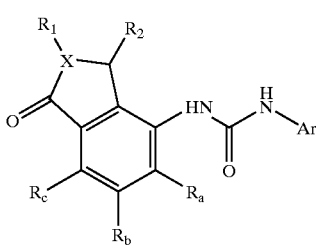

(Ia)

| Example | Ring structure formed by R₁, R₂ and X taken together | Ar | $R_a$ | $R_b$ | $R_c$ |
|---|---|---|---|---|---|
| 32 | benzene | 6-methyl-4-hydroxypyrimidin-2-yl | H | H | H |
| 33 | benzene | 5,6-dimethyl-4-hydroxypyrimidin-2-yl | H | H | H |
| 34 | benzene | pyrazin-2-yl | H | H | H |
| 35 | benzene | 3-phenyl-1H-pyrazol-5-yl | H | H | H |
| 36 | benzene | 3-hydroxy-1H-pyrazol-5-yl | H | H | H |
| 37 | benzene | 1-ethylpyrazol-5-yl | H | H | H |
| 38 | benzene | 1-phenylpyrazol-5-yl | H | H | H |
| 39 | benzene | 3-methyl-1-phenylpyrazol-5-yl | H | H | H |

TABLE 7-continued

(Ia)

| Example | Ring structure formed by R₁, R₂ and X taken together | Ar | $R_a$ | $R_b$ | $R_c$ |
|---|---|---|---|---|---|
| 40 | benzene | 2-thiazolyl | H | H | H |
| 41 | benzene | 4-Me-2-thiazolyl | H | H | H |
| 42 | benzene | 4-(COCO₂Et)-2-thiazolyl | H | H | H |

TABLE 8

(Ia)

| Example | Ring structure formed by R₁, R₂ and X taken together | Ar | $R_a$ | $R_b$ | $R_c$ |
|---|---|---|---|---|---|
| 43 | benzene | 4-(CH₂CO₂Et)-2-thiazolyl | H | H | H |
| 44 | benzene | 4-(CuNOH(CO₂Et))-2-thiazolyl | H | H | H |

TABLE 8-continued

(Ia)

| Example | Ring structure formed by R₁, R₂ and X taken together | Ar | $R_a$ | $R_b$ | $R_c$ |
|---|---|---|---|---|---|
| 45 | benzene | 4-Ph-2-thiazolyl | H | H | H |
| 46 | benzene | 4-Ph(4-Cl)-2-thiazolyl | H | H | H |
| 47 | benzene | 4-(SO₂Ph(4-NO₂))-2-thiazolyl | H | H | H |
| 48 | benzene | 5-Me-2-thiazolyl | H | H | H |
| 49 | benzene | 5-Br-2-thiazolyl | H | H | H |
| 50 | benzene | 5-NO₂-2-thiazolyl | H | H | H |
| 51 | benzene | 2-benzothiazolyl | H | H | H |
| 52 | benzene | 6-Me-2-benzothiazolyl | H | H | H |
| 53 | benzene | 6-F-2-benzothiazolyl | H | H | H |

TABLE 9

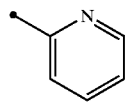
(Ia)

| Example | Ring structure formed by $R_1$, $R_2$ and X taken together or chemical structures of the substituents | Ar | $R_a$ | $R_b$ | $R_c$ |
|---|---|---|---|---|---|
| 54 | 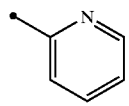 Br | 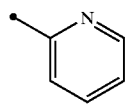 | H | Br | H |
| 55 | $R_1$ = H; $R_2$ = O; X = N | 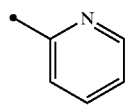 | H | H | H |
| 56 | $R_1$ = Me; $R_2$ = O; X = N | 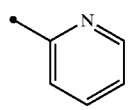 | H | H | H |
| 57 | $R_1$ = Et; $R_2$ = O; X = N | 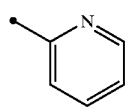 | H | H | H |
| 58 | $R_1$ = n-Pr; $R_2$ = O; X = N | 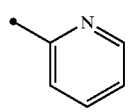 | H | H | H |
| 59 | $R_1$ = i-Pr; $R_2$ = O; X = N | 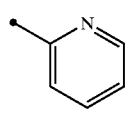 | H | H | H |
| 60 | $R_1$ = n-Bu; $R_2$ = O; X = N | 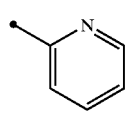 | H | H | H |
| 61 | $R_1$ = (CH$_2$)$_4$OH; $R_2$ = O; X = N | 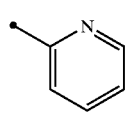 | H | H | H |
| 62 | $R_1$ = CH$_2$CH(CH$_2$OH)$_2$; $R_2$ = O; X = N | 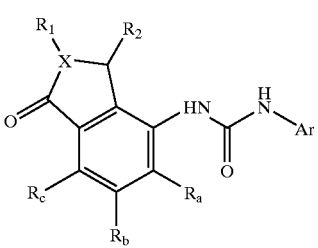 | H | H | H |
| 63 | $R_1$ = CH$_2$COOEt; $R_2$ = O; X = N | 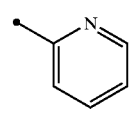 | H | H | H |

TABLE 9-continued

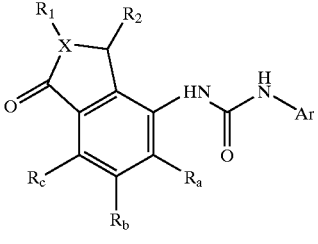
(Ia)

| Example | Ring structure formed by $R_1$, $R_2$ and X taken together or chemical structures of the substituents | Ar | $R_a$ | $R_b$ | $R_c$ |
|---|---|---|---|---|---|
| 64 | $R_1$ = Bn; $R_2$ = O; X = N | 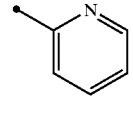 | H | H | H |

TABLE 10

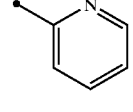
(Ia)

| Example | Chemical structures of the substituents | Ar | $R_a$ | $R_b$ | $R_c$ |
|---|---|---|---|---|---|
| 65 | $R_1$ = (CH$_2$)$_2$Ph; $R_2$ = O; X = N | 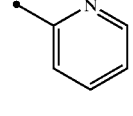 | H | H | H |
| 66 | $R_1$ = CH$_2$Ph(2-NH$_2$); $R_2$ = O; X = N | 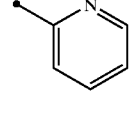 | H | H | H |
| 67 | $R_1$ = CH$_2$Ph(3-NH$_2$); $R_2$ = O; X = N | 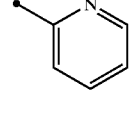 | H | H | H |
| 68 | $R_1$ = CH$_2$(2-Py); $R_2$ = O; X = N | 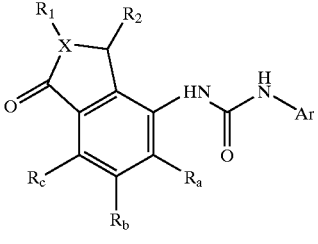 | H | H | H |
| 69 | $R_1$ = CH$_2$(3-Py); $R_2$ = O; X = N | 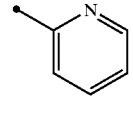 | H | H | H |

TABLE 10-continued (Ia)

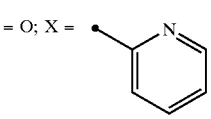

| Example | Chemical structures of the substituents | Ar | $R_a$ | $R_b$ | $R_c$ |
|---|---|---|---|---|---|
| 70 | $R_1$ = CH$_2$(4-Py); $R_2$ = O; X = N | 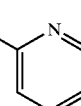 | H | H | H |
| 71 | $R_1$ = CH$_2$Ph(4-MeOCO); $R_2$ = O; X = N | 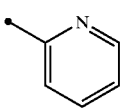 | H | H | H |
| 72 | $R_1$ = 2-cyclohexen-1-yl; $R_2$ = O; X = N | 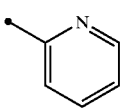 | H | H | H |
| 73 | $R_1$ = cyclohexylmethyl; $R_2$ = O; X = N | 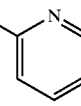 | H | H | H |
| 74 | $R_1$ = N-methylpiperidin-4-yl; $R_2$ = O; X = N | 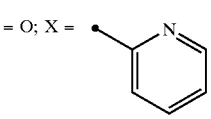 | H | H | H |

TABLE 10-continued (Ia)

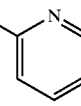

TABLE 11

(Ia)

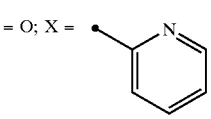

| Example | Ring structure formed by $R_1$, $R_2$ and X taken together | Ar | $R_a$ | $R_b$ | $R_c$ |
|---|---|---|---|---|---|
| 79 | 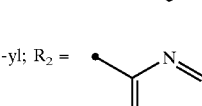 |  | H | H | H |
| 80 | 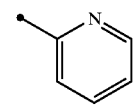 |  | H | H | H |

TABLE 11-continued

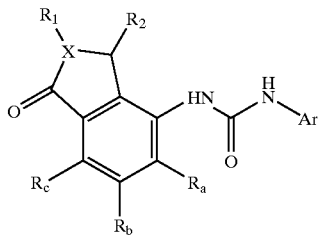
(Ia)

| Example | Ring structure formed by R₁, R₂ and X taken together | Ar | $R_a$ | $R_b$ | $R_c$ |
|---|---|---|---|---|---|
| 81 | pyrrolidine (N-linked) | pyridin-4-yl (2-CH₂CH₂OH) | H | H | H |
| 82 | pyrrolidine (N-linked) | pyridin-4-yl (2-CH₂NH₂) | H | H | H |
| 83 | pyrrolidine (N-linked) | pyridin-4-yl (2-CH₂CH₂NH₂) | H | H | H |
| 84 | pyrrolidine (N-linked) | pyridin-4-yl (2-CH₂NHn-Bu) | H | H | H |
| 85 | pyrrolidine (N-linked) | pyridin-4-yl (2-CH₂NH(CH₂)₃OH) | H | H | H |
| 86 | pyrrolidine (N-linked) | pyridin-4-yl (2-CH₂NHBn) | H | H | H |
| 87 | pyrrolidine (N-linked) | pyridin-4-yl (2-CH₂NHCH₂Ph(4-NH₂)) | H | H | H |

TABLE 11-continued

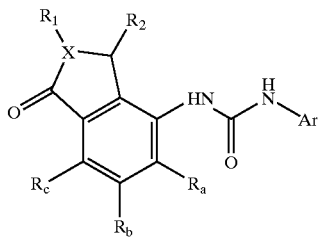
(Ia)

| Example | Ring structure formed by $R_1$, $R_2$ and X taken together | Ar | $R_a$ | $R_b$ | $R_c$ |
|---|---|---|---|---|---|
| 88 | pyrrolidine (N-linked) | 2-Py-4-CH$_2$NH(CH$_2$)$_2$Ph(4-NH$_2$) | H | H | H |
| 89 | pyrrolidine (N-linked) | 2-Py-4-CH$_2$NHCH$_2$Ph(4-SO$_2$NH$_2$) | H | H | H |

30

TABLE 12

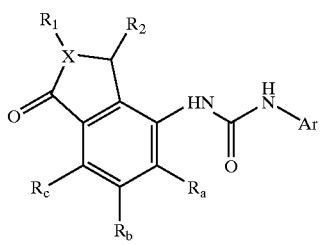
(Ia)

| Example | Ring structure formed by $R_1$, $R_2$ and X taken together | Ar | $R_a$ | $R_b$ | $R_c$ |
|---|---|---|---|---|---|
| 90 | pyrrolidine (N-linked) | 2-Py-4-CH$_2$NH(CH$_2$)$_2$Ph(4-SO$_2$NH$_2$) | H | H | H |
| 91 | pyrrolidine (N-linked) | 2-Py-4-CH$_2$NHCH$_2$-4-Py | H | H | H |

TABLE 12-continued (Ia)

| Example | Ring structure formed by R₁, R₂ and X taken together | Ar | $R_a$ | $R_b$ | $R_c$ |
|---|---|---|---|---|---|
| 92 | pyrrolidine (N-linked) | 2-pyridyl with CH₂NH(CH₂)₂-4-Py at 4-position | H | H | H |
| 93 | pyrrolidine (N-linked) | 2-pyridyl with CH₂NHCHply-(4-imidazolyl) at 4-position | H | H | H |
| 94 | pyrrolidine (N-linked) | 2-pyridyl with CH₂NH-(trans-4-hydroxycyclohexyl) at 4-position | H | H | H |
| 95 | pyrrolidine (N-linked) | 2-pyridyl with (CH₂)₂NH(CH₂)₂NH₂ at 4-position | H | H | H |
| 96 | pyrrolidine (N-linked) | 2-pyridyl with (CH₂)₂NH(CH₂)₂CH₃ at 4-position | H | H | H |
| 97 | pyrrolidine (N-linked) | 2-pyridyl with (CH₂)₂NH(CH₂)₃CH₂ at 4-position | H | H | H |

TABLE 12-continued (Ia)

| Example | Ring structure formed by R₁, R₂ and X taken together | Ar | R$_a$ | R$_b$ | R$_c$ |
|---|---|---|---|---|---|
| 98 | pyrrolidine | pyridine-4-yl, (CH₂)₂NH(CH₂)₇CH₃ | H | H | H |
| 99 | pyrrolidine | pyridine-4-yl, (CH₂)₂NHCH₂CHO | H | H | H |
| 100 | pyrrolidine | pyridine-4-yl, (CH₂)₂NHCH₂CO₂H | H | H | H |

TABLE 13

(Ia)

| Example | Ring structure formed by R₁, R₂ and X taken together | Ar | R$_a$ | R$_b$ | R$_c$ |
|---|---|---|---|---|---|
| 101 | pyrrolidine | pyridine-4-yl, (CH₂)₂NHCH₂CO₂Bn | H | H | H |

TABLE 13-continued (Ia)

| Example | Ring structure formed by R₁, R₂ and X taken together | Ar | $R_a$ | $R_b$ | $R_c$ |
|---|---|---|---|---|---|
| 102 | pyrrolidine | 2-pyridyl, 4-(CH₂)₂NHCH₂Ph(4-HNO) | H | H | H |
| 103 | pyrrolidine | 2-pyridyl, 4-(CH₂)₂NHCH₂-3-Py | H | H | H |
| 104 | pyrrolidine | 2-pyridyl, 4-(CH₂)₂NHCH₂-3-Py | H | H | H |
| 105 | pyrrolidine | 2-pyridyl, 4-(CH₂)₂NHCH₂-4-Py | H | H | H |
| 106 | pyrrolidine | 2-pyridyl, 4-(CH₂)₂NH(CH₂)₃Ph | H | H | H |
| 107 | pyrrolidine | 2-pyridyl, 4-(CH₂)₂NH(CH₂)₂Ph(4-OH) | H | H | H |
| 108 | pyrrolidine | 2-pyridyl, 4-(CH₂)₂NH(CH₃)₂-4-Py | H | H | H |

TABLE 13-continued (Ia)

| Example | Ring structure formed by R₁, R₂ and X taken together | Ar | $R_a$ | $R_b$ | $R_c$ |
|---|---|---|---|---|---|
| 109 | pyrrolidine | pyridine-(CH₂)₂HNa₂ | H | H | H |
| 110 | pyrrolidine | pyridine-(CH₂)₂NHCO(CH₃)₂CH₃ | H | H | H |
| 111 | pyrrolidine | pyridine-(CH₂)₂NHCOOH₂Ph | H | H | H |

TABLE 14

(Ia)

| Example | Ring structure formed by R₁, R₂ and X taken together | Ar | $R_a$ | $R_b$ | $R_c$ |
|---|---|---|---|---|---|
| 112 | pyrrolidine | pyridine-(CH₂)₂NHCOPh | H | H | H |

TABLE 14-continued (Ia)

| Example | Ring structure formed by $R_1$, $R_2$ and X taken together | Ar | $R_a$ | $R_b$ | $R_c$ |
|---|---|---|---|---|---|
| 113 | pyrrolidine | 2-pyridyl-4-(CH$_2$)$_2$NHSO$_2$Bn | H | H | H |
| 114 | pyrrolidine | 2-pyridyl-4-(CH$_2$)$_2$NHSO$_2$Ph | H | H | H |
| 115 | pyrrolidine | 2-pyridyl-4-(CH$_2$)$_2$NHSO$_2$Ph(4-NO$_2$) | H | H | H |
| 116 | pyrrolidine | 2-pyridyl-4-(CH$_2$)$_2$OPh | H | H | H |
| 117 | pyrrolidine | 3-phenyl-1H-pyrazol-5-yl | H | H | H |
| 118 | pyrrolidine | 3-(2-CO$_2$Me-phenyl)-1H-pyrazol-5-yl | H | H | H |

TABLE 14-continued
(Ia)
| Example | Ring structure formed by R₁, R₂ and X taken together | Ar | $R_a$ | $R_b$ | $R_c$ |
|---|---|---|---|---|---|
| 119 | 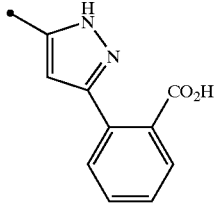 |  | H | H | H |
| 120 | 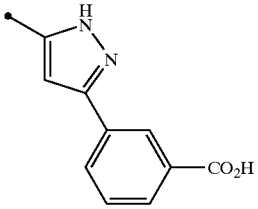 |  | H | H | H |
| 121 | 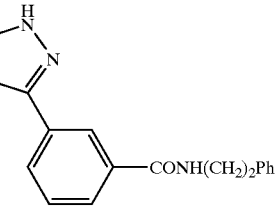 | 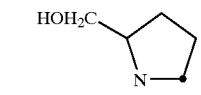 | H | H | H |
TABLE 15
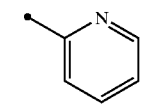
(Ia)
| Example | Ring structure formed by R₁, R₂ and X taken together | Ar | $R_a$ | $R_b$ | $R_c$ |
|---|---|---|---|---|---|
| 122 | HOH₂C—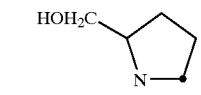 | 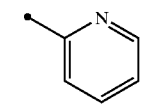 | H | H | H |
| 123 | H₃C(HO)HC—[pyrrolidine] | [pyridine] | H | H | H |

TABLE 15-continued

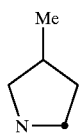 (Ia)

Ring structure formed by

| Example | R₁, R₂ and X taken together | Ar | $R_a$ | $R_b$ | $R_c$ |
|---|---|---|---|---|---|
| 124 | 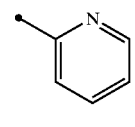 | 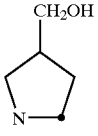 | H | H | H |
| 125 | 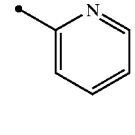 | 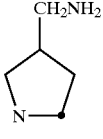 | H | H | H |
| 126 | 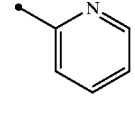 |  | H | H | H |
| 127 | 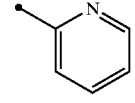 | 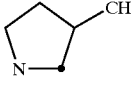 | H | H | H |
| 128 | 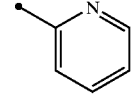 |  | H | H | H |
| 129 | 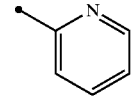 | 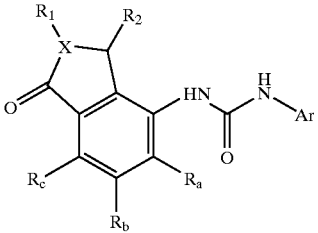 | H | H | H |
| 130 |  | 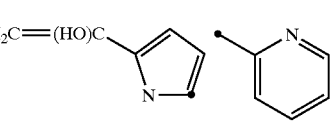 | H | H | H |
| 131 | 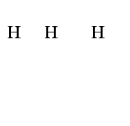 | 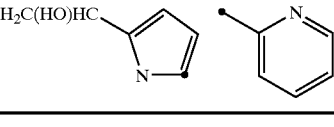 | H | H | H |
| 132 | 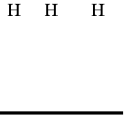 | 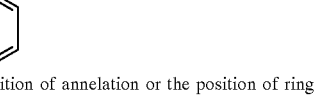 | H | H | H |

Notes:
1. The symbol "*" in

means the position of annelation or the position of ring condensation. Accordingly the product of Example 54 means

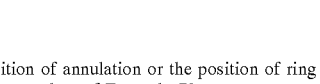

2. The symbol "*" in

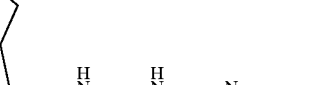

means the position of annelation or the position of ring condensation. Accordingly the product of Example 79 means

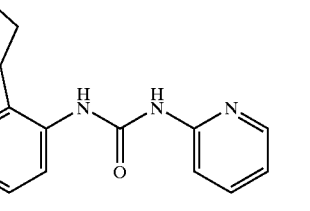

TABLE 16

| Example | Y | R₁ R₂ R₃ or ring structure formed by X, Z, R₁, R₂ and/or R₃ taken together | Ar | R'₁ | R'₂ |
|---|---|---|---|---|---|
| 133 | CO | pyrrolidine (N) | pyridine with R'₁, R'₂ substituents | -CH₂CH₂-S-CH₂CH₂CH₃ | H |
| 134 | CO | same as the above | same as the above | -CH₂CH₂-NH-CH(CH₃)₂ | H |
| 135 | CO | same as the above | same as the above | -CH₂CH₂-NH-cyclopentyl | H |
| 136 | CO | same as the above | same as the above | -CH₂CH₂-NH-cyclohexyl | H |
| 137 | CO | same as the above | same as the above | -CH₂CH₂-NH-CH₂-(2-(OC(S(CH₃)₂)(C₆H₅)₂)phenyl) | H |
| 138 | CO | same as the above | same as the above | -CH₂CH₂-NH-CH₂-(2-hydroxyphenyl) | H |
| 139 | CO | same as the above | same as the above | -CH₂CH₂-NH-CH₂-(2-butoxyphenyl) | H |

TABLE 16-continued

| Example | Y | R₁ R₂ R₃ or ring structure formed by X, Z, R₁, R₂ and/or R₃ taken together | Ar | R'₁ | R'₂ |
|---|---|---|---|---|---|
| 140 | CO | same as the above | same as the above | [2-methoxybenzyl-aminoethyl group] | H |
| 141 | CO | same as the above | same as the above | [bis(2-methoxybenzyl)aminoethyl group] | H |
| 142 | CO | same as the above | same as the above | [3-methyl-4,5-dihydroisoxazol-5-yl group] | H |
| 143 | CO | same as the above | same as the above | [3-methyl-4,5-dihydroisoxazol-5-yl group] | H |

TABLE 17

| Example | Y | R₁ R₂ R₃ or ring structure formed by X, Z, R₁, R₂ and/or R₃ taken together | Ar | R'₁ | R'₂ |
|---|---|---|---|---|---|
| 144 | CO | pyrrolidinyl | pyridyl with R'₁, R'₂ | [3-ethyl-4,5-dihydroisoxazol-5-yl group] | H |

TABLE 17-continued
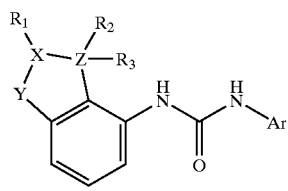
| Example | Y | R₁ R₂ R₃ or ring structure formed by X, Z, R₁, R₂ and/or R₃ taken together | Ar | R'₁ | R'₂ |
|---|---|---|---|---|---|
| 145 | CO | same as the above | same as the above | | H |
| 146 | CO | same as the above | same as the above | | H |
| 147 | CO | same as the above | same as the above | | H |
| 148 | CO | same as the above | same as the above | | H |
| 149 | CO | same as the above | same as the above | | H |
| 150 | CO | same as the above | same as the above | | H |

TABLE 17-continued
| Example | Y | R₁ R₂ R₃ or ring structure formed by X, Z, R₁, R₂ and/or R₃ taken together | Ar | R'₁ | R'₂ |
|---|---|---|---|---|---|
| 151 | CO | same as the above | same as the above | 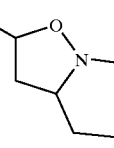 | H |
| 152 | CO | same as the above | same as the above | 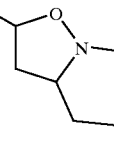 | H |
| 153 | CO | same as the above | same as the above | 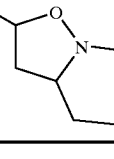 | H |
| 154 | CO | same as the above | same as the above |  | H |
TABLE 18
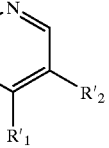
| Example | Y | R₁ R₂ R₃ or ring structure formed by X, Z, R₁, R₂ and/or R₃ taken together | Ar | R'₁ | R'₂ |
|---|---|---|---|---|---|
| 155 | CO | 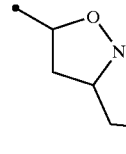 | H |  | H |

TABLE 18-continued

| Example | Y | R₁ R₂ R₃ or ring structure formed by X, Z, R₁, R₂ and/or R₃ taken together | Ar | R'₁ | R'₂ |
|---|---|---|---|---|---|
| 156 | CO | same as the above | same as the above | 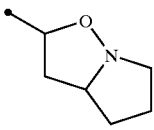 | H |
| 157 | CO | same as the above | same as the above | 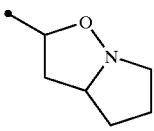 | H |
| 158 | CO | same as the above | same as the above | 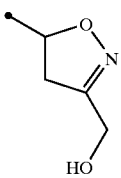 | H |
| 159 | CO | same as the above | same as the above | 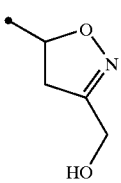 | H |
| 160 | CO | same as the above | same as the above | 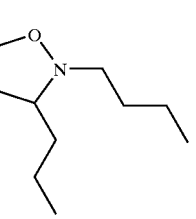 | H |
| 161 | CO | same as the above | same as the above | 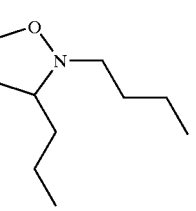 | H |
| 162 | CO | same as the above | same as the above | 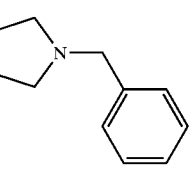 | H |

TABLE 18-continued

[Structure: R1, R2, R3 substituents on X-Z with Y, fused to benzene ring bearing NH-C(O)-NH-Ar group]

| Example | Y | R₁ R₂ R₃ or ring structure formed by X, Z, R₁, R₂ and/or R₃ taken together | Ar | R'₁ | R'₂ |
|---|---|---|---|---|---|
| 163 | CO | same as the above | same as the above | 3-(N-benzyl)pyrrolidinyl | H |
| 164 | CO | same as the above | same as the above | 3-(N-benzyl)pyrrolidinyl | H |
| 165 | CO | same as the above | same as the above | 3-(N-benzyl)pyrrolidinyl | H |

TABLE 19

[Structure: same general scaffold as above]

| Example | Y | R₁ R₂ R₃ or ring structure formed by X, Z, R₁, R₂ and/or R₃ taken together | Ar | R'₁ | R'₂ |
|---|---|---|---|---|---|
| 166 | CO | pyrrolidinyl (N-attached) | pyridyl with R'₁, R'₂ substituents | 3-(N-methyl)pyrrolidinyl | H |
| 167 | CO | same as the above | same as the above | 3-(N-methyl)pyrrolidinyl | H |

TABLE 19-continued

| Example | Y | R₁ R₂ R₃ or ring structure formed by X, Z, R₁, R₂ and/or R₃ taken together | Ar | R'₁ | R'₂ |
|---|---|---|---|---|---|
| 168 | CO | same as the above | same as the above | 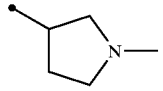 | H |
| 169 | CO | same as the above | same as the above | 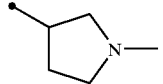 | H |
| 170 | CO | same as the above | same as the above | 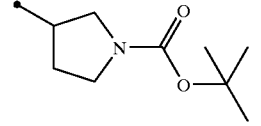 | H |
| 171 | CO | same as the above | same as the above | 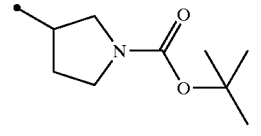 | H |
| 172 | CO | same as the above | same as the above | 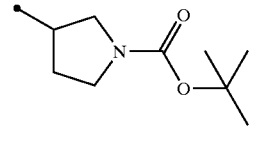 | H |
| 173 | CO | same as the above | same as the above | 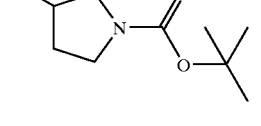 | H |
| 174 | CO | same as the above | same as the above | 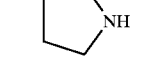 | H |
| 175 | CO | same as the above | same as the above | 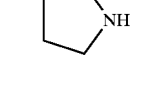 | H |
| 176 | CO | same as the above | same as the above | 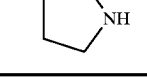 | H |

TABLE 20

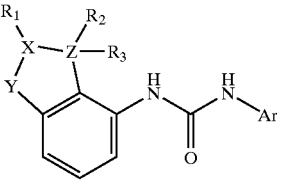

| Example | Y | R₁ R₂ R₃ or ring structure formed by X, Z, R₁, R₂ and/or R₃ taken together | Ar | R'₁ | R'₂ |
|---|---|---|---|---|---|
| 177 | CO |  | 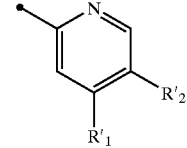 | 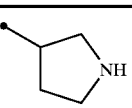 | H |
| 178 | CO | same as the above | same as the above | 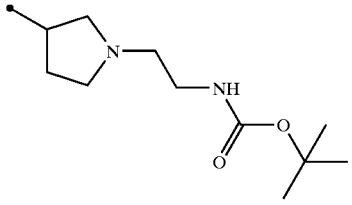 | H |
| 179 | CO | same as the above | same as the above | 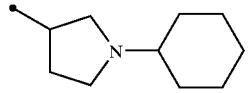 | H |
| 180 | CO | same as the above | same as the above | 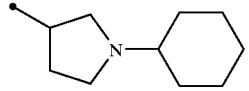 | H |
| 181 | CO | same as the above | same as the above | 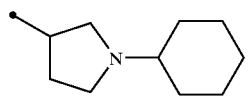 | H |
| 182 | CO | same as the above | same as the above | 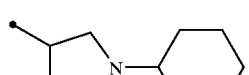 | H |
| 183 | CO | same as the above | same as the above | 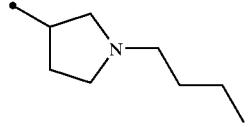 | H |
| 184 | CO | same as the above | same as the above | 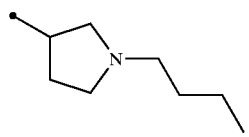 | H |
| 185 | CO | same as the above | same as the above | 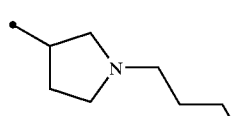 | H |

TABLE 20-continued
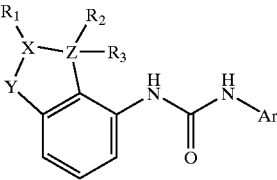
| Example | Y | R₁ R₂ R₃ or ring structure formed by X, Z, R₁, R₂ and/or R₃ taken together | Ar | R'₁ | R'₂ |
|---|---|---|---|---|---|
| 186 | CO | same as the above | same as the above | 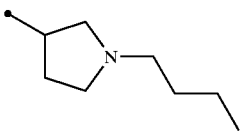 | H |
| 187 | CO | same as the above | same as the above | 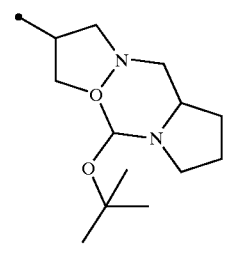 | H |
TABLE 21
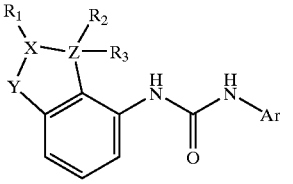
| Example | Y | R₁ R₂ R₃ or ring structure formed by X, Z, R₁, R₂ and/or R₃ taken together | Ar | R'₁ | R'₂ |
|---|---|---|---|---|---|
| 188 | CO | 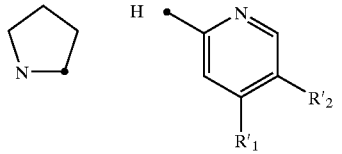 | H 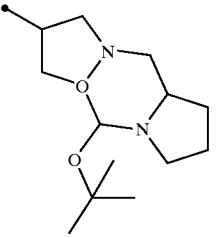 |  | H |

TABLE 21-continued
| Example | Y | R₁ R₂ R₃ or ring structure formed by X, Z, R₁, R₂ and/or R₃ taken together | Ar | R'₁ | R'₂ |
|---|---|---|---|---|---|
| 189 | CO | same as the above | same as the above | 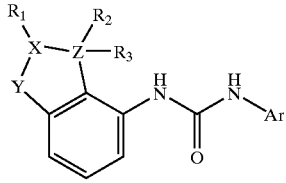 | H |
| 190 | CO | same as the above | same as the above | 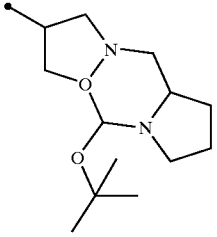 | H |
| 191 | CO | same as the above | same as the above | 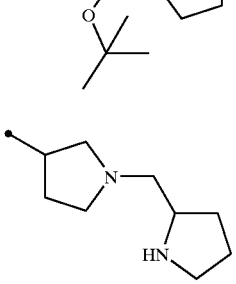 | H |
| 192 | CO | same as the above | same as the above | 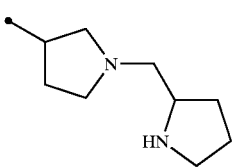 | H |
| 193 | CO | same as the above | same as the above | 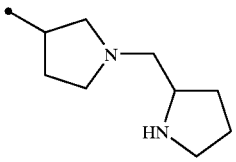 | H |
| 194 | CO | same as the above | same as the above | 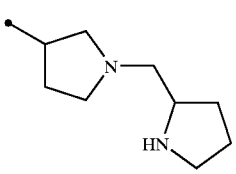 | H |

TABLE 21-continued

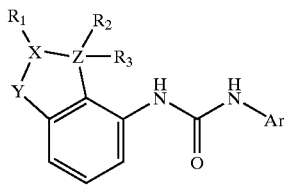

| Example | Y | R₁ R₂ R₃ or ring structure formed by X, Z, R₁, R₂ and/or R₃ taken together | Ar | R'₁ | R'₂ |
|---|---|---|---|---|---|
| 195 | CO | same as the above | same as the above | ![pyrrolidine-cyclooctane] | H |
| 196 | CO | same as the above | same as the above | ![pyrrolidine-cyclooctane] | H |
| 197 | CO | same as the above | same as the above | ![pyrrolidine-cyclooctane] | H |
| 198 | CO | same as the above | same as the above | ![pyrrolidine-cyclooctane] | H |

TABLE 22

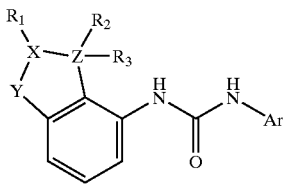

| Example | Y | R₁ R₂ R₃ or ring structure formed by X, Z, R₁, R₂ and/or R₃ taken together | Ar | R'₁ | R'₂ |
|---|---|---|---|---|---|
| 199 | CO | pyrrolidine | pyridine with R'₁, R'₂ | H | ![pyrrolidine-dibutyl] |

TABLE 22-continued

| Example | Y | R₁ R₂ R₃ or ring structure formed by X, Z, R₁, R₂ and/or R₃ taken together | Ar | R'₁ | R'₂ |
|---|---|---|---|---|---|
| 200 | CO | same as the above | same as the above | pyrrolidin-3-yl attached to nonan-5-yl | H |
| 201 | CO | same as the above | same as the above | pyrrolidin-3-yl attached to nonan-5-yl | H |
| 202 | CO | same as the above | same as the above | pyrrolidin-3-yl attached to nonan-5-yl | H |
| 203 | CO | same as the above | same as the above | 1-(indan-2-yl)pyrrolidin-3-yl | H |
| 204 | CO | same as the above | same as the above | 1-(indan-2-yl)pyrrolidin-3-yl | H |
| 205 | CO | same as the above | same as the above | 1-(indan-2-yl)pyrrolidin-3-yl | H |

TABLE 22-continued

| Example | Y | R₁ R₂ R₃ or ring structure formed by X, Z, R₁, R₂ and/or R₃ taken together | Ar | R'₁ | R'₂ |
|---|---|---|---|---|---|
| 206 | CO | same as the above | same as the above | [pyrrolidinyl-indane] | H |
| 207 | CO | same as the above | same as the above | [pyrrolidinyl-(1-benzylpiperidin-4-yl)] | H |
| 208 | CO | same as the above | same as the above | [pyrrolidinyl-(1-benzylpiperidin-4-yl)] | H |
| 209 | CO | same as the above | same as the above | [pyrrolidinyl-(1-benzylpiperidin-4-yl)] | H |

TABLE 23

| Example | Y | R₁ R₂ R₃ or ring structure formed by X, Z, R₁, R₂ and/or R₃ taken together | Ar | R'₁ | R'₂ |
|---|---|---|---|---|---|
| 210 | CO | [pyrrolidine] | H | [pyridine with R'₁, R'₂] | [pyrrolidinyl-(1-benzylpiperidin-4-yl)] | H |

TABLE 23-continued

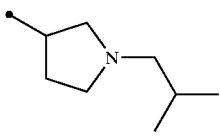

| Example | Y | R₁ R₂ R₃ or ring structure formed by X, Z, R₁, R₂ and/or R₃ taken together | Ar | R'₁ | R'₂ |
|---|---|---|---|---|---|
| 211 | CO | same as the above | same as the above | 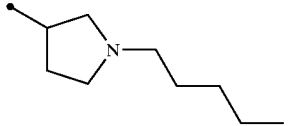 | H |
| 212 | CO | same as the above | same as the above | 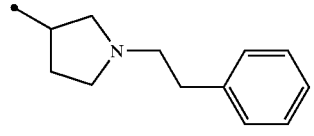 | H |
| 213 | CO | same as the above | same as the above | 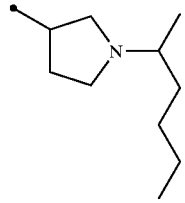 | H |
| 214 | CO | same as the above | same as the above | 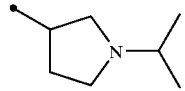 | H |
| 215 | CO | same as the above | same as the above | 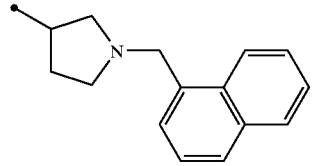 | H |
| 216 | CO | same as the above | same as the above | 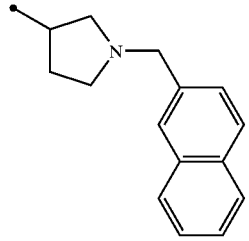 | H |
| 217 | CO | same as the above | same as the above |  | H |

TABLE 23-continued

[Structure: R₁-X, R₂-Z-R₃, Y, with phenyl-NH-C(O)-NH-Ar]

| Example | Y | R₁ R₂ R₃ or ring structure formed by X, Z, R₁, R₂ and/or R₃ taken together | Ar | R'₁ | R'₂ |
|---------|-----|------|------|------|-----|
| 218 | CO | same as the above | same as the above | pyrrolidin-3-yl with N-CH₂CH₂C(O)CH₃ | H |
| 219 | CO | same as the above | same as the above | pyrrolidin-3-yl with N-cyclopentyl | H |
| 220 | CO | same as the above | same as the above | pyrrolidin-3-yl with N-CH₂-cyclohexyl | H |

TABLE 24

[Structure: R₁-X, R₂-Z-R₃, Y, with phenyl-NH-C(O)-NH-Ar]

| Example | Y | R₁ R₂ R₃ or ring structure formed by X, Z, R₁, R₂ and/or R₃ taken together | Ar | R'₁ | R'₂ |
|---------|-----|------|------|------|-----|
| 221 | CO | pyrrolidine | pyridine with R'₁, R'₂ | pyrrolidin-3-yl with N-propyl | H |
| 222 | CO | same as the above | same as the above | pyrrolidin-3-yl with N-(tetrahydropyran-4-yl) | H |

TABLE 24-continued
| Example | Y | R₁ R₂ R₃ or ring structure formed by X, Z, R₁, R₂ and/or R₃ taken together | Ar | R'₁ | R'₂ |
|---|---|---|---|---|---|
| 223 | CO | same as the above | same as the above | 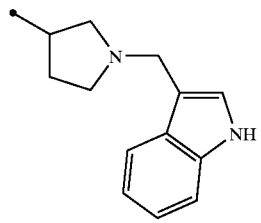 | H |
| 224 | CO | same as the above | same as the above | 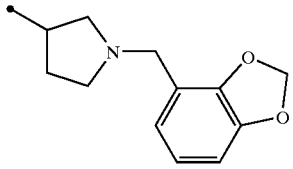 | H |
| 225 | CO | same as the above | same as the above | 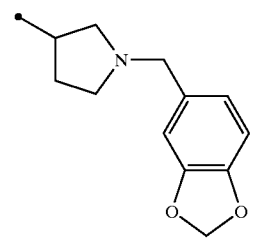 | H |
| 226 | CO | same as the above | same as the above | 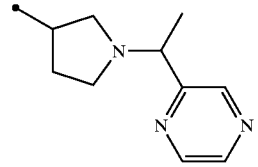 | H |
| 227 | CO | same as the above | same as the above | 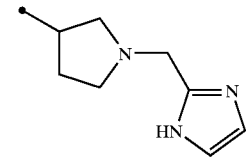 | H |
| 228 | CO | same as the above | same as the above | 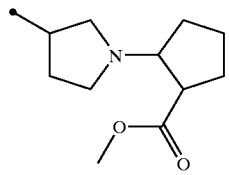 | H |

TABLE 24-continued
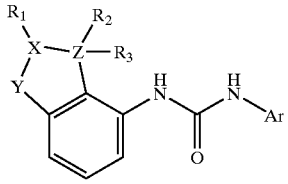
| Example | Y | R₁ R₂ R₃ or ring structure formed by X, Z, R₁, R₂ and/or R₃ taken together | Ar | R'₁ | R'₂ |
|---|---|---|---|---|---|
| 229 | CO | same as the above | same as the above | 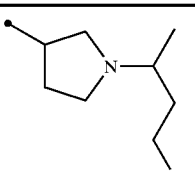 | H |
| 230 | CO | same as the above | same as the above | 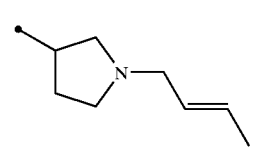 | H |
| 231 | CO | same as the above | same as the above | 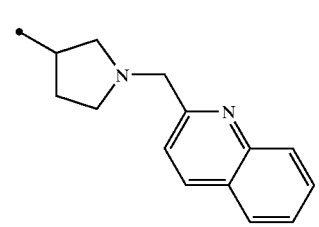 | H |
TABLE 25
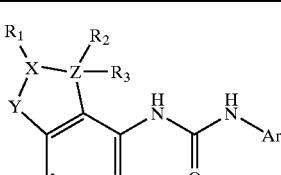
| Example | Y | R₁ R₂ R₃ or ring structure formed by X, Z, R₁, R₂ and/or R₃ taken together | Ar | R'₁ | R'₂ |
|---|---|---|---|---|---|
| 232 | CO | 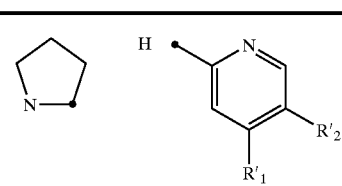 | 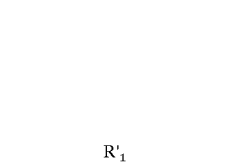 |  | H |

TABLE 25-continued

| Example | Y | R₁ R₂ R₃ or ring structure formed by X, Z, R₁, R₂ and/or R₃ taken together | Ar | R'₁ | R'₂ |
|---|---|---|---|---|---|
| 233 | CO | same as the above | same as the above | 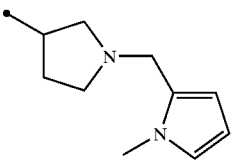 | H |
| 234 | CO | same as the above | same as the above | 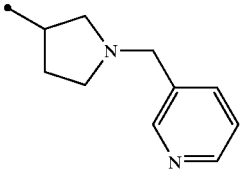 | H |
| 235 | CO | same as the above | same as the above | 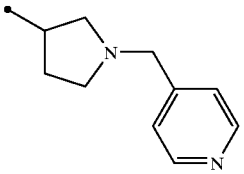 | H |
| 236 | CO | same as the above | same as the above | 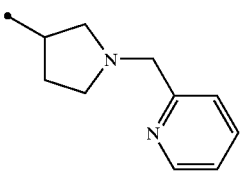 | H |
| 237 | CO | same as the above | same as the above | 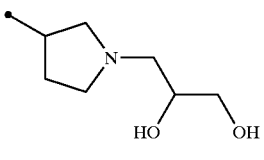 | H |
| 238 | CO | same as the above | same as the above | 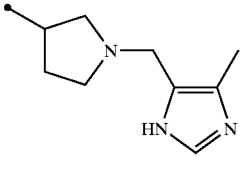 | H |
| 239 | CO | same as the above | same as the above | 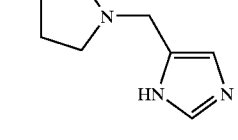 | H |

TABLE 25-continued

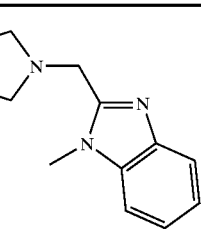

| Example | Y | R₁ R₂ R₃ or ring structure formed by X, Z, R₁, R₂ and/or R₃ taken together | Ar | R'₁ | R'₂ |
|---|---|---|---|---|---|
| 240 | CO | same as the above | same as the above | 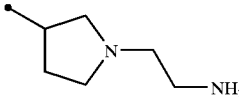 | H |
| 241 | CO | same as the above | same as the above | 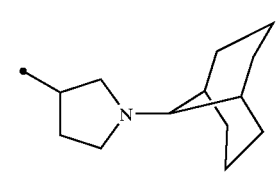 | H |
| 242 | CO | same as the above | same as the above |  | H |

TABLE 26

| Example | Y | R₁ R₂ R₃ or ring structure formed by X, Z, R₁, R₂ and/or R₃ taken together | Ar | R'₁ | R'₂ |
|---|---|---|---|---|---|
| 243 | CO | <image /> | <image /> | 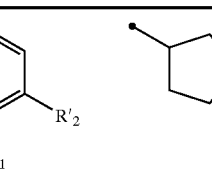 | H |
| 244 | CO | same as the above | same as the above | 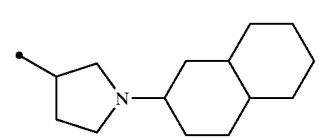 | H |

TABLE 26-continued

| Example | Y | R₁ R₂ R₃ or ring structure formed by X, Z, R₁, R₂ and/or R₃ taken together | Ar | R'₁ | R'₂ |
|---|---|---|---|---|---|
| 245 | CO | same as the above | same as the above | pyrrolidin-3-yl linked to N-azabicyclic group | H |
| 246 | CO | same as the above | same as the above | pyrrolidin-3-yl linked to N-norbornyl | H |
| 247 | CO | same as the above | same as the above | pyrrolidin-3-yl with N-CH₂-(4-hydroxyphenyl) | H |
| 248 | CO | same as the above | same as the above | pyrrolidin-3-yl with N-C(O)-CH₂-phenyl | H |
| 249 | CO | same as the above | same as the above | pyrrolidin-3-yl with N-C(O)-(2,6-dichlorophenyl) | H |
| 250 | CO | same as the above | same as the above | pyrrolidin-3-yl with N-C(O)-cyclohexyl | H |
| 251 | CO | same as the above | same as the above | pyrrolidin-3-yl with N-C(O)-(2-pyridyl) | H |

TABLE 26-continued
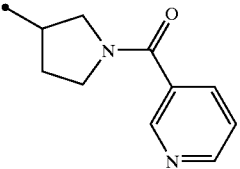
| Example | Y | R₁ R₂ R₃ or ring structure formed by X, Z, R₁, R₂ and/or R₃ taken together | Ar | R'₁ | R'₂ |
|---|---|---|---|---|---|
| 252 | CO | same as the above | same as the above | 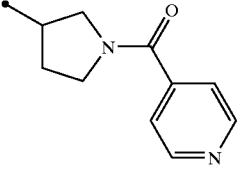 | H |
| 253 | CO | same as the above | same as the above |  | H |
TABLE 27
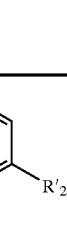
| Example | Y | R₁ R₂ R₃ or ring structure formed by X, Z, R₁, R₂ and/or R₃ taken together | Ar | R'₁ | R'₂ |
|---|---|---|---|---|---|
| 254 | CO |  | H | 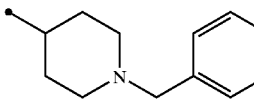 | H |
| 255 | CO | same as the above | same as the above | 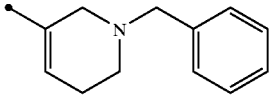 | H |
| 256 | CO | same as the above | same as the above |  | H |

TABLE 27-continued

| Example | Y | R₁ R₂ R₃ or ring structure formed by X, Z, R₁, R₂ and/or R₃ taken together | Ar | R'₁ | R'₂ |
|---|---|---|---|---|---|
| 257 | CO | same as the above | same as the above | 3-(1-benzylpiperidinyl) | H |
| 258 | CO | same as the above | same as the above | 1,2,3,6-tetrahydropyridin-3-yl | H |
| 259 | CO | same as the above | same as the above | 1-acetyl-1,2,3,6-tetrahydropyridin-3-yl | H |
| 260 | CO | same as the above | same as the above | 1,2,3,6-tetrahydropyridin-4-yl | H |
| 261 | CO | same as the above | same as the above | 1-acetyl-1,2,3,6-tetrahydropyridin-4-yl | H |
| 262 | CO | same as the above | same as the above | 1-cyclohexyl-1,2,3,6-tetrahydropyridin-4-yl | H |
| 263 | CO | same as the above | same as the above | 1-(indan-2-yl)-1,2,3,6-tetrahydropyridin-4-yl | H |
| 264 | CO | same as the above | same as the above | pyridin-3-yl | H |

TABLE 28

| Example | Y | R₁ R₂ R₃ or ring structure formed by X, Z, R₁, R₂ and/or R₃ taken together | Ar | R'₁ | R'₂ |
|---|---|---|---|---|---|
| 265 | CO | pyrrolidinyl | pyridin-2-yl (with R'₁, R'₂) | phenyl | H |
| 266 | CO | same as the above | same as the above | indenyl | H |
| 267 | CO | same as the above | same as the above | pyridin-2-yl | H |
| 268 | CO | same as the above | same as the above | pyridin-4-yl | H |
| 269 | CO | same as the above | same as the above | thiazol-2-yl | H |
| 270 | CO | same as the above | same as the above | thiophen-2-yl | H |
| 271 | CO | same as the above | same as the above | 1-benzylpyrazol-4-yl | H |
| 272 | CO | same as the above | same as the above | naphthalen-2-yl | H |
| 273 | CO | same as the above | same as the above | naphthalen-1-yl | H |

TABLE 28-continued

| Example | Y | R₁ R₂ R₃ or ring structure formed by X, Z, R₁, R₂ and/or R₃ taken together | Ar | R'₁ | R'₂ |
|---|---|---|---|---|---|
| 274 | CO | same as the above | same as the above | 3-thienyl | H |
| 275 | CO | same as the above | same as the above | cyclohex-1-enyl | H |

TABLE 29

| Example | Y | R₁ R₂ R₃ or ring structure formed by X, Z, R₁, R₂ and/or R₃ taken together | Ar | R'₁ | R'₂ |
|---|---|---|---|---|---|
| 276 | CO | pyrrolidinyl | pyridyl (with R'₁, R'₂) | 3,6-dihydro-2H-thiopyran-4-yl | H |
| 277 | CO | same as the above | same as the above | 4-tert-butylcyclohex-1-enyl | H |
| 278 | CO | same as the above | same as the above | -CH₂-NH-C(O)-CH₂CH₃ | H |
| 279 | CO | same as the above | same as the above | -CH₂-O-C(O)-CH₂CH₃ | H |

TABLE 29-continued

| Example | Y | R₁ R₂ R₃ or ring structure formed by X, Z, R₁, R₂ and/or R₃ taken together | Ar | R'₁ | R'₂ |
|---|---|---|---|---|---|
| 280 | CO | same as the above | same as the above | ![cyclohexyl ester] | H |
| 281 | CO | same as the above | same as the above | ![cyclohexyl amide via CH2NH] | H |
| 282 | CO | same as the above | same as the above | ![N-butyl amide] | H |
| 283 | CO | same as the above | same as the above | ![N-cyclohexyl amide] | H |
| 284 | CO | same as the above | same as the above | ![4-pyridylmethyl amide] | H |
| 285 | CO | same as the above | same as the above | ![3-pyridylmethyl amide] | H |
| 286 | CO | same as the above | same as the above | ![2-pyridylmethyl amide] | H |

TABLE 30

Structure: Core scaffold with R₁ on X, R₂ and R₃ on Z, Y attached to benzene ring, which bears an NH-C(=O)-NH-Ar urea group. Ar is a pyridine bearing R'₁ and R'₂ substituents.

| Example | Y | R₁, R₂, R₃ or ring structure formed by X, Z, R₁, R₂ and/or R₃ taken together | Ar | R'₁ | R'₂ |
|---|---|---|---|---|---|
| 287 | CO | pyrrolidine (N-linked) | 2-pyridyl with R'₁ at 4-position and R'₂ at 5-position | phenyl | — |
| 288 | CO | same as the above | same as the above | cyclohexyl | — |
| 289 | CO | same as the above | same as the above | pyrrolidin-2-yl (NH) | H |
| 290 | CO | same as the above | same as the above | N-methylpyrrolidin-2-yl | H |
| 291 | CO | same as the above | same as the above | N-acetylpyrrolidin-2-yl | H |
| 292 | CO | same as the above | same as the above | 3,4-dihydro-2H-pyrrol-5-yl | H |
| 293 | CO | same as the above | same as the above | (Z)-CH=CH-C(=O)-O-ethyl | H |
| 294 | CO | same as the above | same as the above | (E)-CH=CH-C(=O)-O-ethyl | H |
| 295 | CO | same as the above | same as the above | (E)-CH=CH-CH₂-OH | H |
| 296 | CO | same as the above | same as the above | -CH₂-CH₂-C(=O)-O-ethyl | H |

TABLE 30-continued

| Example | Y | R₁ R₂ R₃ or ring structure formed by X, Z, R₁, R₂ and/or R₃ taken together | Ar | R'₁ | R'₂ |
|---|---|---|---|---|---|
| 297 | CO | same as the above | same as the above | (allyl alcohol group) | H |

TABLE 31

| Example | Y | R₁ R₂ R₃ or ring structure formed by X, Z, R₁, R₂ and/or R₃ taken together | Ar | R'₁ | R'₂ |
|---|---|---|---|---|---|
| 298 | CO | pyrrolidine | pyridine with R'₁, R'₂ | acrylic acid group | H |
| 299 | CO | same as the above | same as the above | vinyl | H |
| 300 | CO | same as the above | same as the above | (N-benzyl pyrrolidine ethyl ester) | H |
| 301 | CO | same as the above | same as the above | (N-benzyl pyrrolidine ethyl ester) | H |
| 302 | CO | same as the above | same as the above | (hydroxymethyl pyrrolidine) | H |

TABLE 31-continued

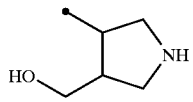

| Example | Y | R₁ R₂ R₃ or ring structure formed by X, Z, R₁, R₂ and/or R₃ taken together | Ar | R'₁ | R'₂ |
|---|---|---|---|---|---|
| 303 | CO | same as the above | same as the above | 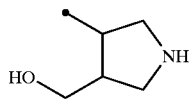 | H |
| 304 | CO | same as the above | same as the above | 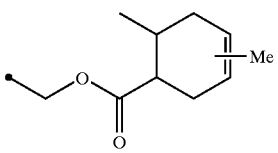 | H |
| 305 | CO | same as the above | same as the above | 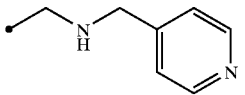 | H |
| 306 | CO | same as the above | same as the above | 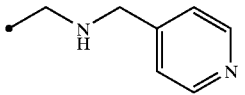 | H |
| 307 | CO | same as the above | same as the above | 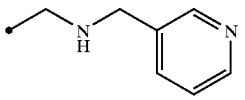 | H |
| 308 | CO | same as the above | same as the above |  | H |

TABLE 32

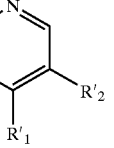

| Example | Y | R₁ R₂ R₃ or ring structure formed by X, Z, R₁, R₂ and/or R₃ taken together | Ar | R'₁ | R'₂ |
|---|---|---|---|---|---|
| 309 | CO | 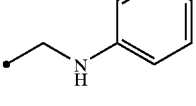 | H | | H |

TABLE 32-continued

| Example | Y | R₁ R₂ R₃ or ring structure formed by X, Z, R₁, R₂ and/or R₃ taken together | Ar | R'₁ | R'₂ |
|---|---|---|---|---|---|
| 310 | CO | same as the above | same as the above | (tetrahydroisoquinolin-5-ylamino-ethyl) | H |
| 311 | CO | same as the above | same as the above | (pyridin-2-ylmethylamino-ethyl) | H |
| 312 | CO | same as the above | same as the above | (pyridin-2-ylmethylamino-ethyl) | H |
| 313 | CO | same as the above | same as the above | (N-methyl-N-(pyridin-4-ylmethyl)amino-ethyl) | H |
| 314 | CO | same as the above | same as the above | cyclopentyl | |
| 315 | CO | same as the above | same as the above | 4-methylcyclohexyl (R₁, R₂) | |
| 316 | CO | same as the above | same as the above | 1-methylpiperidin-4-yl (R₁, R₂) | |
| 317 | CO | same as the above | same as the above | 1-benzylpiperidin-4-yl (R₁, R₂) | |
| 318 | CO | same as the above | same as the above | 1-benzylpiperidin-4-yl (R₁, R₂) | |

TABLE 32-continued

[Structure: benzene ring with X(R1)(Y)-Z(R2)(R3) fused substituent at positions, and NH-C(=O)-NH-Ar at adjacent position]

| Example | Y | R₁ R₂ R₃ or ring structure formed by X, Z, R₁, R₂ and/or R₃ taken together | Ar | R'₁ | R'₂ |
|---|---|---|---|---|---|
| 319 | CO | same as the above | same as the above | [N-Boc pyrrolidine] | |

TABLE 33

[Structure: benzene ring with X(R1)(Y)-Z(R2)(R3) fused substituent, and NH-C(=O)-NH-Ar]

| Example | Y | R₁ R₂ R₃ or ring structure formed by X, Z, R₁, R₂ and/or R₃ taken together | Ar | R'₁ | R'₂ |
|---|---|---|---|---|---|
| 320 | CO | [pyrrolidine with N] | H, [pyridine with R'₁, R'₂] | [pyrrolidine NH] | |
| 321 | CO | same as the above | same as the above | [N-cyclopentyl pyrrolidine] | |
| 322 | CO | same as the above | same as the above | [N-methyl pyrrolidine] | |
| 323 | CO | same as the above | same as the above | —CH₂CH₂CH₂NH₂ | H |
| 324 | CO | same as the above | same as the above | —CH₂CH₂CH₂NH₂ | H |
| 325 | CO | same as the above | same as the above | —CH₂CH₂CH₂OH | H |

TABLE 33-continued

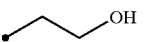

| Example | Y | R₁ R₂ R₃ or ring structure formed by X, Z, R₁, R₂ and/or R₃ taken together | Ar | R'₁ | R'₂ |
|---|---|---|---|---|---|
| 326 | CO | same as the above | same as the above | 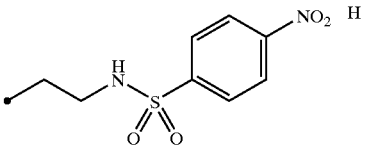 | H |
| 327 | CO | same as the above | same as the above | 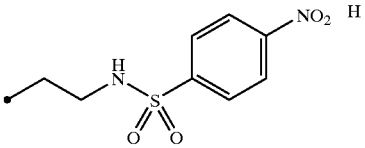 | H |
| 328 | CO | same as the above | same as the above | 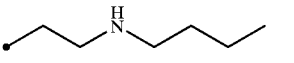 | H |
| 329 | CO | same as the above | same as the above | 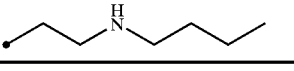 | H |
| 330 | CO | same as the above | same as the above |  | H |

TABLE 34

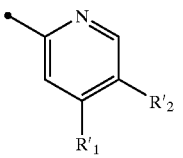

| Example | Y | R₁ R₂ R₃ or ring structure formed by X, Z, R₁, R₂ and/or R₃ taken together | Ar | R'₁ | R'₂ |
|---|---|---|---|---|---|
| 331 | CO | 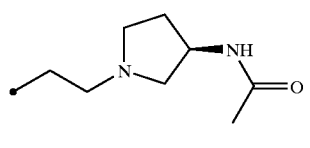 | H | | H |
| 332 | CO | same as the above | same as the above | | H |

TABLE 34-continued

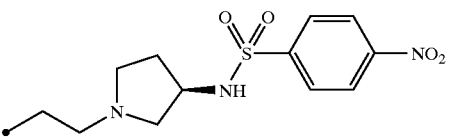

| Example | Y | R$_1$ R$_2$ R$_3$ or ring structure formed by X, Z, R$_1$, R$_2$ and/or R$_3$ taken together | Ar | R'$_1$ | R'$_2$ |
|---|---|---|---|---|---|
| 333 | CO | same as the above | same as the above | 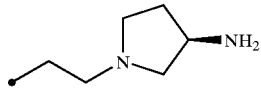 | H |
| 334 | CO | same as the above | same as the above | 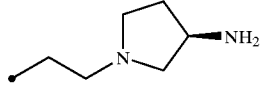 | H |
| 335 | CO | same as the above | same as the above | 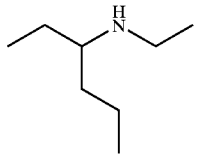 | H |
| 336 | CO | same as the above | same as the above | 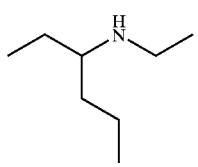 | H |
| 337 | CO | same as the above | same as the above | 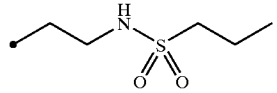 | H |
| 338 | CO | same as the above | same as the above | 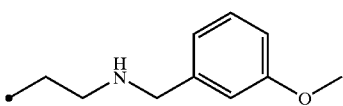 | H |
| 339 | CO | same as the above | same as the above | 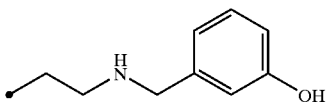 | H |
| 340 | CO | same as the above | same as the above | 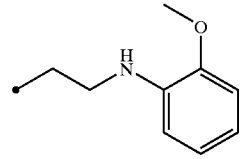 | H |
| 341 | CO | same as the above | same as the above |  | H |

TABLE 35
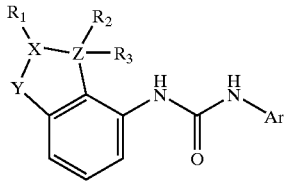
| Example | Y | R₁ R₂ R₃ or ring structure formed by X, Z, R₁, R₂ and/or R₃ taken together | Ar | R'₁ | R'₂ |
|---|---|---|---|---|---|
| 342 | CO |  | 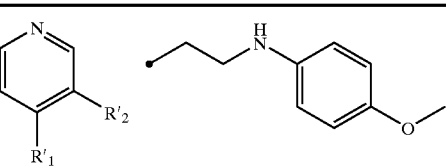 | 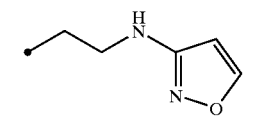 | H |
| 343 | CO | same as the above | same as the above | 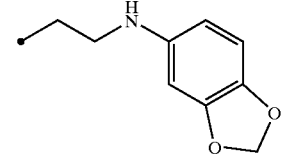 | H |
| 344 | CO | same as the above | same as the above | 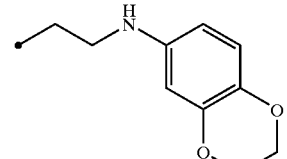 | H |
| 345 | CO | same as the above | same as the above | 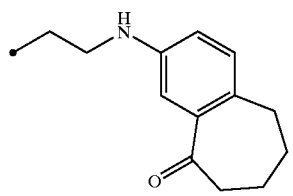 | H |
| 346 | CO | same as the above | same as the above | 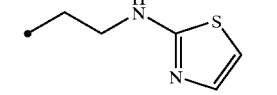 | H |
| 347 | CO | same as the above | same as the above | 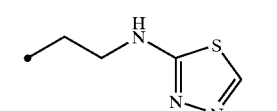 | H |
| 348 | CO | same as the above | same as the above | 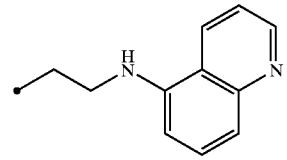 | H |
| 349 | CO | same as the above | same as the above |  | H |

TABLE 35-continued
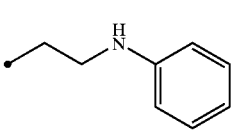
| Example | Y | R₁ R₂ R₃ or ring structure formed by X, Z, R₁, R₂ and/or R₃ taken together | Ar | R'₁ | R'₂ |
|---|---|---|---|---|---|
| 350 | CO | same as the above | same as the above | 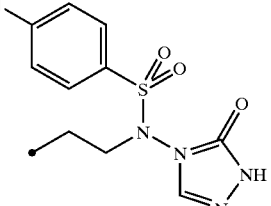 | H |
| 351 | CO | same as the above | same as the above | 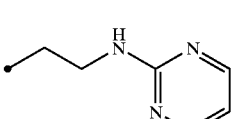 | H |
| 352 | CO | same as the above | same as the above |  | H |
TABLE 36
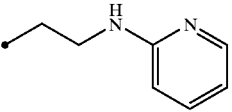
| Example | Y | R₁ R₂ R₃ or ring structure formed by X, Z, R₁, R₂ and/or R₃ taken together | Ar | R'₁ | R'₂ |
|---|---|---|---|---|---|
| 353 | CO | 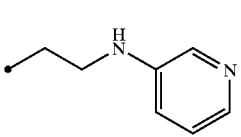 | 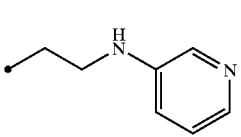 | 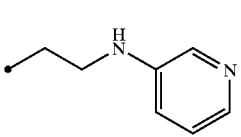 | H |
| 354 | CO | same as the above | same as the above | 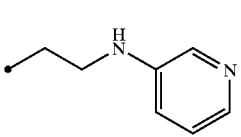 | H |

TABLE 36-continued

| Example | Y | R₁ R₂ R₃ or ring structure formed by X, Z, R₁, R₂ and/or R₃ taken together | Ar | R'₁ | R'₂ |
|---|---|---|---|---|---|
| 355 | CO | same as the above | same as the above | –CH₂CH₂–NH-(4-pyridyl) | H |
| 356 | CO | same as the above | same as the above | –CH₂CH₂–NH-(8-quinolinyl) | H |
| 357 | CO | same as the above | same as the above | –CH₂CH₂–NH-(4-pyrimidinyl) | H |
| 358 | CO | same as the above | same as the above | –CH₂CH₂–NH-(1H-inden-6-yl) | H |
| 359 | CO | same as the above | same as the above | –CH₂CH₂–NH-(8-quinolinyl) | H |
| 360 | CO | same as the above | same as the above | –CH₂CH₂–NH-(2-pyrazinyl) | H |
| 361 | CO | same as the above | same as the above | –CH₂CH₂–S-phenyl | H |
| 362 | CO | same as the above | same as the above | –CH₂CH₂–Cl | H |
| 363 | CO | same as the above | same as the above | –CH₂CH₂–NH-(6-quinolinyl) | H |

TABLE 37

| Example | Y | R₁ R₂ R₃ or ring structure formed by X, Z, R₁, R₂ and/or R₃ taken together | Ar | R'₁ | R'₂ |
|---|---|---|---|---|---|
| 364 | CO | pyrrolidine | H | pyridine with R'₁, R'₂ | imidazole-ethyl | H |
| 365 | CO | same as the above | same as the above | 4-(2-dimethylaminoethoxy)benzyl-aminoethyl | H |
| 366 | CO | same as the above | same as the above | 4-(pyridin-3-ylmethoxy)benzyl-aminoethyl | H |
| 367 | CO | same as the above | same as the above | 4-(2-pyrrolidin-1-ylethoxy)benzyl-aminoethyl | H |
| 368 | CO | same as the above | same as the above | 4-[2-(1-methylpyrrolidin-2-yl)ethoxy]benzyl-aminoethyl | H |
| 369 | CO | same as the above | same as the above | 4-(2-morpholinoethoxy)benzyl-aminoethyl | H |
| 370 | CO | same as the above | same as the above | 4-(pyridin-4-ylmethoxy)benzyl-aminoethyl | H |
| 371 | CO | same as the above | same as the above | 4-[3-(pyridin-4-yl)propoxy]benzyl-aminoethyl | H |

TABLE 37-continued
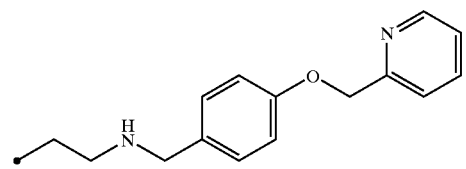
| Example | Y | R₁ R₂ R₃ or ring structure formed by X, Z, R₁, R₂ and/or R₃ taken together | Ar | R'₁ | R'₂ |
|---|---|---|---|---|---|
| 372 | CO | same as the above | same as the above | 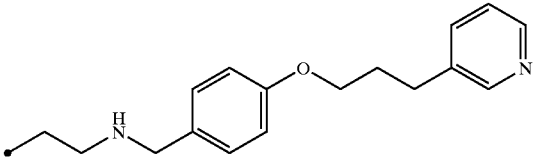 | H |
| 373 | CO | same as the above | same as the above | 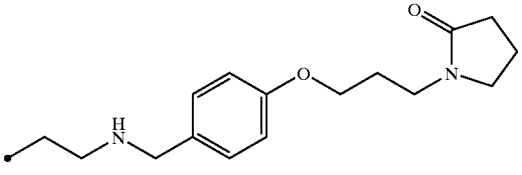 | H |
| 374 | CO | same as the above | same as the above | 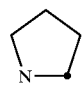 | H |
TABLE 38
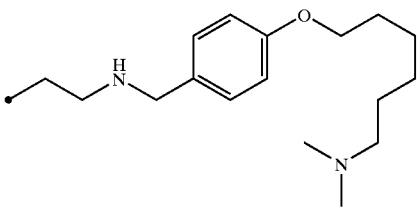
| Example | Y | R₁ R₂ R₃ or ring structure formed by X, Z, R₁, R₂ and/or R₃ taken together | Ar | R'₁ | R'₂ |
|---|---|---|---|---|---|
| 375 | CO |  |  |  | H |

TABLE 38-continued

| Example | Y | R₁ R₂ R₃ or ring structure formed by X, Z, R₁, R₂ and/or R₃ taken together | Ar | R'₁ | R'₂ |
|---|---|---|---|---|---|
| 376 | CO | same as the above | same as the above | *-CH₂CH₂-NH-CH₂-(4-phenyl)-O-CH₂CH₂CH₂-(2-pyridyl) | H |
| 377 | CO | same as the above | same as the above | *-CH₂CH₂-NH-CH₂-(3-phenyl)-O-CH₂-(2-pyridyl) | H |
| 378 | CO | same as the above | same as the above | *-CH₂CH₂-NH-CH₂-(3-phenyl)-O-CH₂-(3-pyridyl) | H |
| 379 | CO | same as the above | same as the above | *-CH₂CH₂-NH-CH₂-(3-phenyl)-O-CH₂-(4-pyridyl) | H |
| 380 | CO | same as the above | same as the above | *-CH₂CH₂-NH-CH₂-(3-phenyl)-O-CH₂CH₂CH₂-(3-pyridyl) | H |
| 381 | CO | same as the above | same as the above | *-CH₂CH₂-NH-CH₂-(3-phenyl)-O-CH₂CH₂CH₂-phenyl | H |
| 382 | CO | same as the above | same as the above | *-CH₂CH₂-NH-CH₂-(3-phenyl)-O-CH₂CH₂-N(CH₃)₂ | H |

TABLE 38-continued

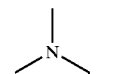

| Example | Y | R₁ R₂ R₃ or ring structure formed by X, Z, R₁, R₂ and/or R₃ taken together | Ar | R'₁ | R'₂ |
|---|---|---|---|---|---|
| 383 | CO | same as the above | same as the above | 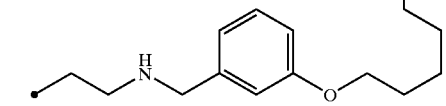 | H |
| 384 | CO | same as the above | same as the above | 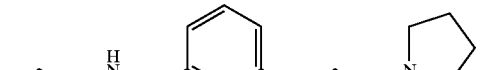 | H |
| 385 | CO | same as the above | same as the above |  | H |

TABLE 39

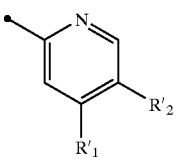

| Example | Y | R₁ R₂ R₃ or ring structure formed by X, Z, R₁, R₂ and/or R₃ taken together | Ar | R'₁ | R'₂ |
|---|---|---|---|---|---|
| 386 | CO | 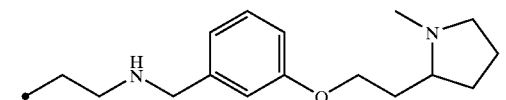 | 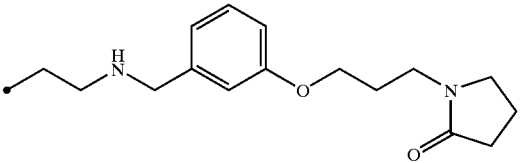 | (structure continued in R'₁ column) | H |
| 387 | CO | same as the above | same as the above | (structure shown) | H |

TABLE 39-continued

| Example | Y | R₁ R₂ R₃ or ring structure formed by X, Z, R₁, R₂ and/or R₃ taken together | Ar | R'₁ | R'₂ |
|---|---|---|---|---|---|
| 388 | CO | same as the above | same as the above | (pyridylpropoxy-benzyl-aminoethyl group) | H |
| 389 | CO | same as the above | same as the above | H | CH₂OH |
| 390 | CO | same as the above | same as the above | H | CH₂NHCH₃ |
| 391 | CO | same as the above | same as the above | H | CH₂NHC₂H₅ |
| 392 | CO | same as the above | same as the above | H | CH₂NHC₃H₇ |
| 393 | CO | same as the above | same as the above | H | NH₂ |
| 394 | CO | same as the above | same as the above | H | N-methylpiperazinyl |
| 395 | CO | same as the above | same as the above | H | CH₂CH₂NHCH₃ |
| 396 | CO | same as the above | same as the above | H | CH₂NHCH₃ |

TABLE 40

| Example | Y | R₁ R₂ R₃ or ring structure formed by X, Z, R₁, R₂ and/or R₃ taken together | Ar | R'₁ | R'₂ |
|---|---|---|---|---|---|
| 397 | CO | pyrrolidinyl | H | pyridyl (with R'₁, R'₂) | H | NHCH₃ |

TABLE 40-continued

| Example | Y | R₁ R₂ R₃ or ring structure formed by X, Z, R₁, R₂ and/or R₃ taken together | Ar | R'₁ | R'₂ |
|---|---|---|---|---|---|
| 398 | CO | same as the above | same as the above | H |  |
| 399 | CO | same as the above | same as the above | H |  |
| 400 | CO | same as the above | same as the above | $CO_2Me$ |  |
| 401 | CO | same as the above | same as the above | $CO_2Me$ | 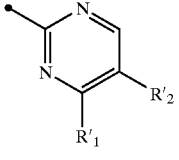 |
| 402 | CO | same as the above | 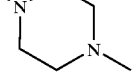 | H | H |
| 403 | CO | same as the above | same as the above | 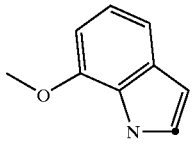 | H |
| 404 | CO | 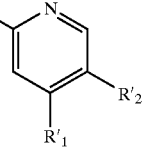 | 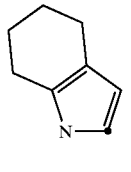 | H | |
| 405 | CO | 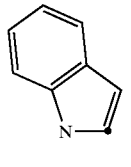 | same as the above | H | |
| 406 | CO | 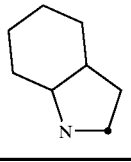 | same as the above | H | |
| 407 | CO |  | same as the above | H | |

TABLE 41

[Structure: phenyl ring fused with X-Z bearing R1, R2, R3 substituents and Y; connected via NH-C(O)-NH-Ar]

| Example | Y | R₁, R₂, R₃ or ring structure formed by X, Z, R₁, R₂ and/or R₃ taken together | | | Ar | R'₁ | R'₂ |
|---------|----|----|----|----|----|----|----|
| 408 | CO | indoline (fused ring) | | H | pyridine with R'₁, R'₂ | H | H |
| 409 | CO | H | -CH₂OH | H | same as the above | H | H |
| 410 | CO | Me | same as the above | H | same as the above | H | H |
| 411 | CO | ethyl | same as the above | H | same as the above | H | H |
| 412 | CO | propyl | same as the above | H | same as the above | H | H |
| 413 | CO | butyl | same as the above | H | same as the above | H | H |
| 414 | CO | benzyl | same as the above | H | same as the above | H | H |
| 415 | CO | NC-CH₂-CH₂- | same as the above | H | same as the above | H | H |
| 416 | CO | isobutyl | same as the above | H | same as the above | H | H |
| 417 | CO | isopentyl | same as the above | H | same as the above | H | H |
| 418 | CO | Cl-(CH₂)₃- | same as the above | H | same as the above | H | H |

TABLE 42

[Structure: benzene ring with NH-C(=O)-NH-Ar substituent, and X-Z ring with R1, R2, R3, Y substituents]

| Example | Y | R₁, R₂ or ring structure formed by X, Z, R₁, R₂ and/or R₃ taken together | R₃ | Ar | R'₁ | R'₂ |
|---|---|---|---|---|---|---|
| 419 | CO | phenethyl | CH₂OH | H | pyridin-2-yl (with R'₁, R'₂) | H | H |
| 420 | CO | 5,5,5-trifluoropentyl | same as the above | H | same as the above | H | H |
| 421 | CO | cyclohexylmethyl | same as the above | H | same as the above | H | H |
| 422 | CO | cyclohex-2-enyl | same as the above | H | same as the above | H | H |
| 423 | CO | cyclohexyl-CH₂- | same as the above | H | same as the above | H | H |
| 424 | CO | Me | Me | H | same as the above | H | H |
| 425 | CO | ethyl | same as the above | H | same as the above | H | H |
| 426 | CO | n-butyl | same as the above | H | same as the above | H | H |
| 427 | CO | benzyl | same as the above | H | same as the above | H | H |
| 428 | CO | cyclohexyl | same as the above | H | same as the above | H | H |
| 429 | CO | phenyl | same as the above | H | same as the above | H | H |

TABLE 43

[Structure: core scaffold with R1 on X, R2 and R3 on Z, Y attached to benzene ring bearing NH-C(O)-NH-Ar]

| Example | Y | R1, R2, R3 or ring structure formed by X, Z, R1, R2 and/or R3 taken together | | Ar | R'1 | R'2 |
|---|---|---|---|---|---|---|
| 430 | CO | 2,2-dimethyl-oxazolidine | H | pyridyl (with R'1, R'2) | H | H |
| 431 | CO | 2-ethyl-oxazolidine | H | same as the above | H | H |
| 432 | CO | 2-phenyl-oxazolidine | H | same as the above | H | H |
| 433 | CO | 2-(hydroxymethyl)-oxazolidine | H | same as the above | H | H |
| 434 | CO | oxazolidine | H | same as the above | H | H |
| 435 | CO | 2-(2-methoxyphenyl)-oxazolidine | H | same as the above | H | H |
| 436 | CO | 2-(3-methoxyphenyl)-oxazolidine | H | same as the above | H | H |
| 437 | CO | 2-(4-methoxyphenyl)-oxazolidine | H | same as the above | H | H |
| 438 | CO | ethyl | OH | same as the above | H | H |
| 439 | CO | ethyl | OMe | same as the above | H | H |

TABLE 43-continued

| Example | Y | R₁, R₂ or ring structure formed by X, Z, R₁, R₂ and/or R₃ taken together | | R₃ | Ar | R'₁ | R'₂ |
|---|---|---|---|---|---|---|---|
| 440 | CO | (propyl) | (—OCH₂CH₃) | H | same as the above | H | H |

TABLE 44

| Example | Y | R₁, R₂ or ring structure formed by X, Z, R₁, R₂ and/or R₃ taken together | | R₃ | Ar | R'₁ | R'₂ |
|---|---|---|---|---|---|---|---|
| 441 | CO | (propyl) | (—O-iPr) | H | (pyridine with R'₁, R'₂) | H | H |
| 442 | CO | same as the above | (—O-n-propyl) | H | same as the above | H | H |
| 443 | CO | same as the above | (—O-sec-butyl) | H | same as the above | H | H |
| 444 | CO | same as the above | (—O-neopentyl) | H | same as the above | H | H |
| 445 | CO | same as the above | (—O-CH₂-cyclopropyl) | H | same as the above | H | H |
| 446 | CO | same as the above | (—O-CH₂-cyclopentyl) | H | same as the above | H | H |
| 447 | CO | same as the above | (—O-cyclopentyl) | H | same as the above | H | H |
| 448 | CO | same as the above | (—O-CH₂-phenyl) | H | same as the above | H | H |

TABLE 44-continued
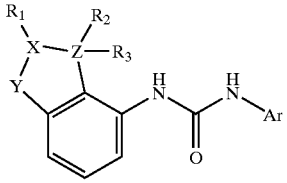
| Example | Y | $R_1$ $R_2$ $R_3$ or ring structure formed by X, Z, $R_1$, $R_2$ and/or $R_3$ taken together | | | Ar | $R'_1$ | $R'_2$ |
|---|---|---|---|---|---|---|---|
| 449 | CO | 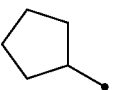 |  | H | same as the above | H | H |
| 450 | CO | 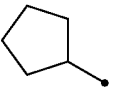 | 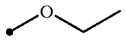 | H | same as the above | H | H |
| 451 | CO | 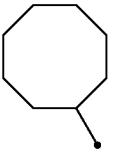 | H | H | same as the above | H | H |
TABLE 45
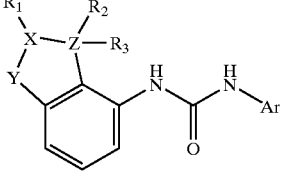
| Example | Y | $R_1$ $R_2$ $R_3$ or ring structure formed by X, Z, $R_1$, $R_2$ and/or $R_3$ taken together | | | Ar | $R'_1$ | $R'_2$ |
|---|---|---|---|---|---|---|---|
| 452 | CO | 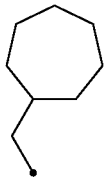 | H | H | 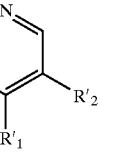 | H | H |
| 453 | CO | 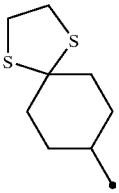 | H | H | same as the above | H | H |

TABLE 45-continued

| Example | Y | R₁ or ring structure formed by X, Z, R₁, R₂ and/or R₃ taken together | R₂ | R₃ | Ar | R'₁ | R'₂ |
|---|---|---|---|---|---|---|---|
| 454 | CO | 2,3-dimethoxybenzyl | H | H | same as the above | H | H |
| 455 | CO | 2,5-dimethoxybenzyl | H | H | same as the above | H | H |
| 456 | CO | Me | H | H | same as the above | H | H |
| 457 | CO | propyl | H | H | same as the above | H | H |
| 458 | CO | butyl | H | H | same as the above | H | H |
| 459 | CO | isobutyl | H | H | same as the above | H | H |
| 460 | CO | cyclopropylmethyl | H | H | same as the above | H | H |
| 461 | CO | cyclobutylmethyl | H | H | same as the above | H | H |
| 462 | CO | 2-hydroxypropyl | H | H | same as the above | H | H |

TABLE 46

[Structure: core scaffold with R1, R2, R3, X, Z, Y substituents and urea-Ar linker]

| Example | Y | R₁ R₂ R₃ or ring structure formed by X, Z, R₁, R₂ and/or R₃ taken together | | | Ar | R'₁ | R'₂ |
|---|---|---|---|---|---|---|---|
| 463 | CO | —O-CH₂CH₂CH₂– | H | H | pyridine with R'₁, R'₂ | H | H |
| 464 | CO | ClCH₂CH₂CH₂– | H | H | same as the above | H | H |
| 465 | CO | cyclopropylmethyl- | H | H | same as the above | H | H |
| 466 | CO | (1-methylcyclopropyl)methyl- | H | H | same as the above | H | H |
| 467 | CO | cyclopentyl- | H | H | same as the above | H | H |
| 468 | CO | tetrahydrofuran-3-yl | H | H | same as the above | H | H |
| 469 | CO | spiro cyclopentane-oxazolidine | | H | same as the above | H | H |
| 470 | CO | methyl oxazolidine-4-carboxylate | | H | same as the above | H | H |
| 471 | CO | 4-phenyloxazolidine | | H | same as the above | H | H |

TABLE 46-continued
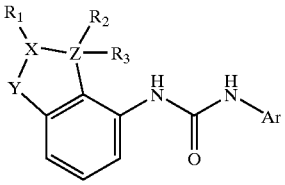
| Example | Y | R₁ R₂ R₃ or ring structure formed by X, Z, R₁, R₂ and/or R₃ taken together | Ar | R'₁ | R'₂ |
|---|---|---|---|---|---|
| 472 | CO | 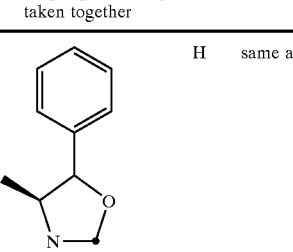 | H | same as the above | H | H |
| 473 | CO | 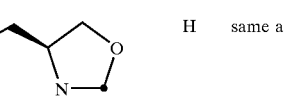 | H | same as the above | H | H |
TABLE 47
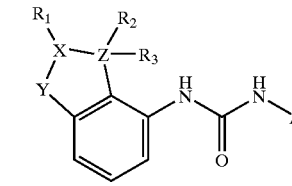
| Example | Y | R₁ R₂ R₃ or ring structure formed by X, Z, R₁, R₂ and/or R₃ taken together | Ar | R'₁ | R'₂ |
|---|---|---|---|---|---|
| 474 | CO | 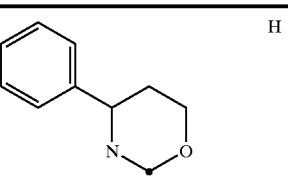 | H | 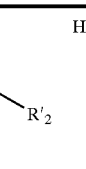 | H | H |
| 475 | CO | 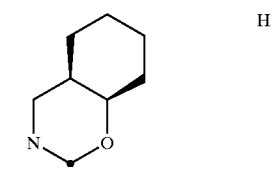 | H | same as the above | H | H |
| 476 | CO | 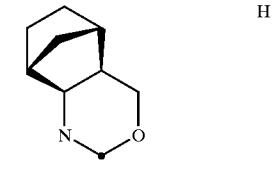 | H | same as the above | H | H |
| 477 | CO | 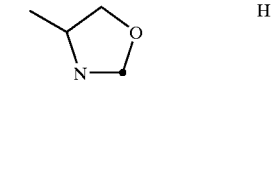 | H | same as the above | H | H |

TABLE 47-continued
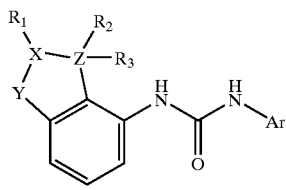
| Example | Y | R₁ R₂ R₃ or ring structure formed by X, Z, R₁, R₂ and/or R₃ taken together | Ar | R'₁ | R'₂ |
|---|---|---|---|---|---|
| 478 | CO | 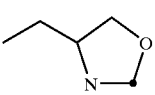 | H same as the above | H | H |
| 479 | CO | 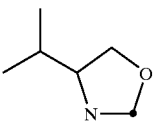 | H same as the above | H | H |
| 480 | CO | 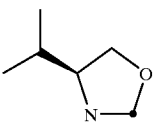 | H same as the above | H | H |
| 481 | CO | 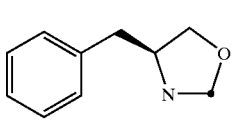 | H same as the above | H | H |
| 482 | CO | 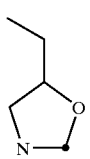 | H same as the above | H | H |
| 483 | CO | 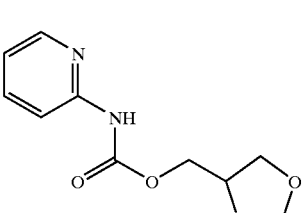 | H same as the above | H | H |
| 484 | CO | 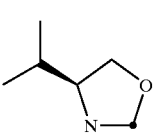 | H same as the above | H | H |

TABLE 48
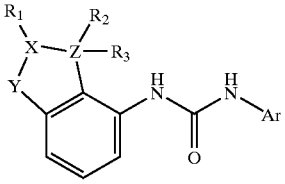
| Example | Y | R₁ R₂ R₃ or ring structure formed by X, Z, R₁, R₂ and/or R₃ taken together | Ar | R'₁ | R'₂ |
|---|---|---|---|---|---|
| 485 | CO | 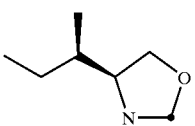 | H 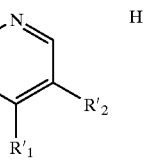 | H | H |
| 486 | CO | 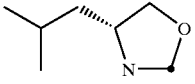 | H same as the above | H | H |
| 487 | CO | 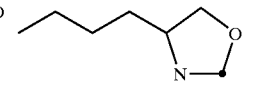 | H same as the above | H | H |
| 488 | CO | 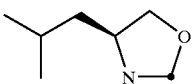 | H same as the above | H | H |
| 489 | CO | 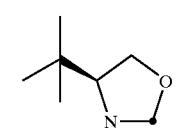 | H same as the above | H | H |
| 490 | CO | 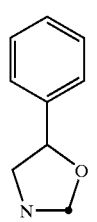 | H same as the above | H | H |
| 491 | CO | 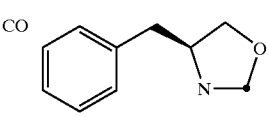 | H same as the above | H | H |
| 492 | CO | 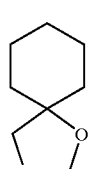 | H same as the above | H | H |
| 493 | CO | 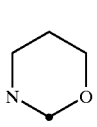 | H same as the above | H | H |

TABLE 48-continued

| Example | Y | R₁, R₂, R₃ or ring structure formed by X, Z, R₁, R₂ and/or R₃ taken together | Ar | R'₁ | R'₂ |
|---|---|---|---|---|---|
| 494 | CO | (1,4-oxazepane) | H | same as the above | H | H |
| 495 | CO | (5-hydroxymethyl-oxazolidine) | H | same as the above | H | H |

TABLE 49

| Example | Y | R₁, R₂, R₃ or ring structure formed by X, Z, R₁, R₂ and/or R₃ taken together | Ar | R'₁ | R'₂ |
|---|---|---|---|---|---|
| 496 | CO | (4-hydroxymethyl-oxazolidine) | H (pyridine with R'₁, R'₂) | H | H |
| 497 | CO | (4-(1H-indol-3-ylmethyl)-oxazolidine) | H same as the above | H | H |
| 498 | CO | (4-methyl-oxazolidine) | H same as the above | H | H |
| 499 | CO | (4-ethyl-oxazolidine) | H same as the above | H | H |

TABLE 49-continued
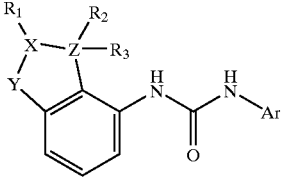
| Example | Y | R₁, R₂, R₃ or ring structure formed by X, Z, R₁, R₂ and/or R₃ taken together | Ar | R′₁ | R′₂ |
|---|---|---|---|---|---|
| 500 | CO | 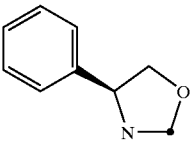 | H | same as the above | H | H |
| 501 | CO | 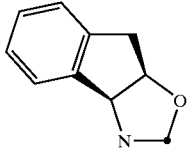 | H | same as the above | H | H |
| 502 | CO | 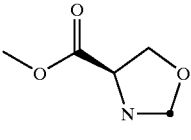 | H | same as the above | H | H |
| 503 | CO | 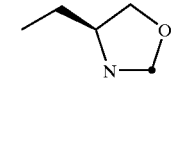 | H | same as the above | 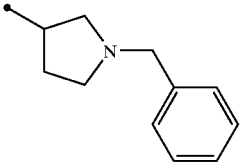 | H |
| 504 | CO | 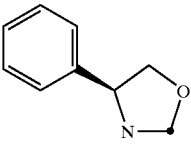 | H | same as the above | same as the above | H |
| 505 | CO | 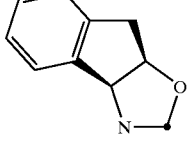 | H | same as the above | same as the above | H |
| 506 | CO | 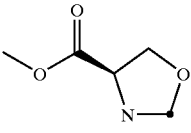 | H | same as the above | same as the above | H |

TABLE 50

| Example | Y | R₁ R₂ R₃ or ring structure formed by X, Z, R₁, R₂ and/or R₃ taken together | Ar | R'₁ | R'₂ |
|---|---|---|---|---|---|
| 507 | CO | cyclopentane-spiro-oxazolidine | pyridine with R'₁, R'₂ | N-benzyl pyrrolidin-3-yl | H |
| 508 | CO | 4-(methoxycarbonyl)oxazolidine | H | same as the above | same as the above | H |
| 509 | CO | 4-phenyloxazolidine | H | same as the above | same as the above | H |
| 510 | CO | 4-methyl-5-phenyloxazolidine | H | same as the above | same as the above | H |
| 511 | CO | 4-ethyloxazolidine | H | same as the above | same as the above | H |
| 512 | CO | 3-phenylmorpholine | H | same as the above | same as the above | H |
| 513 | CO | hexahydrobenzo[e][1,3]oxazine | H | same as the above | same as the above | H |
| 514 | CO | bicyclic oxazine | H | same as the above | same as the above | H |

TABLE 50-continued

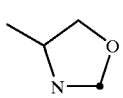

| Example | Y | R₁ R₂ R₃ or ring structure formed by X, Z, R₁, R₂ and/or R₃ taken together | Ar | R'₁ | R'₂ |
|---|---|---|---|---|---|
| 515 | CO | 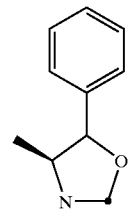 | H | same as the above | same as the above | H |
| 516 | CO | 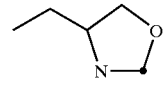 | H | same as the above | same as the above | H |
| 517 | CO | 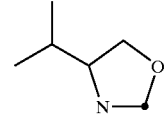 | H | same as the above | same as the above | H |

TABLE 51

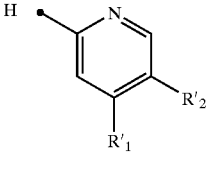

| Example | Y | R₁ R₂ R₃ or ring structure formed by X, Z, R₁, R₂ and/or R₃ taken together | Ar | R'₁ | R'₂ |
|---|---|---|---|---|---|
| 518 | CO | 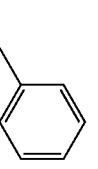 | H | 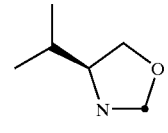 | 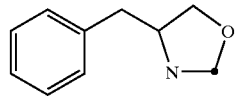 | H |
| 519 | CO | (same structure) | H | same as the above | same as the above | H |
| 520 | CO | (benzyl oxazolidine) | H | same as the above | same as the above | H |

TABLE 51-continued

| Example | Y | $R_1$, $R_2$, $R_3$ or ring structure formed by X, Z, $R_1$, $R_2$ and/or $R_3$ taken together | Ar | $R'_1$ | $R'_2$ |
|---|---|---|---|---|---|
| 521 | CO | 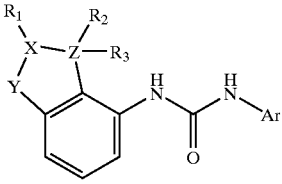 | H | same as the above | same as the above | H |
| 522 | CO | 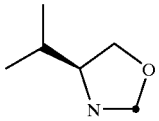 | H | same as the above | same as the above | H |
| 523 | CO | 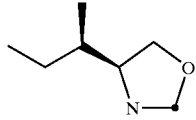 | H | same as the above | same as the above | H |
| 524 | CO | 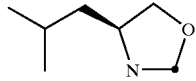 | H | same as the above | same as the above | H |
| 525 | CO | 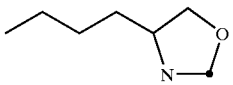 | H | same as the above | same as the above | H |
| 526 | CO | 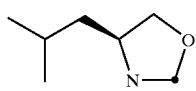 | H | same as the above | same as the above | H |
| 527 | CO | 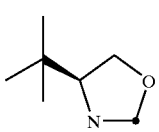 | H | same as the above | same as the above | H |
| 528 | CO | 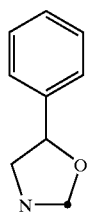 | H | same as the above | same as the above | H |

TABLE 52

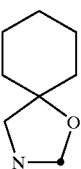

| Example | Y | R₁ R₂ R₃ or ring structure formed by X, Z, R₁, R₂ and/or R₃ taken together | | Ar | R'₁ | R'₂ |
|---|---|---|---|---|---|---|
| 529 | CO | 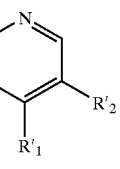 | H | 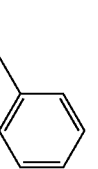 | 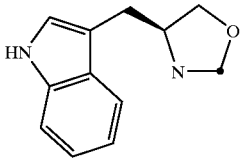 | H |
| 530 | CO |  | H | same as the above | same as the above | H |
| 531 | CO |  | H | same as the above | same as the above | H |
| 532 | CO | 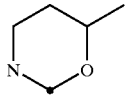 | H | same as the above | same as the above | H |
| 533 | CO | 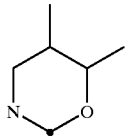 | H | same as the above | same as the above | H |
| 534 | CO | 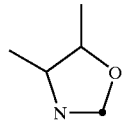 | H | same as the above | same as the above | H |
| 535 | CO | 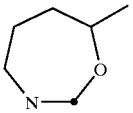 | H | same as the above | same as the above | H |
| 536 | CO | 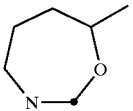 | H | same as the above | same as the above | H |
| 537 | CO |  | H | same as the above | same as the above | H |

TABLE 52-continued

| Example | Y | R₁ R₂ R₃ or ring structure formed by X, Z, R₁, R₂ and/or R₃ taken together | Ar | R'₁ | R'₂ |
|---|---|---|---|---|---|
| 538 | CO | (N–O 8-membered ring with methyl) | H | same as the above | same as the above | H |
| 539 | CO | (N–O 6-membered ring) | (pentyl chain) | same as the above | same as the above | H |

TABLE 53

| Example | Y | R₁ R₂ R₃ or ring structure formed by X, Z, R₁, R₂ and/or R₃ taken together | Ar | R'₁ | R'₂ |
|---|---|---|---|---|---|
| 540 | CO | (oxazolidine with methyl) | H | pyridine with R'₁, R'₂ | N-benzyl pyrrolidine | H |
| 541 | CO | (N–O 6-membered ring with methyl) | H | same as the above | same as the above | H |
| 542 | CO | (N–O 6-membered ring with two methyls) | H | same as the above | same as the above | H |
| 543 | CO | (N–O 7-membered ring with methyl) | H | same as the above | same as the above | H |
| 544 | CO | (N–O 7-membered ring with methyl) | H | same as the above | same as the above | H |

TABLE 53-continued

Structure: Ar-NH-C(=O)-NH-phenyl with fused ring containing X-Y, Z with R1, R2, R3 substituents

| Example | Y | R₁ R₂ R₃ or ring structure formed by X, Z, R₁, R₂ and/or R₃ taken together | Ar | R'₁ | R'₂ |
|---------|-----|---|-----|------|------|
| 545 | CO | 7-membered ring with N, O, methyl | H | same as the above | same as the above | H |
| 546 | CO | 6-membered ring with two N (piperidazine) | H | same as the above | same as the above | H |
| 547 | CO | 5-membered ring with N-N (pyrazolidine) | H | same as the above | same as the above | H |

TABLE 54

| Example | Y | R₁ R₂ R₃ or ring structure formed by X, Z, R₁, R₂ and/or R₃ taken together | Ar | R'₁ | R'₂ | R'₃ |
|---------|-----|---|-----|------|------|------|
| 548 | CO | pyrrolidine | pyrazole with R'₁, R'₂, R'₃ | H | —CH₂OH | H |
| 549 | CO | same as the above | same as the above | H | —CH₂-piperazine-N-CH₃ | H |
| 550 | CO | same as the above | same as the above | H | —CH₂-piperazine-N-CH₃ | H |
| 551 | CO | same as the above | same as the above | H | —CH₂-NH-CH(Et)₂ | H |

TABLE 54-continued

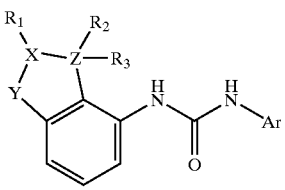

|  |  | R₁ R₂ R₃ or ring structure formed by X, Z, R₁, R₂ and/or R₃ taken |  |  |  |  |
|---|---|---|---|---|---|---|
| Example | Y | together | Ar | R'₁ | R'₂ | R'₃ |
| 552 | CO | same as the above | same as the above | H | 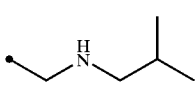 | H |
| 553 | CO | same as the above | same as the above | H | 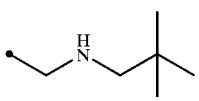 | H |
| 554 | CO | same as the above | same as the above | H | 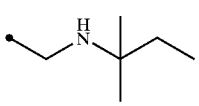 | H |
| 555 | CO | same as the above | same as the above | H | 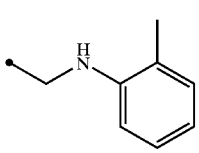 | H |
| 556 | CO | same as the above | same as the above | H | 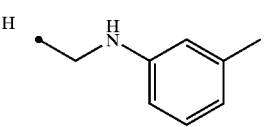 | H |
| 557 | CO | same as the above | same as the above | H | 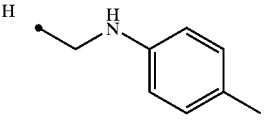 | H |
| 558 | CO | same as the above | same as the above | H | 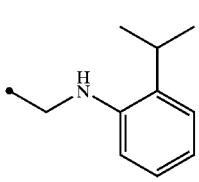 | H |

TABLE 55

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 559 | CO | pyrrolidine (N-) | pyrazole with R'₁, R'₂, R'₃ | H | CH₂-NH-(3-isopropylphenyl) | H |
| 560 | CO | same as the above | same as the above | H | CH₂-NH-(4-isopropylphenyl) | H |
| 561 | CO | same as the above | same as the above | H | CH₂-NH-(indan-1-yl) | H |
| 562 | CO | same as the above | same as the above | H | CH₂-NH-CH(CH₃)-phenyl | H |
| 563 | CO | same as the above | same as the above | H | CH₂-NH-CH(CH₃)-C₅H₁₁ | H |
| 564 | CO | same as the above | same as the above | H | CH₂-NH-C(CH₃)₂-CH₂-C(CH₃)₃ | H |
| 565 | CO | same as the above | same as the above | H | CH₂-NH-(indan-2-yl) | H |
| 566 | CO | same as the above | same as the above | H | CH₂-NH-CH(CH₂Ph)-CH₂OH | H |
| 567 | CO | same as the above | same as the above | H | CH₂-NH-CH(CH₂CH₃)-CH₂OH | H |

TABLE 55-continued

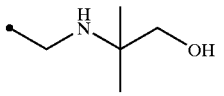

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 568 | CO | same as the above | same as the above | H | 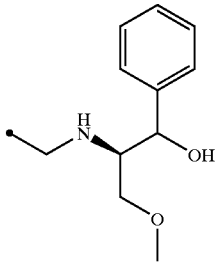 | H |
| 569 | CO | same as the above | same as the above | H |  | H |

TABLE 56

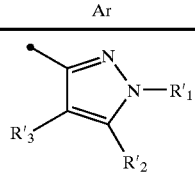

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 570 | CO | 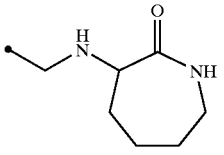 | H | 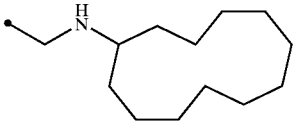 | H | 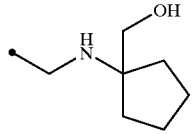 | H |
| 571 | CO | same as the above | same as the above | H | (cyclododecylamine group) | H |
| 572 | CO | same as the above | same as the above | H | (1-hydroxymethylcyclopentylamine group) | H |

TABLE 56-continued

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 573 | CO | same as the above | same as the above | H | ![structure] | H |
| 574 | CO | same as the above | same as the above | H | ![structure] | H |
| 575 | CO | same as the above | same as the above | H | ![structure] | H |
| 576 | CO | same as the above | same as the above | H | ![structure] | H |
| 577 | CO | same as the above | same as the above | H | ![structure] | H |
| 578 | CO | same as the above | same as the above | H | ![structure] | H |
| 579 | CO | same as the above | same as the above | H | ![structure] | H |
| 580 | CO | same as the above | same as the above | H | ![structure] | H |

TABLE 57
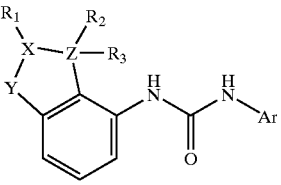
| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 581 | CO |  | 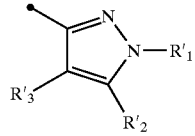 | H | 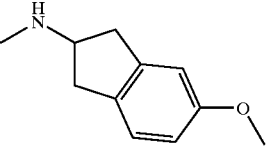 | H |
| 582 | CO | same as the above | same as the above | H | 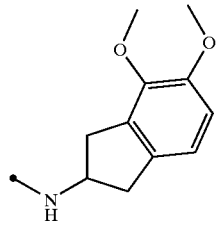 | H |
| 583 | CO | same as the above | same as the above | H | 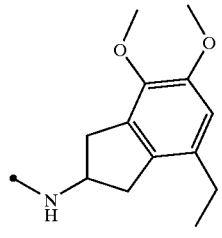 | H |
| 584 | CO | same as the above | same as the above | H | 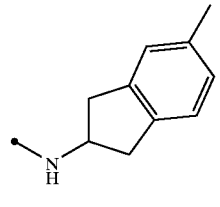 | H |
| 585 | CO | same as the above | same as the above | H | 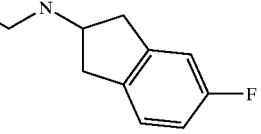 | H |
| 586 | CO | same as the above | same as the above | H | 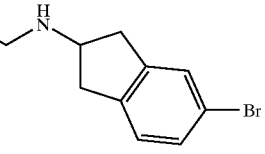 | H |

TABLE 57-continued
| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 587 | CO | same as the above | same as the above | H | 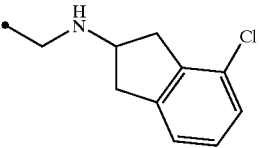 | H |
| 588 | CO | same as the above | same as the above | H | 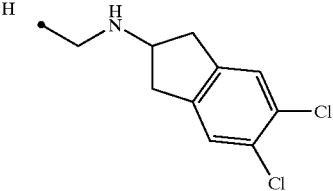 | H |
| 589 | CO | same as the above | same as the above | H | 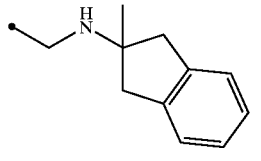 | H |
| 590 | CO | same as the above | same as the above | H | 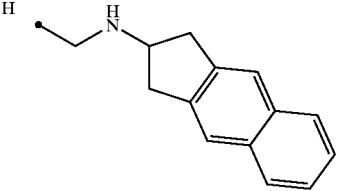 | H |
| 591 | CO | same as the above | same as the above | H | 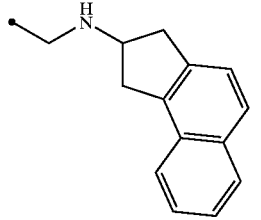 | H |

TABLE 58
|  |  | R₁ R₂ R₃ or ring structure formed by X, Z, R₁, R₂ and/or R₃ taken |  |  |  |  |
|---|---|---|---|---|---|---|
| Example | Y | together | Ar | R'₁ | R'₂ | R'₃ |
| 592 | CO | 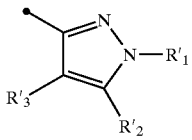 | 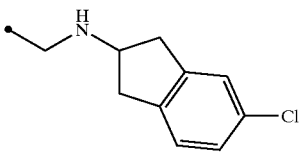 | H | 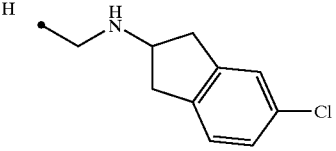 | H |
| 593 | CO | same as the above | same as the above | H | 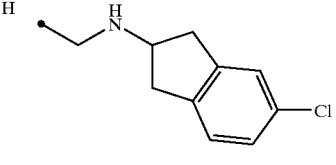 | H |
| 594 | CO | same as the above | same as the above | H | 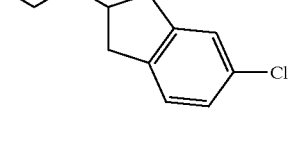 | H |
| 595 | CO | same as the above | same as the above | H | 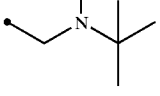 | H |
| 596 | CO | same as the above | same as the above | H | 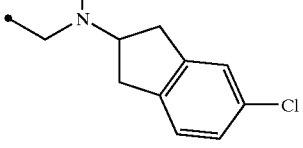 | H |
| 597 | CO | same as the above | same as the above | H | 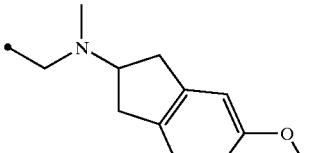 | H |
| 598 | CO | same as the above | same as the above | H |  | H |

TABLE 58-continued

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 599 | CO | same as the above | same as the above | H | (2-benzylpyrrolidinyl) | H |
| 600 | CO | same as the above | same as the above | H | (2-benzylpyrrolidinyl) | H |
| 601 | CO | same as the above | same as the above | H | (2-benzylpyrrolidinyl) | H |
| 602 | CO | same as the above | same as the above | H | (2-benzylpyrrolidinyl) | H |

TABLE 59

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 603 | CO | pyrrolidinyl | pyrazolyl (with R'₁, R'₂, R'₃) | H | 2-methylphenyl | H |

TABLE 59-continued

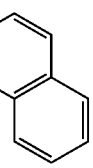

R₁ R₂ R₃
or ring structure
formed by X, Z, R₁,
R₂ and/or R₃ taken

| Example | Y | together | Ar | R'₁ | R'₂ | R'₃ |
|---------|-----|------------------|------------------|-----|-----|-----|
| 604 | CO | same as the above | same as the above | H | 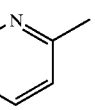 | H |
| 605 | CO | same as the above | same as the above | H | 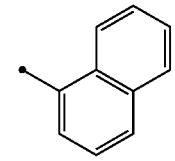 | H |
| 606 | CO | same as the above | same as the above | H | 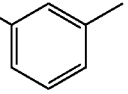 | H |
| 607 | CO | same as the above | same as the above | H | 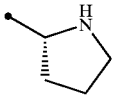 | H |
| 608 | CO | same as the above | same as the above | H | 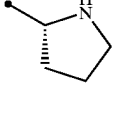 | H |
| 609 | CO | same as the above | same as the above | H | 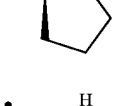 | H |
| 610 | CO | same as the above | same as the above | H | 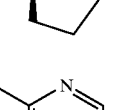 | H |
| 611 | CO | same as the above | same as the above | H | 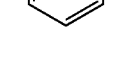 | H |
| 612 | CO | same as the above | same as the above | H |  | H |

TABLE 59-continued

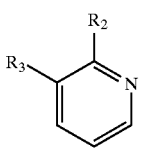

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 613 | CO | same as the above | same as the above | H | ![](R₂, R₃ on pyridine) | H |

TABLE 60

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 614 | CO | pyrrolidine | pyrazole with R'₁, R'₂, R'₃ | H | N-benzyl imidazole | H |
| 615 | CO | same as the above | same as the above | H | thiophene | H |
| 616 | CO | same as the above | same as the above | H | cyclopentyl | H |
| 617 | CO | same as the above | same as the above | H | cyclopentyl | H |

TABLE 60-continued

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 618 | CO | same as the above | same as the above | H | 2-pyrrolidinyl, 4-benzyloxy | H |
| 619 | CO | same as the above | same as the above | H | 2-pyrrolidinyl, 4-benzyloxy (other stereo) | H |
| 620 | CO | same as the above | same as the above | H | 2-pyrrolidinyl, 4-hydroxy | H |
| 621 | CO | same as the above | same as the above | H | 2-pyrrolidinyl, 4-hydroxy (other stereo) | H |
| 622 | CO | same as the above | same as the above | H | 1-benzyl-5-oxopyrrolidin-3-yl | H |
| 623 | CO | same as the above | same as the above | H | 1-benzyl-5-oxopyrrolidin-3-yl (other stereo) | H |

TABLE 60-continued
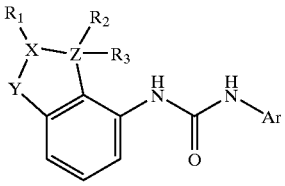
R₁ R₂ R₃
or ring structure
formed by X, Z, R₁,
R₂ and/or R₃ taken
| Example | Y | together | Ar | R'₁ | R'₂ | R'₃ |
|---|---|---|---|---|---|---|
| 624 | CO | same as the above | same as the above | H | 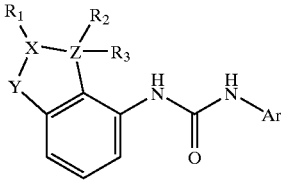 | H |
TABLE 61
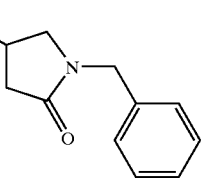
R₁ R₂ R₃
or ring structure
formed by X, Z, R₁,
R₂ and/or R₃ taken
| Example | Y | together | Ar | R'₁ | R'₂ | R'₃ |
|---|---|---|---|---|---|---|
| 625 | CO |  | 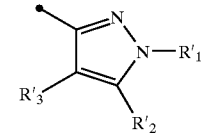 | H | 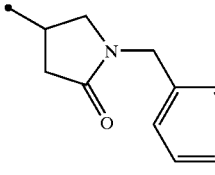 | H |
| 626 | CO | same as the above | same as the above | H | 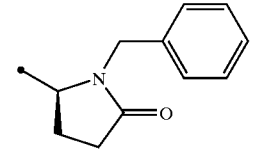 | H |
| 627 | CO | same as the above | same as the above | H | 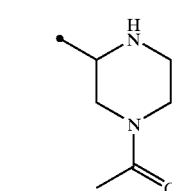 | H |

TABLE 61-continued

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 628 | CO | same as the above | same as the above | H | 3-acetylpiperazin-2-yl | H |
| 629 | CO | same as the above | same as the above | H | 3-acetylpiperazin-2-yl | H |
| 630 | CO | same as the above | same as the above | H | 1-formylpyrrolidin-2-yl | H |
| 631 | CO | same as the above | same as the above | H | 1-formylpyrrolidin-2-yl | H |
| 632 | CO | same as the above | same as the above | H | 1-methylpyrrolidin-2-yl | H |
| 633 | CO | same as the above | same as the above | H | 1-methylpyrrolidin-2-yl | H |
| 634 | CO | same as the above | same as the above | H | 1-(butylamino)ethyl | H |
| 635 | CO | same as the above | same as the above | H | 1-(cyclohexylamino)ethyl | H |

TABLE 62

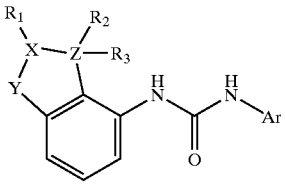

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 636 | CO |  | 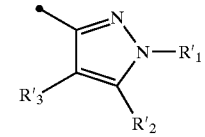 | H |  | H |
| 637 | CO | same as the above | same as the above | H | 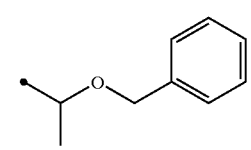 | H |
| 638 | CO | same as the above | same as the above | H | 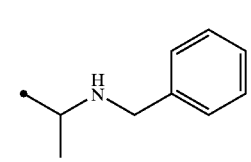 | H |
| 639 | CO | same as the above | same as the above | H | 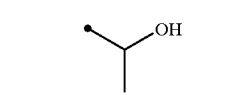 | H |
| 640 | CO | same as the above | same as the above | H | 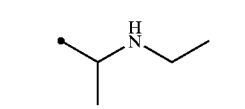 | H |
| 641 | CO | same as the above | same as the above | H | 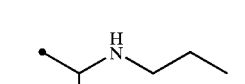 | H |
| 642 | CO | same as the above | same as the above | H | 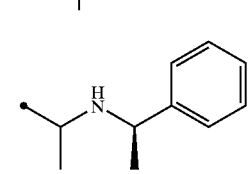 | H |
| 643 | CO | same as the above | same as the above | H | 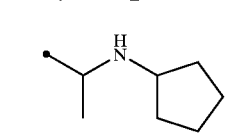 | H |
| 644 | CO | same as the above | same as the above | H | 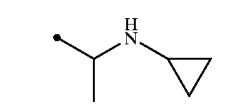 | H |
| 645 | CO | same as the above | same as the above | H | 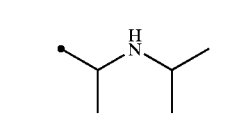 | H |

TABLE 62-continued

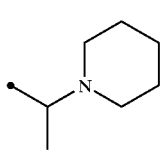

|  |  | $R_1$ $R_2$ $R_3$ or ring structure formed by X, Z, $R_1$, $R_2$ and/or $R_3$ taken |  |  |  |  |
|---|---|---|---|---|---|---|
| Example | Y | together | Ar | $R'_1$ | $R'_2$ | $R'_3$ |
| 646 | CO | same as the above | same as the above | H | ![piperidinyl-ethyl](piperidine with CH attached) | H |

TABLE 63

![structure same as above]

|  |  | $R_1$ $R_2$ $R_3$ or ring structure formed by X, Z, $R_1$, $R_2$ and/or $R_3$ taken |  |  |  |  |
|---|---|---|---|---|---|---|
| Example | Y | together | Ar | $R'_1$ | $R'_2$ | $R'_3$ |
| 647 | CO | pyrrolidine | pyrazole with $R'_1$, $R'_2$, $R'_3$ | Me | pyrrolidine-2-yl | H |
| 648 | CO | same as the above | same as the above | Me | pyrrolidine-2-yl | H |
| 649 | CO | same as the above | same as the above | Me | indan-2-yl-aminomethyl | H |
| 650 | CO | same as the above | same as the above | Me | CH(OMe)$_2$ | H |
| 651 | CO | same as the above | same as the above | Me | CH$_2$OH | H |

TABLE 63-continued

[Structure diagram showing:
R₁-X-Z(-R₃)(-R₂) fused with benzene ring bearing NH-C(=O)-NH-Ar, with Y connecting X and the benzene ring]

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 652 | CO | same as the above | same as the above | Me | -CH₂-NH-(2-indanyl-6-OMe) | H |
| 653 | CO | same as the above | same as the above | Me | -CH₂-NH-(2-indanyl-6-F) | H |
| 654 | CO | same as the above | same as the above | Me | -CH₂-NH-(2-indanyl-6-Br) | H |
| 655 | CO | same as the above | same as the above | Me | -CH₂-NH-(2-indanyl-6-Cl) | H |
| 656 | CO | same as the above | same as the above | Me | -CH₂-NH-(2-indanyl-4-Cl) | H |
| 657 | CO | same as the above | same as the above | H | -CH₂-NH-n-butyl | H |

TABLE 64

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 658 | CO | pyrrolidine | pyrazole | H | -CH₂-NH-cyclohexyl | H |
| 659 | CO | same as the above | same as the above | H | -CH₂-NH-CH₂-phenyl | H |
| 660 | CO | same as the above | same as the above | H | -CH₂-NH-propyl | H |
| 661 | CO | same as the above | same as the above | H | -CH₂-NH-isopropyl | H |
| 662 | CO | same as the above | same as the above | H | -CH₂-NH-tert-butyl | H |
| 663 | CO | same as the above | same as the above | H | -CH₂-N(CH₃)₂ | H |
| 664 | CO | same as the above | same as the above | H | -CH₂-piperidinyl | H |
| 665 | CO | same as the above | same as the above | H | -CH₂-pyrrolidinyl | H |
| 666 | CO | same as the above | same as the above | H | -CH₂-NH-CH₃ | H |
| 667 | CO | same as the above | same as the above | H | -CH₂-NH-cycloheptyl | H |
| 668 | CO | same as the above | same as the above | H | -CH₂-NH-cyclopentyl | H |

TABLE 65

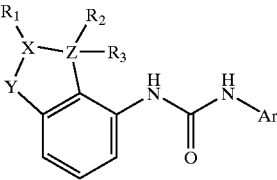

| Example | Y | R₁ R₂ R₃ or ring structure formed by X, Z, R₁, R₂ and/or R₃ taken together | Ar | R'₁ | R'₂ | R'₃ |
|---------|---|---|---|---|---|---|
| 669 | CO |  | 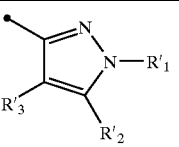 | H | 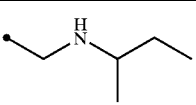 | H |
| 670 | CO | same as the above | same as the above | H | 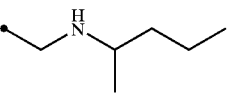 | H |
| 671 | CO | same as the above | same as the above | H | 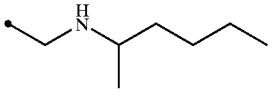 | H |
| 672 | CO | same as the above | same as the above | H | 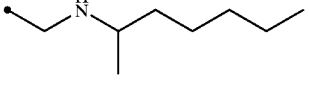 | H |
| 673 | CO | same as the above | same as the above | H | 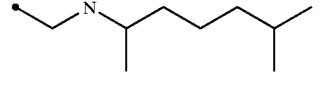 | H |
| 674 | CO | same as the above | same as the above | H | 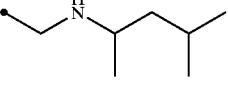 | H |
| 675 | CO | same as the above | same as the above | H | 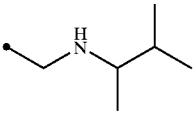 | H |
| 676 | CO | same as the above | same as the above | H | 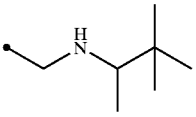 | H |
| 677 | CO | same as the above | same as the above | H | 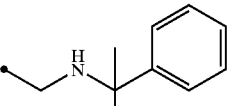 | H |
| 678 | CO | same as the above | same as the above | H | 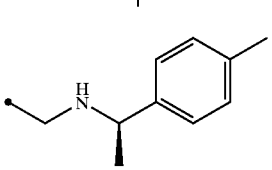 | H |

TABLE 65-continued

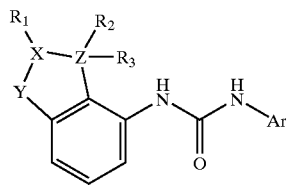

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 679 | CO | same as the above | same as the above | H | | H |

TABLE 66

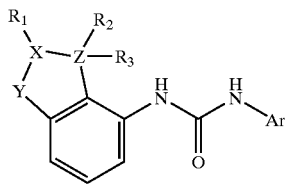

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 680 | CO | pyrrolidine | pyrazole with R'₁, R'₂, R'₃ | H | (S)-1-(naphthalen-1-yl)ethylamine | H |
| 681 | CO | same as the above | same as the above | H | (R)-1-(naphthalen-1-yl)ethylamine | H |
| 682 | CO | same as the above | same as the above | H | 1-cyclohexylethylamine | H |
| 683 | CO | same as the above | same as the above | H | 4-(diethylamino)butan-2-amine | H |

TABLE 66-continued
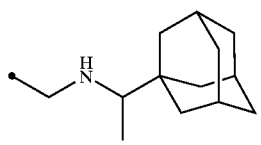
| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 684 | CO | same as the above | same as the above | H | 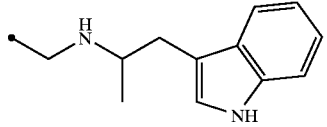 | H |
| 685 | CO | same as the above | same as the above | H | 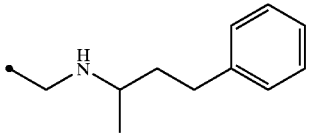 | H |
| 686 | CO | same as the above | same as the above | H | 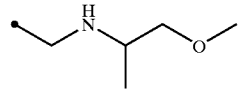 | H |
| 687 | CO | same as the above | same as the above | H | 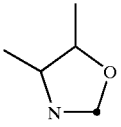 | H |
| 688 | CO | 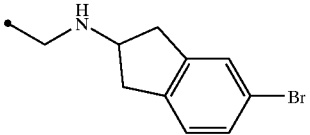 | H | same as the above | H | 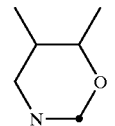 | H |
| 689 | CO | 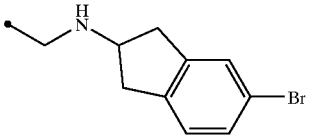 | H | same as the above | H | 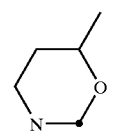 | H |
| 690 | CO | 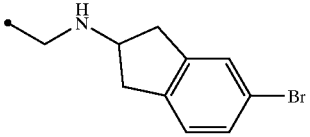 | H | same as the above | H |  | H |

TABLE 67

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 691 | CO | pyrrolidine | pyrazole with R'₁, R'₂, R'₃ | H | 3-benzamido-N-(2-(2-(2-aminoethoxy)ethoxy)ethyl) | H |
| 692 | CO | same as the above | same as the above | H | 3-benzamido-N-(3-aminopropyl) | H |
| 693 | CO | same as the above | same as the above | H | 3-benzamido-N-(4-aminocyclohexyl) | H |
| 694 | CO | same as the above | same as the above | H | 3-benzamido-N-(3-amino-2-hydroxypropyl) | H |
| 695 | CO | same as the above | same as the above | H | 3-benzamido-N-(2-methylcyclohexyl) | H |
| 696 | CO | same as the above | same as the above | H | 3-benzamido-N-(3-aminocyclohexyl) | H |
| 697 | CO | same as the above | same as the above | H | 3-benzamido-N-(2-(indolin-3-yl)ethyl) | H |

TABLE 67-continued

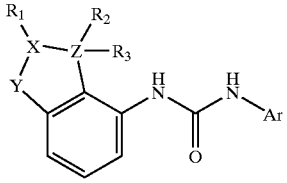

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 698 | CO | same as the above | same as the above | H | 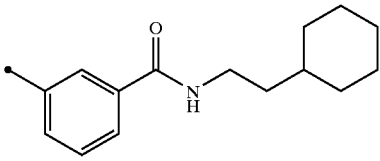 | H |
| 699 | CO | same as the above | same as the above | H | 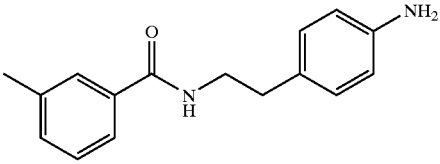 | H |
| 700 | CO | same as the above | same as the above | H | 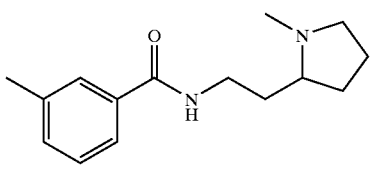 | H |

TABLE 68

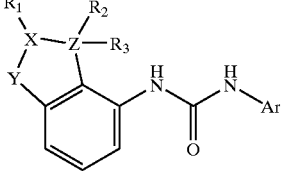

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 701 | CO |  | 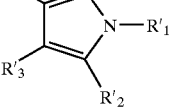 | H | H | H |
| 702 | CO | same as the above | same as the above | H | H | 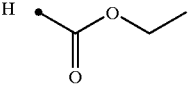 |

TABLE 68-continued

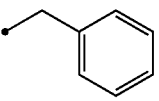

| Example | Y | R₁ R₂ R₃ or ring structure formed by X, Z, R₁, R₂ and/or R₃ taken together | Ar | R'₁ | R'₂ | R'₃ |
|---|---|---|---|---|---|---|
| 703 | CO | same as the above | same as the above | benzyl | H | H |
| 704 | CO | same as the above | same as the above | benzyl | H | CH₂OH |
| 705 | CO | same as the above | same as the above | Me | H | H |

TABLE 69

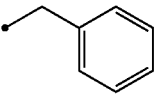

| Example | Y | R₁ R₂ R₃ R₄ R₅ or ring structure formed by X, Z, R₁, R₂ and/or R₃ taken together | Ar | R'₁ | R'₂ |
|---|---|---|---|---|---|
| 706 | CO | pyrrolidine, H, Cl, H | pyridyl with R'₁, R'₂ | H | H |

TABLE 69-continued

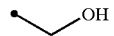

| Example | Y | R₁ R₂ R₃ R₄ R₅ or ring structure formed by X, Z, R₁, R₂ and/or R₃ taken together | Ar | R'₁ | R'₂ |
|---|---|---|---|---|---|
| 707 | CO | same as the above | Br H same as the above | H | H |
| 708 | CO | same as the above | Br Br same as the above | H | H |
| 709 | CO | same as the above | Cl Cl same as the above | H | H |

TABLE 70

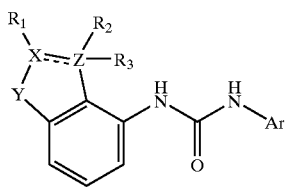

| Example | Y | X—R₁ or ring structure formed by X, Z, R₁, R₂ and/or R₃ taken together | | R₂ | R₃ | Ar | R'₁ | R'₂ |
|---|---|---|---|---|---|---|---|---|
| 710 | $SO_2$ | isopropyl-N | | CO | | 2-pyridyl with R'₁, R'₂ | H | H |
| 711 | $SO_2$ | N= | O-isopropyl | | | same as the above | H | H |
| 712 | $SO_2$ | cyclopentyl-N | | CO | | same as the above | H | H |
| 713 | $SO_2$ | N= | O-cyclopentyl | | | same as the above | H | H |
| 714 | $SO_2$ | NH | | H | H | same as the above | H | H |
| 715 | $SO_2$ | ethoxycarbonyl-N | | H | H | same as the above | H | H |

Note 1: N = means that a double bond is formed by nitrogen atom together with Z. Accordingly the compound of Example 711 is shown by the formula:

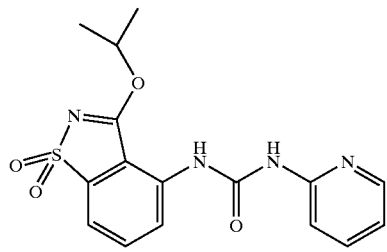

Note 2: The thick letter N means that the nitrogen atom forms a chemical bond with each of Y and Z. Accordingly the compound of Example 710 is shown by the formula:

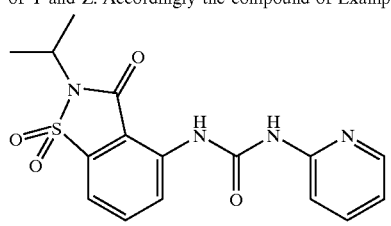

Working Example No.1

To 4-amino-9-fluorenone (29 mg, 0.15 mmol) a solution of 2-pyridinecarbonylazide (22 mg, 0.15 mmol) in tetrahydrofuran (0.5 ml) was added at room temperature. The reaction mixture was refluxed for 2 hours and then cooled to room temperature. To the reaction mixture, a mixture of hexane and ethyl acetate was added for crystalization. The resulting crude product was washed with ethyl acetate and methanol successively and the crude product was filtrated to afford the titled compound (the compound of working example No.1) (34 mg) as yellow powder.

$^1$H-NMR(DMSO-d$_6$)δ:7.07(1H,J=8.3 Hz,5.1 Hz), 7.34–7.45(4H,m), 7.64–7.69(2H,m), 7.78–7.84(1H,m), 8.04 (1H,d,J=7.9 Hz), 8.08 (1H,d,J=7.7 Hz), 8.29(1H,dd,J=5.0 Hz,1.2 Hz), 10.0(1H,s), 11.1(1H,brs).

mass:316(M+1)$^+$.

Working Examples No.2 to 8

According to the procedure described in the working example No.1, the compounds of working examples from No.2 to No.8 were prepared.

Working Example No.2

$^1$H-NMR(DMSO-d$_6$)δ:2.35(3H, s), 7.02–7.11(1H,m) 7.34–7.48 (3H,m), 7.60–7.74(3H,m), 8.02–8.22(3H,m), 8.19(1H,m), 8.92 (1H,m), 12.1(1H,m).

mass:330(M+1)$^+$.

Working Example No.3

$^1$H-NMR(DMSO-d$_6$) δ:7.01(1H,dd,J=5.6 Hz,8.0 Hz), 7.26 (1H,dd,J=2.0 Hz,8.0 Hz), 7.35–7.46 (3H,m), 7.67 (2H, d,J=7.3 Hz), 7.81(1H,dd,J=2.0 Hz,5.6 Hz), 8.11(1H,dd,J= 1.8 Hz,7.3 Hz), 8.15(1H,d,J=7.3 Hz), 8.40(1H,s), 11.8(1H, s).

mass:332(M+1)$^+$.

Working Example No.4

$^1$H-NMR(DMSO-d$_6$)δ:3.28(2H,s), 7.36–7.46(6H,m), 7.56(3H,d,J=7.6 Hz), 7.62–7.70(2H,m), 7.69(1H,dd,J=5.0 Hz,8.0 Hz), 7.88(1H,d,J=5.0 Hz), 8.04–8.14(2H,m), 8.48 (1H,s), 11.8(1H,s).

mass:422(M+1)$^+$.

Working Example No.5

$^1$H-NMR(DMSO-d$_6$)δ:7.23–7.28(1H,m), 7.39–7.48(3H, m), 7.65–7.70(2H,m), 8.07–8.10(2H,m), 8.48(1H,dt,J=7.8 Hz,1.6 Hz), 8.56(1H,d,J=5.0 Hz).

mass:360(M+1)$^+$.

Working Example No.6

$^1$H-NM(DMSO-d$_6$)δ:2.35(3H,s), 6.96(1H,d,J=5.0 Hz), 7.15(1H,s), 7.36–7.49(3H,m), 7.64–7.74(2H,m), 8.08–8.15 (2H,m), 8.19 (1H,d,J=5.0 Hz), 10.0(1H,s), 11.3(1H,brs).

mass:330(M+1)$^+$.

Working Example No.7

$^1$H-NMR(DMSO-d$_6$)δ:7.18(1H,d,J=6.0 Hz), 7.35–7.45 (3H,m), 7.57(1H,s), 7.62–7.67(2H,m), 7.93(1H,d,J=7.0 Hz), 7.98 (1H,d,J=7.0 Hz), 8.28(1H,d,J=4.0 Hz), 10.1(1H,s), 10.4(1H,s).

Working Example No.8

$^1$H-NMR(DMSO-d$_6$)δ:2.97(6H,s), 6.43(1H,s), 6.43(1H, dd,J=7.3 Hz, 2.0 Hz), 7.33–7.41(3H,m), 7.62–7.67(2H,m), 7.88(1H,d,J=6.0 Hz), 8.14(1H,d,J=6.7 Hz), 8.20(1H,d,J=6.7 Hz), 9.63(1H,s).

Working Example No.9

According to the procedure described in the working example No.26, the compound of reference example No.1 and 2-amino-4-(N-ethoxycarbonyl)amonopyridine were used to afford the intermediate (50 mg, 0.12 mmol), which was dissloved in the ethanol (2 ml). 5N aqueous sodium hydroxide (2.0 ml, 10 mmol) was added at room tmperature. The whole was refluxed for 1 hour. The reaction mixture was cooled to room temperature and water was added. The whole was extracted with ethyl acetate-tetrahydrofuran. The organic layer was washed with saturated brine and dried over magnesium sulfate. After filtration, the filtrate was concentrated to afford a residue, which was purified by column chromatography on silica gel. The fraction eluted with chloroform-methanol (100:0–95:5) provided the titled compound (8 mg) as yellow crystals.

$^1$H-NMR(DMSO-d$_6$)δ:6.19(1H,s), 6.25(1H,d,J=5.9 Hz), 6.28 (2H,s), 7.34–7.41(3H,m), 7.62–7.69(2H,m), 7.74(1H, d,J=5.7 Hz), 8.15(1H,d,J=7.1 Hz), 8.21(1H,d,J=7.1 Hz), 9.66(1H,s), 12.3(1H,br).

mass:331(M+1)$^+$.

Working Example No.10

The compound (33 mg, 0.10 mmol) of working example No.9 was dissloved in tetrahydrofuran (3 ml). N-butylaldehyde (27 μl, 0.30 mmol) and sodium triacetoxyborohydride (63 mg, 0.30 mmol) were added at room temperature. The mixture was stirred for 6 hours at the same temperature. To the reaction mixture, saturated aqueous sodium hydogencarbonate was added. The whole was extrated with ethyl acetate-tetrahydrofuran. The organic layer was washed with saturated brine and dried over magnesium sulfate. After filtration, the filtrate was concentrated to afford a residue, which was purified by TLC. The fraction eluted with chloroform-tetrahydrofuran (70:30) provided the titled compound (23 mg) as yellow crystals.

$^1$H-NMR(DMSO-d$_6$)δ:0.90(3H,t,J=7.2 Hz), 1.31–1.40 (2H,m), 1.48–1.53(2H,m), 2.98–3.02(2H,m), 6.19(1H,s), 6.28(1H,d,J=6.1 Hz, 1.9 Hz), 6.79(1H,dt), 7.31–7.40(3H,m), 7.62–7.68(2H,m), 7.75 (1H,d,J=6.2 Hz), 8.14(1H,dd,J=7.1 Hz,1.9 Hz), 8.20(1H,d,J=8.2 Hz), 9.60(1H,s), 12.3(1H,br).

mass:387(M+1)$^+$.

Working Example No.11

According to the procedure described in working example No.80(3), 4-amino-9-flurorene which replaces the compound of reference example No.3 and the compound of working example No.80(2) were used to afford the crude compound. According to the procedure described in working example No.80(4), the crude compound was used to afford the titled compound (21 mg) as colorless crystals.

1H-NMR(CDCl$_3$)δ:4.52(2H,d,J=5.3 Hz), 5.47(1H,t,J=5.3 Hz), 7.00(1H, d,J=4.7 Hz), 7.28–7.69(6H,m), 8.05–8.22(3H, m), 10.0(1H,s), 11.4(1H,s).

mass:346(M+1)$^+$.

Working Examples No.12 to 17

According to the procedure described in the working example No.1, the compounds of working examples from No.12 to No.17 were prepared.

Working Example No.12

$^1$H-NMR(DMSO-d$_6$)δ:2.28(3H,s), 7.25(1H,d,J=7.6 Hz), 7.16–7.45 (3H,m), 7.63–7.72(3H,m), 8.04–8.14(3H,m), 9.92(1H,s), 11.1(1H,br).

mass:330(M+1)$^+$.

Working Example No.13

$^1$H-NMR(DMSO-d$_6$)δ:7.34–7.47(3H,m), 7.58(1H,d,J=8.9 Hz), 7.66 (2H,m), 7.95(1H,d,J=7.8 Hz), 7.99(2H,m), 8.31(1H,d,J=2.6 Hz), 10. 0(1H,br).

mass:350,352(M+1)$^+$.

Working Example No.14

$^1$H-NMR(DMSO-d$_6$)δ:7.35–7.48(3H,m), 7.54(1H,d,J=8.9 Hz), 7.62–7.72(2H,m), 7.93(1H,d,J=9.2 Hz), 7.96(1H,d,J=5.1 Hz), 8.00(1H,dd, J=8.9 Hz,2.2 Hz), 8.39(1H,d,J=2.8 Hz), 10.1(1H,m).

mass:394,396(M+1)$^+$.

Working Example No.15

$^1$H-NMR(DMSO-d$_6$)δ:7.36–7.56(4H,m), 7.64–7.74(2H, m), 7.96 (2H,t,J=8.6 Hz), 7.94–8.02(1H,m), 8.60(1H,m), 9.16(1H,m).

mass:361(M+1)$^+$.

Working Example No.16

$^1$H-NMR(DMSO-d$_6$)δ:7.39–7.49(6H,m), 7.68–7.73(3H, m), 7.99–8.08(3H,m), 8.23–8.26(1H,m), 8.80(1H,s).

mass:359(M+1)$^+$.

Working Example No.17

$^1$H-NMR(DMSO-d$_6$)δ:7.37–7.48(3H,m), 7.55(1H,d,J=8.8 Hz), 7.62–7.69(2H,m), 7.95(1H,d,J=7.9 Hz), 8.02(1H,d,J=6.9 Hz), 8.25(1H,dd,J=8.8 Hz,2.3 Hz), 8.79(1H,d,J=2.2 Hz).

mass:360(M+1)$^+$.

Working Example No.18

(1) According to the procedure described in the working example No.26, the compound of reference example No.1 and 2-amino-5-(N-tert-butoxycarbonyl) aminopyridine were used to afford an intermediate (0.613 g, 1.40 mmol), to which was added trifluoroacetic acid (10 ml) at room temperature. The mixture was stirred for 6 hours at the same temperature. To the reaction mixture was added saturated aqueous sodium hydrogencarbonate.

The whole was extrated with ethyl acetate-tetrahydrofuran. The organic layer was washed with saturated brine and dried over magnesium sulfate. After filtration, the filtrate was concentrated to afford a residue, which was purified by column chromatography on silica gel. The fraction eluted with chloroform-methanol (100:0–90:10) provided crude crystals. According to the procedure described in working example No.80(3), a crude crystal (0.431 g), which was further washed with ether to afford the compound as yellow crystals (0.302 g).

(2) According to the procedure described in the working example No.10, the titled compound (3.4 mg) as a yellow crystal was prepared from the compound (33 mg) obtained above in (1).

$^1$H-NMR(DMSO-d$_6$)δ:0.93(3H,t,J=7.2 Hz), 1.37–1.43 (2H,m), 1.50–1.57(2H,m), 2.97–3.03(2H,m), 5.59(1H,t), 7.11–7.13(2H,m), 7.35–7.45(3H,m), 7.64–7.70(3H,m), 8.11–8.16(2H,m), 9.61(1H,s).

mass:387(M+1)$^+$.

Working Examples No.19 to 20

According to the procedure described in the working example No.26, the compounds of working examples from No.19 to No.20 were prepared.

Working Example No.19

$^1$H-NMR(DMSO-d$_6$)δ:3.81(3H,s), 7.05(2H,d,J=8.8 Hz). 7.38–7.47 (4H,m), 7.64–7.70(4H,m), 8.02–8.13(3H,m), 8.54(1H,d,J=2.6 Hz), 10.1(0.3H,s), 11.0(0.2H,br).

mass:422(M+1)$^+$.

Working Example No.20

$^1$H-NMR(DMSO-d$_6$)δ:2.51(3H,s), 7.04(1H,d,J=7.1 Hz), 7.21–7.27 (1H,m), 7.47–7.59(3H,m), 7.72–7.84(3H,m), 8.00–8.04(1H,m), 8.17(1H,d,J=7.6 Hz), 10.1(1H,s), 11.3 (1H,brs).

mass:330(M+1)$^+$.

Working Example No.21

According to the procedure described in the working example No.18 (1), the compound of reference example No.1 and 2-amino-6-(N-tert-butoxycarbony)aminopyridine was used to afford the titled compound.

$^1$H-NMR(DMSO-d$_6$)δ:6.07–6.10(2H,m), 6.28(1H,d,J=7.5 Hz), 7.34–7.41(4H,m), 7.46–7.48(1H,m), 7.52–7.57(1H, m), 7.65(1H,d,J=6.7 Hz), 7.77(1H,d,J=7.1 Hz), 7.93(1H,d, J=7.6 Hz), 9.55(1H,s), 11.6(1H,brs).

mass:331(M+1)$^+$.

Working Example No.22

According to the procedure described in the working example No.10, the compound of working example No.21 was prepared.

$^1$H-NMR(DMSO-d$_6$)δ:0.68(3H,t,J=7.4 Hz), 1.03–1.15 (2H,m), 1.32–1.42(2H,m), 2.99–3.05(2H,m), 6.07(1H,d,J=8.2 Hz). 6.31(1H,d, J=7.8 Hz), 6.65(1H,t,J=5.4 Hz), 7.34–7.40(3H,m), 7.48(1H,d,J=6.3 Hz), 7.55(1H,dd,J=7.6 Hz,6.4 Hz), 7.65(1H,d,J=7.3 Hz), 7.70(1H d,J=7.2 Hz), 7.81(1H,d,J=7.4 Hz), 9.56(1H,s), 11.4(1H,br).

mass:387(M+1)$^+$.

Working Examples No.23 to 25

According to the procedure described in the working example No.26, the compounds of working examples from No.23 to No.25 were prepared.

Working Example No.23

$^1$H-NMR(DMSO-d$_6$)δ:1.16(3H,t,J=7.4 Hz), 2.36(3H,s), 2.73(2H,q, J=7.6 Hz), 6.94(1H,d,J=7.7 Hz), 7.36–7.47(3H, m), 7.57–7.68 (3H,m), 7.88(1H,d,J=7.9 Hz), 8.06(1H,d,J=7.0 Hz).

mass:358(M+1)$^+$.

Working Example No.24

¹H-NMR(DMSO-d₆)δ:2.26(3H,s), 2.34(3H,s), 6.77(1H,s), 6.89 (1H,s), 7.38–7.43(3H,m), 7.63–7.68(2H,m), 7.90 (1H,dd,J=8.0 Hz, 1.9 Hz), 8.05(1H,d,J=7.5 HZ), 9.92(1H,s), 11.4–11.5 (1H,br).

mass:344(M+1)⁺.

Working Example No.25

¹H-NMR(DMSO-d₆)δ:2.39(3H,s), 2.41(3H,s), 6.94(1H,s), 7.37–7.48(3H,m), 7.60–7.69(2H,m), 7.88(1H,d,J=7.9 Hz), 8.04(1H,d, J=7.6 Hz), 8.11(2H,brs), 8.77(0.7H,s), 9.02 (0.3H,s).

mass:387(M+1)⁺.

Working Example No.26

To a solution of 2-aminopyridine (13 mg, 0.14 mmol) in tetrahydrofuran (1 ml) a solution of the compound (1.25 mg, 0.1 mmol) In tetrahydrofuran (1 ml), was added. The mixture was refluxed for 30 minutes. The crystals precipitated were collected by filtration. The crude product was washed with chloroform and then dried to afford the titled compound (10 mg) as yellow crystals.

¹H-NMR(DMSO-d₆)δ:7.23(1H,t,J=4.9 Hz), 7.38–7.50 (3H,m), 7.67–7.72(2H,m), 8.06–8.10(2H,m), 8.74(2H,d,J= 4.9 Hz), 10.6(0.3H, s), 11.6(0.3H,s).

mass:317(M+1)⁺.

Working Examples No.27 to 53

According to the procedure described in the working example No.26, the compounds of working examples from No.27 to No.53 were prepared.

Working Example No.27

¹H-NMR(DMSO-d₆)δ:7.36–7.95(9H,m)

mass:333(M+1)⁺.

Working Example No.28

¹H-NMR(DMSO-d₆)d:3.28(3H,s), 7.07(1H,d,J=5.3 Hz), 7.36–7.97(6H,m), 8.05(1H,d,J=7.3 Hz), 8.53(1H,d).

mass:331(M+1)⁺.

Working Example No.29

¹H-NMR(DMSO-d₆)δ:2.38(3H,s), 2.52(3H,s), 7.27–7.35 (3H,m), 7.53–7.57(2H,m), 7.81(1H,d,J=7.9 Hz), 7.90(1H,d, J=7.6 Hz), 9.00(1H,s).

mass:373(M+1)⁺.

Working Example No.30

¹H-NMR(DMSO-d₆)δ:2.27(3H,s), 2.38(3H,s), 7.36–7.48 (3H,m), 7.65–7.70(2H,m), 7.75–7.78(1H,m), 7.92(1H,d,J= 7.4 Hz), 9.02(1H,brs).

mass:345(M+1)⁺.

Working Example No.31

¹H-NMR(DMSO-d₆)δ:3.34(3H,s), 3.92(3H,s), 7.39–7.51 (4H,m), 7.69–7.81(3H,m), 7.99(1H,d,J=7.6 Hz).

mass:377(M+1)⁺.

Working Example No.32

¹H-NMR(DMSO-d₆)δ:2.19(3H,s), 5.95(1H,br), 6.75(1H,br), 7.39–7.44(2H,m), 7.49–7.52(1H,m), 7.63–7.69(2H,m), 7.78–7.81 (1H,m), 7.94–7.97(1H,m).

mass:347(M+1)⁺.

Working Example No.33

¹H-NMR(DMSO-d₆)δ:1.76,1.89(3H,sx2), 2.01,2.18(3H, sx2), 7.37–7.50(5H,m), 7.61–7.67(2H,m), 7.77–7.80(1H, m), 7.93–7.97(1H,m).

mass:361(M+1)⁺.

Working Example No.34

¹H-NMR(DMSO-d₆)δ:7.43–7.53(3H,m), 7.68–7.73(2H, m), 7.94–8.02(2H,m), 8.34–8.39(2H,m), 8.99(1H,s).

mass:317(M+1)⁺.

Working Example No.35

¹H-NMR(DMSO-d₆)δ:6.60(1H,brs), 7.33–7.49(7H,m), 7.63–7.75 (4H,m), 7.91–8.05(2H,m).

mass:381(M+1)⁺.

Working Example No.36

¹H-NMR(DMSO-d₆)δ:5.85(2H,brs), 7.30–7.45(5H,m)m 7.61–7.69 (2H,m), 8.13–8.20(1H,m).

mass:321(M+1)⁺.

Working Example No.37

¹H-NMR(DMSO-d₆)δ:1.34(3H,t,J=7.5 Hz), 4.05(2H,q,J= 7.5 Hz), 6.18(1H,m), 7.33–7.46(4H,m), 7.63–7.73(3H,m), 7.84(1H,d, J=7.5 Hz).

mass:333(M+1)⁺.

Working Example No.38

¹H-NMR(DMSO-d₆)δ:6.45(1H,s), 7.31–7.47(4H,m), 7.54–7.63 (8H,m), 7.69(1H,d,J=7.5 Hz), 8.79(1H,s), 8.95 (1H,s).

mass:381(M+1)⁺.

Working Example No.39

¹H-NMR(DMSO-d₆)δ:1.39(3H,s), 5.45(1H,s), 6.49–6.61 (4H,m), 6.69–6.85(8H,m), 7.91(1H,brs), 8.06(1H,brs).

mass:395(M+1)⁺.

Working Example No.40

¹H-NMR(DMSO-d₆)δ:6.33(1H,d,J=3.8 Hz), 6.55–6.66 (4H,m), 6.81–6.85(2H,m), 7.00–7.04(1H,m), 7.08(1H,d,J= 7.6 Hz), 8.03(1H,brs).

mass:322(M+1)⁺.

Working Example No.41 mass:336(M+1)⁺.

Working Example No.42 mass:422(M+1)⁺.

Working Example No.43 mass:408(M+1)⁺.

Working Example No.44

$^1$H-NMR(DMSO-d$_6$)δ:1.30(3H,t,J=7.5 Hz), 4.31(2H,q,J=7.5 Hz), 7.36–7.50(4H,m), 7.60–7.69(1H,m), 7.83(1H,d,J=7.5 Hz), 7.90(1H,d,J=7.5 Hz), 8.72(1H,s).

mass:437(M+1)$^+$.

Working Example No.45

$^1$H-NMR(DMSO-d$_6$)δ:7.29–7.50(6H,m), 7.55(1H,s), 7.60–7.66 (2H,m), 7.81–7.94(4H,m).

mass:398(M+1)$^+$.

Working Example No.46

$^1$H-NMR(DMSO-d$_6$)δ:7.40(2H,t), 7.49(3H,d), 7.60–7.66 (3H,m), 7.83(1H,d,J=7.6 Hz), 7.91(3H,d,J=7.6 Hz).

mass:432(M+1)$^+$.

Working Example No.47

$^1$H-NMR(DMSO-d$_6$)δ:7.35–7.43(2H,m), 7.48–7.52(1H, m), 7.60–7.66(2H,m), 7.72(1H,d,J=7.6 Hz), 7.81(1H,d,J=7.6 Hz), 8.20–8.28(3H,m), 8.38–8.44(2H,m), 8.89–9.02 (0.2H,br).

mass:507(M+1)$^+$.

Working Example No.48

$^1$H-NMR(DMSO-d$_6$)δ:2.45(3H,s), 6.51–6.70(3H,m), 6.79–6.97 (4H,m), 7.13–7.37(1H,m), 7.80(0.3H,s), 8.20 (0.3H,s).

mass:336(M+1)$^+$.

Working Example No.49

$^1$H-NMR(DMSO-d$_6$)δ:7.36–7.43(2H,m), 7.47(2H,d,J=7.5 Hz), 7.61–7.65(2H,m), 7.77(1H,d,J=7.5 Hz), 7.84(1H,d,J=7.5 Hz).

mass:400,402(M+1)$^+$.

Working Example No.50

$^1$H-NMR(DMSO-d$_6$)δ:7.35–7.45(2H,m), 7.52(1H,d,J=6.9 Hz), 7.60–7.67(2H,m), 7.77(1H,d,J=8.0 Hz), 7.85(1H,d,J=7.5 Hz), 8.60(1H,s).

mass:367(M+1)$^+$.

Working Example No.51

$^1$H-NMR(DMSO-d$_6$)δ:7.25(1H,t), 7.40(3H,t), 7.48(1H,d, J=7.6 Hz) 7.60–7.68(3H,m), 7.86–7.93(3H,m), 9.15(0.5H, br).

mass:372(M+1)$^+$.

Working Example No.52

$^1$H-NMR(DMSO-d$_6$)δ:1.49(3H,s), 6.41(1H,d,J=7.5 Hz), 6.57–6.90 (7H,m), 7.00–7.05(1H,brm), 7.10–7.15(1H,brm).

mass:386(M+1)$^+$.

Working Example No.53

$^1$H-NMR(DMSO-d$_6$)δ:6.45(1H,dt), 6.60(2H,t), 6.70(1H, d,J=7.6 Hz), 6.80–6.90(3H,m), 7.00–7.10(3H,m).

mass:390(M+1)$^+$.

Working Examples No.54 and 55

According to the procedure described in the working example No.1, the compounds of working examples of No.54 and No.55 were prepared.

Working Example No.54

$^1$H-NMR(DMSO-d$_6$)δ:7.07–7.11(1H,m), 7.34–7.38(1H, m), 7.53 (1H,s), 7.78–7.84(2H,m), 7.92–7.95(1H,m), 8.07 (1H,d,J=8.3 Hz), 8.32(1H,d,J=1.8 Hz), 8.38(1H,s).

Working Example No.55

$^1$H-NMR(DMSO-d$_6$)δ:7.06(1H,dd,J=7.2 Hz,5.1 Hz), 7.20–7.23(1H,m), 7.42(1H,d,J=7.3 Hz), 7.71–7.80(2H,m), 8.35(1H,dd,J=5.0 Hz,1.9 Hz), 8.74(1H,d,J=8.5 Hz), 12.0 (0.4H,s), 11.3(0.4H,brs), 12.6(br).

Working Example No.56

A mixture of compound (56 mg, 0.20 mmol) of working example No.55, triphenylphosphine (157 mg, 0.6 mmol) and methanol (19 mg, 0.60 mmol) was dissolved in dimethylformamide (5 ml). To the mixture was added a 60% solution (0.17 ml) of diethylazodicarboxylate (0.60 mmol) in toluene at room temperature. The mixture was stirred for 30 minutes at the same temperature. The reaction mixture was diluted with ethyl acetate and washed with water. The organic layer was separated. The crystals precipitated were collected by filtration to afford the titled compound (41 mg).

$^1$H-NMR(DMSO-d$_6$)δ:3.03(3H,s), 7.04–7.09(1H,m), 7.19(1H,brd, J=7.9 Hz), 7.45(1H,dd,J=7.2 Hz,0.8 Hz), 7.70–7.81(2H,m), 8.39 (1H,dd,J=5.0 Hz,1.9 Hz), 8.74(1H, d,J=8.6 Hz), 10.2(0.3H,s), 12.7 (0.3H,br).

Working Examples No.57 to 74

According to the procedure described in the working example No.56, the compounds of working examples from No.57 to No.74 were prepared.

Working Example No.57

$^1$H-NMR(DMSO-d$_6$)δ:1.18(3H,t,J=7.2 Hz), 3.60(2H,q,J=7.2 Hz), 7.07(1H,dd,J=7.3 Hz,5.0 Hz), 7.19–7.21(1H,m), 7.42(1H,d, J=7.2 Hz), 7.71–7.81(2H,m), 8.39(1H,m), 8.75 (1H,d,J=8.6 Hz), 10.2(0.3H,s), 12.7(0.3H,br).

Working Example No.58

$^1$H-NMR(DMSO-d$_5$)δ:0.87(3H,t,J=7.4 Hz)1.62(2H,q,J=7.3 Hz), 3.53 (2H,t,J=7.1 Hz), 7.07(1H,dd,J=7.3 Hz,5.1 Hz), 7.22(1H,m), 7.46(1H d,J=7.3 Hz), 7.71–7.81(2H,m), 8.38 (1H,m), 8.75(1H,d,J=8.5 Hz), 10.2(0.3H,s), 12.6(0.3H,br).

Working Example No.59

$^1$H-NMR(DMSO-d$_6$)δ:1.42(6H,d,J=6.9 Hz), 4.37–4.42 (1H,m), 7.05–7.09(1H,m), 7.21–7.23(1H,brm), 7.43(1H,d, J=7.2 Hz), 7.70–7.81(2H,m), 8.39(1H,m), 8.74(1H,d,J=8.5 Hz), 10.2(0.2H,s), 12.6(0.2H,br).

Working Example No.60

$^1$H-NMR(DMSO-d$_6$)δ:0.90(3H,t,J=7.3 Hz), 1.26–1.36 (2H,m), 1.54–1.63(2H,m), 3.57(2H,t,J=7.0 Hz), 7.07(1H, ddd,J=7.3 Hz,5.0 Hz,1.0 Hz), 7.20(1H,d,J=7.9 Hz), 7.46 (1H,d,J=7.2 Hz), 7.71–7.81 (2H,m), 8.38(1H,dd,J=5.0 Hz,1.8 Hz), 8.75(1H,d,J=8.5 Hz), 10.2 (1H,s), 12.6(1H,br).

Working Example No.61

$^1$H-NMR(DMSO-d$_6$)δ:1.40–1.47(2H,m), 1.61–1.68(2H, m), 3.39(2H,t, J=6.4 Hz), 3.58(2H,t,J=6.8 Hz), 4.38(0.3H, m), 7.04–7.09(1H,m), 7.19–7.22(1H,m), 7.41–7.47(1H,m), 7.71–7.82(2H,m), 8.34–8.39 (1H,m), 8.75(1H,d,J=8.2 Hz), 10.2(0.5H,s), 12.6(0.4H,br).

Working Example No.62

$^1$H-NMR(DMSO-d$_6$)δ:3.34–3.48(3H,m), 3.59(2H,d,J=7.5 Hz) 4.43 (2H,m), 7.05–7.09(1H,m), 7.20(1H,d,J=8.2 Hz), 7.46(1H,d, J=6.9 Hz), 7.71–7.81(2H,m), 8.38(1H,dd, J=4.8 Hz,1.6 Hz), 8.74 (1H,d,J=8.6 Hz), 10.2(11H,s), 12.6 (1H,br).

Working Example No.63

$^1$H-NMR(DMSO-d$_6$)δ:1.21(3H,t,J=7.1 Hz), 4.16(2H,q,J=7.1 Hz), 4.42(2H,s), 7.07(1H,dd,J=7.2 Hz,5.1 Hz), 7.18–7.21(1H,m), 7.54(1H,d,J=7.3 Hz), 7.75–7.83(2H,m), 8.35–8.38(1H,m), 8.81 (1H,d,J=8.6 Hz), 10.2(0.5H,s), 12.7 (0.4H,br).

Working Example No.64

$^1$H-NMR(DMSO-d$_6$)δ:4.78(2H,s), 7.06(1H,ddd, J=7.3 Hz, 5.0 Hz, 1.0 Hz), 7.19–7.36(6H,m), 7.50(1H,d,J=7.1 Hz), 7.74–7.80(2H,m), 8.36(1H,dd,J=4.9 Hz,1.9 Hz), 8.77(1H,d, J=8.6 Hz), 10,2(0.3H,s), 12.6(0.3H,br).

Working Example No.65

$^1$H-NMR(DMSO-d$_6$)δ:2.94(2H,t,J=7.3 Hz), 3.81(2H,t,J=7.3 Hz). 7.08(1H,dd,J=7.2 Hz,5.0 Hz), 7.15–7.33(6H,m), 7.43(1H,d, J=7.3 Hz), 7.70–7.81(2H,m), 8.37(1H,dd,J=4.8 Hz,1.4 Hz), 8.73 (1H,d,J=8.6 Hz), 10.2(0.3H,s), 12.6(0.3H, br).

Working Example No.66

$^1$H-NMR(DMSO-d$_6$)δ:4.61(2H,s), 6.50(1H,t,J=7.2 Hz), 6.67(1H,d, J=7.7 Hz), 6.93–7.09(4H,m), 7.17–7.22(1H,m), 7.41–7.71(2H,m), 7.74–7.80(2H,m), 8.36(1H,d,J=4.7 Hz), 8.78(1H,d,J=8.6 Hz), 10.2(0.5H,s), 12.6(0.5H,br).

Working Example No.67

$^1$H-NMR(DMSO-d$_6$)δ:4.62(2H,s), 6.41–6.46(3H,m), 6.95(1H,t, J=7.9 Hz), 7.06(1H,dd,J=7.2 Hz,5.0 Hz), 7.19–7.22(1H,m), 7.50 (1H,d,J=7.2 Hz), 7.74–7.80(2H,m), 8.37(1H,d,J=5.6 Hz), 8.77 (1H,d,J=8.4 Hz), 10.2(0.3H,s), 12.6(0.3H,br).

Working Example No.68

$^1$H-NMR(DMSO-d$_6$)δ:4.91(2H,s), 7.03(1H,dt,J=6.3 Hz,1.1 Hz), 7.17–7.29(2H,m), 7.42(1H,dd,J=7.9 Hz,1.0 Hz), 7.52(1H,d,J=7.2 Hz), 7.73–7.82(3H,m), 8.31(1H,dd,J=4.5 Hz,1.5 Hz), 8.44(1H,dd, J=4.5 Hz,1.8 Hz), 8.79(1H,d,J=8.6 Hz), 10.2(0.3H,s), 12.6(0.2H,br).

Working Example No.69

$^1$H-NMR(DMSO-d$_6$)δ:4.81(2H,s), 7.06(1H,dd,J=7.2 Hz, 5.0 Hz), 7.09–7.22(1H,m), 7.35(1H,dd,J=7.8 Hz,4.8 Hz), 7.49(1H,d, J=6.9 Hz), 7.72–7.80(3H,m), 8.37(1H,d,J=3.9 Hz), 8.48(1H,dd, J=4.8 Hz,1.6 Hz), 8.60(1H,s), 8.76(1H,d, J=8.0 Hz), 10.2(0.3H,s), 12.6(0.3H,br).

Working Example No.70

$^1$H-NMR(DMSO-d$_6$)δ:4.81(2H,s), 7.04(1H,dd,J=6.9 Hz,5.5 Hz), 7.18–7.21(1H,m), 7.33(2H,d,J=5.7 Hz), 7.51 (1H,d,J=7.2 Hz), 7.74–7.81(2H,m), 8.33(1H,d,J=3.9 Hz), 8.51(2H,d,J=6.0 Hz), 8.78(1H,d, J=8.6 Hz), 10.2(0.4H,s), 12.6(0.3H,br).

Working Example No.71

$^1$H-NMR(DMSO-d$_6$)δ:3.82(3H,s), 4.85(2H,s), 7.04(1H, dd,J=6.2 Hz, 1.1 Hz), 7.07–7.21(1H,m), 7.47(2H,d,J=8.5 Hz), 7.51(1H,d, J=7.3 Hz), 7.74–7.80(2H,m), 7.92(2H,d,J=8.5 Hz), 8.34(1H,d, J=4.0 Hz), 8.78(1H,d,J=8.6 Hz), 10.2 (0.2H,s), 12.6(0.2H,br).

Working Example No.72

$^1$H-NMR(DMSO-d$_6$)δ:1.65–1.68(1H,brm), 1.82–1.98 (2H,brm), 2.04–112.14(3H,brm), 4.72–4.76(1H,brm), 5.61 (1H,dd,J=10 Hz,1.2 Hz), 5.82–5.86(1H,m), 7.03–7.06(1H, brm), 7.21–7.27(1H,brm), 7.42–7.45(1H,m), 7.70–7.80(2H, m), 8.36(1H,brs), 8.72–8.74(1H,m), 10.2(0.4H,brs). 12.4 (0.4H,br).

Working Example No.73

$^1$H-NMR(DMSO-d$_6$)δ:0.93–1.11(2H,brm), 1.13–1.16 (3H,brm), 1.63–1.74(6H,brm), 3.42(2H,d,J=6.9 Hz), 7.08 (1H,dt,J=6.2 Hz,1.1 Hz), 7.19–7.23(1H,brm), 7.47(1H,d,J=7.1 Hz), 7.72–7.82(2H,m), 8.38 (1H,d,J=4.9 Hz), 8.75(1H, d,J=8.6 Hz), 10.2(0.5H,s), 12.7(0.4H,br

Working Example No.74

$^1$H-NMR(DMSO-d$_6$)δ:2.28(4H,m), 2.49(4H,m), 4.49 (3H,s), 5.76–5.85(1H,m), 7.04–7.09(1H,m), 7.17–7.21(1H, brm), 7.48(1H,d, J=7.2 Hz), 7.71–7.80(2H,m), 8.35(1H,d, J=4.2 Hz), 8.76(1H,d, J=8.6 Hz), 10.2(0.5H,s), 12.6(0.5H, br).

Working Example No.79

According to the procedure described in the working example No.1, the compound of the reference example No.3 and 2-pyridine carbonylazide was used to afford the titled compound.

$^1$H-NMR(DMSO-d$_6$)δ:1.06–1.20(1H,m), 2.30–2.43(2H, brm), 2.52–2.57(1H,m), 3.28–3.35(1H,m), 3.50–3.60(1H, m), 4.83(1H,dd, J=10 Hz,5.7 Hz), 7.06(1H,dd,J=7.2 Hz,5.1 Hz), 7.28–7.33(2H,m), 7.46(1H,t,J=7.7 Hz), 7.76–7.82(1H, m), 8.29–8.32(2H,m), 9.95 (1H,s), 11.2(1H,br).

mass:309(M+1)$^+$.

Working Example No.80

(1) Ethyl 4-hydroxymethylpicolinate (2.00 g, 11.0 mol) was dissolved in dimethylformamide (80 ml). To the solution, imidazole (1.88 g. 27.0 mmol) and chloro-tert-butyldiphenylsilan (7.60 ml, 27.0 mmol) were added at room temperature. The mixture was stirred for 2 hours at the same temperature. The reaction mixture was diluted with hexane-ethyl acetate (1:1) and washed saturated brine and dried over magnesium sulfate. After filtration, the filtrate was concentrated to afford a residue, which was purified by column chromatography on silica gel. The fraction was eluted with hexane-ethyl acetate (95:5–70:30) to provide a crude compound (4.27 g) as colorless solid.

(2) The compound (3.14 g, 7.40 mmol) obtained in (1) was dissolved in methanol (60 ml). To the solution was added hydrazine monohydrate (1.80 ml, 37.0 mmol) at room temperature. The mixture was stirred for 12 hours at the same temperature. The reaction mixture was concentrated to afford a residue, which was dissolved in chloroform. The organic layer was washed with saturated brine and then concentrated to afford an oily compound, which was used in the next reaction without further purification.

(3) The compound obtained in (2) was dissolved in chloroform (10 ml). To the solution was added 1N hydrochloric acid (22.2 ml, 22.2 mmol) at room temperature. The mixture was cooled in an ice-bath and sodium nitrite (1.02 g, 14.8 mmol) was added at the same temperature. The mixture was stirred for 30 minutes at the same temperature. The reaction mixture was extracted with chloroform. The organic layer was separated and washed with saturated brine and dried over magnesium sulfate. After filtration, the filtrate was concentrated to afford a residue. To the residue, a solution of the compound (0.622 g, 3.30 mmol) obtained in the reference example No.3 in tetrahydrofuran (50 ml) was added at room temperature. The reaction mixture was refluxed over night. The reaction mixture was concentrated to afford a residue, which was purified by column chromatography on silica gel. The fraction eluted with chloroform-tetrahydrofuran (10:0–9:1) provided the compound (2.03 g) as a brown amorphous.

(4) The compound (2.03 g, 3.30 mml) obtained in (3) was dissolved in tetrahydrofuran (10 ml). To the solution was added a solution (6.60 ml) of n-butylammonium fluoride (1.0 M, 6.60 mmol) in tetrahydrofuran at room temperature. The mixture was stirred for 1 hour at the same temperature. The reaction mixture was diluted with tetrahydrofuran, ethyl acetate and then washed with saturated brine. The organic layer was concentrated to afford light yellow crystals by filtration. The filtrate was purified by column chromatography on silica gel. The fraction eluted with chloroform-methanol (100:0–95:5) provided yellow crystals, which were combined with the crystal obtained by filtration to afford the titled compound (1.02 g).

$^1$H-NMR(DMSO-$d_6$)δ:1.07–1.20(1H,m), 2.31–2.44(2H, m), 2.45–2.58(1H,m), 3.28–3.35(1H,m), 3.50–3.60(1H,m), 4.52(2H,d, J=5.6 Hz), 4.83(1H,dd,J=10 Hz,5.3 Hz), 5.47 (1H,t,J=5.7 Hz), 6.99(1 H,d,J=4.7 Hz), 7.26(1H,s), 7.32(1H, d,J=7.5 Hz), 7.47(1H,t,J=7.8H z), 8.23(1H,d,J=5.3 Hz), 8.33 (1H,d,J=7.6 Hz), 9.96(1H,s), 11.4(1H,br).

mass:339(M+1)$^+$.

Working Example No.81

To a solution of the compound (3.50 g) of the reference example No.5 in tetrahydrofuran (35 ml), a solution (7.10 ml) of tetra-n-butylammonium fluoride solution (1.0 M, 7.10 mmol) was added at room temperature. The reaction mixture was stirred for 1 hour at the same temperature. The reaction mixture was concentrated and diluted with ether. The whole was washed with water and saturated brine, and then dried over magnesium sulfate. After filtration the filtrate was concentrated to afford a residue, which was washed with ether to afford the titled compound (1.66 g) as colorless solid.

$^1$H-NMR(DMSO-$d_6$)δ:1.02–1.22(1H,m), 2.26–2.31(2H, brm), 2.46–2.62(1H,m), 2.70(2H,t,J=6.3 Hz), 3.22–3.40(1H, m), 3.48–3.71 (3H,m), 4.71(1H,brt), 4.79–4.90(1H,m), 6.95 (1H,d,J=6.3 Hz), 7.11(1H,s), 7.30(1H,d,J=6.3 Hz), 7.44(1H, t,J=7.9 Hz), 8.19(1H,d, J=6.3 Hz), 8.30(1H,d,J=7.9 Hz), 9.86(1H,s), 11.4(1H,br).

mass:353(M+1)$^+$.

Working Example No.82

(1) The compound (45 mg, 0.13 mmol) of the working example No.80 was dissolved in pyridine (1 ml). To the solution, methanesulfonyl chloride (40 μL 1, 0.52 ml) was added at room temperature. The reaction mixture was stirred for 1 hour at the same temperature. The reaction mixture was made acidic by adding 1N hydrochloric acid. The mixture was extracted with a mixture of ethyl acetate and tetrahydrofuran. The organic layer was washed with 1N hydrochloric acid, saturated sodium hydrogencarbonate and saturated brine successively and then dried over maganesium sulfate. After filtration, the filtrate was concentrated to afford a residue, which was dissolved in dimethylformamide (1 ml). To the solution sodium azide (85 mg, 1.3 mmol) was added at room temperature. The reaction mixture was stirred for 30 minutes at 80° C. The reaction mixture was diluted with chloroform and washed with saturated brine. The organic layer was separated and concentrated to afford a light yellow solid (35 mg), which was used for the next reaction without further purification.

(2) The compound (35 mg) obtained above in (1) was dissolved in a mixture (7 ml) of methanol and tetrahydrofuran (5:2). To the solution, was added 10% palladium carbon catalyst (5 mg) at room temperature. The reaction vessel was filled with hydrogen. The reaction mixture was stirred over night under the hydrogen atomosphere at room temperature. The reaction mixture was filtrated through celite and the filtrate was concentrated. The crystals precipitated were collected by filtration to afford light yellow crystals (13 mg).

$^1$H-NMR(DMSO-$d_6$)δ:1.02–1.10 (1H,m), 2.21–2.60(4H, m), 3.45–3.52 (2H,m), 4.06–4.09(2H,m), 4.79–4.85(1H,m), 5.16–5.20(1H,m), 6.93(1H,d,J=5.9 Hz), 7.20(1H,s), 7.26 (1H,d,J=7.6 Hz), 7.39–7.45 (1H,m), 8.10(1H,d,J=4.9 Hz), 8.27(1H,d,J=7.7 Hz), 10.3(1H,br), 11.7(1H,br).

mass:338(M+1)$^+$.

Working Example No.83

The compound (260 mg) of the reference example No.9 was dissolved in a solution (10 ml) of methanol and tetrahydrofuran (1:1). 10% palladium carbon catalyst (200 mg) was added to the solution at room temperature. The reaction vessel was filled with hydrogen. The reaction mixture was stirred overnight under the hydrogen atomosphere at room temperature. The insoluble material was filtered and the filtrate was concentrated to afford the titled compound (105 mg).

$^1$H-NMR(DMSO-$d_6$)δ:1.01–1.22(1H,m), 2.28–2.40(3H, brm), 2.62–2.72(2H,m), 2.80–2.88(2H,m), 3.18(2H,s), 3.45–3.60(2H,m), 4.82(1H,dd,J=9.8 Hz,6.2 Hz), 6.95(1H,d, J=6.2 Hz), 7.12(1H,s), 7.30(1H,d,J=6.8 Hz), 7.45(1H,t,J=7.4 Hz), 8.20(1H,d,J=5.5 Hz), 8.30(1H,d,J=6.2 Hz), 9.94(1H, br), 11.4(1H,br).

mass:352(M+1)$^+$.

Working Example No.84

(1) The compound (1.02 g, 3.02 mmol) of the working example No.80 was dissolved in a solution (90 ml) of dimethylformamide-tetrahydrofuran (1:8). To the solution was added manganese dioxide (3.92 g, 45.1 mmol) at room temperature. The reaction mixture was stirred for 6 hours at the same temperature. The reaction mixture was filtrated by celite and filtrate was concentrated. The crystals precipitated were collected by filtration to afford yellow crystals (0.211 g).

(2) The compound (34 mg, 0.10 mmol) obtained above in (1) and n-butylamine (22 mg, 0.30 mmol) were dissolved in chloroform (5 ml). To the solution was added sodium triacetoxyborohydride (212 mg, 1.0 mmol) at room temperature. The reaction mixture was stirred for 24 hours at the same temperature. The reaction mixture was neutralized with 3N hydrochloric acid and extracted with chloroform. The organic layer was washed with saturated brine and dried over magnesium sulfate and then concentrated. The crystals precipitated were collected by filtration to affod the titled compound (13 mg).

¹H-NMR(DMSO-d₆)δ:0.88(3H,t,J=7.3 Hz), 1.08–1.17 (1H,m), 1.28–1.38(2H,m), 1.42–1.51(2H,m), 2.31–2.39(3H, m), 2.47–2.54 (2H,m), 2.59(2H,t,J=7.2 Hz), 3.50–3.57(1H, m), 3.81(2H,s), 4.83(1H,dd,J=11 Hz,5.5 Hz), 7.09(1H,d,J= 5.3 Hz), 7.31–7.33 (2H,m), 7.47(1H,t,J=7.9 Hz), 8.26(1H, d,J=5.3 Hz), 8.31(1H,d, J=8.1 Hz), 9.98(1H,s), 11.2(1H,br).

mass:394(M+1)⁺.

Working Examples No.85 to 94

According to the procedure described in working example No.84, the compounds from the working examples No.85 to No.94 were prepared.

Working Example No.85

¹H-NMR(DMSO-d₆)δ:1.11–1.18(1H,m), 2.22–2.44(5H, m), 2.58(2H,t, J=5.8 Hz), 3.46–3.58(3H,m), 3.73(2H,s), 4.51(1H,t,J=5.4 Hz), 4.84(1H,dd,J=10 Hz.5.6 Hz), 7.05(1H, d, J=5.4 Hz), 7.26(1H,s), 7.33(1H,d,J=7.4 Hz), 7.48(1H,t, J=7.9 Hz), 8.24(1H,d,J=5.3 Hz), 8.34(1H,d,J=8.2 Hz), 9.93 (1H,s), 11.4 (1H,br).

mass:382(M+1)⁺.

Working Example No.86

¹H-NMR(DMSO-d₆)δ:1.06–1.20(1H,m), 2.28–2.43(2H, m), 2.48–2.60(1H,m), 3.00(1H,br), 3.28–3.40(1H,m), 3.50–3.60(1H,m), 3.71(4H,s), 4.83(1H,m), 7.06(1H,d,J=4.6 Hz), 7.25(1H,d,J=7.4 Hz), 7.29–7.39(6H,m), 7.46(1H,t,J= 7.4 Hz), 8.23(1H,d,J=5.5 Hz), 8.34(1H,d,J=7.4 Hz), 9.97 (1H,s), 11.5(1H,br).

mass:428(M+1)⁺.

Working Example No.87

¹H-NMR(DMSO-d₆)δ:1.06–1.20(1H,m), 2.29–2.43(2H, m), 2.49–2.60 (1H,m), 3.32(2H,s), 3.49(2H,s), 3.53–3.60 (1H,m), 3.64(2H,s), 4.83(1H,dd,J=11 Hz,5.6 Hz), 4.91(2H, s), 6.51(2H,d,J=8.3 Hz), 6.99(1H,d,J=8.2 Hz), 7.04(2H,d,J= 5.4 Hz), 7.26(1H,s), 7.32(1H,d, J=7.4 Hz), 7.47(1H,t,J=7.8 Hz), 8.22(1H,d,J=5.4 Hz), 8.33(1H,d,J=8.1 Hz), 9.94(1H,s), 11.5(1H,br).

mass:443(M+1)⁺.

Working Example No.88

¹H-NMR(DMSO-d₆)δ:1.07–1.18(1H,m), 2.32–2.44(2H, m), 2.51–2.66(5H,m), 3.28–3.40(2H,m), 3.54–3.61(1H,m), 3.72(2H,s), 4.82(3H,s), 6.48(2H,d,J=8.2 Hz), 6.86(2H,d,J= 8.2 Hz), 7.03 (1H,d, J=5.2 Hz), 7.24(1H,s), 7.32(1H,d,J=7.3 Hz), 7.48(1H,t,J=7.6 Hz), 8.22(1H,d,J=5.0 Hz), 8.34(1H,d, J=8.3 Hz), 9.94(1H,s), 11.4(1H,br).

mass:457(M+1)⁺.

Working Example No.89

¹H-NMR(DMSO-d₆)δ:1.12–1.21(1H,m), 2.33–2.42(2H, m), 2.50–2.59(2H,m), 2.90–3.15(1H,br), 3.51–3.58(1H,m), 3.70(2H,s), 3.77(2H,s), 4.84(1H,dd,J=11 Hz,5.6 Hz), 7.08 (1H,d,J=5.3 Hz), 7.28–7.46(4H,m), 7.48(1H,t,J=7.8 Hz), 7.57(2H,d,J=8.2 Hz), 7.79(2H, d,J=8.3 Hz), 8.25(1H,d,J=5.3 Hz), 8.34(1H,d,J=8.2 Hz), 9.96(11H,s) 11.4(1H,br).

mass:507(M+1)⁺.

Working Example No.90

¹H-NMR(DMSO-d₆)δ:1.08–1.15(1H,m), 2.30–2.57(5H, m), 2.71–2.83(4H,m), 3.48–3.55(1H,m), 3.71(2H,s), 4.78–4.83(1H,m), 6.99(1H,d,J=5.3 Hz), 7.23–7.25(3H,m), 7.30(1H,d,J=7.6 Hz), 7.39(2H,d,J=8.0 Hz). 7.45(1H,t,J=7.8 Hz), 7.71(2H,d,J=7.9 Hz), 8.20(1H,d,J=4.9 Hz), 8.31(1H,d, J=8.0 Hz), 9.91(1H,s), 11.4(1H,br).

mass:521(M+1)⁺.

Working Example No.91

¹H-NMR(DMSO-d₆)δ:1.05–1.18(1H,m), 2.26–2.40(2H, m), 2.46–2.60(2H,m), 3.00(1H,br), 3.50–3.58(1H,m), 3.69 (2H,s), 3.71 (2H,s), 4.82(1H,dd,J=10 Hz,5.9 Hz), 7.05(1H, d,J=5.3 Hz), 7.31(2H, d,J=7.5 Hz), 7.38(2H,d,J=5.5 Hz), 7.46(1H,t,J=7.9 Hz), 8.23(1H,d, J=5.4 Hz), 8.32(1H,d,J=8.1 Hz), 8.50(2H,d,J=5.9 Hz), 9.95(1H,s), 11.4(1H,br).

mass:429(M+1)⁺.

Working Example No.92

¹H-NMR(DMSO-d₆)δ:1.03–1.17(1H,m), 2.28–2.40(3H, m), 2.47–2.54 (1H,m), 2.73(4H,s), 3.26–3.34(1H,m), 3.50–3.58(1H,m), 3.70 (2H,s), 4.80(1H,dd,J=11 Hz,5.6 Hz), 6.98(1H,d,J=5.5 Hz), 7.23 (2H,d,J=6.1 Hz), 7.23(1H,s), 7.29(1H,d,J=6.6 Hz), 7.44(1H,t,J=7.8 Hz), 8.19(1H,d,J=5.3 Hz), 8.30(1H,d,J=7.3 Hz), 8.42(2H,d,J=5.9H z), 9.91(1H,s), 11.4(1H,br).

mass:443(M+1)⁺.

Working Example No.93

¹H-NMR(DMSO-d₆)δ:1.05–1.25(1H,m), 2.27–2.644H, m), 3.20–3.41 (3H,m), 3.49–3.60(2H,m), 4.24(2H,brm), 4.84–4.92(1H,m), 7.33–7.63(6H,m), 8.29(1H,d,J=7.7 Hz), 8.40(1H,d,J=5.5 Hz), 9.08(1H,s), 9.85(2H,brm), 10.3(1H,s), 10.7(1H,brm).

mass:432(M+1)⁺.

Working Example No.94

¹H-NMR(DMSO-d₆)δ:0.99–1.14(5H,m), 1.75–1.85(4H, m), 2.25–2.38 (3H,m), 2.47–2.55(1H,m), 3.26–3.35(2H,m), 3.48–3.57(1H,m), 3.71(2H,s), 4.44(1H,d,J=4.4 Hz), 4.81 (11H,dd,J=10 Hz, 5.6 Hz), 7.02(1H,d,J=5.5 Hz), 7.23(1H,s), 7.29(1H,d,J=7.4 Hz), 7.45(1H,t,J=7.7 Hz), 8.19(1H,d,J=5.3 Hz), 8.30(1H,d,J=8.2 Hz), 9.90(1H,s), 11.4(1H,br).

mass:436(M+1)⁺.

Working Example No.95

According to the procedure described in working example No.96, tert-butyl N-(2-aminoethyl) carbamate was used to afford the titled compound.

¹H-NMR(DMSO-d₆)δ:1.01–1.15(1H,m), 2.25–2.61(3H, brm), 2.97–3.03(2H,brm), 3.14–3.35(6H,brm), 3.50–3.59 (1H,m), 3.80–4.00 (1H,brm), 4.80–4.86(1H,m), 7.05(1H, brd), 7.25–7.34(2H,m), 7.46(1H,dd), 8.21–8.30(4H,m), 9.48 (2H,br), 10.2(1H,brs), 10.9 (1H,br).

mass:395(M+1)⁺.

Working Example No.96

(1) A solution of 4-nitrobenzenesulfonylchloride (844 mg, 3.81 mmol) in chloroform (9 ml) was cooled in an ice-bath. Triethylamine (0.531 ml, 3.81 mmol) was added to the solution. The reaction mixture was warmed up to room temperature. A solution (0.3 ml) of n-propylamine (10 μL 1, 0.122 mmol) in chloroform was added to the solution (0.3 ml) at room temperature. The reaction mixture was stirred overnight at the same temperature. The reaction mixture was purified by TLC eluted with chloroform-methanol(19:1) to afford the titled compound.

(2) To the compound obtained in (1), a solution of the compound (38 mg) of the reference example No.7 and triphenylphosphine (29 mg, 0.111 mmol) in chloroform (0.6 ml) was added. A 40% solution (0.047 ml, 0.108 mmol) of diethylazodicarboxylate in toluene was added to the reaction mixture. The reaction mixture was stirred for 3 days at room temperature. The reaction mixture was purified by TLC eluted with chloroform-methanol (19:1) to afford the titled compound.

(3) The compound obtained in (2) was dissolved in dimethylformamide (1 ml). To the solution, sodium carbonate (35 mg, 0.330 mmol) and thiophenol (11 µl, 0.107 mmol) were added at room temperature. The reaction mixture was stirred for 1 day at the same temperature. The insoluble material was filtated and the filtrate was dissolved in tetrahydrofuran (3 ml). To the reaction mixture, 1N hydrochloric acid (1 ml) was added at room temperature. The whole was stirred for one hour at room temperature. The reaction mixture was concentrated to provide a residue, which was boiled with toluene by heating. To the mixture, methanol-ether was added to afford the titled compound.

$^1$H-NMR(DMSO-d$_6$)δ:0.93(3H,t,J=7.5 Hz), 1.03–1.17 (1H,m), 1.58–1.70(2H,m), 2.26–2.40(2H,brm), 2.55–2.65 (1H,brm), 2.85–2.95 (2H,brm), 2.96–3.03(2H,m), 3.12–3.22 (2H,brm), 2.28–2.35(1H, m), 3.50–3.60(1H,m), 4.80–4.86 (1H,m), 7.06(1H,d,J=5.2 Hz), 7.30–7.35(2H,m), 7.48(1H,t, J=7.9 Hz), 8.27–8.32(2H,m), 8.86(2H, br), 10.4(1H,brs), 10.9(1H,br).

mass:394(M+1)$^+$.

Working Examples No.97 and 98

According to the procedure described in the working example No.96, the compounds of the working example No.97 and No.98 were prepared.

Working Example No.97

$^1$H-NMR(DMSO-d$_6$)δ:0.89(3H,t,J=7.8 Hz), 1.01–1.17 (1H,m), 2.26–2.40(2H,m), 2.52–2.63(2H,m), 2.26–2.39(2H, m), 2.50–2.61 (1H,m), 2.88–3.00(4H,m), 3.10–3.21(2H,m), 3.26–3.34(1H,m), 3.50–3.60(1H,m), 4.80–4.86(1H,m), 7.02 (1H,d,J=4.6 Hz), 7.26–7.34(2H,m), 7.46(1H,t,J=7.8 Hz), 8.26–8.30(2H,m), 8.80(2H,m), 10.2(1H,s), 11.0(1H,br).

mass:408(M+1)$^+$.

Working Example No.98

$^1$H-NMR(DMSO-d$_6$)δ:0.86(3H,t), 1.00–1.20(1H,m), 1.21–1.34 (4H,m), 1.54–1.66(2H,m), 2.26–2.38(2H,m), 2.40–2.63(1H,m), 2.85–3.00(4H,m), 3.08–3.23(2H,m), 3.26–3.35(1H,m), 3.50–3.60 (1H,m), 4.80–4.86(1H,m), 7.03(1H,d,J=4.3 Hz), 7.26–7.35(2H,m), 7.46(1H,t,J=7.8 Hz), 8.26–8.30(2H,m), 8.81(2H,brm), 10.3(1H,s), 11.0(1H, br).

mass:422(M+1)$^+$.

Working Example No.99

According to the procedure described in the working example No.96, glycolaldehydediethylacetal was used to afford the titled compound.

$^1$H-NMR(DMSO-d$_6$)δ:1.05–1.15(1H,m), 2.25–2.40(3H, m), 2.43–2.63 (1H,m), 2.90–3.37(6H,m), 3.48–3.60(1H,m), 4.77–4.85(1H,m), 6.97–7.02(1H,m), 7.23–7.34(2H,m), 7.40–7.50(1H,m), 8.23–8.32(2H,m), 8.66(0.5H,brm), 9.00–9.23(1H,brm), 10.1(1H,s), 11.0(1H,br).

mass:394(M+1)$^+$.

Working Example No.100

According to the procedure described in the working example No.96, glycine tert-butyl ester was used to afford the titled compound.

$^1$H-NMR(DMSO-d$_6$)δ:1.03–1.10(1H,m), 2.23–2.40(2H, brm), 2.54–2.65(1H,brm), 2.97–3.05(2H,brm), 3.17–3.40 (3H,m), 3.50–3.59(1H,m), 3.94(2H,brs), 4.81–4.86(1H,m), 7.03(1H,d,J=5.5 Hz), 7.28–7.34(2H,m), 7.46(1H,t,J=7.8 Hz), 8.26(2H,d,J=6.5 Hz), 9.23(2H,br), 10.4(1H,br), 10.9 (1H,br).

mass:466(M+1)$^+$.

Working Examples No.101 to 108

According to the procedure described in the working example No.96, the compounds from the working example No.101 to 108 were prepared.

Working Example No.101

$^1$H-NMR(DMSO-d$_6$)δ:1.03–1.15(1H,m), 2.25–2.63(3H, m), 2.95–3.05 (2H,m), 3.19–3.37(3H,m), 3.50–3.61(1H,m), 4.10–4.19(2H,m), 4.80–4.86(1H,m), 5.26(2H,s), 7.00(1H,d, J=5.5 Hz), 7.28–7.49(8H,m), 8.26–8.32(2H,m), 9.37(2H, brm), 10.2(1H,s), 10.9 (1H,br).

mass:500(M+1)$^+$.

Working Example No.102

$^1$H-NMR(DMSO-d$_6$)δ:1.03–1.17(1H,m), 2.26–2.63(3H, brm), 2.97–3.05(2H,brm), 3.10–3.21(2H,brm), 3.26–3.37 (1H,brm), 3.50–3.60(1H,m), 3.78(3H,s), 4.06–4.17(2H, brm), 4.80–4.88(1H,m), 6.98–7.03(3H,m), 7.26(1H,brm), 7.34(1H,d,J=8.3 Hz), 7.43–7.50(3H,m), 8.25–8.30(2H,m), 9.18(2H,brm), 10.3(1H,brs), 10.9(1H,br).

Working Example No.103

$^1$H-NMR(DMSO-d$_6$)δ:1.02–1.18(1H,m), 2.25–2.40(3H, m), 2.44–2.63(2H,m), 3.06–3.09(2H,m), 3.25–3.35(3H,m), 3.50–3.59 (1H,m), 4.82–4.88(1H,m), 7.04(1H,dd,J=6.0 Hz,1.1 Hz), 7.30–7.35(2H,m), 7.45–7.55(3H,m), 7.92(1H,t), 8.28(2H,d,J=7.0 Hz), 8.67(1H,m), 9.39(2H,brm), 10.4(1H, brm), 10.9(1H,br).

mass:443(M+1)$^+$.

Working Example No.104

$^1$H-NMR(DMSO-d$_4$)δ:1.01–1.15(1H,m), 2.30–2.40(3H, m), 2.41–2.56 (1H,m), 2.57–2.64(1H,m), 3.04–3.11(2H,m), 3.20–3.36(3H,m), 3.50–3.59(1H,m), 4.82–4.87(1H,m), 7.07 (1H,d,J=6.6 Hz), 7.31–7.35(2H,m), 7.48(1H,t,J=7.8 Hz). 7.83–7.90(1H,m), 8.25–8.29 (2H,m), 8.46(1H,d), 8.83(1H, dd,J=5.3 Hz,1.3 Hz), 8.98(1H,s), 9.79 (2H,brm), 10.3(1H, br), 10.9(1H,br).

mass:443(M+1)$^+$.

Working Example No.105

$^1$H-NMR(DMSO-d$_6$)δ:1.03–1.17(1H,m), 2.26–2.40(2H, m), 2.50–2.65 (1H,m), 3.05–3.15(2H,m), 3.21–3.37(3H,m), 3.50–3.61(1H,m), 4.40–4.45(2H,m), 4.81–4.89(1H,m), 7.05 (1H,d,J=4.6 Hz), 7.25–7.35(2H,m), 7.46(1H,t,J=8.3 Hz), 7.99(2H,d,J=7.4 Hz), 8.28(2H,d, J=7.4 Hz), 8.86(2H,d,J=6.5 Hz), 9.90–10.0(2H,m), 10.3(1H,s), 10.9(1H,br).

mass:443(M+1)$^+$.

Working Example No.106

$^1$H-NMR(DMSO-d$_6$)δ:1.03–1.17(1H,m), 2.25–2.37(2H, m), 2.40–2.60(1H,m), 2.91–3.01(4H,m), 3.14–3.35(5H,m), 3.49–3.59 (1H,m), 4.80–4.85(1H,m), 7.02(1H,d,J=5.3 Hz), 7.26–7.37 (7H,m), 7.46(1H,t), 8.26–8.29(2H,m), 8.94(2H, brm), 10.2(1H, s), 11.0(1H,br).

mass:456(M+1)$^+$.

Working Example No.107

$^1$H-NMR(DMSO-d$_6$)δ:1.03–1.17(1H,m), 2.26–2.50(3H, brm), 2.54–2.63(1H,brm), 2.83(2H,t), 3.00(2H,t), 3.06–3.23 (3H,brm), 3.26–3.37(1H,m), 3.50–3.58(11H,m), 4.80–4.86 (1H,m), 6.72(2H,d, J=8.3 Hz), 7.05(3H,d,J=8.3 Hz), 7.28–7.35(2H,m), 7.46(1H,t,J=7.8 Hz), 8.26–8.32(2H,m), 8.94(2H,brm), 10.3(1H,s), 11.0(1H,br).

mass:472(M+1)$^+$.

Working Example No.108

$^1$H-NMR(DMSO-d$_6$)d:1.05–1.15(1H,m), 2.26–2.40(2H, brm) 2.43–2.63(2H,brm), 2.98–3.06(2H,m), 3.20–3.43(6H, brm), 3.50–3.65 (1H,m), 4.81–4.88(1H,m), 7.03(1H,d,J=5.5 Hz), 7.30–7.35(2H,m), 3.45–3.50(1H,m), 7.95(2H,d,J=5.5 Hz), 8.28(2H,d, J=5.5 Hz), 8.86(2H,d,J=5.5 Hz), 8.72(2H, brm), 10.2(1H,s), 10.9(1H,br).

mass:457(M+1)$^+$.

Working Example No.109

According to the procedure described in the reference example No.8, the titled compound (80 mg) was obtained.

$^1$H-NMR(DMSO-d$_6$)δ:1.03–1.25(2H,m), 2.26–2.43(2H, brm), 2.50–2.65(1H,m), 2.57(6H,s), 2.88–3.06(3H,m), 3.26–3.40(1H,m), 3.50–3.59(1H,m), 4.82–4.86(1H,m), 7.00 (1H,d,J=5.5 Hz), 6.26–6.34 (2H,m), 7.46(1H,t,J=7.8 Hz), 8.23(1H,d,J=5.5 Hz), 8.30(1H,d,J=8.3 Hz), 10.0(1H,s), 10.5 (0.5H,br), 11.1(1H,br).

mass:380(M+1)$^+$.

Working Example No.110

To a solution of the compound (30 mg, 0.038 mmol) of the reference example No.11 in chloroform (1 ml), n-butanoylchloride (6 μl, 0.058 mmol) and triethylamine (13 μl, 0.093 mmol) were added at room temperature. The reaction mixture was stirred for 1 hour at the same temperature. To the reaction mixture, n-butanoyl chloride (6 μl, 0.058 mmol) and triethylamine (10 μl, 0.072 mmol) were added at room temperature. The reaction mixture was stirred for 10 minutes at the same temperature. To the reaction mixture, water (1 ml) was added and the organic layer was separated. The organic layer was washed with water (1 ml) and dried over magnesium sulfate. After filtration, the filtrate was concentrated to give a residue, which was dissolved in tetrahydrofuran (1 ml). To the mixture, 1N hydrochloric acid (1 ml) was added at room temperature. The reaction mixture was stirred for 15 minutes at the same temperature. The reaction mixture was concentrated to afford a residue, to which methanol-ether was added. The titled compound precipitated was obtained.

$^1$H-NMR(DMSO-d$_6$)δ:0.80(3H,t,J=7.8 Hz), 1.03–1.15 (1H,m), 1.42–1.54(2H,m), 2.00(2H,t,J=6.9 Hz), 2.25–2.40 (2H,brm), 2.55–2.63 (1H,brm), 2.70–2.78(2H,brm), 3.28–3.39(3H,brm), 3.50–3.60(1H, brq), 4.80–4.86(1H,m), 7.01(1H,d,J=4.6 Hz), 7.14(1H,s), 7.34 (1H,d,J=8.3 Hz), 7.48(1H,t,J=7.8 Hz), 7.88(2H,brm), 8.23(1H,d,J=4.6 Hz), 8.26(1H,d,J=8.3 Hz), 10.4(1H,br), 11.1(1H,br).

mass:422(M+1)$^+$.

Working Examples No.111 to 114

According to the procedure described in the working example No.110, the compounds from the working example No.111 to 114 were prepared.

Working Example No.111

$^1$H-NMR(DMSO-d$_6$)δ:1.00–1.23(1H,m), 2.26–2.60(3H, m), 2.70(2H, br), 3.15(2H,br), 3.40–3.60(2H,m), 4.34(2H,s), 4.80–4.90(1H, m), 6.97(1H,d,J=4.9 Hz), 7.15(1H,s), 7.30 (1H,d,J=8.0 Hz), 7.40–7.52(6H,m), 8.23(1H,d,J=4.3 Hz), 8.30(1H,d,J=8.0 Hz), 8.54–8.63(1H,m), 9.94(1H,s), 11.4 (1H,br).

mass:470(M+1)$^+$.

Working Example No.112

$^1$H-NMR(DMSO-d$_6$)δ:1.00–1.20(1H,m), 2.26–2.40(2H, m), 2.41–2.60(1H,m), 2.83(2H,brt), 3.15(1H,s), 3.20–3.40 (1H,m), 3.43–3.57(2H,m), 4.75–4.86(1H,m), 6.97(1H,d,J= 7.6 Hz), 7.15(1H,s), 7.30(1H,d,J=11 Hz), 7.40–7.52(4H,m), 7.80(2H,d,J=10 Hz), 8.21 (1H,d,J=6.7 Hz), 8.30(1H,d,J=11 Hz), 8.59(1H,brt), 9.94(1H,s),11.4(1H,br).

mass:456(M+1)$^+$.

Working Example No.113

$^1$H-NMR(DMSO-d$_6$)δ:1.06–1.20(1H,m), 2.25–2.41(2H, m), 2.72(2H.

t), 3.10–3.20(2H,m), 3.26–3.42(1H,m), 3.48–3.60(1H,m), 3.75–3.90(1H,m), 4.36(2H,s), 4.80–4.86(1H,m), 6.99 (1H,d,J=5.7 Hz), 7.13(1H,s), 7.19–7.40(7H,m), 7.46 (1H,t,J=7.6 Hz), 8.23(1H,d, J=3.8 Hz), 8.28(1H,d,J=8.6 Hz), 10.0(1H,s), 11.2(1H,br).

Working Example No.114

$^1$H-NMR(DMSO-d$_6$)δ:1.43–1.60(1H,m), 2.50–3.00(3H, brm), 3.03–3.15(2H,brm), 3.34–3.48(2H,brm), 3.65–3.80 (1H,brm), 3.85–4.00(1H,m), 5.17–5.26(1H,m), 7.31(1H,d, J=5.4 Hz), 7.46(1H, s), 7.72(1H,dd,J=6.8 Hz,0.6 Hz), 7.87 (1H,t), 7.94–8.03(3H, m), 8.10–8.20(3H,m), 8.58(1H,d,J= 4.7 Hz), 8.70(1H,d,J=8.1 Hz), 10.4(1H,s), 11.7(1H,br).

mass:492(M+1)$^+$.

Working Example No.115

According to the procedure described in the working example No.96(1), the compound of the working example No.83 was used to afford the titled compound.

$^1$H-NMR(DMSO-d$_6$)δ:1.04–1.19(1H,m), 2.26–2.41(2H, m) 2.48–2.60(1H,m), 2.66–2.74(2H,m), 3.10–3.20(2H,m), 3.28–3.39 (1H,m), 3.51–3.59(1H,m), 4.79–4.82(1H,m), 6.90(1H,d,J=4.6 Hz), 7.01(1H,s), 7.32(1H,d,J=8.3 Hz), 7.46 (1H,t,J=8.3 Hz), 7.97 (2H,d,J=9.2 Hz), 8.17(2H,m), 8.29–8.37(3H,m), 9.90(1H,s), 11.2 (1H,br).

mass:537(M+1)$^+$.

Working Example No.116

According to the procedure described in the working example No.56, phenol and the compound of the reference example No.7 were used to afford the compound, which was subjected to the similar manner to that described in the working example No.124 to provide the titled compound.

$^1$H-NMR(DMSO-d$_6$)δ:1.08(1H,t,J=7.4 Hz), 2.25–2.40 (2H,m), 2.60–2.69(1H,m), 3.10(2H,t,J=5.5 Hz), 3.25–3.35 (1H,m), 3.54(1H,q, J=9.2 Hz), 4.25(2H,t,J=5.5 Hz), 4.80–4.86(1H,m), 6.92(1H,d, J=12 Hz), 6.94(2H,d,J=7.4 Hz), 7.20(1H,d,J=5.5 Hz), 7.25–7.37 (4H,m), 7.48(1H,t,J= 7.4 Hz), 8.23–8.28(2H,m), 10.5–11.0(2H,br).

mass:429(M+1)$^+$.

Working Example No.117

(1) To a solution of 3-amino-5-phenylpyrazole (544 mg, 3.4 mmol) in dimethylformmamide (10 ml), sodium hydride (64 mg, 4.1 mmol), benzylchloride (0.45 ml, 3.8 mmol) were added at room temperature. The reaction mixture was stirred for 6 hours at room temperature. Saturated aqueous ammonium chloride was added and extracted with ethyl acetate. The organic layer was separated and washed with water and saturated brine and dried over magenisum sulfate. After filtration, the filtrate was concentrated to afford a residue, which was purified by column chromatography on silica gel. The fraction eluted with hexane-ethyl acetate (4:1) provided the titled compound (509 mg).

(2) To a solution of the compound (509 mg, 2.0 mmol) obtained in (1) in pyridine (5.0 ml) was added methyl chloroformate (0.19 ml, 2.5 mmol) at room temperature. The mixture was stirred for 2 hours at room temperature. To the reaction mixture, 1N hydrochloric acid was added. The mixture was extracted with ethyl acetate. The organic layer was separated and washed with saturated sodium hydrogencarbonate, saturated brine and then dried over magnesium sulfate. After filtration, the filtrate was concentrated to afford a residue, which was purified by column chromatography on silica gel. The fraction eluted with hexane-ethyl acetate (4:1–2:1) provided the titled compound (450 mg).

(3) To a solution of the compound (440 mg, 1.4 mmol) obtained in (2) in toluene (5.0 ml), triethylamine (0.40 ml, 2.9 mmol) was added. The mixture was stirred for 10 minutes at 80° C. B-chlorocatecolboran (450 mg, 2.9 mmol) was added and the mixture was stirred for 10 minutes at the same temperature. The compound (290 mg, 1.5 mmol) of the reference example No.3 was added and the mixture was stirred for 30 minutes at the same temperature. B-chlorocatecolboran (440 mg, 2.9 mmol) was added and the mixture was stirred for 1 hour at 100° C. To the reaction mixture 1N hydrochloric acid was added. The mixture was extracted with chloroform. The organic layer was separated and washed with 1N sodium hydroxide, saturated brine and dried over magnesium sulfate. After filtration, the filtrate was concentrated to afford a residue. To the residue, was added chloroform-ether to afford the crystal (400 mg) by filtration.

(4) The compound (400 mg, 0.87 mmol) obtained in (3), was dissolved in methanol-tetrahydrofuran (1:1, 20 ml). 10% paradium carbon catalyst (200 mg) was added. The reaction vessel was filled with hydrogen and the mixture was stirred overnight at 50° C. The reaction mixture was filtrated by celite. The filtrate was concentrated to afford a residue. To the residue, ether-ethyl acetate was added to provide cystals as the titled compound (220 mg).

$^1$H-NMR(DMSO-d$_6$)δ:1.02–1.10(1H,m), 2.27–2.37(2H, brm), 2.62–2.67(1H,brm), 3.26–3.37(1H,m), 3.48–3.57(1H, m), 4.75(1H,dd. J=11 Hz,5.7 Hz), 6.60(1H,brs), 7.28(1H,d, J=7.5 Hz), 7.30–7.48 (4H,m), 7.73(2H,d,J=7.3 Hz), 8.26 (1H,d,J=8.2 Hz), 9.61(1H,s), 12. 8(1H,br).

Working Example No.118

(1) A mixture of α-cyano-o-iodoacetophenone (3.81 g, 13.3 mmol), benzylhydrazine 2 hydrogen chloride (7.80 g, 40.0 mmol), triethylamine (18.0 ml, 129 mmol) and n-butanol (50 ml) was stirred overnight at 120° C. The raction mixture was cooled to room temperature and concentrated to afford a residue. The residue was dissolved in ether. The solution was washed with water and then dried over magnesium sulfate. After filtration, the filtrate was concentrated to afford a residue, which was purified by column chromatography on silica gel. The fraction eluted with hexane-ethyl acetate (5:1–2:1) provided the compound (2.61 g) as light yellow crystals.

(2) A mixture of the compound (1.23 g, 3.27 mmol) obtained in (1), p-nitrophenyl chloroformate (0.859 mg, 4.26 mmol), 4-dimethylaminopyridine (1.00 g, 8.19 mmol) and chloroform (10 ml) was stirred for 30 minutes at room temperature. To the reaction mixture, the compound (0.920 g, 4.96 mol) prepared in the reference example No.3 was added. The reaction mixture was stirred overnight at 100° C. The reaction mixture was diluted with chloroform. The whole was washed with 1N sodium hydroxide, 1N hydrochloric acid and saturated brine respectively and then dried over magnesium sulfate. After filtration, the filtrate was concentrated to afford a residue, which was purified by column chromatography on silica gel. The fraction eluted with chloroform-methanol (98:2–97:3) provided yellow solid (1.60 g).

(3) The compound (236 mg, 0.461 mmol) obtained in (2), pallolium acetate (11 mg, 0.0490 mmol), 1,1-bis (diphenylphosphino)ferrocene (30 mg, 0.0541 mmol) and sodium hydrogencarbonate (71 mg, 0.845 mmol) were mixted with methanol (4 ml) and the reaction vessel was filled with carbon monoxide. The reaction mixture was refluxed for 7 hours. The reaction mixture was filtrated by celite. The filtrate was concentrated to afford a residue, which was purified by column chromatography on silica gel. The fraction eluted with chloroform-methanol (98:2–97:3) provided a yellow solid (180 mg).

(4) The compound (40 mg) obtained above in (3) was dissolved in ethanol (5 ml). To the solution, palladium hydroxide (10 mg) was added at room temperature. The reaction vessel was filled with hydrogen. The reaction mixture was stirred overnight at 70° C. The reaction mixture was filtered through celite. The filtrate was concentrated to afford a residue, which was purified by column chromatography on silica gel. The fraction eluted with chloroform-methanol (10:1) provided the titled compound (8.6 mg).

$^1$H-NMR(DMSO-d$_6$)δ:1.03–1.15(1H,m), 2.25–2.40(2H, m), 2.62–2.77(1H,m), 3.43–3.58(2H,m), 3.73(3H,s), 4.74–4.78(1H,m), 6.25(1H,m), 7.27(1H,d,J=7.6 Hz), 7.41–7.74(5H,m), 8.23–8.26 (1H,m), 8.31(1H,s), 9.59(1H, s).

mass:432(M+1)$^+$.

Working Example No.119

(1) The compound (140 mg, 0.268 mmol) obtained from the working example No.118(3) was dissolved in methanol (3 ml). To the solution was added 1N sodium hydroxide (1.00 ml, 1.00 mmol) at room temperature. The reaction mixture was stirred for a while at room temperature and furtherly stirred for 2 hours at 50° C. The reaction mixture was made acidic by adding 1N hydrochloric acid. The whole was concentrated to afford a residue, which was dissolved in chloroform. The solution was washed with water. The aqueous layer was further extracted with chloroform twice. The organic layers were combined and dried over magnesium sulfate. After filtration, the filtrate was concentrated to afford a residue. Adding ether and chloroform to the residue resulted in the formation of the crystals. After filtration, the crystals (73 mg) were collected.

(2) The compound (36 mg, 0.0699 mmol) obtained above in (1) was dissolved in ethanol (4 ml). To the solution, palladium hydroxide (10 mg) was added. The reaction vessel was filled with hydrogen and the reaction mixture was stirred overnight at 70° C. The reaction mixture was filtrated by celite. The filtrate was concentrated to afford a residue. Ether and chloroform were added to the residue to afford the titled compound (13 mg) as crystals.

¹H-NMR(DMSO-d₆)δ:1.01–1.14(1H,m), 2.25–2.34(2H, m), 2.65–2.68(1H,m), 3.35–3.53(2H,m), 4.74(1H,dd,J=10 Hz.5.8 Hz), 6.34(1H,br), 7.27(2H,d,J=7.5 Hz), 7.43(2H,t,J=7.8 Hz), 7.54(1H,d,J=3.8 Hz), 7.70(1H,d,J=7.4 Hz), 8.26 (1H,d,J=8.1 Hz), 9.59(1H,s).

mass:418(M+1)⁺.

Working Example No.120

(1) According to the procedures described in the working example No.118(1) to (3), a-cyano-m-iodoacetophenone was used to afford the compound, which was furtherly subjected to the reaction described in the working example No.119(1) to afford the titled compound.

(2) According to the procedure described in the working example No.119(2), the compound obtained in (1) was used to afford the titled compound.

¹H-NMR(DMSO-d₆)δ: 1.02–1.17(1H,m), 2.25–2.40(1H, m), 2.63–2.72(2H,m), 3.34–3.41(2H,m), 4.74–4.80(1H,m), 6.65(1H,br), 7.28(1H,d,J=7.6 Hz), 7.44(1H,t,J=7.6 Hz), 7.58 (1H,t,J=7.7 Hz), 7.91(1H,d,J=8.0 Hz), 7.97(1H,d,J=7.9 Hz), 8.25(1H,d,J=8.2 Hz), 8.30 (1H,d,J=4.3 Hz), 9.68(1H,s).

mass:418(M+1)⁺.

Working Example No.121

(1) The compound (56 mg, 0.11 mmol) obtained from the working example No.120 was dissolved in dimethylformamide (1.5 ml). To the solution, 1,1-dicarbonyldiimidazole (25 mg, 0.15 mmol) was added at room temperature. The reaction mixture was stirred for 30 minutes at room temperature. To the mixture phenylethylamine (42 μl, 0.33 mmol) was added at room temperature and the mixture was heated from room temperature to 70° C. and furtherly stirred for 10 minutes. The reaction mixture was concentrated to afford a residue, which was purified by thin layer chromatography. The elution with chloroform-methanol (10:1) provided a crude compound, which was used for the next reaction without further purification.

(2) The compound (51 mg, 0.084 mmol) obtained above in (1) was dissolved in methanol-tetrahydrofuran (2:1) (3 ml). To the solution was added paradium hydroxide (51 mg) at room temperature. The reaction vessel was filled with hydrogen and the reaction mixture was stirred overnight at room temperature. The reaction mixture was filtered by celite. The filtrate was concentrated to afford the titled compound (25 mg).

¹H-NMR(DMSO-d₆)δ:1.02–1.10(1H,m), 2.25–2.36(2H, m), 2.43–2.56 (1H,m), 2.65(2H,t,J=7.1 Hz), 2.87(2H,t,J=7.5 Hz), 3.16–3.25 (2H,m), 4.73–4.79(1H,m), 6.70(1H,br), 7.16–7.33(7H,m), 7.44 (1H,t,J=7.9 Hz), 7.54(1H,t,J=7.7 Hz), 7.79(1H,d,J=7.0 Hz), 7.87(1H,d,J=6.3 Hz), 8.19(1H,s), 8.26(1H,d,J=7.7 Hz), 8.72(1H,br), 9.69 (1H,br).

mass:521(M+1)⁺.

Working Example No.122

(1) According to the procedure described in the reference example No.2(1), 2-bromo-3-nitrobenzoic acid (10.0 g, 40.7 mmol), pyrrole-2-carboxy aldehyde (7.74 g. 81.4 mmol), triethylamine (20.0 ml, 143 mmol) and thionyl chloride (30 ml) were used to provide the titled compound (9.07 g).

(2) A solution of the compound (9.07 g, 28.0 mmol) obtained above in (1) in tetrahydrofuran (400 ml) was cooled to −78° C. To the solution, a solution (33.6 ml) of diisopropylammonium hydride (1.0 M, 33.6 mmol) in toluene was added at the same temperature. The reaction mixture was stirred for 2 hours at the same temperature. To the reaction mixture was added a saturated aqueous ammonium chloride (15 ml) at the same temperature. The reaction mixture was warmed up to room temperature and stirred for 2 hours. The organic layer was separated and dried over magnesium sulfate. After filtration, the filtrate was concentrated to afford a residue, which was dissolved in methylene chloride (200 ml). To the solution was added chloro-tert-butyl dimethylsilan (6.32 g, 41.9 mmol) and imidazole (3.80 g, 55.8 mmol). The reaction mixture was stirred overnight at room temperature. The reaction mixture was diluted with ethyl acetate. The organic layer was washed with water (200 ml) for 3 times and saturated brine respectively and then dried over magnesium sulfate. After filtration, the filtrate was concentrated to afford a residue, which was purified by column chromatography on silica gel (Wakogel C-300). The fraction eluted with hexane-ethyl acetate (10:1–5:1) provided a colorless oily compound (9.34 g).

(3) The compound (9.34 g. 21.3 mmol) obtained above in (2) and diisopropylethylamine (8.24 g, 63.8 mmol) were dissolved in dimethyl formamide (200 ml). The reaction vessel was filled with nitrogen. To the reaction mixture tetrakistriphenylphosphine palladium (2.46 g, 2.13 mmol) was added. The reaction mixture was stirred for 2 hours at 130° C. The reaction mixture was added ethyl acetate (1 L) and water (500 ml). The organic layer was separated. The aqeous layer was further extracted with ethyl acetate (300 ml). The combined organic layers were washed with water and saturated brine respectively and dried over magnesium sulfate. After filtration, the filtrate was concentrated to afford a residue, which was purified by column chromatography on silica gel (wakogel C-300). The fraction eluted with hexane-ethyl acetate (20:1–5:1) provided a yellow solid compound (4.73 g).

(4) The compound (4.73 g, 13.2 mmol) obtained above in (3) was dissolved in methanol-tetrahydrofuran (1:1) (400 ml). To the solution was added 10% palladium carbon catalyst (500 mg) at room temperature. The reaction vessel was filled with hydrogen. The whole was stirred for 2 hours at room temperature. The reaction mixture was filtrated by celite. After filtration, the filtrate was concentrated to afford a residue, which was purified by column chromatography on silica gel (Wakogel C-300). The elution with hexane-ethyl acetate (2:1–1:1) provided fraction 1 (less polar compound) as pyrrole compound (1.20 g) and fraction 2 (more polar compound) as pyrrolidine compound (2.40 g).

Fraction 1 (less polar compound)

¹H-NMR(CDCl₃)δ:0.14(6H,s), 0.95(9H,s), 3.84(2H,brs), 4.88(2H,s), 5.98(1H,d,J=3.1 Hz), 6.09–6.11(1H,m), 6.78 (1H,d, J=7.1 Hz), 7.02(1H,t,J=7.7 Hz), 7.14(1H,d,J=7.3 Hz).

Fraction 2 (more polar compound)

¹H-NMR(CDCl₃)δ:0.02(6H,s), 0.74(9H,s), 1.60–1.70 (1H,m), 2.15–2.23(1H,m), 2.42–2.50(2H,m), 3.68(2H,brs), 3.95–4.02(2H,m), 4.36(1H,dd,J=10 Hz,5.2 Hz), 4.63(1H,dd, J=12 Hz,5.5 Hz), 6.80(1H,d,J=7.0 Hz), 7.20–7.24(2H,m).

(5) According to the procedure described in the working example No.1, the polar compound (2.40 g, 7.23 mmol) from the fraction 2 obtained above in (4) was used to afford a yellow solid compound (2.71 g).

(6) The compound (2.71 g, 6.00 mmol) obtained above in (5) was suspended to the methanol-tetrahydrofuran (1:1,200 ml). To the mixture was added 2N hydrochloric acid (10 ml) at room temperature and the reaction mixture was stirred for 6 hours at the same temperature. The reaction mixture was concentrated to afford a residue, which was dehydrated by heating with toluene twice to remove water. The crude compound obtained was recrystallized from hexane-ethylacetate-tetrahydro furan to afford the titled compound (1.85 g).

$^1$H-NMR(DMSO-d$_6$)δ:1.27–1.40(1H,m), 1.72–1.78(1H, m), 2.20–2.27(1H,m), 2.40–2.50(1H,m), 2.53–2.62 (1H,m), 3.59 (1H,t,J=7.5 Hz), 3.85–3.93(1H,m), 4.90(1H,dd,J=8.0 Hz,5.5 Hz), 5.97 (1H,br), 7.17–7.22(1H,m), 7.33(1H,d,J= 8.0 Hz), 7.40 (1H,d, J=9.0 Hz), 7.47(1H,t,J=7.5 Hz), 7.98 (1H,t,J=8.0 Hz), 8.18(1H,d,J=7.0 Hz), 8.30(1H,d,J=4.0 Hz), 10.6(1H,br), 11.0(1H,br).

mass:339(M+1)$^+$.

Working Example No.123

(1) According to the procedure described in the working example No.122(2), the compound (4.50 g, 13.4 mmol) obtained from the working example No.131(1) was used to afford a yellow solid compound (3.94 g).

(2) According to the procedure described in the working example No.122(3) and (4), the compound (3.94 g, 8.47 mmol) obtained above in (1) was used to afford fraction 1 (less polar compound, 238 mg) and fraction 2 (more polar compound, 1.14 g).

Fraction 1(less polar compound):

$^1$H-NMR(CDCl$_3$—CD$_3$OD)δ:0.08(3H,s), 0.11(3H,s), 0.93(9H,s), 1.51 (3H,d,J=6.2 Hz), 3.84(2H,br), 5.26(1H,m), 5.96(1H,d,J=3.3 Hz), 6.10(1H,dd,J=3.1 Hz,1.0 Hz), 6.78 (1H,d,J=8.0 Hz), 7.01(1H,t,J=7.7H z), 7.13(1H,d,J=7.3 Hz).

Fraction 2(more polar compound):

$^1$H-NMR(CDCl$_3$)δ:0.07(3H,s), 0.11(3H,s), 0.85–0.95 (1H,m), 0.92 (9H,s), 1.24–1.35(2H,m), 1.52(3H,d,J=6.3 Hz), 1.52–1.55(1H,m), 5.27(1H,q), 6.28(1H,d,J=3.4 Hz), 7.07(1H,d,J=3.6 Hz), 7.31(1H,dd,J=8.5 Hz,7.3 Hz), 7.92 (1H,dd,J=7.3 Hz.1.0 Hz), 8.28(1H,dd,J=8.5H z,1.0 Hz).

(3) According to the procedure described in the working example No.1, the polar compound (300 mg, 0.87 mmol) from the fraction 2 obtained above in (2) was used to afford a yellow solid compound (389 mg).

(4) According to the procedure described in the reference example No. 7, the compound (200 mg, 0.429 mmol) obtained above in (3) was used to afford the titled compound (92 mg).

$^1$H-NMR(DMSO-d$_6$)δ:0.80–0.95(1H,m), 1.14(3H,d,J= 6.3 Hz), 1.17–1.28(1H,m), 2.25–2.40(2H,m), 3.70–3.74(1H, m), 3.80–3.90 (1H,m), 4.78–4.85(2H,m), 7.06(1H,dd,J=7.2 Hz,5.0 Hz), 7.33 (2H,t,J=7.4 Hz), 7.46(1H,t,J=7.9 Hz), 7.76–7.82(1H,m), 8.26–8.30(2H,m), 9.90(1H,s), 11.0(1H, br).

Working Example No.124

The more polar compound (14 mg) obtained from the fraction 2 of the working example No.128(5) was dissolved in methanol-tetrahydrofuran (1:1, 2 ml). To the solution was added 1N hydrochloric acid (1.0 ml) at room temperature and the reaction mixture was stirred for 30 minutes at the same temperature. The reaction mixture was neutralized with saturated aqueous sodium hydrogencarbonate and then extracted with chloroform. After being dried over magnesium sulfate, the mixture was filtered. The filtrate was concentrated to afford a residue, which was purified by thin layer chromatography (ethyl acetate-methanol, 30:1) to provide the titled compound (4.1 mg) as well as the compound (3.8 mg) of the working example No. 127.

$^1$H-NMR(DMSO-d$_6$)δ:0.92–1.09(1H,m), 1.18(2H,d,J= 6.6 Hz), 1.60–1.74(1H,br), 2.68–2.76(1H,m), 2.80–3.00(1H, m), 3.28(1H,dd, J=11 Hz,9.0 Hz), 3.63(1H,dd,J=11 Hz,8.5 Hz), 4.87(1H,dd,J=11 Hz,5.2 Hz), 6.97(1H,d,J=4.6 Hz), 6.99–7.05(1H,m), 7.45–7.60(2H,m), 7.68–7.76(1H,m), 8.19–8.23(1H,m), 8.32(1H,dd,J=7.7 Hz,1.3 Hz), 8.94(1H, br), 12.00(1H,br).

mass:323(M+1)$^+$.

Working Example No.125

(1) The compound (12.3 g, 38.2 mmol) of the working example No. 128(1) was dissolved in tetrahydrofuran (150 ml). The mixture was cooled to −78° C. A solution (46.0 ml) of diisobutylaluminum hydride in toluene (1.0 M, 46.0 mmol) was added at the same temperature. The reaction mixture was stirred for 15 minutes and saturated aqueous ammonium chloride (25 ml) was added at the same temperature. The whole was warmed up to room temperature. To the reaction mixture was added magnesium sulfate and the whole was filtered. The filtrate was concentrated to afford a residue, which was dissolved in chloroform (150 ml), and imidazole (5.20 g, 81.1 mmol) and chlorotriisopropylsilane (9.40 g. 43.9 mmol) were added. The reaction vessel was filled with nitorogen. The whole was stirred for 12 hours at room temperature. The reaction mixture was diluted with ethyl acetate and washed with water and brine respectively and then dried over magnesium sulfate. After filtration, the filtrate was concentrated to afford a residue, which was purified by column chromatography on silica gel. Elution with hexane-ethyl acetate (10:1) provided a yellow solid compound (17.2 g).

(2) The compound (17.2 g, 15.6 mmol) obtained above in (1) was subjected to the reaction described in the reference example No. 2(2) to afford a yellow solid compound (4.9 g).

(3) The compound (4.90, 12.2 mmol) obtained above in (2) was dissolved in tetrahydrofuran (70 ml). To the solution was added 6N hydrochloric acid (20 ml) at room temperature. The reaction mixture was stirred for 1 hour at the same temperature. The reaction mixture was alkalized by adding 1N sodium hydroxide. The whole was extracted with ethyl acetate and the organic layer was dried over magnesium sulfate. After filtration, the filtrate was concentrated to afford a crystal, which was washed with hexane-ethyl acetate and dried. A yellow solid compound (2.94 g) was obtained.

(4) The compound (180 mg, 0.73 mmol) obtained above in (3) was dissolved in methanol (5.0 ml) and tetrahydrofuran (16 ml). To the solution was added triethylamine (0.20 ml) and 10% paradium carbon catalyst (100 mg). The whole was stirred for 1 hour at 50° C. under an atomosphere of hydrogen. The reaction mixture was filtered by celite and the filtrate was concentrated to afford a colorless solid compound (163 mg).

(5) According to the procedure described in the working example No.1, the compound (163 mg, 0.75 mmol) obtained above in (4) and 2-pyridinecarbonylazide (107 mg, 0.72 mmol) were used to afford the titled compound (7 mg).

$^1$H-NMR(DMSO-d$_6$)δ:1.03–1.10(1H,m), 3.02–3.21(1H, m), 3.30–3.65 (4H,m), 3.87–3.89(1H,m), 4.95–5.02(1H,m), 7.06–8.45(7H,m), 9.02(1H,br), 11.9(1H,br).

mass:339(M+1)$^+$.

Working Example No.126

(1) To a solution of the compound (85 mg, 0.251 mmol) of the working example No. 125 and triphenylphosphine (132 mg, 0.503 mmol) in tetrahydrofuran (6 ml) were added diphenylphosphorylazide (0.140 ml, 0.650 mmol) and a 40% solution (0.220 ml, 0.505 mmol) of diethylazodicarbolxylate at room temperature. The reaction mixture was stirred for 1 hour at the same temperature and diluted with ethyl acetate. The mixture was washed with water and brine respectively. The organic layer was dried over magnesium sulfate. After filtration, the filtrate was concentrated to afford a residue, which was purified by thin layer column chromatography eluted with chloroform-methanol (10:1). Ether was added to the crude compound to afford a crystal (24 mg).

(2) The compound (24 mg) obtained above In (1) was dissolve in methanol-tetrahydrofuran (1:1, 2 ml). To the solution was added 10% paradium carbon catalyst (10 mg) at room temperature. The reaction vissel was filled with hydrogen. The mixture was stirred at room temperature under an atomosphere of hydrogen until the disappearance of the starting material. The reaction mixture was filtered by celite. The filtrate was concentrated to afford a residue. To the residue, was added ether to afford the crystal. The crystal was collected by filtration, washed with ethyl acetate and chloroform, and then dried to afford the tilted compound (4.6 mg).

$^1$H-NMR(DMSO-d$_6$)δ:0.97–1.10(1H,m), 2.72–2.82(1H, m), 2.87–3.00 (2H,m), 3.10–3.20(1H,m), 3.30–3.60(2H,m), 4.96–5.01(1H,m), 7.03–7.14(1H,m), 7.31–7.34(1H,m), 7.40–7.50(2H,m), 7.77–7.83 (1H,m), 8.16(2H,br), 8.26(1H, d,J=8.1 Hz), 8.37(1H,d,J=4.0 Hz), 10.1(1H,s), 11.2(1H,br).

mass:338 (M+1)$^+$.

Working Example No.127

According to the procedure described in the working example No.124, the titled compound was obtained.

$^1$H-NMR(DMSO-d$_6$)δ:0.45(2H,d,J=7.0 Hz), 1.55–1.70 (1H,br), 2.08–2.19(1H,m), 2.48–2.68(1H,m), 2.88–3.02(1H, m), 3.41–3.53 (1H,m), 3.66–3.80(1H,m), 4.96(1H,d,J=5.3 Hz), 6.92(1H,d, J=8.3 Hz), 6.99–7.05(1H,m), 7.46–7.60(2H, m), 7.72–7.77(1H,m), 8.20–8.23(1H,m), 8.32–8.37(1H,m), 8.66(1H,br), 12.00(1H,br).

mass:323(M+1)$^+$.

Working Example No.128

(1) According to the procedure described in the reference example No.2(1), pyrrole-3-carboxyaldehyde was used to afford the titled compound.

(2) According to the procedure described in the working example No.122(2), the compound (139 mg, 0.433 mmol) obtained above in (1) was used to afford the titled compound.

(3) According to the procedure described in the reference example No.2(2), the compound obtained above in (2) was used to afford the titled compound as a mixture of isomers in a ratio of 2 to 1.

(4) According to the procedure described in the working example No.122(4), the compound obtained above in (3) was used to afford a mixture, which was used for the next reaction without further purification.

(5) The mixture (22 mg) obtained above in (4) and 2-pyridinecarbonylazide (26 mg. 0.17 mmol) were subjected in the similar manner to that described in the working example No.1. The reaction mixture was concentrated to afford a residue, which was purified by thin layer chromatography eluted with hexane-ethyl acetate (1:2) to afford fraction 1 (less polar compound) and fraction 2 (more polar compound).

(6) The fraction 1 (less polar compound, 11 mg) obtained above in (5) was dissolved in methanol-tetrahydrofuran (1:5, 1.2 ml). To the solution was added 1N hydrochloric acid (1.0 ml). The reaction mixture was stirred at the same temperature and concentrated to afford a residue. The residue was diluted with ethyl acetate and washed with saturated sodium hydrogencarbonate and brine respectively. The organic layer was dried over magnesium sulfate. After filtration, the filtrate was concentrated to afford a residue, which was purified by thin layer chromatography eluted with chloroform-methanol (10:1) to provide the titled compound (3.1 mg).

$^1$H-NMR(acetone-d$_6$)δ:1.29(1H,br), 2.52–2.61(2H,m) 3.00–3.10 (2H,m), 3.29–3.41(1H,m), 3.54–3.70(2H,m), 5.08(1H,d,J=5.4 Hz), 7.05–7.12(1H,m), 7.23(1H,d,J=8.4 Hz), 7.32–7.36(1H,m), 7.45 (1H,t,J=7.7 Hz), 7.78–7.87(1H, m), 8.36–8.42(2H,m), 8.96(1H, br), 11.9(1H,br).

Working Example No.129

(1) To a solution of the compound (100 mg, 0.467 mmol) obtained from the reference example No.2(2) in methanol (15 ml) was added iron powder (200 mg, 3.58 mmol) and 6N hydrochloric acid (0.500 ml, 3.00 mmol). The reaction mixture was stirred for 30 minutes at room temperature and diluted with ethyl acetate (200 ml). The whole was washed with saturated aqueous sodium hydrogencarbonate (100 ml), water and brine respectively. The organic layer was dried over magnesium sulfate. After filtration, the filtrate was concentrated to afford a residue, which was purified by column chromatography on silica gel (wakogel C-300). Elution with hexane-ethyl acetate (5:1) afforded a light green solid (71 mg).

(2) According to the procedure described in the working example No.1, the compound (50 mg) obtained above in (1) was used to afford the titled compound (65 mg).

$^1$H-NMR(DMSO-d$_6$)δ:6.34(1H,t,J=3.1 Hz), 6.65(1H,d,J= 3.1 Hz), 7.08(1H,dd,J=6.7 Hz,5.6 Hz), 7.24–7.29(3H,m), 7.38(1H,d, J=7.3 Hz), 7.77–7.83(1H,m), 8.27(1H,d,J=8.2 Hz), 8.31(1H,dd, J=5.1 Hz 1.1 Hz), 10.1(1H,brs), 11.0(1H, br).

Working Example No.130

According to the procedure described in the working example No.122(5) and (6), the fraction 1 (less polar compound, 300 mg, 0.91 mmol) obtained from the working example 122(4) was used to afford the titled compound (216 mg).

$^1$H-NMR(DMSO-d$_6$)δ:4.60(2H,s), 5.65(1H,br), 6.20(1H, s), 6.68 (1H,s), 7.14–7.20(1H,m), 7.25(1H,t,J=7.4 Hz), 7.35–7.43(2H, m), 7.94(1H,t,J=6.9 Hz), 8.20(1H,d,J=7.4 Hz), 8.34(1H,d,J=5.5 Hz), 10.8(2H,br).

Working Example No.131

(1) According to the procedure described in the reference example No.2(1). 2-bromo-3-nitrobenzonic acid (10.0 g, 40.7 mmol) and 2-acetylpyrrole (8.90 g, 81.6 mmol) were used to afford a yellow solid (9.20 g).

(2) According to the procedure described in the reference example No.2(2), the compound (2.00 g, 5.93 mmol) obtained above in (1) was used to afford a light green solid (941 mg).

(3) According to the procedure described in the working example No.129, the compound (300 mg, 1.17 mmol) obtained above in (2) was used to afford the titled compound (277 mg).

$^1$H-NMR(DMSO-d$_6$)δ:6.32–6.35(1H,m), 6.74(1H,s), 7.07(1H,dd, J=7.2 Hz,5.2 Hz), 7.19(1H,s), 7.26(1H,s), 7.40 (1H,t,J=8.0 Hz), 7.47(1H,d,J=8.6 Hz), 7.66(1H,dd,J=7.9 Hz,1.5 Hz), 7.78–7.83(1H,m), 8.25(1H,dd,J=5.2 Hz,1.6 Hz), 8.47(11H,dd,J=8.0 Hz,1.6 Hz), 10.1(1H,s), 10.8(1H,brs), 12.0(1H,s).

mass:347(M+1)$^+$.

Working Example No.132

(1) According to the procedure described in the working example No.122(2), the compound (4.5 g, 13.4 mmol) obtained from the working example No.131(1) was used to afford the titled compound (3.94 g).

(2) According to the procedures described in the working example No.122(3) and (4), the compound (3.94 g, 8.47 mmol) obtained above in (1) was used to afford the fraction 1 (less polar compound, 238 mg) and the fraction 2 (more polar compound, 1.14 g).

(3) According to the procedure described in the working example No.1, the fraction 1 (less polar compound, 200 mg, 0.58 mmol) obtained above in (2) was used to afford a crystal (247 mg).

(4) According to the procedure described in the reference example No.7, the compound (247 mg, 0.53 mmol) obtained above in (3) was used to afford the titled compound (85 mg).

$^1$H-NMR(DMSO-d$_6$)δ:1.58(3H,d,J=7 Hz), 5.02(1H,q,J=7 Hz), 6.07(1H,d,J=3 Hz), 6.55(1H,d,J=3 Hz), 6.96(1H,brd, J=8 Hz), 7.06(1H,t,J=5 Hz), 7.22(1H,t,J=7 Hz), 7.43(1H,d, J=7 Hz), 7.69–7.75 (1H,m), 8.23–8.27(2H,m).

Working Example No.133

(1) To a solution of the compound (16 mg) of the working example No.299(1) in ethanol (0.2 ml) were added 1-butanethiol (4.2 μl) and sodium ethoxide (2.6 mg). The reaction mixture was stirred for 15 hours at room temperature and concentrated. The residue was purified by TLC (Merck Art5744) eluted with hexane-ethyl acetate (1:5) to afford the titled compound (8 mg).

(2) To a solution of the compound (8 mg) obtained above in (1) in tetrehydrofuran (2 ml) was added 1N hydrochloric acid (1 ml). The mixture was stirred for 15 minutes at room temperature. The reaction mixture was concentrated to afford a residue, which was crystallized from ether-methanol to afford the titled compound (4 mg) as a white solid.

1H-NMR(DMSO-d$_6$) 0.87(3H,t,J=7.2 Hz), 1.07–1.24 (1H,m), 1.28–1.40(2H,m), 1.49 (2H,tt,J=7.3, 7.7 Hz), 2.25–2.58(5H,m), 2.71–2.88(4H,m), 3.27–3.34(1H,m), 3.38–3.82(1H,m), 4.82(1H,dd,J=5.4,11 Hz), 7.03 (1H,d,J= 5.4 Hz), 7.17(1H,s), 7.32(1H,d,J=7.5 Hz), 7.47(1H,t,J=7.8 Hz), 8.22(1H,d,J=5.4 Hz), 8.28(1H,d,J=8.4 Hz), 10.1(1H, br),11.1(1H,br).

mass:425(M+1)$^+$.

Working Example No.134

(1) According to the procedure described in the working example No.289(6), the compound of the reference example No.8 was used to afford the titled compound.

(2) A solution of the compound (19 mg) obtained above in (1), isopropanol (15 μl) and triphenylphosphine (50 mg) in tetrahydrofuran (0.2 ml) were cooled to 0° C. To the mixture was added diethyl azodicarboxylate (82 μl). The reaction mixture was stirred for 30 minutes at room temperature and diluted with chloroform. The whole was washed with water and brine and dried over magnesium sulfate. After filtration, the filtrate was concentrated to afford a residue, which was purified by TLC (Merck Art5744) eluted with chloroform-methanol (20:1) to afford the titled compound (18 mg).

(3) The compound (18 mg) obtained above in (2) was subjected to the similar reaction to that described in the reference example No.11 to afford the compound, which was further subjected to the reaction described in the working example No.133(2) to afford a hydrochloride of the titled compound (5 mg) as a white solid.

$^1$H-NMR(DMSO-d$_6$) 1.06–1.20(1H,m), 1.24(6H,sx2), 2.25–2.44(3H,m), 2.93–2.99 (2H,m), 3.11–3.16(2H,m), 3.21–3.36(2H,m), 3.49–3.59(1H,m), 4.80–4.86(1H,m), 7.04–7.06(1H,m), 7.26–7.33(2H,m), 7.46 (1H,t,J=7.8 Hz), 8.26–8.29(2H,m), 8.78(2H,br), 10.2(1H,s), 10.9(1H,br).

mass:394(M+1)$^+$.

Working Examples No.135–136

According to the procedure described in the working example No.134, the compounds of the working examples No.135 and No.136 were prepared.

mass:420(M+1)$^+$.

Working Example No.136 mass:434(M+1)$^+$.

Working Example No.137

(1) According to the procedure described in the working example No.84(2), the compound of the reference example No.8 and tert-butyldiphenylsilylether of salicylaldehyde were used to afford the titled compound.

(2) According to the procedure described in the working example No.133(2), the compound obtaine above in (1) was used to afford the titled compound (3 mg) as a white solid.

mass:696 (M+1)$^+$.

Working Example No.138

(1) The compound of the working example No.137 (1) was subjected to the reaction described in the reference example No.7 to afford the titled compound.

(2) The compound obtained above in (1) was subjected to the reaction described in the working example No.133(2) to afford the hydrochloride of the titled compound (4 mg) as a white solid.

$^1$H-NMR(DMSO-d$_6$) 1.06–1.24(1H,m), 2.25–2.48(2H, m), 2.49–2.63(1H,m), 2.98–3.03 (2H,m), 3.13–3.27(2H,m), 3.27–3.35(1H,m), 3.45–3.79(1H,m), 4.11–4.14(2H,m), 4.80–4.85(1H,m), 6.83–7.01(3H,m), 7.22–7.38 (3H,m), 7.44–7.49(1H,m), 8.25–8.29(2H,m), 8.90(2H,br), 10.1 (1H, br), 10.2(1H,br), 11.0(1H,br).

mass:458(M+1)$^+$.

Working Example No.139

(1) A mixture of the compound (29 mg) of the working example No.137(1), ditert-butyldicarbonate (16 mg), triethylamine (15 μl) and chloroform (0.2 ml) was stirred for 3 hours at room temperature. The reaction mixture was concentrated to afford a residue, which was purified by TLC (Merck Art5744) eluted with chloroform-methanol (20:1) to afford the titled compound (32 mg).

(2) According to the procedure described in the reference example No.7, the compound (35 mg) obtained above in (1) was used to afford the titled compound (24 mg).

(3) According to the procedure described in the working example No.134(2), the compound (24 mg) obtained above in (2) and 1-butanol (5 μl) were used to afford the titled compound (3 mg).

(4) The compound (8 mg) obtained above in (3) was subjected to the reaction procedure described in the working example No.133(2) to afford the hydrochloride of the titled compound (3 mg).

$^1$H-NMR(DMSO-d$_6$) 0.91(3H,t,J=7.5 Hz), 1.06–1.24(1H, m), 1.43(2H,tt,J=6.6, 7.5 Hz), 1.73(2H,tt,J=6.6, 6.6 Hz), 2.25–2.59(3H,m), 2.9873.05 (2H,m), 3.14–3.24(2H,m), 3.27–3.35(1H,m), 3.43–3.65(1H,m), 4.03(2H,t,J=6.6 Hz), 4.15(2H,brt,J=5.4 Hz), 4.79–4.86(1H,m), 6.97–7.10(3H,m), 7.27–7.49(5H,m), 8.25–8.29(2H,m), 9.01 (1H,br), 10.1(1H, br), 10.9(1H,br).

mass:514(M+1)$^+$.

Working Example No.140

(1) According to the procedure described in the working example No.84(2), the compound (30 mg) of the reference example No.8 and o-anisaldehyde (9 al) were used to afford the monoalkyl compound (A) (16 mg) and dialkyl compound (B) (11 mg).

(2) According to the procedure described in the working example No.133(2), the compound (A) (16 mg) obtained above in (1) was used to afford the hydrochloride of the titled compound (12 mg) as a light yellow solid.

$^1$H-NMR(DMSO-d$_6$) 1.05–1.12(1H,m), 2.26–2.61(3H, m), 2.99–3.05(2H,m), 3.14–3.21 (2H,m), 3.22–3.35(1H,m), 3.49–3.84(1H,m), 3.85(3H,s), 4.13–4.17 (2H,m), 4.81–4.86 (1H,m), 6.98–7.03(2H,m), 7.10(1H,d,J=4.8 Hz), 7.27–7.34 (2H,m), 7.40–7.49(3H,m), 8.26–8.29(2H,m), 9.01 (2H,br), 10.3(1H,br), 10.9(1H,br).

mass:472(M+1)$^+$.

Working Example No.141

The compound (B) (7 mg) obtaine from the working example No.140(1) was subjected to the reaction described in the working example No.133(2) to afford the hydrochloride of the titled compound (4 mg) as a light yellow solid.

$^1$H-NMR(DMSO-d$_6$) 1.03–1.10(1H,m), 2.26–2.81(3H, m), 3.16–3.40(4H,m), 3.70 (3H,s), 3.75(3H,s), 3.43–3.99 (2H,m), 4.29–4.46(4H,m), 4.81–4.86(1H,m), 6.90–7.13(5H, m), 7.27–7.35(2H,m), 7.42–7.51 (5H,m), 8.22–8.28(2H,m), 8.93(1H,br), 10.3(1H,br), 10.8(1H,br).

mass:592(M+1)$^+$.

Working Example No.142

(1) The compound (30 mg) of the working example No.164(3) was dissolved in acetonitrile-methylenedichloride (3:1, 0.4 ml). The reaction vessel was filled with nitrogen. To the solution were added (Boc)$_2$O (0.12 ml), nitroethane (25 µl) and 4-dimethylaminopyridine (4 mg). The reaction mixture was stirred for 1 hour at room temperature. To the reaction mixture was added water and the whole was extracted with chloroform. The organic layer was washed with water and brine and dried over magnesium sulfate. After filtration, the filtrate was concentrated to afford a residue, which was purified by TLC (Merck art5744) eluted with chloroform-methanol (30:1) to afford the adducts (32 mg). The diastereomer adducts were resolved by HPLC [CHIRALPAK AD, Dicel Chem. Ind. Co., 0.46×25 cm, hexane-ethanol (20:80), 1.0 ml/min] to afford the fraction (A) (12 mg) at R$_t$=9.64 min and the fraction (B) (13 mg) at R$_t$=14.58 min.

(2) According to the procedure described in working example No.133(2), the compound of the working example No.142 was prepared from the (1)-A as a light yellow powder and the compound of the working example No.143 was prepared from the (1)-B as a light yellow powder.

MASS:392(M+1)$^+$.

Working Example No.143

The compound of the working example No.143 was obtained from the diastermer of the working example No.142.

mass:392(M+1)$^+$.

Working Examples No.144–147

According the procedure described in the working example No.142, the compounds of working examples from No.144 to No.147 were prepared.

Working Example No.144

$^1$H-NMR(CDCl$_3$) 1.18(3H,t,J=7.5 Hz), 1.16–1.44(1H,m), 2.40(2H,q,J=7.5 Hz), 2.36–2.44(2H,m), 2.57–2.65(1H,m), 2.87(1H,dd,J=7.2, 17 Hz), 3.42–3.53(2H,m), 3.73–3.82(1H, m), 4.80(1H,dd,J=5.7, 11 Hz), 5.54(1H,dd,J=7.2,11 Hz), 6.97(1H,d,J=9.0 Hz), 6.98(1H,br), 7.56–7.57(2H,m), 8.20 (1H,d,J=5.1 Hz), 8.37(1H,d,J=7.2 Hz), 9.05(1H,br), 11.9 (1H,br).

mass:406(M+1)$^+$.

Working Example No.145 mass:406(M+1)$^+$.

Working Example No.146 mass:406(M+1)$^+$.

Working Example No.147 mass:406(M+1)$^+$.

Working Examples No.148–151

According to the procedure described in the working example No.142, the compounds of the working examples from No.148 to No.151 were prepared as a mixture of diasteomer.

Working Example No.148 mass:420(M+1)$^+$.

Working Example No.149 mass:420(M+1)$^+$.

Working Example No.150 mass:448(M+1)$^+$.

Working Example No.151 mass:448(M+1)$^+$.

Working Examples No.152–155

According to the procedure described in the working example No.156, the compounds of the working examples from No.152 to No.155 were prepared as a single isomer.

Working Example No.152 mass:434(M+1)$^+$.

Working Example No.153 mass:434(M+1)$^+$.

Working Example No.154 mass:434(M+1)$^+$.

Working Example No.155 mass:434(M+1)$^+$.

Working Example No.156

(1) A mixture of the compound (30 mg) obtained from the working example No.164(3), 1-pyrroline-N-oxide (59 mg) and chloroform (2 ml) was stirred for 23 hours at 80° C. The reaction mixture was cooled to room temperature and then extracted with chloroform. The organic layer was washed with water and brine and dried over magnesium sulfate. After filtration, the filtrate was concentrated to afford a residue, which was purified by TLC (Merck Art5744) eluted with chloroform-methanol (20:1) to afford a light yellow oily compound (24 mg).

(2) Accroding to the procedure described in the working example No.133(2), the compound (6 mg) obtained above in (1) was used to afford the tilted compound (5 mg).

$^1$H-NMR(CDCl$_3$) 1.22–1.35(1H,m), 1.58–1.86(3H,m), 1.99–2.17(2H,m), 2.35–2.62(4H,m), 3.13–3.22(1H,m), 3.33–3.49(2H,m), 3.72–3.84 (2H,m), 4.79(1H,dd,J=5.7,11 Hz), 5.08(1H,t,J=7.2 Hz), 6.95–7.01(2H,m), 7.47(1H,t,J= 7.5 Hz), 7.54(1H,d,J=6.3 Hz), 8.09(1H,s), 8.16(1H,d,J=5.1 Hz), 8.32(1H,d,J=6.6 Hz), 11.9(1H,s).

mass:420(M+1)$^+$.

Working Example No.157

According to the procedure described in the working example No.156, the optical isomer obtained form the working example No.164(3) was used to afford the titled compound.

mass:420(M+1)$^+$.

Working Example No.158

(1) According to the procedure described in the working example No.142, the compound (30 mg) obtained from the working example No.164(3) and 2-(2-nitroethoxide) tetrahydropyran (53 μl) were used to afford the titled compound (39 mg).

(2) According to the procedure described in the working example No.133(2), the compound (7 mg) obtained above in (1) was used to afford the titled compound (4 mg) as a light yellow solid.

$^1$H-NMR(CDCl$_3$) 1.22–1.39(1H,m), 2.35–2.62(3H,m), 3.04(1H,dd,J=6.9, 17 Hz). 3.42–3.82(3H,m), 4.47(1H,d,J= 14 Hz), 4.54(1H,d,J=14 Hz), 4.79(1H,dd,J=5.7, 10 Hz), 5.66–5.73(1H,m), 6.85–6.88(1H,m), 6.99(1H,s), 7.22–7.26 (1H,m), 7.48 (1H,t,J=7.8 Hz), 7.54(1H,d,J=7.5 Hz), 8.19 (1H,d,J=5.4 Hz), 8.25–8.30(1H,m), 9.16(1H,br), 11.9(1H,s).

mass:408(M+1)$^+$.

Working Example No.159

According to the procedure described in the working example No.158, the optical isomer obtained from the working example No.164(3) was used to afford the titled compound mass:408(M+1)$^+$.

Working Example No.160

According to the procedure described in the working example No.156, the titled compound of the working example No.160 was prepared as a mixture of diastereomer.

mass:478(M+1)$^+$.

Working Example No.161

According to the procedure described in the working example No.157, the titled compound of the working example No.161 was prepared as a mixture of diastereomer.

mass:478(M+1)$^+$.

Working Example No.162

The compound of the working example No.164(2)-B was subjected to the reactions described in the working examples No.164(3) to (5) afford the compound (7 mg) of the working example No.162 as a light yellow amorphous compound and the compound (9 mg) of the working example No.163 as a light yellow amorphous compound.

mass:468(M+1)$^+$.

Working Example No.163

The compound of the working example No.163 was obtained as a diasteromer of the working example No.162.

mass:468(M+1)$^+$.

Working Example No.164

(1) The compound (3.08 g) of the reference example No.6 was subjected to the optical resolution by HPLC [CHIRALCEL OD (Diecel Chem. Indus. Ltd., 0.46×25 cm, hexane-isopropanol (60:40), 0.4 ml/min) to afford the fraction (A) (1.37 g) at R$_t$=14.54 min and the fraction (B) (1.21 g) at Rt=25.58 min.

(2) (1)-(A) (15.6 g) and (1)-(B) (15.9 g) were subjected to the reaction described in the reference example No.7 to afford (2)-(A) (11.0 g) as a colorless amorphous compound and (2)-(B) (10.9 g) as a colorless amorphous compound.

(3) Accroding to the procedure described in the working example No.299(1), the compound (727 mg) of (2)-(A) was used to afford an amorphous compound (606 mg).

(4) According to the procedure described in the working example No.300(1), the compound (606 mg) obtained above in (3) was used to afford the titled compund (712 mg). The compound was subjected to the optical resolution by HPLC (CHIRALCEL OD Diecel Chem. Indus. Ltd., 0.46×25 cm, ethnaol, 0.5 ml/min) to afford the fraction (A) (360 mg) at Rt=22.58 min and the fraction (B) (329 mg) at R$_t$=38.84 min.

(5) (4)-(A) and (4)-(B) were subjected to the reaction described in the working example No.133(2) respectively.

The compound (291 mg) of the working example No.164 was prepared from (4)-(A) as a light yellow amorphous compound and the compound (235 mg) of the working example No.165 was prepared from (4)-(B) as a light yellow amorphous compound.

mass:468(M+1)$^+$.

Working Example No.165

The compound of the working example No.165 was obtained as a diasteromer of the working example No.164.

¹H-NMR (CDCl₃) 1.24–1.31(1H,m), 1.82–1.99(1H,m), 2.30–2.45(3H,m), 2.58–2.74(3H,m), 2.82(1H,dt,J=5.4, 9 Hz), 2.90(1H,t,J=8.7 Hz), 3.29–3.34(1H,m), 3.41–3.50(1H, m), 3.62–3.81(3H,m), 6.79(1H,dd, J=6,11 Hz), 6.80(1H,s), 6.95(1H,d,J=5.1 Hz), 7.23–7.36(5H,m), 7.45(1H,t,J=7.2 Hz), 7.53(1H,d,J=7.5 Hz), 8.09(1H,d,J=5.4 Hz), 8.25(1H,s), 8.33(1H,d,J=9 Hz), 12.0(1H,s).

mass:468(M+1)⁺.

Working Examples No.166–169

According to the procedure described in the working example No.183, the compounds of the working examples from No.166 to No.169 were prepared.

Working Example No.166 mass:392(M+1)⁺.

Working Example No.167 mass: 392(M+1)⁺.

Working Example No.168 mass:392 (M+1)⁺.

Working Example No.169 mass:392(M+1)⁺.

Working Example No.170

According to the procedure described in the working example No.171, the compound of the working example No.162 was used to afford the titled compound.

mass:478(M+I)⁺.

Working Example No.171

A mixture of the compound (291 mg) of the working example No.164, (Boc)₂O (2.86 ml), 20% palladium hydroxide carbon catalyst (150 mg), ethyl acetate (30 ml) and methanol (5 ml) was stirred for 15.5 hours at 60° C. under an atmosphere of hydrogen. The reaction was filtrated by celite and the filtrate was concentrated to afford a residue, which was purified by column chromatography on silica gel (Wakogel C-300) eluted with hexane-ethyl acetate (1:1–1:5) to afford the titled compound (183 mg) as a colorless amorphous compound.

¹H-NMR(CDCl₃) 1.22–1.44(1H,m), 1.49(9H,s), 1.96–2.04(1H,m), 2.27–2.47 (3H,m), 2.58–2.64(1H,m), 3.30–3.34(2H,m), 3.41–3.49 (2H,m), 3.57–3.89(3H,m), 4.79(1H,dd,J=5.7,11 Hz), 6.81 (1H,s), 6.88(1H,d,J=5.4 Hz), 7.46–7.57(2H,m), 8.15(11H,d, J=5.1 Hz), 8.34(1H,d,J=6.9 Hz), 8.76(0.5H,br), 8.88(0.5H,br), 12.0(1H,br).

mass:478(M+1)⁺.

Working Example No.172

According to the procedure described in the working example No.171, the compound of the working example No.165 was used to afford the titled compound.

mass:478(M+1)⁺.

Working Example No.173

According to the procedure described in the working example No.171, the compound of the working example No.163 was used to afford the titled compound.

mass:478(M+1)⁺.

Working Example No.174

A mixture of the compound (25 mg) of the working example No.170 and 4N hydrochloric acid-dioxane (6 ml) was stirred for 15 minutes at room temperature. The reaction mixture was concentrated and then dried to afford the titled compound (7 mg) as a white solid.

¹H-NMR(DMSO-d₆) 1.07–1.14(1H,m), 1.89–1.97(1H, m), 2.25–2.41(3H,m), 2.42–2.58 (1H,m), 3.04–3.79(7H,m), 4.80–4.86(1H,m), 7.09–7.11(1H,m), 7.31–7.34(2H,m), 7.47 (1H,t,J=7.8 Hz), 8.26–8.29(2H,m), 9.16 (2H,br), 10.1(1H,s), 10.9(1H,br).

mass:378(M+1)⁺.

Working Example No.175

According to the procedure described in the working example No.174, the compound of the working example No.173 was used to afford the titled compound.

mass:378(M+1)⁺.

Working Example No.176

According to the procedure described in the working example No.174, the compound of the working example No.171 was used to afford the titled compound.

mass:378(M+1)⁺.

Working Example No.177

According to the procedure described in the working example No.174, the compound of the working exaple No.172 was used to afford the titled compound mass:378(M+1)⁺.

Working Example No.178

According to the procedure described in the working example No.84(2), the titled compound (5 mg) was prepared from the hydrochloride of racemic compound (5 mg) of the working example No.174 and tert-butyl N-(2-oxoethyl) carbamate (8 mg).

¹H-NMR(CDCl₃) 1.22–1.42(1H,m), 1.45(9H,s), 1.82–1.89(1H,m), 2.29–2.49 (3H,m), 2.51–2.80(4H,m), 2.81–2.98(2H,m), 3.22–3.34(3H,m), 3.41–3.49(1H,m), 3.71–3.81(1H,m), 4.79(1H,dd,J=5.4,11 Hz), 5.04(1H,br), 6.82(1H,s), 6.93(1H,d,J=5.7 Hz), 7.46(1H,t,J=7.8 Hz), 7.54 (1H,d,J=7.2 Hz), 8.10(1H,d,J=5.4 Hz), 8.30(1H,d,J=7.8 Hz), 8.48(1H,br), 12.0(1H,br).

mass:521(M+1)⁺.

Working Examples No.179–182

According to the procedure described in the working example No.183, the compounds of the working examples from No.179 to No.182 were prepared.

Working Example No.179 mass:460(M+1)⁺.

Working Example No.180 mass:460(M+1)⁺.

Working Example No.181 mass:460(M+1)⁺.

Working Example No.182 mass:460(M+1)⁺.

Working Example No.183

According to the procedure described in the working example No.178, the working exaple No.177 and butylaldehyde (7 μl) was used to afford the titled compound (7 mg) as a lightly yellow oil y compound.

$^1$H-NMR (CDCl$_3$) 0.93(3H,t,J=7.2 Hz), 1.25–1.43(3H,m), 1.52(2H,quintet, J=7.8 Hz), 1.71–1.91(1H,m), 2.32–2.66(8H,m), 2.75(1H,t, J=7.2 Hz), 2.96(1H,t,J=8.7 Hz), 3.30–3.35(1H,m), 3.42–3.48 (1H,m), 3.72–3.82(1H,m), 4.79(1H,dd,J=5.4,11 Hz), 6.80 (1H,br), 6.96(1H,d,J=5.7 Hz), 7.47(1H,t,J=7.5 Hz), 7.54(1H,d,J=7.5 Hz), 8.10(1H,d, J=5.7 Hz), 8.34(1H,d,J=8.1 Hz), 8.38(1H,br), 12.0(1H,br).

mass:434(M+1)$^+$.

Working Examples No.184–190

According to the procedure described in the working example No.183, the compounds of the working examples from No.184 to No.190 were prepared.

Working Example No.184 mass:434(M+1)$^+$.

Working Example No.185 mass:434(M+1)$^+$.

Working Example No.186 mass:434(M+1)$^+$.

Working Example No.187 mass:561(M+1)$^+$.

Working Example No.188 mass:561(M+1)$^+$.

Working Example No.189 mass:561(M+1)$^+$.

Working Example No.190 mass:561(M+1)$^+$.

Working Example No.191

According to the procedure described in the working example No.193, the compound of the working example No.187 was used to afford the titled compound.

mass:461(M+1)$^+$.

Working Example No.192

According to the procedure described in the working example No.193, the compound of the working example No.188 was used to afford the titled compound.

mass:461(M+1)$^+$.

Working Example No.193

According to the procedure described in the working example No.133(2), the compound (6 mg) of the working example No.189 was used to afford the hydrochloride of the titled compound (4 mg) as a yellow solid.

$^1$H-NMR(DMSO-d$_6$) 1.04–1.11(1H,m), 1.65–2.03(3H,m), 2.19–2.59(9H,m), 3.13–3.34(3H,m), 3.36–4.03(6H,m), 4.84(1H,dd,J=5.4, 10 Hz). 7.33(1H,d,J=7.2 Hz), 7.47(1H,t, J=7.8 Hz), 7.16–7.55(2H,m), 8.26(1H,d,J=7.8 Hz), 8.31(1H,d,J=5.4 Hz), 9.52(1H,br), 10.3(1H,b rd,J=10 Hz), 10.8(1H,br), 11.7(1H,br).

mass:461(M+1)$^+$.

Working Example No.194

According to the procedure described in the working example No.193, the compound of the working example No.190 was used to afford the titled compound.

mass:461(M+1)$^+$.

Working Examples No.195–210

According to the procedure described in the working example No.183, the compounds of the working examples from No.195 to No.210 were prepared.

Working Example No.195 mass:488(M+1)$^+$.

Working Example No.196 mass:488(M+1)$^+$.

Working Example No.197 mass:488(M+1)$^+$.

Working Example No.198 mass:488(M+1)$^+$.

Working Example No.199 mass:504(M+1)$^+$.

Working Example No.200 mass:504(M+1)$^+$.

Working Example No.201 mass:504(M+1)$^+$.

Working Example No.202 mass:504(M+1)$^+$.

Working Example No.203 mass:494(M+1)$^+$.

Working Example No.204 mass:494(M+1)$^+$.

Working Example No.205 mass:494(M+1)$^+$.

Working Example No.206 mass:494(M+1)$^+$.

Working Example No.207 mass:551(M+1)$^+$.

Working Example No.208 mass:551(M+1)$^+$.

Working Example No.209 mass:551(M+1)$^+$.

Working Example No.210 mass:551(M+1)$^+$.

Working Examples No.211–240

According to the procedure described in the working example No.178, the compounds of the working examples from No.211 to No.240 were prepared.

Working Example No.211 mass:434(M+1)$^+$.

Working Example No.212 mass:448(M+1)$^+$.

Working Example No.213 mass:482(M+1)$^+$.

Working Example No.214 mass:462(M+1)$^+$.

Working Example No.215 mass:420(M+1)$^+$.

Working Example No.216 mass:518(M+1)$^+$.

Working Example No.217 mass:518(M+1)$^+$.

Working Example No.218 mass:448(M+1)$^+$.

Working Example No.219 mass:446(M+1)$^+$.

Working Example No.220 mass:474(M+1)$^+$.

Working Example No.221 mass:420(M+1)$^+$.

Working Example No.222 mass:462(M+1)$^+$.

Working Example No.223 mass:507(M+1)$^+$.

Working Example No.224 mass:512(M+1)$^+$.

Working Example No.225 mass:512(M+1)$^+$.

Working Example No.226 mass:484(M+1)$^+$.

Working Example No.227 mass:458(M+1)$^+$.

Working Example No.228 mass:504(M+1)$^+$.

Working Example No.229 mass:450(M+1)$^+$.

Working Example No.230 mass:432(M+1)$^+$.

Working Example No.231 mass:519(M+1)$^+$.

Working Example No.232 mass:457(M+1)$^+$.

Working Example No.233 mass:471(M+1)$^+$.

Working Example No.234 mass:469(M+1)$^+$.

Working Example No.235 mass:469(M+1)$^+$.

Working Example No.236 mass:469(M+1)$^+$.

Working Example No.237 mass:452(M+1)$^+$.

Working Example No.238 mass:472(M+1)$^+$.

Working Example No.239 mass:458(M+1)$^+$.

Working Example No.240 mass:522(M+1)$^+$.

Working Example No.241

According to the procedure described in the working example No.133(2), the compound (4 mg) of the working example No.178 was used to afford the hydrochloride of the titled compound (4 mg).

$^1$H-NMR(CD$_3$OD) 1.14–1.28(1H,m), 1.51–1.76(1H,m), 2.30–2.48(3H,m), 2.62–2.75 (2H,m), 3.42–3.76(10H,m), 4.95(1H,dd,J=5.7,11 Hz), 7.55 (1H,br), 7.57–7.59(3H,m), 8.04–8.07(1H,m), 8.30(1H,d,J=6.6 Hz).

mass:421(M+1)$^+$.

Working Examples No.242–247

According to the procedure described in the working example No.178, the compounds of the working examples from No.242 to No.247 were prepared.

Working Example No.242 mass:500(M+1)$^+$.

Working Example No.243 mass:514(M+1)$^+$.

Working Example No.244 mass:514(M+1)$^+$.

Working Example No.245 mass:486(M+1)$^+$.

Working Example No.246 mass:472(M+1)$^+$.

Working Example No.247 mass:484(M+1)$^+$.

Working Example No.248

According to the procedure described in the working example No.249, the title compound was prepard.

mass:496(M+1)$^+$.

Working Example No.249

The hydrochloride of the racemic compound (5 mg) of the working example No.174 was dissolved in acetone-water (2:1) (0.3 ml) and sodium acetate (4 mg) was added. The whole was cooled to 0° C. and 2,6-dichlorobenzoyl chloride (2:1) was added. The reaction mixture was stirred for 4 hours and water was added. The whole was extracted with chloroform and the organic layer was washed with water and saturated brine and dried over magnesium sulfate. After filtration, the filtrate was concentrated to afford a residue, which was purified by TLC (Merck Art5744) eluted with chloroform-methanol (20:1) to afford the titled compound (5 mg) as a white solid.

$^1$H-NMR(CDCl$_3$) 1.21–1.36(1H,m), 2.06–2.18(1H,m), 2.33–2.64(4H,m), 3.24–4.03(6H,m), 4.21–4.27(1H,m), 4.74–4.83(1H,m), 6.74(0.5H,s), 6.82(0.5H,s), 6.88(0.5H,d, J=5.7 Hz), 6.94(0.5H,d,J=5.7 Hz), 7.23–7.38(3H,m), 7.45–7.77(2H,m), 8.16(1H,dd,J=5.4, 12 Hz), 8.31 (1H,t,J=8.4 Hz), 8.53(1H,s), 11.8(0.5H,s), 11.9(0.5H,s).

mass:550(M+1)$^+$.

Working Examples No.250–253

According to the procedure described in the working example No.249, the compounds of the working examples from No.250 to No.253 were prepared.

Working Example No.250 mass:488(M+1)$^+$.

Working Example No.251 mass:483(M+1)$^+$.

Working Example No.252 mass:483(M+1)$^+$.

Working Example No.253 mass:483(M+1)$^+$.

Working Example No.254

(1) According to the procedure described in the working example No.264(3), the compound (3.8 g) of the working example from No.264(1) and enoltriflete (which was prepared from 1-benzyl-4-piperidon, lithium diisopropylamide, N-phenyl trifluoromethanesulfonimide and tetrahydrofuran according the ordinaly procedure) were used to afford a brown oily compound (1.9 g).

(2) According to the procedure described in the working example No.80(2) and (3), the compound obtained above in (1) was used to provide the titled compound (230 mg) as a white solid.

$^1$H-NMR(DMSO-d$_6$) 1.28(1H,m), 2.20–2.80(7H,m), 3.22 (1H,d,J=2.6 Hz), 3.45 (1H,m), 3.67(2H,s), 3.78(1H,m), 4.79 (1H,dd,J=5.6, 11 Hz), 6.36(1H,br), 6.88(1H,s), 7.00(1H,d, J=5.6 Hz), 7.20–7.50(6H,m), 7.50(1H,d, J=7.9 Hz), 8.10 (1H,d,J=5.6 Hz), 8.35(1H,d,J=7.9 Hz), 8.86 (1H,s), 12.0 (1H,br).

mass:480(M+1)$^+$.

Working Example No.255

The compound (160 mg) of the working example from No.254 was subjected to the reaction described in the reference example No.3 to afford a white solid (52 mg).

$^1$H-NMR(DMSO-d$_6$) 1.32(1H,m), 1.70–2.00(4H,m), 2.03 (2H,m), 2.25–2.80(4H,m) 13.08(2H,m), 3.49(1H,m), 3.60 (2H,s), 3.81(1H,m), 4.82(1H,dd, J=5.6,11 Hz), 6.72(1H,s), 6.92(1H,d,J=5.2 Hz), 7.20–7.50(5H,m), 7.49(1H,t,J=7.9 Hz), 7.55(1H,d,J=7.9 Hz), 8.07(1H,s,), 8.15(1H,d,J=5.2 Hz), 8.40(1H,d,J=7.9 Hz), 12.0(1H,br).

mass:482(M+1)$^+$.

Working Example No.256

1-benzyl-3-piperidone was subjected to the reaction described in the working example No.254 to afford a white solid (52 mg).

$^1$H-NMR(DMSO-d$_6$) 1.30(1H,m), 2.20–2.80(7H,m), 3.35 (1H,d,J=2.0 Hz), 3.48 (1H,m), 3.72(2H,s), 3.76(1H,m), 4.81 (1H,dd,J=5.7, 11 Hz), 6.44(1H,m), 6.78(1H,s), 6.95(1H,d, J=5.6 Hz), 7.20–7.40(5H,m), 7.49(1H,d, J=7.9 Hz), 7.53 (1H,d,J=7.9 Hz), 8.11(1H,d,J=5.6 Hz), 8.35(1H,d,J=7.9 Hz), 8.52(1H,s), 12.0(1H,br).

mass:480(M+1)$^+$.

Working Example No.257

The compound (30 mg) of the working example No.56 was subjected to the reaction described in the reference example No.3 to afford a white solid (12 mg).

$^1$H-NMR(DMSO-d$_6$) 1.20–1.40(1H,m), 1.60–2.20(5H, m), 2.20–2.70(3H,m), 2.80–3.00 (3H,m), 3.45(1H,m), 3.55 (2H,s), 3.75(1H,m), 4.78(1H,dd,J=5.6, 11 Hz), 6.71(1H,s), 6.87(1H,d,J=5.2 Hz), 7.10–7.40(5H,m), 7.47 (1H,t,J=7.5 Hz), 7.54(1H,d,J=7.9 Hz), 8.08(1H,d,J=5.2 Hz), 8.12(1H,s), 8.34(1H,d,J=5.2 Hz), 12.0(1H,br).

mass:482(M+1)$^+$.

Working Example No.258

According to the procedure described in the working example No.260, the compound (180 mg) of the working example No.256 was used to afford a yellow solid (17 mg).

$^1$H-NMR(DMSO-d$_6$) 1.25(1H,m), 2.20–2.70(5H,m), 3.01 (2H,m), 3.45(1H,m), 3.70 (2H,s), 3.75(1H,m), 4.79(1H,dd, J=5.6,11 Hz), 6.48(1H,m), 6.67(1H,s), 6.98(1H,d,J=5.2 Hz), 7.46(1H,t,J=7.9 Hz), 7.52(1H,s), 7.58(1H,d,J=7.9 Hz), 8.30 (1H,d,J=7.9 Hz), 12.0(1H,br).

mass:390(M+1)$^+$.

Working Example No.259

According to the procedure described in the working example No.261, the compound (20 mg) of the working example No.258 was used to afford a white solid (5 mg).

¹H-NMR(DMSO-d₆) 1.25(1H,m), 2.20(3H,s), 2.30–2.80 (5H,m), 3.40–3.90(4H,m), 4.42(2H,m), 4.81(1H,dd,J=5.6, 11 Hz), 6.50(1H,m), 5.82(1H,s), 7.00 (1H,d,J=5.2 Hz), 7.48 (1H,t,J=7.9 Hz), 7.55(1H,d,J=7.9 Hz), 8.20(2H,m), 8.35(1H, d,J=7.9 Hz), 11.9(1H,br).

mass:432(M+1)⁺.

Working Example No.260

(1) A mixture of the compound (280 mg) of the working example No.254, chloroethyl chloroformate (100 mg), triethylamine (71 mg) and chloroform (5 ml) was stirred for 30 minutes at room temperature. The reaction mixture was concentrated to afford a residue, which was purified by column chromatography on silica gel (Wakogel C-200) eluted with chloroform-methanol (100:0–98:2) to affod a solid compound (295 mg).

(2) The compound (295 mg) obtained above in (1) was dissolved in methanol (5 ml) and the mixture was refluxed for 3 hours. The reaction mixture was cooled to room temperature and saturated aqueous sodium hydrogencarbonate was added. The whole was extracted with chloroform. The organic layer was washed with brine and then dried over magnesium sulfate. After filtration, the filtrate was concentrated to afford a residue, which was purified by column chromatography on silica gel (FL60D Fujisilysia. Co.) eluted with chloroform-methanol (100:0–95:5) to affod a light yellow solid-compound (160 mg).

¹H-NMR(DMSO-d₆) 1.28(1H,m), 2.40(3H,m), 2.62(1H, m), 3.12(2H,m), 3.45(1H,m), 3.59 (2H,s), 3.77(1H,m), 4.80 (1H,dd,J=5.6,11 Hz), 6.42(1H,m), 6.81(1H,s), 7.02(1H,d,J= 5.3 Hz), 7.26(1H,s), 7.46(1H,t,J=7.9 Hz), 7.55(1 H,d,J=7.9 Hz), 8.13(1H,d,J=5.3 Hz), 8.33(1H,s,), 8.35(1H,d,J=7.9 Hz), 12.0(1H,br).

mass:390(M+1)⁺.

Working Example No.261

A mixture of the compound (30 mg) of the working example No.260, acetyl chloride (6.6 μl), triethylamine (13 μl) and chloroform (3 ml) was stirred for 1 hour at room temperature. The reaction mixture was added saturated aqueous sodium hydrogencarbonate and then extracted with chloroform. The organic layer was washed with brine and then dried over magnesium sulfate. After filtration, the filtrate was concentrated to afford a residue, which was purified by TLC (Merck Art5744) eluted with chloroformmethanol (9:1) to afford a white crystal solid (5 mg).

¹H-NMR(DMSO-d₆) 1.25(1H,m), 2.22(3H,s), 2.20–2.80 (5H,m), 3.40–3.95(4H,m), 4.35(2H,m), 4.82(1H,dd,J=5.6, 11 Hz), 6.40(1H,m), 6.80(1H,s), 7.03(1H,d,J=5.6 Hz), 7.49 (1H,t,J=7.9 Hz), 7.57(1H,t,J=7.9 Hz), 8.20(2H,m), 8.33(1H, d,J=7.9 Hz), 11.9(1H,br).

mass:432(M+1)⁺.

Working Example No.262

Accroding to the procedure described in the working example No.84(2), the compound (20 mg) of the working example No.260 was used to afford a white solid (3 mg).

¹H-NMR(DMSO-d₆) 1.05–2.20(14H,m), 2.20–2.90(6H, m), 3.22–3.50(3H,m), 3.70–3.82(1H,m), 4.78(1H,dd,J=5.8, 11 Hz), 6.37(1H,m), 6.77(1H,s), 7.01 (1H,d,J=5.4 Hz), 7.54 (1H,d,J=7.8 Hz), 8.12(1H,d,J=5.4 Hz), 8.32(1H,d,J=7.8 Hz), 12.0(1H,s).

mass:472(M+1)⁴.

Working Example No.263

Accroding to the procedure described in the working example No.262, the titled compound was prerpared.

mass:506(M+1)⁺.

Working Example No.264

(1) The hydrochloride of methyl 4-chloropyridine-2-carboxylate (3 g) was added to dioxane (140 ml). To the mixture was added hexabutylditin (8.4 g) and tetrakistriphenyl phosphine palladium. The whole was refluxed for 12 hours under an atmosphere of nitrogen. The reaction mixture was cooled to room temperature and a 10% solution of potassium fluoride was added. The whole was stirred for 30 minutes and diluted with ether. After filtration, the filtrate was washed with brine and then dried over magnesium sulfate. After filtration, the filtrate was concentrated to afford a residue, which was purified by column chromatography on silica gel (Wakogel C-200) eluted with hexane-ethyl acetate (1:0~2:1) to afford a colorless oily compound (0.9 g).

(2) Accroding to the procedure described in the working example No.80(2) and (3), the compound (6.3 g) obtained above in (1) was used to afford an oily compound (2.8 g).

(3) The mixture of the compound (60 mg) obtained above in (2). 3-bromopyridine (47 mg), 2-dicyclohexylphosphynobiphenyl (21 mg), lithium chloride (9 mg), tris(benzylidenacetone)dipalladium (21 mg) and tetrahydrofuran (2 ml) was refluxed overnight. To the reaction mixture was added a 10% solution of potassium fluoride and chloroform. The organic layer was separated and washed with water and saturated brine and then dried over magnesium sulfate. After filtration, the filtrate was concentrated to afford a residue, which was purified by TLC (Merck Art5744) eluted with chloroform-methanol (9:1) to affod a white crystal (5 mg).

¹H-NMR(DMSO-d₆) 1.10–1.20(1H,m), 2.33–2.40(1H, m), 2.40–2.78<2H,m>,3.28–3.33 (1H,m), 3.53(1H,m), 4.84 (1H,m), 7.31(1H,d,J=7.7 Hz), 7.43–7.49 (1H,m), 7.56(1H, dd,J=4.5, 7.7 Hz), 7.61(1H,s), 8.10(1H,dd,J=2.3, 7.7 Hz), 8.30(1H,d,J=7.7 Hz), 8.41(1H,d,J=5.5 Hz), 8.68(1H,d,J=5.5 Hz), 8.91(1H,d,J=2.3 Hz), 10.0(1H,s), 11.0(1H,br).

mass:386(M+1)⁺.

Working Examples No.265 to 277

According to the procedure described in the compound of working example No.264, the compounds for working example No.265 to No.277 were obtained.

Working Example No.265 mass:385(M+1)⁺.

Working Example No.266 mass:423(M+1)⁺.

Working Example No.267 mass:386(M+1)⁺.

Working Example No.268 mass:386(M+1)⁺.

Working Example No.269 mass:392(M+1)⁺.

Working Example No.270 mass:391(M+1)⁺.

Working Example No. 271 mass:465(M+1)+.

Working Example No.272 mass:435(M+1)+.

Working Example No.273 mass:435(M+1)+.

Working Example No.274 mass:391(M+1)+.

Working Example No.275 mass:389(M+1)+.

Working Example No.276 mass:407(M+1)+.

Working Example No.277 mass:445(M+1)+.

Working Example No.278

According to the procedure described in the compound of working example No.261, the compound of working example No.82 was used to afford a white solid (9 mg).

$^1$H-NMR(DMSO-$d_6$) 0.89(3H,t,J=7.3 Hz), 1.15(1H,m), 1.57(2H,q,J=7.3 Hz), 2.15(2H,q, J=7.3 Hz), 2.20–2.60(3H, m), 3.30(1H,m), 3.55(1H,m), 4.24(11H,d, J=6.0 Hz), 4.82 (1H,dd,J=5.6, 11 Hz), 6.92(1H,d,J=5.6 Hz), 7.13(1H, s), 7.46(1H,t,J=7.9 Hz), 7.48(1H,d,J=7.9 Hz), 8.23(1H,d,J=5.6 Hz), 8.30(1H,d,J=7.9 Hz), 8.42(1H,t,J=6.0 Hz), 9.97(1H,s), 11.3(1H br).

mass:408(M+1)+.

Working Example No.279

The compound (30 mg) of the working example No.80 and butanoyl chloride were dissolved in dimethylformamide and the mixture was stirred for 30 minutes at 90° C. The reaction mixture was diluted with chloroform, washed with aqueous saturated sodium hydrogencarbonate, saturated brine and then dried over magnesium sulfate. After filtration, the filtrate was concentrated to afford a residue, which was purified by TLC (Merck Art5744) eluted with chloroform-tetrahydrofuran (7:3) to afford white crystals (8 mg).

$^1$H-NMR(DMSO-$d_6$) 0.97(3H,t,J=7.3 Hz), 1.25(1H,m), 1.70(2H,q,J=7.3 Hz), 2.30–2.60 (1H,m), 2.40(2H,q,J=7.4 Hz), 2.30–2.55(2H,m), 2.60(1H,m), 3.45 (1H,m), 3.79(1H, m), 4.80(1H,dd,J=5.6,11 Hz), 5.13(2H,s), 6.84 (1H,s), 6.96 (1H,d,J=5.5 Hz), 7.49(1H,t,J=7.9 Hz), 7.55(1H,d,J=7.9 Hz), 8.19(1H,d,J=5.5 Hz), 8.31(1H,d,J=7.9 Hz), 11.9(1H,br).

mass:409(M+1)+.

Working Example No.280

According to the procedure described in the compound of working example No.279, the compound of working example form No.280 was prepared.

mass:449(M+1)+.

Working Example No.281

According to the procedure described in the compound of working example No.278, the compound of working examples form No.281 was obtained.

mass:448(M+1)+.

Working Example No.282

(1) A mixture of 2-aminopyridine-4-carboxylic acid (1 g), thionylchloride (2.8 ml) and methanol (36 ml) was refluxed overnight. The reaction mixture was concentrated to afford a residue. Saturated aqueous sodium hydrogencarbonate was added to the residue and then extracted with chloroform. The organic layer was washed with brine and then dried over magnesium sulfate. After filtration, the filtrate was concentrated to afford a residue, which was purified by column chromatography on silica gel (Wakogel C-200) eluted with chloroform-methanol (100:0–98:2) to afford the titled compound (1.05 g).

(2) A mixture of the compound (1.8 g) of the reference example No.3, trichloroacetic anhydrate (0.35 ml), triethylamine (0.2 ml), methylen chloride (5 ml) and tetrahydrofuran (10 ml) was stirred for 2 hours at room temperature. Saturated aqueous sodium hydrogencarbonate was added to the reaction mixture and then extracted with chloroform. The extract was washed with brine and then dried over magnesium sulfate. After filtration, the filtrate was concentrated to afford a residue, which was purified by column chromatography on silica gel (Wakogel C-200) eluted with chloroform-tetrahydrofuran (9:1–8:2) to afford an amorphous compound (2.92 g).

A mixture of the compound (1.77 g) obtained above, the compound (1.05 g) obtained above in (1), DBU (1 ml) and dimethylsulfoxide (8 ml) was stirred for 3 hours at 100° C. The reaction mixture was diluted with chloroform and was washed with water and brine and then dried over magnesium sulfate. After filtration, the filtrate was concentrated to afford a residue, which was purified by column chromatography on silica gel (Wakogel C-200) eluted with chloroform-methanol (97:3) to afford the desired compound (1.21 g).

(3) A mixture of the compound (300 mg) obtained above in (2), 1N sodium hydroxide solution (10 ml) and methanol (3 ml) was stirred for 1 hour at 90° C. The pH of the reaction mixture was adjusted to 4 with 1N hydrochloric acid and then extracted with chloroform. The organic layer was washed with brine and then dried over magnesium sulfate. After filtration, the filtrate was concentrated to afford a residue, which was washed with chloroform-ethyl acetate to afford a white solid compound (80 mg).

(4) According to the procedure described in the compound of working example No.409(1), the compound (18 mg) obtained above in (3) was used to afford the titled compound (5 mg) as a white solid.

$^1$H-NMR(DMSO-$d_6$) 0.92(3H,t,J=7.2 Hz), 1.13(1H,m), 1.32(1H,m), 1.53(2H,m), 2.20–2.70(3H,m), 3.20–3.70(4H, m), 4.85(1H,dd,J=5.6,11 Hz), 7.32 (1H,d,J=7.9 Hz), 7.38 (1H,d,J=5.2 Hz), 7.49(1H,t,J=7.9 Hz), 7.75(1 H,s), 8.30(1H, d,=7.9 Hz), 8.43(1H,d,J=5.2 Hz), 8.70(1H,t,J=6.7 Hz), 10.1 (1H,s), 10.8(1H,br).

mass:408(M+1)+.

Working Examples No.283 to No.286

According to the procedure described in the compound of working example No.282, the compounds of working examples form No.283 to No.286 were obtained.

Working Example No.283 mass:434(M+1)$^+$.

Working Example No.284 mass:443(M+1)$^+$.

Working Example No.285 mass:443(M+1)$^+$.

Working Example No.286 mass:443(M+1)$^+$.

Working Example No.287

(1) According to the procedure described in the compound of reference example No.1, isoquinoline-3-carboxylic acid (90 mg) was used to afford a yellow solid compound (14 mg).

(2) According to the procedure described in the compound of working example No.79, the compound (14 mg) obtained above in (1) was used to afford the titled compound (13 mg) as a white solid.

$^1$H-NMR(DMSO-d$_6$) 1.10–1.20(1H,m), 2.25–2.50(2H, m), 2.58–2.70(1H,m), 3.20–3.40 (1H,m), 3.48–3.62(1H,m), 4.83(1H,dd,J=5.6, 10 Hz), 7.33(1H,d, J=7.9 Hz), 7.49(2H, m), 7.70(1H,t,J=7.9 Hz), 7.87(1H,d,J=7.9 Hz), 8.02(1H,s), 8.07(1H,d,J=7.9 Hz), 8.31(1H,d,J=7.9 Hz), 9.18(1H,s), 9.70 (1H,br), 9.90(1H,s).

mass:359(M+1)$^+$.

Working Example No.288

(1) A mixture of isoquinoline 3-carboxylic acid (300 mg), platinum oxide (30 mg), 4N hydrochloric acid-dioxane (5 ml) and methanol (5 ml) was stirred for 6 hours at room temperature. The reaction vessel was filled with hydrogen. The reaction mixture was filtered by celite. The filtrate was concentrated to afford a crude product (32 mg).

(2) According to the procedure described in the compound of working example No.287, the compound (130 mg) obtained above in (1) was used to afford the titled compound (23 mg) as a white solid.

$^1$H-NMR(DMSO-d$_6$) 1.00–1.20(1H,m), 1.60–1.80(4H, m), 2.20–2.70(7H,m), 3.20–3.35 (1H,m), 3.45–3.60(1H,m), 4.77(1H,dd,J=5.5, 10 Hz), 6.95(1H,s), 7.28(1H,d,J=7.9 Hz), 7.43(1H,t,J=7.9 Hz), 8.00(1H,s), 8.29(1H,d,J=7.9 Hz), 9.71 (1H,s), 11.2(1H,br).

mass:363(M+1)$^+$.

Working Example No.289

(1) A solution of dimethylacetal of 4-pyridinecarboxylaldehyde (15 g) in tetrahydrofuran (300 ml) was cooled to −78° C. To the solution was added a solution of n-butyllithium in hexane (1.6 M, 73 ml). The reaction temperature was raised from −78° C. up to 0° C. Tert-butyldimethylsilylether of 3-bromobutanol (25 g) was added at 0° C. The whole was stirred for 3 hours at the same temperature and then warmed up to room temperature. To the reaction mixture was added saturated aqueous sodium hydrogencarbonate. The whole was extracted with chloroform. The organic layer was washed with saturated brine and dried over magnesium sulfate. After filtration, the filtrate was concentrated to afford a residue, which was purified by column chromatography on silica gel (Wakogel C-200) eluted with hexane-ethyl acetate (2:1) to afford an oily compound (17 g).

(2) According to the procedure described in the reference example No.7, the compound (7 g) obtained above in (1) was used to afford an oily compound (3.9 g).

(3) According to the procedure described in the reference example No.8, the compound (3 g) obtained above in (2) was used to afford a brown oily compound (7 g).

(4) To water-tetrahydrofuran (1:10) was added the compound (7 g) obtained above in (3) and triphenylphosphine (5.8 g). The mixture was stirred for 2 hours at 50° C. The reaction mixture was concentrated to afford a residue, which was purified by column chromatography on silica gel (FL60D Fujisilysia. Co.) eluted with chloroform-methanol (100:0–98:2) to afford a brown oily compound (2.1 g).

(5) The compound (2.1 g) obtained above in (4) in chloroform (10 ml) was added to formic acid (5 ml). The mixture was stirred for 2 hours at 80° C. The reaction mixture was concentrated to afford a residue, which was dissolved in methanol (10 ml). To the solution was added sodium borohydride (7.4 g) and the mixture was stirred for 1 hour at room temperature. The reaction mixture was diluted with chloroform and washed with brine and then dried over magnesium sulfate. After filtration the filtrate was concentrated to afford a residue, which was purified by column chromatography on silica gel (FL60D Fujisilysia. Co.) eluted with chloroform-methanol (100:0–98:2) to afford the titled compound (0.57 g).

(6) A mixture of the compound (0.57 g) obtained above in (5), p-nitrobenzenesulfonyl chloride (7 g), dimethylaminopyridine (0.71 g) and chloroform (5 ml) was stirred for 2 hours at room temperature. The reaction mixture was diluted with chloroform and washed with saturated aqueous sodium hydrogencarbonate and brine and then dried over magnesium sulfate. After filtration, the filtrate was concentrated to afford a residue, which was purified by column chromatography on silica gel (Wakogel C-200) eluted with chloroform-methanol (100:0–98:2) to afford the titled compound (0.73 g).

(7) A mixture of the compound 0.73 g) obtained above in (6), manganese dioxide (50 mg), a 30% solution (5 ml) of hydrogen peroxide and chloroform (20 ml) was stirred for 6 hours at room temperature. The reaction mixture was diluted with chloroform and washed with saturated aqueous sodium hydrogencarbonate and brine and then dried over magnesium sulfate. After filtration, the filtrate was concentrated to afford a residue, which was purified by column chromatography on silica gel (Wakogel C-200) eluted with chloroform-methanol (100:0–98:2) to afford the crystalline compound (0.78 g).

(8) A mixture of the compound (0.78 g) obtained above in (7), trimethylsilylcyanide (0.66 ml) and acetonitrile-chloroform was stirred for 3 hours at 80° C. The residue was purified by column chromatography on silica gel (Wakogel C-200) eluted with chloroform-methanol (100:0–98:2) to afford the crystalline compound (0.71 g).

(9) Accroding to the procedures described in the reference examples No.4 and 5, the compound obtained above in (8) was used to afford the titled compound (75 mg).

(10) Accroding to the procedure described in the reference example No.11, the compound (75 mg) obtained above in (9) was used to afford the titled compound (18 mg) as a light yellow solid and the compound (1.4 mg) of the working example No.292 as a yellow solid.

$^1$H-NMR(DMSO-d$_6$) 1.25(1H,m), 1.60–2.00(3H,m), 2.20–2.60(4H,m), 2.64(1H,m), 3.15(2H,m), 3.45(1H,m), 3.78(1H,m), 4.18(1H,t,J=7.2 Hz), 4.80(1H,dd,J=5.6,11 Hz), 6.98(1H,s), 6.99(1H,d,J=5.6 Hz), 7.46(1H,t,J=7.9 Hz), 4.55

(1H,d,J=7.9 Hz), 8.11(1H,d,J=5.6 Hz), 8.39(1H,d,J=7.9 Hz), 8.40(1H,s), 12.0(1H,br).

mass:378(M+1)$^+$.

Working Example No.290

The compound (7 mg) of the working example No.289 was dissolved in methanol (2 ml). To the solution were added formalin (50 µl) and stirred for 4 hours at room temperature. To the reaction mixture was added sodium boron hydride (100 mg) and stirred for 1 hour at room temperature. To the reaction mixture, was added 1N hydrochloric acid to decompose the excess reagent. Saturated aqueous sodium hydrogencarbonate was added and then extracted with chloroform. The organic layer was washed with saturated brine and then dried over magnesium sulfate. After filtration the filtrate was concentrated to afford a residue, which was purified by column chromatography on silica gel (FL60D Fujisilysia. Co.) eluted with chloroform-methanol (9:1) to afford the titled compound (3 mg) as a yellow solid.

$^1$H-NMR(DMSO-d$_6$) 1.25(1H,m), 1.55–2.10(4H,m), 2.22 (3H,s), 2.20–2.40(3H,m), 2.65(1H,m), 3.14(1H,m), 3.25 (1H,m), 3.50(1H,m), 3.79(1H,m), 4.82 (1H,dd,J=5.6, 11 Hz), 6.89(1H,s), 7.03(1H,d,J=5.6 Hz), 7.49(1H,t, J=7.9 Hz), 7.56(1H,d,J=7.9 Hz), 8.05(1H,s), 8.15(1H,d,J=5.6 Hz), 8.35 (1H,d,J=7.9 Hz), 12.0(1H,br).

mass:392(M+1)$^+$.

Working Example No.291

A mixture of the compound (7 mg) of the working example No.289, acetic anhydride (6 mg), dimethylaminopyridine (5 mg) and chloroform (2 ml) was stirred overnight at room temperature. The reaction mixture was diluted with chloroform and washed with saturated aqueous sodiun hydrogencarbonate and saturated brine and then dried over magnesium sulfate. After filtration, the filtrate was concentrated to afford a residue, which was purified by TLC (Merck Art5744) eluted with chloroform-methanol (7:3) to afford the titled compound (3 mg) as a solid.

$^1$H-NMR(DMSO-d$_6$) 1.25(1H,m), 1.80–2.10(3H,m), 2.11 (3H,s), 2.20–2.70(4H,m), 3.30–3.80(4H,m), 4.60–5.20(2H, m), 6.60–6.90(1H,m), 7.40–7.60 (2H,m), 8.00–8.40(2H,m), 9.10(1H,br), 11.9(1H,br).

Working Example No.292

The titled compound was prepared in the last process for preparing the compound of the working example No.289.

$^1$H-NMR (DMSO-d$_6$) 1.20–1.60(3H,m), 2.10(2H,m), 2.40(2H,m), 2.60(1H,m), 2.90(2H,m), 3.45(1H,m), 3.78 (1H,m), 4.80(1H,dd,J=5.6,11 Hz), 7.10–7.60(4H,m), 8.00–8.40(3H,m), 11.8(1H,br).

mass:376(M+1)$^+$.

Working Example No.293

(1) Accroding to the procedure described in the reference example No.6, the compound (9 g) of the working example No.80(3) was used to afford a brown oily compound (8.5 g).

(2) According to the procedure described in the working example No.80(4), the compound (8.5 g) obtained above in (1) was used to afford a brown amorphous compound (4.7 g).

(3) According to the procedure described in the working example No.84(1), the compound (250 mg) obtained above in (2) was used to afford the titled compound (210 mg).

(4) A solution of ethyl di-o-tolylphosphono acetate (38 mg) in tetrahydrofuran (2 ml) was cooled to −78° C. To the solution was added a solution of the compound (43 mg) obtained above in (3) in tetrahydrofuran (1 ml). The whole was stirred for 2 hours at −78° C. To the reaction mixture was added saturated aqueous ammonium chloride. The whole was warmed up to room temperature and extracted with chloroform solution. The organic layer was washed with saturated brine and then dried over magnesium sulfate. After filtration, the filtrate was concentrated to afford a residue, which was purified by column chromatography on silica gel (Wakogel C-200) eluted with chloroform-methanol (100:0–97:3) followed by TLC (Merck Art5744) eluted with chloroform-ethanol (9:1) to afford a colorless oily compound (40 mg).

(5) A mixture of the compound (40 mg) obtained above in (4). 6N hydrochloric acid and tetrahydrofuran (5 ml) was stirred for 15 minutes at room temperature. The reaction mixture was extracted with chloroform and washed with saturated brine and then dried over magnesium sulfate. After filtration, the filtrate was concentrated to afford the titled compound (19 mg) as a colorless solid.

$^1$H-NMR(DMSO-d$_6$) 1.15(3H,t,J=7.1 Hz), 1.09–1.15(1H, m), 2.30–3.38(2H,m), 2.48–2.56(1H,m), 3.20–3.31(11H,m), 3.51–3.55(1H,m), 4.11(2H,q, J=7.1 Hz), 4.79–4.85(1H,m), 6.23(1H,d,J=13 Hz), 7.04(2H,m), 7.30–7.32(2H,m), 7.46 (1H,t,J=7.7 Hz), 8.28–8.30(2H,m), 9.99(1H,s) 11.0(1H,br).

mass:407(M+1)$^+$.

Working Example No.294

(1) A solution of ethyl diethylphosphono acetate (22 mg) in tetrahydrofuran (2 ml) was cooled in an ice-bath. Sodium hydride (4 mg) was added and the mixture was stirred for 30 minutes. To the mixture was added a solution of the compound (43 mg) of the working example No. 293(3) in tetrahydrofuran (1 ml). The whole was stirred for 2 hours and then aqueous saturated ammonium chloride solution was added. The mixture was warmed up to room temperature and extracted with chloroform. The organic layer was washed with saturated brine and then dried over magnesium sulfate. After filtration, the filtrate was concentrated to afford a residue, which was purified by column chromatography on silica gel (Wakogel C-200) eluted with chloroform-methanol (100:0–97:3) to afford a white solid (42 mg).

(2) According to the procedure described in the working example No.293(5), the compound (42 mg) obtained above in (1) was ued to afford the titled compound (21 mg) as a white solid.

$^1$H-NMR(DMSO-d$_6$) 1.00–1.20(1H,m), 1.28(3H,t,J=7.1 Hz), 2.20–2.40(2H,m), 2.40–2.60(1H,m), 3.20–3.40(1H,m), 3.45–3.60(1H,m), 4.23(1H,q, J=7.1 Hz), 4.84(1H,m), 6.78 (1H,d,J=16 Hz), 7.33(1H,d,J=7.9 Hz), 7.40–7.50(3H,m), 7.57(1H,d,J=16 Hz), 8.30(1H,d,J=7.9 Hz), 8.36(1H,d,J=5.6 Hz), 10.0(1H,s), 10.8(1H,br mass:407(M+1)$^+$.

Working Example No.295

To a solution of the compound (50 mg) of the working example No.294(1) in chloroform (5 ml), were added zinc chloride (27 mg) and sodium borohydride (7 mg). The reaction mixture was refluxed for 3 hours and treated according to the procedure described in the working example No.290. The titled compound (32 mg) was obtained as a white solid.

$^1$H-NMR(DMSO-d$_6$) 1.00–1.20(1H,m), 2.20–2.60(3H, m), 3.20–3.60(2H,m), 4.17(2H,m), 4.84(1H,dd,J=5.6,11

Hz), 5.04(1H,t,J=6.3 Hz), 6.53(1H,d,J=16 Hz), 6.66(1H,d, J=16 Hz), 7.15(1H,d,J=5.3 Hz), 7.22(1H,s), 7.31(1H,d,J=7.9 Hz), 7.47(1H,t,J=7.9 Hz), 8.24(1H,d,J=5.3 Hz), 8.32(1H,d, J=7.9 Hz), 9.94(1H,s), 11.3(1H,br).

mass:365(M+1)$^+$.

Working Example No.296

To a solution of the compound (30 mg) of the working example No.294(1) in methanol (10 ml), were added cuprous chloride (10 mg) and sodium borohydride (4 mg). The reaction mixture was stirred until the disappearance of the starting material. The reaction mixture was treated according to the procedure described in the working example No.290. The titled compound (13 mg) was obtained as a white solid.

$^1$H-NMR(DMSO-d$_6$) 1.05–1.25(1H,m), 1.15(3H,t,J=7.1 Hz), 2.20–2.60(3H,m), 2.64(2H,t,J=7.1 Hz), 2.83(2H,t,J= 7.1 Hz), 3.20–3.40(1H,m), 3.45–3.60(1H,m), 4.04(2H,q,J= 7.1 Hz), 4.81(1H,m), 6.96(1H,d,J=5.3 Hz), 7.11(1H,s), 7.30 (1H,d,J=7.9 Hz), 7.45(1H,d,J=7.9 Hz), 8.19(1H,d,J=5.4 Hz), 8.30(1H,d,J=7.9 Hz), 9.90(1H,s), 12.3(1H,br).

mass:409(M+1)$^+$.

Working Example No.297

The compound (60 mg) of the working example No.293 was dissolved in chloroform (30 mL). To the solution, was added a solution of diisopropylaluminum hydride in toluene (1.0 M, 0.9 ml). The mixture was stirred for 30 minutes at −30 to −20° C. The reaction mixture was treated according to the procedure described in the working example No.290 to obtain the titled compound (17 mg) as a white solid.

$^1$H-NMR(DMSO-d$_6$) 1.25(1H,m), 2.20–2.70(3H,m), 3.30 (1H,m), 3.53(1H,m), 4.15–4.40(2H,m), 4.81(1H,dd,J=5.6, 11 Hz), 5.00(1H,m), 6.00(1H,m), 6.38(1H,m), 6.89(1H,d,J= 5.4 Hz), 7.12(1H,s), 7.31(1H,d,J=7.9 Hz), 7.45(1H,t,J=7.9 Hz), 8.28(2H,m), 9.90(1H,m), 11.1(1H,br).

mass:365(M+1)$^+$.

Working Example No.298

A mixture of the compound (40 mg) of the working example No. 294, 2N aqueous sodium hydroxide solution (5 ml), tetrahydrofuran (2 ml) and methanol (2 ml) was stirred for 1 hour at room temperature. To the reaction mixture, was added 1N hydrochloric acid to adjust the pH of the reaction mixture to 3. The whole was extracted with chloroform. The organic layer was washed with saturated brine and then dried over magnesium sulfate. After filtration, the filtrate was concentrated to afford a residue, which was purified by TLC (Merck Art5744, chloroform-methanol (9:1) followed by recrystallization to afford the titled compound (22 mg) as a white solid.

$^1$H-NMR(DMSO-d$_6$) 1.00–1.20(1H,m), 2.20–2.60(3H, m), 3.15(1H,m), 3.45–3.60(1H,m), 4.82(1H,m), 6.68(1H,d, J=16 Hz), 7.20–7.60(5H,m), 8.28(1H,d,J=7.9 Hz), 8.35(1H, d,J=5.6 Hz), 10.2(1H,s), 10.9(1H,br), 12.8(1H,br).

mass:379(M+1)$^+$.

Working Example No.299

(1) A mixture of the compound (727 mg) of the working example No. 7, DBU (1.496 ml) and tetrahydrofuran (10 ml) was cooled to 0° C. and a solution of methanesulfonyl chloride (0.310 ml) in tetrahydrofuran (2 ml) was added. The reaction mixture was stirred for 11 hours at room temperature and water was added. The whole was extracted with chloroform. The organic layer was washed with water and saturated brine and then dried over magnesium sulfate. After filtration, the filtrate was concentrated to afford a residue, which was purified by column chromatography on silica gel (Wakogel C-200, hexane-ethyl acetate (1:1–0:1)) to afford a colorless amorphous compound (606 mg).

(2) According to the procedure described in the working example No.133(2), the titled compound was prepared.

$^1$H-NMR(DMSO-d$_6$) 1.07–1.14(1H,m), 2.29–2.57(3H, m), 3.24–3.88(2H,m), 4.79–4.85(1H,m), 5.58(1H,d,J=11 Hz), 6.08(1H,d,J=18 Hz). 6.74(1H,dd,J=11,18 Hz), 7.22–7.24(1H,m), 7.29–7.34(2H,m), 7.47(1H,t,J=7.5 Hz), 8.22–8.27(2H,m), 10.1(1H,s), 11.0(1H,br).

mass:335(M+1)$^+$.

Working Example No.300

(1) A solution of the compound (80 mg) of the working example No.294(1) in methylene chloride (5 ml) was cooled in an ice-bath. Trifluoroacetic acid (274 mg) and N-(methoxymethyl)-N-trimethylsilylmethyl)benzylamine (190 mg) were added.

The reaction mixture was stirred for 3 hours and diluted with chloroform. The whole was washed aqueous saturated sodium bicarbonate solution and saturated brine and then dried over magnesium sulfate. After filtration, the filtrate was concentrated to afford a residue, which was purified by TLC (Merck Art5744, chloroform-methanol (9:1)) followed by recrystallization to afford a light yellow oily compound (91 mg).

(2) According to the procedure described in the working example No.293(5), the compound (91 mg) obtained above in (1) was used to afford titled compound as a white solid (50 mg).

$^1$H-NMR(DMSO-d$_6$) 1.24(1H,m), 1.24(3H,t,H=7.4 Hz), 2.20–2.75(3H,m), 2.80(1H,m), 2.95(1H,m), 3.05(1H,m), 3.19(1H,m), 3.45(1H,m), 3.60–3.90(4H,m), 4.18(2H,q,J= 7.4 Hz), 4.78(1H,dd,J=5.6,11 Hz), 6.93(1H,s), 7.03(1 H,d, J=5.6 Hz), 7.10–7.45(5H,m), 7.50(1H,t,J=7.9 Hz), 7.55(1H, d,J=7.9 Hz), 8.13(1H,d,J=5.6 Hz), 8.37(1H,d,J=7.9 Hz), 8.82(1H,s), 12.0(1H,br).

mass:540(M+1)$^+$.

Working Example No.301

According to the procedure described in the working example No.300, the titled compound was prepared from the compound of the working example No.293(4).

mass:540(M+1)$^+$.

Working Example No.302

A solution of the compound (30 mg) of the working example No. 300 in tetrahydrofuran (3 ml) was cooled in an ice-bath. To the solution, were added a solution of lithium aluminum hydride in tetrahydrofuran (2 M, 56 µl) and a solution of methanol in tetrahydrofuran (1 M, 0.22 ml). The reaction mixture was stirred for 30 minutes at room temperature. According to the procedure described in the working example No.290, the titled compound (less polar fraction) (1.2 mg) as a white solid and its diastereomer compound (2.3 mg) (more polar fraction), which is the compound of the working example No.303, were prepared.

H-NMR(DMSO-d$_6$) 1.25(1H,m), 2.20–2.60(3H,m), 3.30–4.40(12H,m), 4.78(1H,m), 6.60–7.00(2H,m), 7.20–7.80(7H,m), 8.10–8.40(2H,m), 11.8(1H,br).

mass:498(M+1)$^+$.

Working Example No.303

The titled compound was obtained from the diastereomer of the compound of working example No.302.

$^1$H-NMR(DMSO-d$_6$) 1.25(1H,m), 2.00–2.70(3H,m), 2.80–4.40(12H,m), 4.78(1H,m), 6.75(1H,s), 6.98(1H,d,J=5.4 Hz), 7.20–7.70(7H,m), 8.10(1H,d,J=5.4 Hz), 8.28(1H, d,J=7.9 Hz), 11.8(1H,br).

mass:498(M+1)$^+$.

Working Example No.304

According to the procedure described in the working example No.303, the compound of the working example No.301 was used to afford the titled compound.

mass:498(M+1)$^+$.

Working Example No.305

(1) A mixture of the compound (50 mg) of the working example No. 293(4), isoprene (34 mg) and toluene (3 ml) was reacted in a sealed tube at 120° C. overnight. The reaction mixture was concentrated to afford a residue, which was purified by TLC (Merck Art5744, chloroform-methanol (9:1) to afford adduct (52 mg).

(2) The compound obtained above in (1) was subjected to the reaction described in the working example No.293(5), to afford the titled compound (18 mg) as a white solid.

$^1$H-NMR(DMSO-d$_6$) 1.03(3H,t,J=7.3 Hz), 1.25(1H,m), 1.68(s), 1.72(s), 1.68–1.72(3H), 2.00–3.20(9H,m), 3.42(1H, m), 3.78(1H,m), 3.98(2H,q,J=7.3 Hz), 4.80(1H,dd,J=5.6,11 Hz), 5.49(1H,m), 6.84(2H,m), 7.46(1H,d,J=7.9 Hz), 7.55 (1H,d,J=7.9 Hz), 8.10(1H,d, J=5.2 Hz), 8.40(1H,d,J=7.9 Hz), 9.25(1H,s), 12.0(1H,br).

mass:475(M+1)$^+$.

Working Example No.306

(1) According to the procedure described in the working example No.261, the compound of the working example No.3 and 4-nitrobenzoyl chloride were used to afford a yellow solid.

(2) The compound (22.1 g) obtained above in (1) was subjected to the optical resolution by HPLC (CHIRALPAK AD, hexane-ethanol (1:1–1:4) to afford the compound (A) (11.2 g) at Rt=22 min and the compound (B) (10.1 g) at Rt=30 min.

(3) A mixture of the compound (10 g) of (2)-A, 6N hydrochloric acid (30 ml) and acetic acid (30 ml) was stirred for 3 days at 80° C. The reaction mixture was cooled to room temperature and made alkaline by adding aqueous saturated sodium bicarbonate solution. The mixture was extracted with chloroform.

The organic layer was washed with 1N potassium hydroxide solution and saturated brine and then dried over magnesium sulfate. After filtration, the filtrate was concentrated to afford a residue, which was purified by column chromatography on silica gel (Wakogel C-200, chloroform-methanol (100:0–98:2)) followed by the recrystallization from ethanol to afford a white solid (3.1 g, 98% ee).

(4) According to the procedure described in the working example No.80, the compound obtained above in (3) was used to afford a white solid.

(5) According to the procedure described in the working example No.84, the compound obtained above in (4) was used to afford a white solid, which is the optical isomer of the working example No.91.

mass:429(M+1)$^+$.

Working Example No.307

According to the procedures described in the working example No.306(3) to (5), the compound of the working example No. 306(2)-B was used to afford the titled compound as a white solid.

mass:429(M+1)$^+$.

Working Example No.308

According to the procedure described in the working example No.306, the compound of the working example No.308 was prepared.

mass:429(M+1)$^+$.

Working Example No.309

According to the procedure described in the working example No.307, the compound of the working example No.309 was prepared.

mass:429(M+1)$^+$.

Working Example No.310

According to the procedure described in the working example No.307, the compound of the working example No.310 was prepared.

mass:469(M+1)$^+$.

Working Example No.311

According to the procedure described in the working example No.306, the compound of the working example No.311 was prepared.

mass:429(M+1)$^+$.

Working Example No.312

According to the procedure described in the working example No.307, the compound of the working example No.312 was prepared.

mass:429(M+1)$^+$.

Working Example No.313

According to the procedure described in the working example No.290, the compound (51 mg) of the working example No.91 was used to afford the titled compound (12 mg) as a white solid.

mass:429(M+1)$^+$.

Working Example No.314

(1) A mixture of cyclopentanone (504 mg), pyrrolidine (498 mg), molecular sieves 4A (2 g) and toluene (30 ml) was stirred overnight at room temperature. The reaction mixture was filtered through a celite pad and the filtrate was concentrated to afford a residue, which was dissolved in chloroform (20 ml). To the solution, was added a solution of ethyl 1,2,4-triazine-5-carboxylate in chloroform (10 ml). The mixture was stirred for 30 minutes at room temperature and for 6 hours at 45° C. The reaction mixture was concentrated to afford a residue, which was purified by column chromatography on silica gel (Wakogel C-200, hexane-ethyl acetate (4:1–1:1)) to afford a yellow oily compound (734 mg).

(2) According to the procedure described in the reference example No. 5, the compound (100 mg) obtained above in (1) was used to afford the titled compound (101 mg) as a white solid.

$^1$H-NMR(DMSO-d$_6$) 1.30(1H,m), 2.14(2H,quintet,J=7.5 Hz), 2.40(2H,m), 2.62(1H,m), 2.92(4H,t,J=7.5 Hz), 3.42 (1H,m), 3.75(1H,m), 4.79(1H,dd,J=5.6, 11 Hz), 6.68(1H,s), 7.48(1H,t,J=7.4 Hz), 7.53(1H,d,J=7.4 Hz), 7.66(1H,s), 8.03 (1H,s), 8.33(1H,d,J=7.4 Hz), 12.1(1H,s).

mass:349(M+1)$^+$.

Working Examples No.315–319

According to the procedure described in the working example No.314, the compounds of the working examples No.315 to No.319 were prepared.

Working Example No.315 mass:377(M+1)$^+$.

Working Example No.316 mass:378(M+1)$^+$.

Working Example No.317 mass:454(M+1)$^+$.

Working Example No.318 mass:454(M+1)$^+$.

Working Example No.319 mass:450(M+1)$^+$.

Working Example No.320

A mixture of the compound (100 mg) of the working example No. 319, 4N hydrochloric acid-dioxane (5 ml) and methanol (3 ml) was stirred for 30 minutes at room temperature. To the reaction mixture, was added triethylamine. The whole was concentrated to afford a residue, which was purified by column chromatography on silica gel (FL60D FujiSilysia Co.), chloroform-methanol (100:0–95:5) to afford a white solid (72 mg).

mass:350(M+1)$^+$.

Working Example No.321

According to the procedure described in the working example No.84(2), the compound (17 mg) of the working example No.320 and cyclopentanone (12 mg) were used to afford the titled compound.

mass:418(M+1)$^+$.

Working Example No.322

According to the procedure described in the working example No.321, the compound of the working example No.322 was prepared.

mass:364(M+1)$^+$.

Working Example No.323

(1) According to the procedure described in the reference example No.8, the compound of the working example No.164(2)-A was used to afford the desired compound.

(2) According to the procedure described in the working example No.133(2), the compound obtained above in (1) was used to afford the hydrochloride of the titled compound.

$^1$H-NMR(DMSO-d$_6$) 1.00–1.23(1H,m), 2.20–2.90(7H, m), 3.40–3.61(2H,m), 4.81(1H,m), 6.90–7.51(4H,m), 8.08–8.37(2H,m), 9.95(1H,brs), 11.4(1H,brs).

mass:352(M+1)$^+$.

Working Example No.324

According to the procedure described in the working example No.323, the compound of the working example No.164(2)-B was used to afford the hydrochloride of the titled compound.

mass:352(M+1)$^+$.

Working Example No.325

According to the procedure described in the working example No.133(2), the compound of the working example No.164(2)-A was used to afford the titled compound.

$^1$H-NMR(DMSO-d$_6$) 1.00–1.21(1H,m), 2.25–2.79(5H, m), 3.21–3.72(4H,m), 4.65–4.90(2H,m), 6.90–7.52(4H,m), 8.13–8.38(2H,m), 9.85(1H,s), 11.4(1H,brs).

mass:353(M+1)$^+$.

Working Example No.326

According to the procedure described in the working example No. 133(2), the compound of the working example No.164(2)-B was used to afford the titled compound.

mass:353(M+1)$^+$.

Working Example No.327

(1) According to the procedure described in the working example No.96(1), the compound of the working example No.323(1) was used to afford the desired compound.

(2) According to the procedure described in the working example No.133(2), the compound obtained above in (1) was used to afford the titled compound.

$^1$H-NMR(DMSO-d$_6$) 1.01–1.20(1H,m), 2.22–2.78(5H, m), 3.08–3.20(2H,m), 3.32(1H,m), 3.55(1H,m), 4.81(1H, m), 6.85–7.52(4H,m), 7.92–8.40(7H,m), 9.90(1H,s), 11.2 (1H,brs).

mass:538(M+1)$^+$.

Working Example No.328

(1) According to the procedure described in the working example No.323(1), the compound of the working example No.164(2)-B was used to afford the desired compound.

(2) According to the procedure described in the working example No.327, the compound obtained above in (1) was used to afford the titled compound.

mass:538(M+1)$^+$.

Working Example No.329

According to the procedures described in the working example No.96(2) and (3), the compound of the working example No.327(1) and 1-butanol were used to afford the hydrochloride of the titled compound.

$^1$H-NMR(DMSO-d$_6$) 0.89(3H,t,J=7.8 Hz), 1.01–1.17(1H, m), 1.25–1.41(2H,m), 1.52–1.64(2H,m), 2.26–2.40(2H,m), 2.52–2.63(1H,m), 2.85–3.00(4H,m), 3.08–3.23(2H,m), 3.26–3.35(1H,m), 3.50–3.60(1H,m), 4.80–4.86(1H,m), 7.03 (1H,d,J=4.3 Hz), 7.26–7.35(2H,m), 7.56(1H,t,J=7.8 Hz), 8.26–8.30(2H,m), 8.81(2H,m), 10.3(1H,s), 11.0(1H,brs).

mass:408(M+1)$^+$.

Working Example No.330

(1) According to the procedure described in the working example No.327(1), the compound of the working example No.328(1) was used to afford the desired compound.

(2) According to the procedure described in the working example No.329, the compound obtained above in (1) was used to afford the hydrochloride of the titled compound.

mass:408(M+1)$^+$.

Working Example No.331

According to the procedure described in the working example No.334, the compound of the reference example No.8 and (R)-3-(tert-butoxycarbonylamino)-1,4-dimethanesulfonyloxybutane were used to afford the hydrochloride of the titled compound.

$^1$H-NMR(DMSO-d$_6$) 1.05(1H,m), 2.00–2.75(5H,m), 3.05–4.95(11H,m), 7.12–7.52(4H,m), 8.21–8.80(4H,m), 10.5–11.8(4H,m).

Working Example No.332

A mixture of the compound (15 mg) of the working example No. 331, acetyl chloride (24 μl), triethylamine (92 a 1) and dimethylformamide (0.5 ml) was stirred for 5 minutes at room temperature. The reaction mixture was concentrated to afford a residue, which was purified by TLC (Merck Art5713, chloroform-methanol (19:1)) to afford the titled compound (11 mg) as a light yellow solid.

$^1$H-NMR(CD$_3$OD) 1.10–1.30(1H,m), 1.65(1H,m), 1.90 (3H,s), 2.22(1H,m), 2.40–2.92(11H,m), 3.45(1H,m), 3.65 (1H,m), 4.29(1H,m), 4.86(1H,m), 6.87–7.00(2H,m), 7.39–7.52(2H,m), 8.14–8.30(2H,m).

mass:463(M+1)$^+$.

Working Example No.333

According to the procedure described in the working example No.96(1), the compound (20 mg) of the working example No.331 was used to afford the titled compound (16 mg) as a light yellow solid.

$^1$H-NMR(DMSO-d$_6$) 1.12(1H,m), 1.45(1H,m), 1.89(1H, m), 2.20–2.75(10H,m), 3.25–3.75(4H,m), 4.75–4.85(1H,m), 6.87–7.50(4H,m), 8.00–8.43(6H,m).

Working Example No.334

(1) A mixture of the compound (100 mg) of the working example No. 323(1), (S)-3-(tert-butoxycarbonylamino)-1,4-dimethanesulfonyloxybutane (34 mg), N,N-diisopropyl ethylamine (46 mg) and dimethylformamide (1 ml) was stirred for 1 hour at 80° C. The reaction mixture was cooled to room temperature and diluted with chloroform. The whole was washed with aqueous saturated sodium bicarbonate solution and brine, and then dried over magnesium sulfate. After filtration, the filtrate was concentrated to afford a residue, which was purified by column chromatography on silica gel (Wakogel C-200, chloroform-methanol (1:0–4:1)) to afford an ester (90 mg).

(2) According to the procedure described in the working example No.133(2), the compound (100 mg) obtained above in (1) was used to afford the hydrochloride of the titled compound (50 mg) as a white solid.

$^1$H-NMR(DMSO-d$_6$) 1.05(1H,m), 2.00–2.75(5H,m), 3.05–4.95(11H,m), 7.12–7.52(4H,m), 8.21–8.80(4H,m), 10.5–11.8(4H,m).

mass:421(M+1)$^+$.

Working Example No.335

According to the procedure described in the reference example No.8, the compound of the working example No.164(2)-B was used to afford the compound, which was subjected to the reaction described in the working example No.334 to afford the hydrochloride of the titled compound.

mass:421(M+1)$^+$.

Working Example No.336

(1) A solution of 2-(N-(tert-butoxycarbonyl)amino)-4-methylpyridine (2.26 g) in tetrahydrofuran (100 ml) was cooled to −78° C. A solution of n-butyllithium in hexane (1.5 M, 18.2 ml) was added and then warmed up to room temperature. The reaction mixture was cooled again to −78° C., to which n-butylaldehyde (1.48 ml) was added dropwise and the whole was warmed up to room temperature. To the reaction mixture was added water and then extracted with ethyl acetate. The organic layer was washed with saturated brine and dried over magnesium sulfate. After filtration, the filtrate was concentrated to afford a residue, which was purified by column chromatography on silica gel (Wakogel C-300, hexane-ethyl acetate (1:0–1:1)) to afford a white solid compound (1.37 g).

(2) According to the procedure described in the reference example No.8(1), the compound (1.00 g) obtained above in (1) was used to afford the desired compound (700 mg).

(3) A mixture of the compound (700 mg) obtained above in (2), triphenylphosphine (700 mg), water (2 ml) and tetrahydrofuran (30 ml) was stirred for 30 minutes. To the reaction mixture was added toluene and methanol at room temperature. The whole was concentrated to afford a residue, which was purified by column chromatography on silica gel (Wakogel C-300, chloroform-methanol (1:0–4:1) to afford the desired compound (600 mg).

(4) According to the procedure described in the working example No.96(1), the compound obtained above in (3) was used to afford the desired compound.

(5) According to the procedure described in the working example No.96(2), the compound (100 mg) obtained above in (4) and ethanol were used to afford the desired compound (105 mg).

(6) According to the procedure described in the working example No.118(2), the compound (53 mg) obtained above in (5) was used to afford the urea compound (40 mg), which was resolved by HPLC (CHIRALPAK AD) to afford compound A (19 mg) and compound B (19 mg) in earler order of Rt.

(7) According to the procedure described in the working example No.96(3), the compound (20 mg) obtained above in (6)-A was used to afford the colorless oily compound (3.8 mg).

$^1$H-NMR(DMSO-d$_6$) 0.70–1.42(11H,m), 2.10–2.82(8H, m), 3.05–3.81(2H,m), 4.37–4.88(1H,m), 6.90–6.97(1H,m), 7.10(1H,s), 7.28–7.51(2H,m), 8.15–8.37(2H,m), 9.88(1H,s), 11.8(1H,s).

mass:422(M+1)$^+$.

Working Example No.337

According to the procedure described in the working example No.96(3), the compound of the working example No.336(6)-B was used to afford the titled compound (5.7 mg) as a colorless oil.

mass:422(M+1)$^+$.

Working Example No.338

(1) According to the procedure described in the working example No.84(2), the compound of the reference example No.8 and 2,4-dimethoxybenzaldehyde were used to afford the desired compound.

(2) According to the procedure described in the working example No.96(1), the compound obtained above in (1) and 1-propansulfonylchloride were used to afford the desired compound.

(3) A solution of the compound obtained above in (2) in trifluoroacetic acid was stirred for 15 minutes at room temperature. The reaction mixture was concentrated to afford a residue. The residue was crystallized from ether-methanol to afford the title compound.

mass:458(M+1)$^+$.

Working Example No.339

According to the procedure described in the working example No.140, the compound of the working example No.339 was used to afford the titled compound.

mass:472(M+1)$^+$.

Working Example No.340

According to the procedure described in the working example No.138, the compound of the working example No.340 was used to afford the titled compound.

mass:458(M+1)$^+$.

Working Example No.341

(1) According to the procedure described in the reference example No.10, o-anisidine was used to afford the desired compound.

(2) The compound obtained above in (1) was subjected to the procedure described in the reference example No.11 to afford a crude product, which was dissolved in methanol and treated with 1N hydrochloric acid. The reaction mixture was filtered through a celite pad, and concentrated to afford a residue, which was solidified from ether-methanol to afford the titled compound as a white solid.

mass:458(M+1)$^+$.

Working Examples No.342–360

According to the procedure described in the working example No.341, the compounds of the working examples from No.342 to No.360 were prepared.

Working Example No.342 mass:458(M+1)$^+$.

Working Example No.343 mass:419(M+1)$^+$.

Working Example No.344 mass:472(M+1)$^+$.

Working Example No.345 mass:485(M+1)$^+$.

Working Example No.346 mass:510(M+1)$^+$.

Working Example No.347 mass:435(M+1)$^+$.

Working Example No.348 mass:436(M+1)$^+$.

Working Example No.349 mass:479(M+1)$^+$.

Working Example No.350 mass:428(M+1)$^+$.

Working Example No.351

$^1$H-NMR(DMSO-d$_6$) 1.07(1H,m), 2.25–2.35(2H,m), 2.58 (1H,m), 2.93(2H,t,J=6.9 Hz), 3.29(1H,m), 3.53(1H,m), 3.86 (2H,t,J=6.9 Hz), 4.82(1H,dd,J=5.6,11 Hz), 6.90(1H,d,J=5.5 Hz), 7.08(1H,s), 7.32(1H,d,J=7.6 Hz), 7.46(1H,t,J=7.6 Hz), 7.97(2H,d,J=8.9 Hz), 8.17(1H,s), 8.21(1H,d,J=5.5 Hz), 8.26 (1H,d,J=7.6 Hz), 8.35(2H,d,J=8.9 Hz), 10.3(1H,br), 11.0 (1H,br), 13.0(1H,br).

mass:620(M+1)$^+$.

Working Example No.352 mass:430(M+1)$^+$.

Working Example No.353 mass:429(M+1)$^+$.

Working Example No.354 mass:429(M+1)$^+$.

Working Example No.355 mass:429(M+1)$^+$.

Working Example No.356 mass:479(M+1)$^+$.

Working Example No.357 mass:430(M+1)$^+$.

Working Example No.358 mass:468(M+1)$^+$.

Working Example No.359 mass:479(M+1)$^+$.

Working Example No.360 mass:430(M+1)$^+$.

Working Example No.361

(1) 6-Aminoquinoline was subjected to the reaction described in the reference examples No.10 and No.11 to afford sulfide as a by-product.

(2) According to the procedure described in the working example No.133(2), the compound (64 mg) obtained above in (1) was used to afford the titled compound (21 mg) as a white solid.

mass:445(M+1)$^+$.

Working Example No.362

(1) 6-Aminoquinoline was subjected to the reaction described in the reference examples No.10 and No. 11 to afford chloride as a by-product.

(2) According to the procedure described in the working example No. 133(2), the compound (26 mg) obtained above in (1) was used to afford the titled compound (18 mg) as a white solid.

mass:371(M+1)$^+$.

Working Examples No.363–364

According to the procedure described in the working example No.341, the compounds of the working examples from No.363 to No.364 were prepared.

Working Example No.363 mass:479(M+1)$^+$.

Working Example No.364 mass:418(M+1)$^+$.

Working Example No.365

(1) According to the procedure described in the working example No. 137(1), tert-butyldiphenylsilylether of 4-hydroxybenzaldehyde was used to afford the desired compound.

(2) According to the procedure described in the working example No.139, the compound obtained above in (1) was used to afford the hydrochloride of the titled compound as a white solid.

$^1$H-NMR(DMSO-d$_6$) 1.07–1.16(1H,m), 2.26–2.61(3H, m), 2.80(3H,s), 2.83(3H,s), 3.00–3.17(3H,m), 3.25–3.34 (1H,m), 3.45–3.56(3H,m), 4.11(2H,t,J=4.2 Hz), 4.36(2H,t, J=4.3 Hz), 4.82(2H,dd,J=6.2, 12 Hz), 6.97–7.07(3H,m), 7.25–7.54(5H,m), 8.23–8.28(2H,m), 9.37(2H,br), 10.2(1H, br), 10.4(1H,br), 10.9(1H,br).

mass:529(M+1)$^+$.

Working Examples No.366–375

According to the procedure described in the working example No.365, the compounds of the working examples from No.366 to No.375 were prepared.

Working Example No.366 mass:549(M+1)$^+$.

Working Example No.367 mass:555(M+1)$^+$.

Working Example No.368 mass:569(M+1)$^+$.

Working Example No.369 mass:571(M+1)$^+$.

Working Example No.370 mass:549(M+1)$^+$.

Working Example No.371 mass:577(M+1)$^+$.

Working Example No.372 mass:549(M+1)$^+$.

Working Example No.373 mass:577(M+1)$^4$.

Working Example No.374 mass:583(M+1)$^+$.

Working Example No.375 mass:585(M+1)$^+$.

Working Example No.376

(1) To a solution of 2-pyridinecarboxyaldehyde (510 mg) in benzene (20 ml) was added methyl triphenylphosphoranylidene acetate (1.7 g). The mixture was stirred for 2 hours at room temperature. The reaction mixture was concentrated to leave a residue, which was purified by column chromatography on silica gel (Wakogel C-300, hexane-ethyl acetate (4:1–3:1) to afford the desired compound (621 mg).

(2) According to the procedure described in the working example No. 297, the compound (621 mg) obtained above in (1) was used to afford the desired compound (252 mg).

(3) According to the procedure described in the working example No.365, the compound (20 mg) obtained above in (2) was used to afford the hydrochloride of the titled compound (24 mg) as a yellow solid.

$^1$H-NMR (CD$_3$OD) 1.13(1H,m), 2.42(2H,m), 2.70(1H, m), 3.60–3.82(2H,m), 3.37–3.47(3H,m), 4.03(1H,m), 4.20–4.38(3H,m), 4.96(2H,m), 6.81–8.72(16H,m).

Working Example No.377

(1) According to the procedure described in the working example No.137(1), tert-butyldiphenylsilylether of 3-hydroxybenzaldehyde was used to afford the desired compound.

(2) According to the procedure described in the working example No.139, the compound obtained above in (1) was used to afford the hydrochloride of the titled compound as a white solid.

$^1$H-NMR(DMSO-d$_6$) 1.04(1H,m), 2.23–2.34(2H,m), 2.70 (1H,m), 3.07–3.20(4H,m), 3.28(1H,m), 3.51(1H,m), 4.16 (2H,m), 4.84(1H,dd,J=6.4,10 Hz), 5.39(2H,s), 7.08–7.20 (2H,m), 7.28–7.39(4H,m), 7.43–7.52(2H,m), 7.71(1H,m), 7.86(1H,d,J=8.6 Hz), 8.20–8.28(2H,m), 8.77(1H,m), 9.64 (2H,br), 10.7(1H,br), 11.1(1H,br).

mass:549(M+1)$^+$.

Working Examples No.378–387

According to the procedure described in the working example No.377, the compounds of the working examples from No.378 to No.387 were prepared.

Working Example No.378 mass:549(M+1)$^+$.

Working Example No.379 mass:549(M+1)$^+$.

Working Example No.380 mass:577(M+1)$^+$.

Working Example No.381 mass:577(M+1)$^+$.

Working Example No.382 mass:529(M+1)$^+$.

Working Example No.383 mass:585(M+1)$^+$.

Working Example No.384 mass:571(M+1)$^+$.

Working Example No.385 mass:555(M+1)$^+$.

Working Example No.386 mass:569(M+1)$^+$.

Working Example No.387 mass:583(M+1)$^+$.

Working Example No.388

According to the procedure described in the reference example No.3, the compound (19 mg) of the working example No.376 was used to afford the titled compound (14 mg).

$^1$H-NMR(CD$_3$OD) 1.12(1H,m), 2.24–2.41(3H,m), 2.70 (1H,m), 3.32–3.41(4H,m), 3.55–3.75(2H,m), 4.02–4.32(5H, m), 4.92(3H,m), 6.88(2H,m), 7.22(2H,m), 7.30(1H,m), 7.40–7.50(3H,m), 7.89(1H,m), 8.03(2H,m), 8.22(1H,m), 8.43(1H,m), 8.69(1H,m).

Working Example No.389

(1) A mixture of 6-amnionicotinic acid (1.01 g), lithium aluminum hydride (835 mg) and tetrahydrofuran was refluxed for 23 hours. The reaction mixture was cooled to room temperature and water (840 µl), 1N sodium hydroxide (840 µl) solution and water (840 µl) were added respectively. The whole was filtered through a celite pad and the filtrate was concentrated to leave a residue, which was purified by column chromatography on silica gel (Wakogel C-200, chloroform-methanol (50:1–10:1) to afford the desired compound (223 mg).

(2) A mixture of the compound (223 mg) obtained above in (1), tert-butyldimethylchlorosilane (332 mg), imidazole (244 mg) and dimethylformamide (5 ml) was stirred for 30 minutes at room temperature. To the reaction mixture, was added water and extracted with chloroform. The organic layer was washed with saturated brine and dried over magnesium sulfate.

After filtration, the filtrate was concentrated to leave a residue which was purified by column chromatography on silica gel (Wakogel C-200, hexane-ethyl acetate (3:2) to afford the desired compound (341 mg).

(3) According to the procedure described in the working example No.118(2), the compound (320 mg) obtained above in (2) was used to afford the desired compound (138 mg).

(4) A mixture of the compound (103 mg) obtained above in (3), acetic acid (1 ml), water (1 ml) and tetrahydrofuran (1 ml) was stirred for 3 days at room temperature. The reaction mixture was concentrated to leave a residue, which was purified by TLC (Merck Art5744, chloroform-methanol (10:1)) to afford the titled compound (44 mg) as a white powder.

$^1$H-NMR(DMSO-d$_6$) 1.07(1H,m), 2.22–2.57(3H,m), 3.30 (1H,m), 3.53(1H,m), 4.46(2H,d,J=5.0 Hz), 4.82(1H,dd,J= 5.6, 10 Hz), 5.23(1H,t,J=5.0 Hz), 7.25(1H,d,J=8.6 Hz), 7.31(1H,dd,J=0.9, 8.0 Hz), 7.46(1H,t,J=8.0 Hz), 7.73(1H, dd,J=2.3,8.6 Hz), 8.23(1H,d,J=2.3 Hz), 8.31(1H,dd, J=0.9, 8.0 Hz), 9.92(1H,s), 11.2(1H,br).

mass:339(M+1)$^+$.

Working Example No.390

According to the procedure described in the working example No.498, the compound of the working example No.390 was used to afford the titled compound.

mass:352(M+1)$^+$.

Working Example No.391

(1) To a mixture of the compound (103 mg) of the working example No. 389, triethylamine (0.6 ml) and dimethylsulfoxide (3 ml), was added a sulfur trioxide pyridine complex (265 mg). The mixture was stirred for 4 hours at room temperature. To the reaction mixture, sulfur trioxide pyridine complex (195 mg) was added again and the mixture was stirred for 1 hour at room temperature. The reaction mixture was diluted with chloroform and washed with water and saturated brine and dried over magnesium sulfate. After filtration, the filtrate was concentrated to C7 afford a crude product, which was used in the next reaction without further purification.

(2) According to the procedure described in the working example No.84(2), the compound (36 mg) obtained above in (1) and a solution of ethylamine in methanol (2.0 M, 2 ml) were used to afford the titled compound (20 mg) as a white powder.

$^1$H-NMR(DMSO-d$_6$) 1.15(1H,m), 1.20(3H,t,J=7.3 Hz), 2.32–2.38(2H,m), 2.53(1H,m), 3.00(2H,q,J=7.3 Hz), 3.30 (1H,m), 3.55(1H,m), 4.14(2H,s), 4.79(1H,dd,J=5.6, 10 Hz), 7.33(1H,d,J=7.9 Hz), 7.46(1H,d,J=8.8 Hz), 7.48(1H,t,J=7.9 Hz), 7.88(1H,dd,J=2.3,8.8 Hz), 8.27(1H,d,J=7.9 Hz), 8.36 (1H,d,J=2.3 Hz), 10.1(0.2H,s), 10.6(0.3H,br).

mass:366(M+1)$^+$.

Working Example No.392

According to the procedure described in the working example No.391, the compound of the working example No.392 was prepared.

mass:380(M+1)$^+$.

Working Example No.393

(1) According to the procedure described in the working example No.118(2), 2-amino-5-nitropyridine (139 mg) was used to afford the desired compound.(33 mg).

(2) According to the procedure described in the reference example No.3, the compound (33 mg) obtained above in (1) was used to afford the desired compound (26 mg) as a white powder.

$^1$H-NMR(DMSO-d$_6$) 1.12(1H,m), 2.31–2.45(3H,m), 2.55 (1H,m), 3.53(1H,m). 4.77(1H,dd,J=4.5, 10 Hz), 5.05(2H,s), 6.99(1H,m), 7.07(1H,dd,J=3.1, 8.8 Hz), 7.27(1H,d,J=7.8 Hz), 7.43(1H,t,J=7.8 Hz), 7.67(1H,d,J=3.1 Hz), 8.32(1H,d, J=7.8 Hz), 9.47(1H,s).

mass:324(M+1)$^+$.

Working Example No.394

(1) According to the procedure described in the working example No.118(2). 2-amino-5-bromopyridine (643 mg) was used to afford the desired compound (989 mg).

(2) According to the procedure described in the reference example No.6, the compound (218 mg) obtained above in (1) was used to afford the desired compound (150 mg).

(3) A mixture of the compound (30 mg) obtained above in (2), 1-methylpiperazine (10 µl), tris(dibenzylidenacetone)dipalladium(0)(3 mg), 1,1-bis(diphenylphosphino)ferrocene (3 mg), 2,2-bis(diphenylphosphino)-1.1-binaphthyl (3 mg) and sodium tert-butoxide (9 mg) and tetrahydrofuran (2 ml) was reacted in a sealed tube for 2 hours at 100° C. The reaction mixture was cooled to room temperature and filtered through silica gel and celite. The filtrate was concentrated to leave a residue which was purified by TLC (Merck Art5744, chloroform-methanol (10:1)) to afford the desired compound (17 mg).

(4) According to the procedure described in the working example No.133(2), the compound (17 mg) obtained above in (3) was used to afford the hydrochloride of the titled compound (15 mg) as a white solid.

$^1$H-NMR(DMSO-d$_6$) 1.04(1H,m), 2.23–2.38(2H,m), 2.58 (1H,m), 2.80(s), 2.81(s), 2.80–2.81(3H), 3.06–3.22(4H,m), 3.30(1H,m), 3.48–3.58(3H,m), 3.75–3.79(2H,m), 4.83(1H, dd,J=5.6,10 Hz), 7.30(1H,dd,J=0.9, 8.1 Hz), 7.36(1Hbrd,J= 9.2 Hz), 7.45(1H,t,J=8.1 Hz), 7.65(1H,dd,J=2.7,9.2H z), 7.99(1H,d,J=2.7 Hz), 8.24(1H,dd,J=0.9, 8.1 Hz), 10.1(1H, br), 10.8(1H,br).

mass:407(M+1)$^+$.

Working Examples No.395–397

According to the procedure described in the working example No.394, the compounds of the working examples from No.395 to No.397 were prepared.

Working Example No.395 mass:366(M+1)$^+$.

Working Example No.396 mass:352(M+1)$^+$.

Working Example No.397 mass:338(M+1)$^+$.

Working Example No.398

(1) 2-Amino-5-bromopyridine and tributylvinylthin were subjected to the reaction procedure described in the working example No.429(2) to afford the desired compound.

(2) According to the procedure described in the working example No.118(2), the compound (6 mg) obtained above in (1) was used to afford the titled compound (2 mg) as a white solid.

$^1$H-NMR(DMSO-d$_6$)
0.80–0.92(1H,m), 2.35–2.50(2H,m), 2.55–2.65(1H,m), 3.02–3.50(1H,m), 3.72–3.82(1H,m), 4.77–4.84(1H,m), 5.35(1H,d,J=9.0 Hz), 5.73(1H,d,J=18 Hz), 6.68(1H,dd, J=9.0, 18 Hz), 6.72–7.00(1H,m), 7.45–7.60(3H,m), 7.80(1H,m), 8.17(1H,m), 8.27(1H,d,J=7.0 Hz), 11.8 (1H,br).
mass:335(M+1)$^+$.

Working Example No.399

According to the procedure described in the reference example No.3, the compound (4 mg) of the working example No.398 was used to afford the titled compound (3 mg) as a white solid.

$^1$H-NMR(DMSO-d$_6$) 0.80–0.90(1H,m), 1.22(3H,t,J=7.4 Hz), 2.40–2.50(2H,m), 2.58–2.65(1H,m), 2.62(2H,q,J=7.4 Hz), 3.42–3.50(1H,m), 3.70–3.82(1H,m), 4.80(1H,m), 6.70 (1H,d,J=9.0 Hz), 7.46(11H,t,J=7.0 Hz), 7.50–7.60(2H,m), 8.04(1H,d), 8.30(1H,d,J=7.4 Hz), 11.9(1H,br).

mass:337(M+1)$^+$.

Working Example No.400

(1) To a mixture of methyl 2-acetoaminopyridine-4-carboxylate (19 mg), sodium periodate (7 mg), iodine (12 mg), water (25 µl) and acetic acid (0.12 ml), was added one drop of concentrated sulfuric acid. The mixture was stirred for 23 hours at 85° C. To the reaction mixture was added aqueous sodium thiosulfate solution (5 ml). The mixture was extracted with chloroform. The organic layer was dried over magnesium sulfate. After filtration, the filtrate was concentrated to leave a residue, which was purified by TLC (Merck Art5744, chloroform-methanol (20:1)) to afford the desired compound (15 mg) as a yellow powder.

(2) The compound obtained above in (1) was subjected to the reaction described in the working example No.398 to afford the titled compound (2 mg) as a white solid.

$^1$H-NMR(DMSO-d$_6$) 0.85–0.92(1H,m), 2.37–2.47(2H, m), 2.55–2.59(1H,m), 3.43–3.51(1H,m), 3.74–3.81(1H,m), 3.97(3H,s), 4.82(1H,m), 5.43(1H,d,J=10 Hz), 5.66(1H,dd, J=1.0,10 Hz), 7.22–7.32(1H,m), 7.49(1H,t,J=7.8 Hz), 7.58 (1H,m), 8.05(1H,s), 8.26(1H,d,J=8.0 Hz), 8.43(1H,s), 11.5 (1H,br).

mass:393(M+1)$^+$.

Working Example No.401

According to the procedure described in the reference example No.3, the compound (2 mg) of the working example No.400 was used to afford the titled compound (1 mg) as a white solid.

$^1$H-NMR(DMSO-d$_6$) 0.70–0.80(1H,m), 1.25(3H,t,J=7.5 Hz), 2.30–2.50(2H,m), 2.94(2H,q,J=7.5 Hz), 3.41–3.50(1H, m), 3.74–3.82(1H,m), 3.98(3H,s), 4.24–4.30(1H,m), 4.78–4.820(1H,m), 7.20(1H,s), 7.43–7.60(2H,m), 7.67–7.76 (1H,m), 8.17(1H,s), 8.26(1H,d,J=7.2 Hz), 11.6(1H,br).

mass:395(M+1)$^+$.

Working Example No.402

According to the procedure described in the working example No.118(2), 2-aminopyridine (86 mg) was used to afford the titled compound (15 mg) as a light red solid.

$^1$H-NMR(DMSO-d$_6$) 1.17(1H,m), 2.24–2.40(2H,m), 2.52 (1H,m), 3.30(1H,m), 3.54(1H,m), 4.87(1H,dd,J=5.0, 10 Hz), 7.18(1H,t,J=5.0 Hz), 7.34(1H,dd,J=0.9, 7.8 Hz), 7.49(1H,t, J=7.8 Hz), 8.30(1H,dd,J=0.9, 7.8 Hz), 8.71(2H,d,J=5.0 Hz), 10.4(1H,s), 11.6(1H,s).

mass:310(M+1)$^+$.

Working Example No.403

(1) A mixture of 2-amino-4,6-dichloropyrimidine (1.0 g), 1-methylpiperazine (733 mg), triethylamine (1.3 ml) and 1-butanol (15 ml) was stirred for 22 hours at 80° C. The reaction mixture was concentrated and then diluted with chloroform-methanol (10:1). The whole was filtered through silica gel (Wakogel C-200). The filtrate was concentrated to afford a crude product.

(2) According to the procedure described in the reference example No.3, a solution of the compound obtained above in (1) in ethanol (18 ml) was used to afford the desired compound (390 mg).

(3) According to the procedure described in the working example No.118(2), the compound (74 mg) obtained above in (2) was used to afford the titled compound (14 mg) as a white solid.

¹H-NMR(CDCl₃) 1.27(1H,m), 2.35(3H,m), 2.34–2.60 (7H,m), 3.42(1H,m), 3.64–3.80(5H,m), 4.76(1H,dd,J=5.3, 11 Hz), 5.22(1H,d,J=6.4 Hz), 7.36(1H,s), 7.45(1H,t,J=7.7 Hz), 7.52(1H,dd,J=1.1, 7.7 Hz), 7.94(1H,d,J=6.4 Hz), 8.26 (1H,dd,J=1.1, 7.7 Hz), 11.8(1H,s).

mass:408(M+1)⁺.

Working Examples No.404–405

According to the procedure described in the working example No.406, the compounds of the working examples from No.404 to No.405 were prepared.

Working Example No.404 mass:385(M+1)⁺.

Working Example No.405 mass:359(M+1)⁺.

Working Example No.406

(1) According to the procedure described in the reference example No.2, indole was used to afford the desired compound.

(2) According to the procedure described in the working example No.129, the compound obtained above in (1) was used to afford the titled compound.

mass:355(M+1)⁺.

Working Example No.407

According to the procedure described in the working example No.408, the titled compound was prepared.

mass:363(M+1)⁺.

Working Example No.408

(1) According to the procedure described in the reference example No.3, the compound of the working example No.406(1) was used to afford the desired compound.

(2) According to the procedure described in the working example No.1, the compound obtained above in (1) was used to afford the titled compound.

mass:357(M+1)⁺.

Working Example No.409

(1) A mixture of 2-chloro-3-nitrobenzoic acid (3 g), diethyl aminomalonate hydrochloride (3.47 g), HOBT monohydrate (2,51 g), triethylamine (3.11 ml) and dimethylformamide (36 ml) was cooled in an ice-bath and WSC hydrochloride (3.37 g) was added. The reaction mixture was stirred for 3 hours at room temperature and diluted with ethyl acetate (200 ml). The whole was washed with 1N hydrochloric acid, aqueous saturated sodium bicarbonate solution and saturated brine, and then dried over magnesium sulfate. After filtration, the filtrate was concentrated to leave a crude solid, which was washed with ethyl acetate to afford the first crystal (2.49 g) and the second crystal (0.895 g) was obtained from the mother liquid.

(2) The solution of first crystal (1.50 g) obtained above in (1) in dimethylsulfoxide (30 ml) was cooled in an ice-bath and sodium hydride (230 mg) was added. The reaction mixture was stirred for 10 minutes at 90° C. and aqueous saturated ammonium chloride solution was added. The whole was diluted with ethyl acetate (150 ml). The organic layer was separated. The organic layer was washed with water and saturated brine and then dried over magnesium sulfate. After filtration, the filtrate was concentrated to leave a crude product (1.36 g).

(3) A solution of the crude product (16.47 g) obtained above in (2) in ethanol (600 ml) was heated at 100° C. and 1N sodium hydroxide solution (52 ml) was added. The reaction mixture was stirred for 40 minutes and then cooled. After filtration, the filtrate was concentrated to leave a residue, which was purified by column chromatography on silica gel (Wakogel C-200, hexane-ethyl acetate (1:1–3:5) to afford an ester (5.76 g).

(4) The compound (5.76 g) obtained above in (3) was suspended in methanol (90 ml) and then cooled in an ice-bath. To the cooled mixture, was added sodium borohydride (3.61 g) in four portions. The mixture was stirred for 50 minutes and aqueous saturated ammonium chloride solution (2 ml) was added. After filtration, the solid obtained was washed with methanol to afford a white powder (3.48 g).

(5) To a mixture of the compound (1.00 g) obtained above in (4), imidazole (650 mg) and dimethylformamide (16 ml), was added tert-butyldimethylchlorosilane (1.50 g). The mixture was stirred for 85 minutes at room temperature and then diluted with ethyl acetate (200 ml). The whole was washed with water and saturated brine and then dried over magnesium sulfate. After filtration, the filtrate was concentrated to leave a crude product, which was used for the next reaction without further purification.

(6) The whole crude product obtained above in (5) was dissolved in ethanol (100 ml) and then subjected to the reaction described in the reference example No.3. The crude crystal obtained was washed with ether-hexane to afford an amine (1.13 g).

(7) According to the procedure described in the working example No.1, the compound (1.13 g) obtained above in (6) and 2-pyridine carbonylazide (650 mg) were used to afford the desired compound (1.48 g).

(8) To the solution the compound (1.48 g) obtained above in (7) in methanol (30 ml), was added concentrated hydrochloric acid (4 ml). The mixture was stirred for 30 minutes at room temperature. The solid precipitated was collected by filtration and washed with tetrahydrofuran to afford the titled compound (1.18 g).

¹H-NMR(DMSO-d₆) 3.62(1H,dd,J=5.7 Hz,11 Hz), 3.94 (1H,dd,J=3.9 Hz,11 Hz), 4.75(1H,m), 7.09(1H,m), 7.36(2H, m), 7.44(1H,t,J=7.7 Hz), 7.85(1H,m), 8.14(1H,d,J=7.7 Hz), 8.31(1H,m), 8.60(1H,s), 10.18(1H,s), 10.92(1H,s).

mass:299(M+1)⁺.

Working Examples No.410–413

According to the procedure described in the working example No.414, the compounds of the working examples from No.410 to No.413 were prepared.

Working Example No.410 mass:313(M+1)⁺.

Working Example No.411 mass:327(M+1)⁺.

Working Example No.412 mass:341(M+1)⁺.

Working Example No.413 mass:355(M+1)⁺.

Working Example No.414

(1) The compound (26 mg) of the working example No.409(6) was dissolved in dimethylformamide-tetrahydrofuran (1:1) (1 ml) and sodium hydride (5 mg) and benzylbromide (12 µl) were added. The mixture was stirred for 30 minutes at room temperature and then filtrated with silica gel. The silica gel was washed with hexane-ethyl acetate (1:1). The filtrate and the washing were combined and then concentrated to afford the crude product, which was used for the next reaction.

(2) According to the procedure described in the working example No.1, the compound obtained above in (1) and 2-pyridine carbonylazide were used to afford the desired compound.

(3) The compound obtained above in (2) was subjected to the similar reaction to that described in the working example No. 409(8) to afford the titled compound (25 mg) as a light yellow powder.

$^1$H-NMR(DMSO-d$_6$) 3.92–4.00(2H,m), 4.34(1H,d,J=11 Hz), 4.58(1H,t,J=4.5 Hz), 5.20(1H,d,J=11 Hz), 7.10(1H,m), 7.25–7.38(5H,m), 7.43–7.50(3H,m), 7.86(1H,m), 8.08(1H, m), 8.20(1H,m), 10.2(1H,s), 10.5 (1H,s).

mass:389(M+1)$^+$.

Working Examples No.415–423

According to the procedure described in the working example No.414, the compounds of the working examples from No.415 to No.423 were prepared.

Working Example No.415 mass:338(M+1)$^+$.

Working Example No.416 mass:355(M+1)$^+$.

Working Example No.417 mass:369(M+1)$^+$.

Working Example No.418 mass:375(M+1)$^+$.

Working Example No.419 mass:403(M+1)$^+$.

Working Example No.420 mass:409(M+1)$^+$.

Working Example No.421 mass:395(M+1)$^+$.

Working Example No.422 mass:379(M+1)$^+$.

Working Example No.423 mass:381(M+1)$^+$.

Working Examples No.424–426

According to the procedure described in the working example No.427, the compounds of the working examples from No.424 to No.426 were prepared.

Working Example No.424 mass:297(M+1)$^+$.

Working Example No.425 mass:311(M+1)$^+$.

Working Example No.426 mass:339(M+1)$^+$.

Working Example No.427

(1) A mixture of the compound (11 mg) of the working example No. 414, triethylamine (40 µl) and methanesulfonylchloride (10 µl) was stirred for 20 minutes at room temperature. To the reaction mixture, was added DBU (20 µl). The mixture was stirred for 25 minutes at room temperature and further stirred for 14.5 hours at 80° C. The reaction mixture was cooled to room temperature and filtrated with silica gel. The silica gel was washed with hexane-ethyl acetate (1:1). The filtrate and washing were combined and then concentrated to leave a residue, which was purified by TLC (Merck Art5744, chloroform-methanol (20:1)) to afford the desired compound (6.4 mg).

(2) The compound obtained above in (1) was dissolved in ethanol-tetrahydrofuran and the mixture was subjected to the similar reaction to that described in the reference example No. 3. The crude product obtained was purified by TLC (Merck Art5744, chloroform-methanol (20:1) to afford the titled compound (3.8 mg).

$^1$H-NMR(DMSO-d$_6$) 1.45(3H,d,J=6.6 Hz), 4.40(1H,d,J=16 Hz), 4.55(1H,q,J=6.6 Hz), 5.08(1H,d,J=16 Hz), 7.02(1H, ddd,J=0.9,5.1,7.2 Hz), 7.24–7.39(6H,m), 7.42–7.51(2H,m), 7.75(1H,ddd,J=2.1,7.2,8.7 Hz), 8.13–8.17(2H,m), 9.72(1H, s), 10.73(1H,s).

mass:373(M+1)$^+$.

Working Example No.428

According to the procedure described in the working example No.427, the compound of the working example No.428 was prepared.

mass:365(M+1)$^+$.

Working Example No.429

(1) A mixture of 2-chloro-3-nitrobenzoic acid (1.49 g), concentrated sulfuric acid (50 µl) and methanol (50 ml) was refluxed for 22 hours. The reaction mixture was diluted with chloroform and washed with water and saturated brine and then dried over magnesium sulfate. After filtration, the filtrate was concentrated to afford a crude product (1.56 g).

(2) The compound (50 mg) obtained above in (1) and tetrakistriphenylphosphinepalladium (9 mg) were suspended in tetrahydrofuran (1 ml). After degassing, tributyl (1-ethoxyvinyl)tin (79 µl) was added. The mixture was stirred for 1 hour at room temperature, for 2 hours at 50° C. and further refluxed for 2.5 hours. The reaction mixture was cooled to room temperature and filtrated with silica gel. The silica gel was washed with hexane-ethyl acetate (3;1). The filtrate and the washing were combined and concentrated to leave a residue, which was purified by TLC(Merck Art5744, hexane-ethyl acetate (3:1) to afford the desired compound (53 mg) as a light yellow oil.

(3) To the compound (110 mg) obtained above in (2) in ethanol (2 ml) was added 1N sodium hydroxide solution (437 µl). The reaction mixture was stirred for 17 hours at room temperature and then concentrated to leave a residue. The residue was dissolved in water (4 ml) and washed with hexane. The aqueous layer was concentrated to afford the desired compound (95 mg).

(4) The compound (45 mg) obtained above in (3) and aniline 18 µl) were subjected to the similar reaction to that described in the working example No.409(1) to afford the desired compound (45 mg).

(5) A mixture of the compound (45 mg) obtained above in (4), concentrated hydrochloric acid (20 µl) and ethanol (2 ml) was stirred for 50 minutes at room temperature. The reaction mixture was concentrated to leave a solid, which was washed with chloroform-ethyl acetate (3:1). The washing was purified by TLC (Merck Art5744, hexane-ethyl acetate (3:1) to afford the desired compound.

(6) A mixture of the compound obtained above in (5) and triethylsilane (30 µl) in chloroform was cooled in an ice-bath. To the mixture, was added borontrifluoride ether complex (23 µl). The reaction mixture was stirred for 2 hours and 45 minutes at room temperature. The reaction mixture was purified by TLC (Merck Art5744, hexane-ethyl acetate (3:1) to afford the desired compound.

(7) The compound obtained above in (6) was dissolved in ethanol and then subjected to the similar reaction described in the reference example No.3.

(8) The compound (7 mg) obtained above in (7) and 2-pyridinecarbonylazide (12 mg) were subjected the reaction described in the working example No.1. The crude product was purified by TLC (Merck Art5744, hexane-ethyl acetate (1:1) to afford the titled compound (4 mg).

$^1$H-NMR(DMSO-$d_6$) 1.43(3H,d,J=6.6 Hz), 5.60(1H,q,J= 6.6 Hz), 7.05(1H,m), 7.24–7.33(2H,m), 7.46–7.57(4H,m), 7.68–7.82(2H,m), 8.28–8.33(2H,m), 9.92(1H,s), 11.3(1H,s).

mass:359(M+1)$^+$.

Working Example No.430

According to the procedure described in the working example No.431, the compound of the working example No.430 was prepared.

mass:339(M+1)$^+$.

Working Example No.431

(9) The compound (12 mg) obtained above in (8) and diethyl acetal of propionaldehyde (100 µL 1) were dissolved in chloroform-tetrahydrofuran (1:1) (2 ml) and borontrifluoride ether complex (40/1) was added. The mixture was stirred for 6 hours at 120° C. Diethyl acetal of propionaldehyde (50 µl) was added again. The reaction mixture was stirred for 3 hours at 120° C. Diethyl acetal of propionaldehyde (200 µl) was added again. The reaction mixture was stirred for 2.5 hours at 120° C. The reaction mixture was purified by TLC (Merck Art5744, chloroform-methanol (10:1)) to afford the titled compound (2.3 mg).

$^1$H-NMR (DMSO-$d_6$) 0.98(3H,t,J=7.0 Hz), 1.75(2H,m), 3.19(1H,t,J=10 Hz), 4.49(1H,t,J=10 Hz), 5.18(2H,m), 7.05 (1H,m), 7.35–7.58(3H,m), 7.78(1H,m), 8.29(2H,m), 9.88 (1H,s), 10.8(1H,s).

mass:339(M+1)$^+$.

Working Examples No.432–437

According to the procedure described in the working example No.431,the compounds of the working examples from No.432 to No.437 were prepared.

Working Example No.432 mass:387(M+1)$^+$.

Working Example No.433 mass:341(M+1)$^+$.

Working Example No.434 mass:311(M+1)$^+$.

Working Example No.435 mass:417(M+1)$^+$.

Working Example No.436 mass:417(M+1)$^+$.

Working Example No.437 mass:417(M+1)$^+$.

Working Example No.438

(1) According the procedure described in the working example No.56, 3-nitrophthalimide (2.00 g) and ethanol (800 µl) were used to afford the desired compound (2.11 g).

(2) The compound (2.11 g) obtained above in (1) was dissolved in methanol-tetrahydrofuran (1:4) (50 ml) and cooled to −15° C. Sodium borohydride (360 mg) was added. The mixture was stirred for 1 hour and aqueous saturated ammonium chloride solution was added. The mixture was warmed to room temperature and water was added. The whole was extracted with chloroform. The organic layer was dried over magnesium sulfate. After filtration, the filtrate was concentrated to leave a solid, which was washed with hexane to afford the desired compound (1.134 g).

(3) The compound (120 mg) obtained above in (2) was subjected to the similar reaction to that described in reference example No. 3 to afford the desired compound (70 mg).

(4) According to the procedure described in the working example No.1, the compound (70 mg) obtained above in (3) and 2-pyridinecarbonylazide (65 mg) were used to afford the titled compound (26 mg).

$^1$H-NMR(DMSO-$d_6$) 1.25(3H,t,J=7.2 Hz), 3.42(1H,m), 3.71(1H,m), 6.00(1H,d,J=9.0 Hz), 6.63(1H,d,J=9.0 Hz), 7.10(1H,ddd,J=1.0,5.0,7.0 Hz), 7.30(1H,d, J=7.5 Hz), 7.37 (1H,dd,J=1.0, 7.0 Hz), 7.54(1H,t,J=7.5 Hz), 7.82(1H,ddd,J= 2.1,7.0,7.5 Hz), 8.36–8.39(2H,m), 9.98(1H,s), 11.7(1H,s).

mass:313(M+1)$^+$.

Working Example No.439

According to the procedure described in the working example No.440, the compound of the working example No.439 was prepared.

mass:327(M+1)$^+$.

Working Example No.440

The compound in working example No.438(13 mg) was dissolved in ethanol (2 mL) and catalytic quantity of p-toluensulfonic acid was added. The mixture was stirred at 90° C. for 1 hour. The mixture was concentrated. The solid yielded was recrystallized with hexane-ethyl acetate to afford the titled compound (7.3 mg).

$^1$H-NMR(DMSO-$d_6$) 1.01(3H,t,J=6.9 Hz), 1.20(3H,t,J= 7.1 Hz), 2.85(1H,m), 2.60(1H,m) 3.25(1H,m), 3.64(1H,m), 6.15(1H,s), 7.04(1H,dd,J=5.4, 6.6 Hz), 7.21(1H,d,J=8.0 Hz), 7.36(1H,d,J=7.2 Hz), 7.53(1H,t,J=8.0 Hz), 7.77(1H, ddd,J=2.1,6.6,7.2 Hz), 8.28(1H,dd,J=2.7, 5.4 Hz), 8.36(1H, d,J=8.0 Hz), 9.97(1H,s), 11.8(1H,s).

mass:341(M+1)$^+$.

Working Examples No.441–448

According to the procedure described in the working example No.440, the compounds of the working examples from No.441 to No.448 were prepared.

Working Example No.441 mass:355(M+1)⁺.

Working Example No.442 mass:369(M+1)⁺.

Working Example No.443 mass:369(M+1)⁺.

Working Example No.444 mass:383(M+1)⁺.

Working Example No.445 mass:367(M+1)⁺.

Working Example No.446 mass:395(M+1)⁺.

Working Example No.447 mass:381(M+1)⁺.

Working Example No.448 mass:403(M+1)⁺.

Working Example No.449

(1) According to the procedure described in the working example No.56, 3-nitrophthalimide (2.02 g) and cyclopentanol (1.20 ml) were used to afford the desired compound (2.27 g).

(2) The compound (2.27 g) obtained above in (1) was subjected to the reaction described in the working example No.438(2) to afford the desired compound (1.429 g).

(3) The compound (827 mg) obtained above in (2) was subjected to the reaction described in the working example No.440. The reaction mixture was concentrated to leave a crude product, which was used for the next reaction.

(4) The compound obtained above in (3) was subjected to the similar reaction to that described in the reference example No. 3 to afford the desired compound (772 mg).

(5) According to the procedure described in the working example No.1, the compound (772 mg) obtained above in (4) and 2-pyridinecarbonylazide (600 mg) were used to afford the titled compound (448 mg).

$^1$H-NMR(DMSO-$d_6$) 1.52<8H,m>,2.81<3H,s>,4.21(1H,m), 6.24(1H,s), 7.04(1H,ddd,J=1.0,5.0,7.5 Hz), 7.23(1H,d,J=7.5 Hz), 7.34(1H,dd,J=1.0, 7.0 Hz), 7.52(1H,t,J=7.5 Hz), 7.76(1H,m), 8.24(1H,m), 8.34(1H,m), 9.95(1H,s), 11.6(1H,s).

mass:335(M-MeOH)⁺.

Working Example No.450

The compound in working example No.449(25 mg) was dissolved in ethanol and subjected to the reaction described in the working example No.440 to afford the titled compound (18 mg).

$^1$H-NMR(DMSO-$d_6$) 0.99<3H,t,J=7.5 Hz>, 1.55–2.00<8H,m>,2.78(1H,m), 3.12(1H,m), 4.22(1H,m), 6.21(1H,s), 7.04(1H,ddd,J=1.0,5.0,7.5 Hz), 7.20(1H, d,J=7.5 Hz), 7.33(1H,d,J=7.0 Hz), 7.51(1H,t,J=7.5 Hz), 7.77 (1H,m), 8.27(1H,m), 8.37(1H,d,J=7.5 Hz), 9.96(1H,s), 11.8 (1H,s).

mass:381(M+1)⁺.

Working Examples No.451–466

According to the procedure described in the working example No.467, the compounds of the working examples from No.451 to No.466 were prepared.

Working Example No.451

$^1$H-NMR(DMSO-$d_6$) 1.55–1.99(14H,m), 4.30(1H,m), 4.45(2H,s), 7.03(1H,m), 7.32–7.50(3H,m), 7.76(1H,m), 8.15(1H,d,J=7.8 Hz), 8.28(1H,m), 9.73(1H,s), 10.7(1H,br).

mass:379(M+1)⁺.

Working Example No.452

$^1$H-NMR(DMSO-$d_6$) 1.10–1.70(12H,m), 1.95(1H,m), 3.38(2H,d,J=7.8 Hz), 4.47(2H,s), 7.05(2H,m), 7.33–7.51 (3H,m), 7.78(1H,m), 8.08(1H,d,J=7.5 Hz), 9.75(1H,s), 10.8 (1H,br).

mass:379(M+1)⁺.

Working Example No.453

$^1$H-NMR(DMSO-$d_6$) 1.10–1.25(4H,m), 1.79–1.92(4H, m), 2.10–2.22(4H,m), 4.12(1H,m), 4.45(2H,s), 7.05(1H,m), 7.33–7.57(3H,m), 7.78(1H,m), 8.18(1H,d,J=7.5 Hz), 8.28 (1H,d,J=2.1 Hz), 9.69(1H,s), 10.6(1H,br).

Working Example No.454 mass:419(M+1)⁺.

Working Example No.455 mass:419(M+1)⁺.

Working Example No.456 mass:283(M+1)⁺.

Working Example No.457 mass:297(M+1)⁺.

Working Example No.458 mass:311(M+1)⁺.

Working Example No.459 mass:311(M+1)⁺.

Working Example No.460 mass:323(M+1)⁺.

Working Example No.461 mass:337(M+1)⁺.

Working Example No.462 mass:327(M+1)⁺.

Working Example No.463

$^1$H-NMR(DMSO-$d_6$) 3.62(2H,t,J=7.5 Hz), 3.91(3H,s), 4.34(2H,t,J=7.5 HZ), 4.60(2H,s), 7.02(1H,m), 7.38–7.51 (3H,m), 7.99(1H,m), 8.20(11H,d,J=7.8 Hz), 8.39(1H,d,J= 2.1 Hz), 9.80(1H,s), 11.0(1H,br).

Working Example No.464 mass:331(M+1)$^+$.

Working Example No.465 mass:337(M+1)$^+$.

Working Example No.466 mass:337(M+1)$^+$.

Working Example No.467

(1) A mixture of the compound (20 mg) of the working example No. 449(2), 20% palladium hydroxide-carbon (20 mg), methanol (1 ml) and tetrahydrofuran (1 ml) was stirred for 15 hours at room temperature under an atmosphere of hydrogen. The reaction mixture was filtered through a celite pad and the filtrate was concentrated to leave a residue, which was purified by TLC (Merck Art5744, chloroform-methanol (19:1) to afford the desired compound (5 mg).

(2) According to the procedure described in the working example No.1, the compound (5 mg) obtained above in (1) was used to afford the titled compound (2 mg) as a light yellow solid.

mass:337(M+1)$^+$.

Working Example No.468

According to the procedure described in the working example No.467, the compound of the working example No.468 was prepared.

mass:339(M+1)$^+$.

Working Examples No.469–492

According to the procedure described in the working example No.493, the compounds of the working examples from No.469 to No.492 were prepared.

Working Example No.469 mass:365(M+1)$^+$.

Working Example No.470 mass:369(M+1)$^+$.

Working Example No.471 mass:387(M+1)$^+$.

Working Example No.472 mass:401(M+1)$^+$.

Working Example No.473 mass:407(M+1)$^+$.

Working Example No.474 mass:401(M+1)$^+$.

Working Example No.475 mass:379(M+1)$^+$.

Working Example No.476 mass:391(M+1)$^+$.

Working Example No.477 mass:325(M+1)$^+$.

Working Example No.478 mass:339(M+1)$^+$.

Working Example No.479 mass:353(M+1)$^+$.

Working Example No.480 mass:353(M+1)$^+$.

Working Example No.481 mass:401(M+1)$^+$.

Working Example No.482 mass:339(M+1)$^+$.

Working Example No.483 mass:461(M+1)$^+$.

Working Example No.484 mass:353(M+1)$^+$.

Working Example No.485 mass:367(M+1)$^+$.

Working Example No.486 mass:367(M+1)$^+$.

Working Example No.487 mass:367(M+1)$^+$.

Working Example No.488 mass:367(M+1)$^+$.

Working Example No.489 mass:367(M+1)$^+$.

Working Example No.490 mass:387(M+1)$^+$.

Working Example No.491 mass:401(M+1)$^+$.

Working Example No.492 mass:379(M+1)$^+$.

Working Example No.493

(1) A solution of 3-nitrophthalic acid anhydride (125 g) in tetrahydrofuran (2.5 L) was cooled to −78° C. and sodium borohydride (48.8 g) was added. The mixture was stirred for 1 hour and 1N hydrochloric acid was added. The reaction mixture was warmed to room temperature and extracted with ethyl acetate. The organic layer was washed with water and brine and then dried over magnesium sulfate. After filtration, the filtrate was concentrated to leave a residue, which was purified by column chromatography on silica gel (Wakogel C-200, hexane-ethyl acetate (2:1) to afford the desired compound (88.4 g).

(2) A mixture of the compound (200 mg) obtained above in (1), 3-amino-1-propanol (90 mg), molecular sieves 3A (500 mg) and tetrahydrofuran (3 ml) was refluxed overnight. The reaction mixture was filtered through a celite pad and the filtrate was concentrated to leave a residue, which was purified by TLC(Merck Art5744, hexane-ethyl acetate (1:1) to afford the desired compound (180 mg).

(3) According to the procedure described in the reference example No.3, the compound (180 mg) obtained above in (2) was used to afford the desired compound (139 mg).

(4) According to the procedure described in the working example No.1, the compound (30 mg) obtained above in (3) was used to afford the titled compound (36 mg).

$^1$H-NMR(DMSO-d$_6$) 1.50–4.30(6H,m), 5.86(1H,s), 7.05 (1H,t,J=5.0 Hz), 7.19(1H,d,J=8.0 Hz), 7.36(1H,d,J=6.0 Hz), 7.53(1H,t,J=8.0 Hz), 7.78(1H,t,J=8.0 Hz), 8.32(1H,d,J=5.0 Hz), 8.38(1H,d,J=8.0 Hz), 9.99 (1H,s).

mass:325(M+1)$^+$.

Working Examples No.494–502

According to the procedure described in the working example No.493, the compounds of the working examples from No.494 to No.502 were prepared.

Working Example No.494 mass:339(M+1)$^+$.

Working Example No.495 mass:341(M+1)$^+$.

Working Example No.496 mass:341(M+1)$^+$.

Working Example No.497 mass:340(M+1)$^+$.

Working Example No.498 mass:325(M+1)$^+$.

Working Example No.499 mass:339(M+1)$^+$.

Working Example No.500 mass:387(M+1)$^+$.

Working Example No.501 mass:399(M+1)$^+$.

Working Example No.502 mass:369(M+1)$^+$.

Working Examples No.503–530

According to the procedure described in the working example No.531, the compounds of the working examples from No.503 to No.530 were prepared.

Working Example No.503 mass:498(M+1)$^+$.

Working Example No.504 mass:546(M+1)$^+$.

Working Example No.505 mass:558(M+1)$^+$.

Working Example No.506 mass:528(M+1)$^+$.

Working Example No.507 mass:524(M+1)$^+$.

Working Example No.508 mass:528(M+1)$^+$.

Working Example No.509 mass:546(M+1)$^+$.

Working Example No.510 mass:560(M+1)$^+$.

Working Example No.511 mass:566(M+1)$^+$.

Working Example No.512 mass:560(M+1)$^+$.

Working Example No.513 mass:538(M+1)$^+$.

Working Example No.514 mass:550(M+1)$^+$.

Working Example No.515 mass:484(M+1)$^+$.

Working Example No.516 mass:560(M+1)$^+$.

Working Example No.517 mass:498(M+1)$^+$.

Working Example No.518 mass:512(M+1)$^+$.

Working Example No.519 mass:512(M+1)$^+$.

Working Example No.520 mass:560(M+1)$^+$.

Working Example No.521 mass:512(M+1)$^+$.

Working Example No.522 mass:526(M+1)$^+$.

Working Example No.523 mass:526(M+1)$^+$.

Working Example No.524 mass:526(M+1)$^+$.

Working Example No.525 mass:526(M+1)$^+$.

Working Example No.526 mass:526(M+1)$^+$.

Working Example No.527 mass:546(M+1)$^+$.

Working Example No.528 mass:560(M+1)$^+$.

Working Example No.529 mass:538(M+1)$^+$.

Working Example No.530 mass:599(M+1)$^+$.

Working Example No.531

(1) A mixture of picolinic acid (150 g), dimethylformamide (20 ml) and thionylchloride (500 ml) was stirred for 1 hour at 100° C. The reaction mixture was cooled to 0° C. and methanol (200 ml) was added. The mixture was diluted with ethyl acetate and saturated aqueous sodium bicarbonate was added. The organic layer was separated and washed with water and brine, and then dried over magnesium sulfate. After filtration, the filtrate was concentrated to leave a residue, which was purified by column chromatography on silica gel (Wakogel C-100, hexane-ethyl acetate (2:1–1:1)) to afford the desired compound (148 g).

(2) The compound (18 g) obtained above in (1) and tributyl vinyltin (35 g) were subjected to the reaction described in the working example No.429(2) to afford the desired compound (16 g).

(3) According to the procedure described in the working example No.300, the compound (16 g) obtained above in (2) was used to afford the desired compound (19.7 g).

(4) According to the procedures described in the reference example No.5(1) and (2), the compound (19.7 g) obtained above in (3) was used to afford the titled compound (14.1 g).

$^1$H-NMR(CDCl$_3$) 1.85(1H,m), 2.30–2.90(5H,m), 3.48 (1H,quintet,J=7.0 Hz), 3.68(2H,d,J=7.0 Hz), 7.20–7.40(5H, m), 7.45(1H,d,J=8.0 Hz), 8.09(1H,s), 8.59(1H,d,J=8.0 Hz).

(5) According to the procedure described in the working example No.1, the compound (50 mg) obtained above in (4) and the compound (30 mg) of the working example No. 493(3) were used to afford the titled compound (41 mg).

$^1$H-NMR(CDCl$_3$) 1.60–4.60(15H,m), 5.69(1H,s), 6.83 (1H,s), 6.91(1H,d,J=5.0 Hz), 7.20–7.60(6H,m), 8.13(1H,d, J=5.0 Hz), 8.45(11H,d,J=5.0 Hz), 8.77(1H,s).

mass:484(M+1)$^+$.

Working Example No.532

According to the procedure described in the working example No.531, the compound of the working example No.532 was prepared.

mass:498(M+1)$^+$.

Working Example No.533

(1) According to the procedures described in the working example No.438(1) and (2), 3-nitrophthalimide (2.00 g) in 4-hydroxy-2-butanone (1.37 g) were used to afford the desired compound (1.78 g).

(2) A mixture of the compound (1,78 g) obtained above in (1), molecular sieve 3A (5 g), and trifluoroacetic acid (1 ml) in tetrahydrofuran (25 ml) was stirred overnight at 100° C. The reaction mixture was cooled to room temperature and filtrated. The filtrate was concentrated to leave a residue, which was purified by column chromatography on silica gel (Wakogel C-300, hexane-ethyl acetate (1:1)) to afford the desired compound (963 mg).

(3) According to the procedure described in the reference example No.3, the compound (963 mg) obtained above in (2) was used to afford the desired compound (680 mg).

(4) According to the procedure described in the working example No.1, the compound (30 mg) obtained above in (3) was used to afford the titled compound (28 mg).

$^1$H-NMR(DMSO-d$_6$) 1.16(3H,d,J=7.0 Hz), 1.70–4.30 (5H,m), 5.95(1H,s), 6.90–8.70(7H,m), 10.0(1H,s), 11.6(1H, br).

mass:339(M+1)$^+$.

Working Example No.534 mass:353(M+1)$^+$.

Working Example No.535 mass:339(M+1)$^+$.

Working Example No.536 mass:353(M+1)$^+$.

Working Example No.537 mass:353(M+1)$^+$.

Working Example No.538 mass:367(M+1)$^+$.

Working Example No.539

(1) A mixture of the compound (1,70 g) of the working example No. 493(3), (Boc)$_2$O (5.50 g), and 4-dimethylaminopyridine (3.00 g) in tetrahydrofuran (40 ml) was stirred overnight at room temperature. The reaction mixture was concentrated to leave a residue, which was purified by column chromatography on silica gel (Wakogel C-300, hexane-ethyl acetate (10:1–5:1)) to afford the desired compound (2.56 g).

(2) A solution of the compound (500 mg) obtained above in (1) in tetrahydrofuran (25 ml) was cooled to −78° C. and butyliodide (400 μl) and lithium hexamethyldisilazide in tetrahydrofuran (1.0 M, 3.6 ml) were added. The reaction mixture was warmed up to room temperature slowly and saturated aqueous ammonium chloride was added. The whole was extracted with ethyl acetate. The organic; layer was washed with water and brine and then dried over magnesium sulfate. After filtration, the filtrate was concentrated to leave a residue, which was purified by column chromatography on silica gel (Wakogel C-300, hexane-ethyl acetate (10:1)) to afford the desired compound (484 mg).

(3) A mixture of the compound (484 mg) obtained above in (2), trifluoroacetic acid (4 ml) and water (0.4 ml) was stirred for 10 minutes at room temperature. The reaction mixture was concentrated to leave a residue, which was purified by column chromatography on silica gel (Wakogel C-300, hexane-ethyl acetate (10:1)) to afford the desired compound (249 mg).

(4) According to the procedure described in the working example No.1, the compound (50 mg) obtained above in (3) was used to afford the titled compound (48 mg).

$^1$H-NMR(DMSO-d$_6$) 0.61(1H,m), 0.63(3H,t,J=7.0 Hz), 1.00–3.80(8H,m), 3.95(1H,brd,J=11 Hz), 4.18(1H,brd,J=11 Hz), 4.39(1H,dt,J=2.0, 11 Hz), 7.00–7.20(2H,m), 7.37(1H,d,J=7.0 Hz), 7.50(1H,t,J=8.0 Hz), 7.78(1H,t,J=8.0 Hz), 8.23 (1H,d,J=5.0 Hz), 8.38(1H,d,J=8.0 Hz), 10.0(1H,s), 11.8(1H, br).

mass:381(M+1)$^+$.

Working Example No.540

According to the procedure described in the working example No.541, the compound of the working example No.540 was prepared.

mass:498(M+1)$^+$.

Working Example No.541

According to the method in the working example No.1, the titled compound (48 mg) was obtained using the compound in working example No.533(3) (30 mg) and the compound in working example No.531(4) (50 mg).

$^1$H-NMR(DMSO-d$_6$) 1.17(3H,d,J=7.0 Hz), 1.20–2.90 (10H,m), 3.66(2H,s), 4.21(2H,m), 5.94(1H,s), 7.04(1H,d,J= 5.0 Hz), 7.18(1H,s), 7.20–7.40(6H,m), 7.56(1H,t,J=8.0 Hz), 8.22(1H,d,J=5.0 Hz), 8.45(1H,d,J=8.0 Hz), 9.96(1H,s), 11.7 (1H,br).

mass:498(M+1)$^+$.

Working Examples No.542–545

According to the procedure described in the working example No.541, the compounds of the working examples from No.542 to No.545 were prepared.

Working Example No.542 mass:512(M+1)$^+$.

Working Example No.543 mass:512(M+1)$^+$.

Working Example No.544 mass:512(M+1)$^+$.

Working Example No.545 mass:526(M+1)$^+$.

Working Example No.546

(1) According to the procedure described in working example No.121(1), the desired compound (9.00 g) was prepared using 2-chloro-3-nitrobenzoic acid (10.1 g) and hydrazine monohydrate (4.85 mL).

(2) The compound (9.00 g) obtained above in (1) in ethanol (1 L) was sealed in sealed tube and stirred at 150° C. for 15 hours. After the mixture was cooled to room tempeture, the precipitated crystal was filtrated and dried to afford the desired compound (5.00 g).

(3) A mixture of the compound (40 mg) obtained above in (2), 1,4-butanediiodine (29 μl) and dimethylformamide (1 ml) was refluxed for 15 hours. The reaction mixture was cooled to room temperature and diluted with ethyl acetate. The whole was washed with saturated aqueous sodium bicarbonate, water and brine, and then dried over magnesium sulfate. After filtration, the filtrate was concentrated to leave a residue, which was purified by TLC (Merck Art5744, hexane-ethyl acetate (1:2)) to afford the desired compound (44 mg).

(4) According to the procedure described in reference example No.3, the desired compound was afforded using the compound (49 mg) obtained above in (3).

(5) According to the procedure described in working example No.1, the titled compound was obtained as a white solid using the compound (25 mg) afforded above in (4).

$^1$H-NMR(DMSO-d$_6$) 1.65–1.78(2H,m), 1.88–2.11(2H, m), 3.39–3.50(2H,m), 3.80–3.96(2H,m), 7.00–7.13(1H,m), 7.20–7.39(2H,m), 7.40–7.49(1H,m), 7.75–7.85(1H,m), 8.15–8.22(1H,m), 8.32(1H,s), 9.93(1H,s), 11.1(1H,s).

mass:324(M+1)$^+$.

Working Example No.547

According to the methods described in working example No.546 from (3) to (5), the titled compound was obtained as a white solid using the compound in working example No.546(2) and 1,3-propandiiodine.

$^1$H-NMR(DMSO-d$_6$) 2.49(2H,m), 3.55–3.71(2H,m), 3.71–3.81(2H,m), 7.01–7.10(1H,m), 7.18–7.22(1H,m), 7.28–7.40(2H,m), 7.76–7.82(1H,m), 8.08–8.35(2H,m), 9.97 (1H,s), 11.1(1H,s).

Working Example No.548

(1) A mixture of ethyl glycolate (9.64 g), 4-methoxybenzyl chloride (13.2 ml), and sodium hydride (3.89 g) in dimethylformamide (200 ml) was stirred overnight at 0° C. The reaction mixture was diluted with ethyl acetate. The whole was washed with water and brine and then dried over magnesium sulfate. After filtration, the filtrate was concentrated to leave a residue, which was purified by column chromatography on silica gel (Wakogel C-200, hexane-ethyl acetate (20:1)) to afford the desired compound (16.0 g).

(2) A solution of acetonitrile (4.11 ml) in tetrahydrofuran (400 ml) was cooled to −78° C. To the cooled solution, was added n-butyllithium in hexane (1.6 M, 46.3 ml) and the compound (16.0 g) obtained above in (1) in tetrahydrofuran (150 ml) was added.

The reaction mixture was warmed up from −78° C. to room temperature and stirred until the disappearence of the starting material. To the reaction mixture, was added water and made acidic by the addition of 1N hydrochloric acid. The whole was extracted with ethyl acetate. To the organic layer, was added ethanol (200 ml) and hydrazine monohydrate (20 ml). The mixture was refluxed overnight. The reaction mixture was concentrated to leave a residue, which was purified by column chromatography on silica gel (Wakogel C-200, chloroform-methanol (98:2) to afford the desired compound (13.9 g).

(3) A mixture of the compound (13.9 g) obtained above in (2), (Boc)$_2$O (15.1 ml), and sodium hydride (2.62 g) in dimethylformamide (300 ml) was stirred at room temperature until the disappearence of the starting material. To the reaction mixture was added saturated aqueous ammonium chloride and then extracted with ethyl acetate. The organic layer was washed with brine and dried over magnesium sulfate. After filtration, the filtrate was concentrated to leave a residue, which was purified by column chromatography on silica gel (Wakogel C-200, hexane-ethyl acetate (10:1–1:1) to afford the desired compound (7.32 g).

(4) According to the procedure in working example No.118(2), the desired compound (4.16 g) was obtained using the compound (7.32 g) obtained above in (3).

(5) A mixture of the compound (4.16 g) obtained above in (4), and 10% Pd-carbon (3 g) in methanol-tetrahydrofuran (1:1)(140 ml) was stirred for 3 hours at 50° C. under an atmosphere of hydrogen. The reaction mixture was filtered through a celite pad and the filtrate was concentrated to leave a residue, which was purified by column chromatography on silica gel (Wakogel C-300, chloroform-methanol (98:2–80:20) to afford the compound A (602 mg), which is protected by Boc and the titled compound (593 mg).

$^1$H-NMR(DMSO-d$_6$) 0.98–1.18(1H,m), 2.20–2.41(2H, m), 2.60–2.78(1H,m), 3.03–3.60(2H,m), 4.44(2H,d,J=5.5 Hz), 4.61–4.79(1H,m), 5.29(1H,t,J=5.5 Hz), 6.00(1H,s), 7.26(1H,d,J=6.7 Hz), 7.42(1H,dd,J=6.7, 7.9 Hz), 8.27(1H, d,J=7.9 Hz), 9.41(1H,s), 12.3(1H,s).

mass:328(M+1)$^+$.

Working Example No.549

(1) According to the procedure in working example No.84(1), the desired compound (295 mg) was prepared from the compound (510 mg) in working example No.548.

(2) A mixture of the compound (121 mg) obtained above in (1) 1-methylpiperazine (414 µl), and molecular sieve 3A (100 mg) in chloroform-methanol (1:1) (4 ml) was stirred for 12 hours at room temperature. To the reaction mixture, was added sodium hydrite (41 mg) and the mixture was stirred until the disapperance of the starting material. The reaction mixture was filtered through a celite pad and the filtrate was concentrated to leave a residue, which was purified by column chromatography on silica gel (Wakogel C-300, chloroform-methanol (20:1–4:1)) to afford the recemic compound (139 mg).

(3) The recemic compound was subjected to optical resolution by HPLC (CHIRALPAK AD (DAICEL Chemical Industries, Ltd.)) to afford the titled compound (A)(6 mg) at Rt=8.3 min (CHIRALPAK AD (DAICEL Chemical Industries, Ltd., 0.46φ×25 cm), ethanol, 0.5 ml/min) and the compound (B)(19 mg) of the working example No.550 at Rt=11.1 min.

$^1$H-NMR(DMSO-d$_6$). 0.98–1.13(1H,m), 2.13(3H,s), 2.22–2.47(10H,m), 2.51–2.72(1H,m), 3.42(2H,s), 3.23–3.60 (2H,m), 4.62–4.78(1H,m), 5.96(1H,s), 7.26(1H,d,J=7.5 Hz), 7.42(1H,dd,J=7.5,7.9 Hz), 8.26(1H,d,J=7.9 Hz), 9.44(1H,s), 12.3(1H,s).

mass:410(M+1)$^+$.

Working Example No.550

The compound of the working example No.550 was obtained as the optical isomer of working example No.549.

mass:410(M+1)$^+$.

Working Examples No.551–591

According to the procedure described in the working example No.549(2), the compounds of the working examples from No.551 to No.591 were prepared.

Working Example No.551

$^1$H-NMR(DMSO-d$_6$) 0.82(6H,t,J=7.5 Hz), 0.98–1.14(1H, m), 1.36(4H,dq,J=7.2, 7.5 Hz), 2.21–2.40(2H,m), 2.48–2.65 (2H,m), 3.23–3.60(2H,m), 3.67(2H,s), 4.63–4.74(1H,m), 6.02(1H,s), 7.26(1H,d,J=6.7 Hz), 7.42(1H,dd,J=6.7, 8.0 Hz), 8.26(1H,d,J=8.0 Hz), 9.41(1H,s), 12.2(1H,s).

mass:397(M+1)$^+$.

Working Example No.552 mass:383(M+1)$^+$.

Working Example No.553 mass:397(M+1)$^+$.

Working Example No.554 mass:397(M+1)$^+$.

Working Example No.555 mass:417(M+1)$^+$.

Working Example No.556 mass:417(M+1)$^+$.

Working Example No.557 mass:417(M+1)$^+$.

Working Example No.558 mass:445(M+1)$^+$.

Working Example No.559

$^1$H-NMR(DMSO-d$_6$) 0.98–1.14(1H,m), 1.14(6H,d,J=6.9 Hz), 2.24–2.40(2H,m), 2.59–2.70(1H,m), 2.74(1H,dq,J=6.9, 6.9 Hz), 3.22–3.60(2H,m), 4.22(1H,d,J=6.0 Hz), 4.64–4.73 (1H,m), 5.94(1H,t,J=6.0 Hz), 6.08(1H,s), 6.40(1H,d,J=7.0 Hz), 6.44(1H,d,J=7.1 Hz), 6.51(1H,s), 6.98(1H,dd,J=7.0, 7.1 Hz), 7.26(1H,d,J=7.0 Hz), 7.42(1H,dd,J=7.0,8.2 Hz), 8.25(1H,d,J=8.2 Hz), 9.40(1H,s), 12.3(1H,s).

Working Example No.560 mass:445(M+1)$^+$.

Working Example No.561 mass:443(M+1)$^+$.

Working Example No.562 mass:431(M+1)$^+$.

Working Example No.563 mass:439(M+1)$^+$.

Working Example No.564 mass:439(M+1)$^+$.

Working Example No.565 mass:443(M+1)$^+$.

Working Example No.566 mass:461(M+1)$^+$.

Working Example No.567 mass:399(M+1)$^+$.

Working Example No.568 mass:399(M+1)$^+$.

Working Example No.569 mass:491(M+1)$^+$.

Working Example No.570 mass:438(M+1)$^+$.

Working Example No.571 mass:493(M+1)$^+$.

Working Example No.572 mass:425(M+1)$^+$.

Working Example No.573 mass:427(M+1)$^+$.

Working Example No.574 mass:500(M+1)$^+$.

Working Example No.575 mass:436(M+1)$^+$.

Working Example No.576 mass:413(M+1)$^+$.

Working Example No.577 mass:506(M+1)$^+$.

Working Example No.578 mass:503(M+1)$^+$.

Working Example No.579 mass:477(M+1)$^+$.

Working Example No.580 mass:473(M+1)$^+$.

Working Example No.581 mass:473(M+1)$^+$.

Working Example No.582 mass:489(M+1)$^+$.

Working Example No.583 mass:489(M+1)$^+$.

Working Example No.584 mass:443(M+1)$^+$.

Working Example No.585 mass:461(M+1)$^+$.

Working Example No.586 mass:522,524(M+1)$^+$.

Working Example No.587 mass:477(M+1)$^+$.

Working Example No.588 mass:512(M+1)$^+$.

Working Example No.589 mass:457(M+1)$^+$.

Working Example No.590 mass:493(M+1)$^+$.

Working Example No.591 mass:493(M+1)$^+$.

Working Examples No.592–595

According to the procedures described in the working example No.549(2) and (3), the compounds of the working examples from No.592 to No.595 were prepared.

Working Example No.592 mass:477(M+1)$^+$.

Working Example No.593 mass:477(M+1)$^+$.

Working Example No.594 mass:477(M+1)$^+$.

Working Example No.595 mass:477(M+1)$^+$.

Working Example No.596

According to the method in working example No.290, the titled compound (15 mg) was obtained using the compound (62 mg) in working example No.662.

mass:397(M+1)$^+$.

Working Example No.597

According to the procedure described in the working example No.596, the compound of the working example No.597 was prepared.

mass:491(M+1)$^+$.

Working Example No.598

According to the method in working example No. 596, the compound of the working example No.598 was prepared from the compound in working example No.649(2).

mass:501(M+1)$^+$.

Working Example No.599

(1) According to the procedures in working example No.548(2) and (3), the desired compound was prepared from L-N-benzylproline ethyl ester.

(2) According to the procedure in working example No.118(2), the desired compound was prepared (408 mg) from the above compound (1)(623 mg).

(3) A solution of the compound (288 mg) obtained above in (2) in hydrochloric acid-methanol (5 ml) was stirred for 15 minutes at room temperature. The reaction mixture was concentrated and diluted with chloroform. The whole was washed with saturated aqueous sodium bicarbonate and brine, and dried over magnesium sulfate. After filtration, the filtrate was concentrated to leave a residue, which was purified by column chromatography on silica gel (Wakogel C-200, chloroform-methanol (99:1)) to afford the desired compound (119 mg) as a mixture.

(4) The compound obtained above in (3) was subjected to optical resolution by HPLC to afford the titled compound (38 mg) as fraction (A) at Rt=14.6 min (CHIRALCEL OD (DAICEL Chemical Industries, Ltd., 0.46φ×25 cm), hexane-ethanol (80:20), 0.6 ml/min) and the compound (39 mg) of the working example No.600 as fraction (B) at Rt=18.3 min.

mass:457(M+1)$^+$.

Working Example No.600

Compound of working example No.600 was obtained as the diastereomer of the compound in working example No.599.

$^1$H-NMR(DMSO-d$_6$) 0.98–1.04(1H,m), 1.64–1.80(3H, m), 2.04–2.40(4H,m), 2.59–2.90(2H,m), 3.16(1H,d,J=13 Hz), 3.42–3.60(3H,m). 3.76(1H,d,J=13 Hz), 4.62–4.68(1H, m), 6.09(1H,brs), 7.20–7.36(6H,m), 7.42(1H,dd,J=7.9, 8.0 Hz), 8.26(1H,d,J=7.9 Hz), 9.43(1H,s), 12.4(1H,s).

mass:457(M+1)$^+$.

Working Example No.601

According to the procedures described in the working examples No.599 and No.600, D-N-benzylproline ethyl ester was used to afford the titled compound (68 mg) as fraction (A) at Rt=14.0 min (CHIRALCEL OD (DAICEL Chemical Industries, Ltd., 0.46ϕ×25 cm), hexane-ethanol (80:20), 0.6 ml/min) and the compound (64 mg) of the working example No.602 as fraction (B) at Rt=16.8 min.

mass:457(M+1)$^+$.

Working Example No.602

Compound of working example No.602 was obtained as the diastereomer of the compound in working example No.601.

mass:457(M+1)$^+$.

Working Examples No.603–607

According to the procedures described in the working example No.599(1) to (3), the compounds of the working examples from No.603 to No.607 were prepared.

Working Example No.603 mass:388(M+1)$^+$.

Working Example No.604 mass:424(M+1)$^+$.

Working Example No.605 mass:389(M+1)$^+$.

Working Example No.606 mass:424(M+1)$^+$.

Working Example No.607 mass:388(M+1)$^+$.

Working Example No.608

A mixture of the compound (610 mg) of the working example No.599, 10% Pd-carbon catalyst (300 mg), and ammonium formate (800 mg) in ethanol (15 ml) was refluxed for 4 hours. The reaction mixture was cooled to room temperature and then filtered through a celite pad. The filtrate was concentrated to leave a residue, which was purified by column chromatography on silica gel (Silica gel 60N (spherial neutral)(Kanto Kagaku Co. Ltd., chloroform-methanol (98:2–5:1)) to afford the titled compound (290 mg).

mass:367(M+1)$^+$.

Working Example No.609 mass:367(M+1)$^+$.

Working Example No.610 mass:367(M+1)$^+$.

Working Example No.611 mass:367(M+1)$^+$.

Working Example No.612

According to the procedures described in the working example No.599(1) to (3), the compound of the working example No.612 was prepared.

mass:375(M+1)$^+$.

Working Example No.613

(1) According to the procedure in working example No.118(1), the desired compound (1.35 g) was prepared from 2-chloro-3-cyanopyridine (1.87 g).

(2) According to the procedure in working example No.548(3), the N-protected compound (618 mg) was prepared from the above compound (1)(818 mg).

(3) According to the procedure in working example No.118(2), the titled compound was obtained (45 mg) using the compound (294 mg) described above in (2).

$^1$H-NMR(DMSO-d$_6$) 1.04–1.20(1H,m), 2.30–2.41(2H, m), 2.62–2.71(11H,m), 3.28–3.35(1H,m), 3.48–3.59(1H,m), 4.74–4.82(1H,m), 7.12–7.20(1H,m), 7.33(1H,d,J=7.6 Hz), 7.48(1H,dd,J=7.6, 7.9 Hz), 8.32(1H,d,J=7.9 Hz), 8.51–8.54 (2H,m), 9.80(1H,s), 10.2(1H,s).

mass:349(M+1)$^+$.

Working Examples No.614–615

According to the procedures described in the working example No.599(1) to (3), the compounds of the working examples from No.614 to No.615 were prepared.

Working Example No.614 mass:468(M+1)$^+$.

Working Example No.615 mass:380(M+1)$^+$.

Working Examples No.616–619

According to the procedures described in the working example No.599(1) to (3), compounds of working examples from No.616 to No.619 were prepared from the compounds in working examples No.306(3) and compounds synthesized according to the procedures in working examples No.306 (2)-B to (3).

Working Example No.616 mass:366(M+1)$^+$.

Working Example No.617 mass:366(M+1)$^+$.

Working Example No.618 mass:473(M+1)$^+$.

Working Example No.619 mass:473(M+1)$^+$.

Working Examples No.620–621

According to the procedures described in the working example No.548(5), the compounds of the working examples from No.620 to No.621 were prepared using compounds in working examples No.618 and No.619.

Working Example No.620 mass:383(M+1)$^+$.

Working Example No.621 mass:383(M+1)$^+$.

Working Examples No.622–625

The compounds of the working example No.306(3) and the compounds synthesized in the working examples No.306 (2)-B to No.306(3), were used to afford the corresponding diastereomers, which were subjected to resolution by HPLC (CHIRALPAK AD (DAICEL Chemical Industries, Ltd., 2φ×25 cm)) following the the procedures described in the working example No.599(1) to (3) to afford the compounds of the working examples No. 622 to 625.

Working Example No.622 mass:471(M+1)$^+$.

Working Example No.623 mass:471(M+1)$^+$.

Working Example No.624 mass:471(M+1)$^+$.

Working Example No.625 mass:471(M+1)$^+$.

Working Example No.626

According to the procedures described in the working example No.599(1) to (3), the compounds of the working example No.626 was prepared.

mass:471(M+1)$^+$.

Working Example No.627

According to the procedure described in the working example No.622, the compound of the working example No.627 was prepared.

mass:424(M+1)$^+$.

Working Examples No.628–629

According to the procedure described in the working example No.622, the compounds of the working examples No.628 and No.629 were prepared.

Working Example No.628 mass:424(M+1)$^+$.

Working Example No.629 mass:424(M+1)$^+$.

Working Example No.630

(1) According to the procedure in working example No.610, the desired compound was prepared from the compound in working example No.599(3).

(2) A mixture of the compound (85 mg) obtained above in (1) and N-(diethylcarbamoyl)-N-methoxyformamide (81 μl) in chloroform (2 ml) was stirred for 2 hours at 60° C. The reaction mixture was cooled to room temperature and diluted with chloroform. The whole was washed with water and brine and dried over magnesium sulfate. After filtration, the filtrate was concentrated to leave a residue, which was purified by TLC (Merck Art5744, chloroform-methanol (10:1)) to afford a mixture of diastereomers, which was subjected to resolution following the procedure described in the working example No.549(3) to afford the titled compound (4 mg) and the compound (3 mg) of the working example No.631.

mass:395(M+1)$^+$.

Working Example No.631 mass:395(M+1)$^+$.

Working Example No.632

(1) Diastereomer mixture (70 mg) was prepared from the compound in working example No.630(171 mg) according to the procedure in working example No.295.

(2) The above compound was resolved in the same way as that in the working example No.549(3) to afford the compounds of working examples No.632(13 mg) and No.633(26 mg).

mass:381(M+1)$^+$.

Working Example No.633

The compound of working example No.633 was obtained as the diastereomer of the compound of working example No.632.

mass:381(M+1)$^+$.

Working Example No.634

The compound in working example No.636(42 mg) and 1-butylamine (120 μL) were reacted according to the procedure in working example No.549(2). The mixture was treated with 10% HCl-MeOH and dried to afford the titled compound as a hydrochloride (22 mg).

mass:397(M+1)$^+$.

Working Example No.635

According to the procedure described in the working example No.634, the compound of the working examples No.635 was prepared.

Working Example No.636

After the compound of working example No.639(2)(1.20 g) was reacted according to the procedure described in working example No.84(1), the compound obtained above was reacted according to the procedure described in working example No.599(3) to afford the titled compound (591 mg).

mass:340(M+1)$^+$.

Working Example No.637

According to the procedure described in the working example No.599(3), the titled compound (708 mg) was obtained from the compound in working example No.639 (1).

mass:432(M+1)$^+$.

Working Example No.638

According to the procedure described in the working example No.634, the compound of the working examples No.638 was prepared.

Working Example No.639

(1) According to the procedures in working example No.599(1) and (2), the desired compound was prepared from ethyl 2-benzyloxypropionate.

(2) The compound obtained above in (1)(4.30 g) was reacted in the same conditions as that described in working example No.548(5). 10% HCl-MeOH was added to the mixture to remove Boc group. Ethyl acetate was added and the crystal precipitated was filtrated and then dried to afford the titled compound (2.21 g).

mass:342(M+1)$^+$.

Working Examples No.640–646

According to the procedure described in the working example No.634, the compounds of the working examples from No.640 to No.646 were prepared.

Working Example No.640 mass:369(M+1)$^+$.

Working Example No.641 mass:383(M+1)$^+$.

Working Example No.642 mass:445(M+1)$^+$.

Working Example No.643 mass:409(M+1)$^+$.

Working Example No.644 mass:381(M+1)$^+$.

Working Example No.645 mass:383(M+1)$^+$.

Working Example No.646 mass:409(M+1)$^+$.

Working Example No.647

(1) According to the procedure in working example No.548(2), the desired compound was prepared from L-N-benzylproline ethyl ester.

(2) A mixture of the compound (1.34 g) obtained above in (1), sodium hydride (243 mg), and methyliodine (0.38 ml) in dimethylformamide (20 ml) was stirred at room temperature until the diappearence of the starting material. To the reaction mixture, was added saturated aqueous ammonium chloride and the whole was extracted with ethyl acetate. The organic layer was washed with water and then dried over magnesium sulfate. After filtration, the filtrate was concentrated to leave a residue, which was purified by column chromatography on silica gel (Wakogel C-300, chloroform-methanol (98:2) to afford the desired compound (350 mg).

(3) The compound obtained above in (2)(340 mg) was treated according to the procedure in working example No.118(2) to afford the desired compound (252 mg).

(4) According to the procedure in working example No.610, the diastereomer mixture (86 mg) was prepared from the compound obtained above in (3)(252 mg). The mixture was resolved in the same procedure as that in working example No.549 to afford the titled compound (20 mg) and its diestereomer (17 mg) which is the compound in working example No.648.

mass:381(M+1)$^+$.

Working Example No.648

The compound of working example No.648 was obtained together with the compound in working example No.647.

mass:381(M+1)$^+$.

Working Example No.649

(1) According to the procedures in working example No.548(1) and (2), the desired compound was prepared from ethyl glycolate and benzylbromide.

(2) The mixture of the compound obtained above in (1)(1.31 mg), sodium hydride (271 mg), and methyliodine (421 µL) in dimethyl formamide (30 mL) was stirred at 0° C. for 60 minutes and then treated by the general method. The residue was purified by column chromatography on silica gel (Wakogel C-200, chloroform-methanol (99:1 to 98:2) to afford the desired compound (593 mg).

(3) According to the procedure in working example No.118(2), the desired compound (535 mg) was prepared using the compound (593 mg) obtained above in (2).

(4) According to the procedures in working examples No.548(5) and followed by 84(1), the desired compound (176 mg) was prepared using the compound obtained above in (3).

(5) Using the compound obtained above in (4)(30 mg) and 2-aminoindan (31 mg), the titled compound (31 mg) and the compounds in working examples No.650(11 mg) and No.651(12 mg) were obtained according to the procedure in working examples No.549(2).

$^1$H-NMR(DMSO-d$_6$) 0.93–1.10(1H,m), 2.24–2.38(2H, m), 2.52–2.63(1H,m), 2.67(1H,d,J=6.6 Hz), 2.72(1H,d,J= 6.6 Hz), 3.02(1H,d,J=7.0 Hz), 3.08(1H,d,J=7.0 Hz), 3.28–3.58(3H,m), 3.72(3H,s), 3.74(2H,s), 4.71–4.80(1H,m), 6.08(1H,s), 7.06–7.18(4H,m), 7.26(1H,d,J=7.4 Hz), 7.43 (1H,dd,J=7.4, 7.9 Hz), 8.26(1H,d,J=7.9H z), 9.43(1H,s).

mass:457(M+1)$^+$.

Working Example No.650

The compound of working example No.650 was obtained as a by-product of the compound of working example No.649.

mass:386(M+1)$^+$.

Working Example No.651

The compound of working example No.651 was obtained as a by-product of the compound of working example No.649.

mass:342(M+1)$^+$.

Working Examples No.652–656

According to the procedure described in the working example No.649, the compounds of the working examples from No.652 to No.656 were prepared.

Working Example No.652 mass:487(M+1)$^+$.

Working Example No.653 mass:475(M+1)$^+$.

Working Example No.654 mass:535,537(M+1)⁺.

Working Example No.655 mass:491(M+1)⁺.

Working Example No.656 mass:491(M+1)⁺.

Working Examples No.657–687

According to the procedure described in the working example No.549(2), the compounds of the working examples from No.657 to No.687 were prepared.

Working Example No.657 mass:383(M+1)⁺.

Working Example No.658 mass:409(M+1)⁺.

Working Example No.659 mass:417(M+1)⁺.

Working Example No.660 mass:369(M+1)⁺.

Working Example No.661 mass:369(M+1)⁺.

Working Example No.662

$^1$H-NMR(DMSO-$d_6$) 0.95–1.12(1H,m), 1.36(9H,s), 2.22–2.38(2H,m), 2.62–2.75(1H,m), 3.23–3.37(1H,m), 3.42–3.60(1H,m), 4.10(2H,m), 4.79(1H,dd,J=5.9,10 Hz), 6.47(1H,s), 7.29(1H,d,J=7.3 Hz), 7.45(1H,t,J=7.3 Hz), 8.22 (1H,d,J=7.3 Hz), 9.09(3H,br), 9.91(1H,s).
mass:383(M+1)⁺.

Working Example No.663 mass:355(M+1)⁺.

Working Example No.664 mass:395(M+1)⁺.

Working Example No.665 mass:381(M+1)⁺.

Working Example No.666 mass:341(M+1)⁺.

Working Example No.667 mass:324(M+1)⁺.

Working Example No.668

$^1$H-NMR(DMSO-$d_6$) 0.90–1.20(1H,m), 1.20–2.00(8H,m), 2.20–2.70(4H,m), 3.00–3.40(1H,m), 3.40–3.60(1H,m), 3.74(2H,m), 4.69(1H,m), 7.25(1H,d,J=7.9 Hz), 7.41(1H,t,J=7.9 Hz), 8.21(1H,d,J=7.9 Hz), 9.44(1H,br), 12.2(1H,br).
mass:395(M+1)⁺.

Working Example No.669 mass:383(M+1)⁺.

Working Example No.670 mass:397(M+1)⁺.

Working Example No.671

$^1$H-NMR(DMSO-$d_6$) 0.70–0.95(6H,m), 0.95–1.15(1H,m), 1.15–1.50(8H,m), 2.10–2.70(4H,m), 3.10–3.40(1H,m), 3.40–3.60(1H,m), 3.66(2H,s), 4.70(1H,dd,J=6.0,11 Hz), 6.01(1H,br), 7.27(1H,d,J=7.9 Hz), 7.43(1H,t,J=7.9 Hz), 8.27 (1H,d,J=7.9 Hz), 9.40(1H,s), 12.1(11H,br).
mass:425(M+1)⁺.

Working Example No.672 mass:425(M+1)⁺.

Working Example No.673 mass:439(M+1)⁺.

Working Example No.674 mass:411(M+1)⁺.

Working Example No.675 mass:397(M+1)⁺.

Working Example No.676 mass:411(M+1)⁺.

Working Example No.677 mass:445(M+1)⁺.

Working Example No.678 mass:445(M+1)⁺.

Working Example No.679 mass:445(M+1)⁺.

Working Example No.680 mass:481(M+1)⁺.

Working Example No.681 mass:481(M+1)⁺.

Working Example No.682 mass:437(M+1)⁺.

Working Example No.683 mass:468(M+1)⁺.

Working Example No.684 mass:489(M+1)⁺.

Working Example No.685 mass:484(M+1)⁺.

Working Example No.686 mass:459(M+1)⁺.

Working Example No.687 mass:399(M+1)⁺.

Working Example No.688

(1) A mixture of 2-aminoindan hydrochloride (1.93 g), bromine (5.0 ml) and acetic acid (30 ml) was stirred for 3 days at 50° C. The reaction mixture was concentrated to leave a residue, which was dissolved in chloroform (50 ml). (Boc)$_2$O (4 ml) and triethylamine (15 ml) were added and the reaction mixture was stirred until the disappearance of the starting material. The mixture was washed with 1N hydrochloric acid. The organic layer was concentrated to leave a residue, which was purified by column chromatography on silica gel (Wakogel C-200) to afford the desired compound (1.38 g).

(2) According to the procedure in working example No.599(3), the titled compound (553 mg) was prepared using the compound (1.38 g) obtained above in (1).

(3) A mixture of the compound (14 g) obtained above in (2), ethyl bromoacetate (5.85 ml), and triethylamine (14.7 ml) in toluene (100 ml) was stirred at room temperature overnight. The mixture was diluted with ether-ethyl acetate. The whole was washed with brine and dried over magnesium sulfate. After filtration, the filtrate was concentrated to leave a residue, which was dissolved in chloroform (150 ml) and (Boc)$_2$O (12.6 ml) was added again. The reaction mixture was stirred at room temperature until the disappearance of the starting material. The mixture was concentrated to leave a residue, which was purified by column chromatography on silica gel (Wakogel C-200, hexane-ethyl acetate) to afford the desired compound (11.68 g).

(4) According to the procedure in working example No.548(2), the compound (10.13 g) obtained above in (3) was used to afford the desired compound (1.95 g).

(5) Urea was prepared according to the procedure in working example No.118(2) using the compound obtained above in (4) and amine synthesized from 3-hydroxy-2-butanone according to the procedures in working example No.533(1) to (3).

(6) The compound obtained above in (5) was treated by 4N HCl-dioxane to remove the Boc-protected group and the titled compound was obtained.

mass:551,553(M+1)$^+$.

Working Examples No.689–690

According to the procedure described in the working example No.688, the compounds of the working examples No.689 and No.690 were prepared.

Working Example No.689

$^1$H-NMR(DMSO-d$_6$) 0.78–1.20(7H,m), 2.24–2.78(4H, m), 2.89–3.10(2H,m), 3.40–3.59(1H,m), 3.72(2H,s), 4.10–4.22(1H,m), 4.78(1H,s), 6.10(1H,brs), 7.27(1H,d,J= 6.5 Hz), 7.29(1H,d,J=7.7 Hz), 7.35(1H, d,J=6.5 Hz), 7.40 (1H,s), 7.48(1H,dd,J=7.7, 8.5 Hz), 8.32(1H,d,J=8.5 Hz), 9.55(1H,s), 12.1(1H,brs).

mass:565,567(M+1)$^+$.

Working Example No.690 mass:551,553(M+1)$^+$.

Working Examples No.691–692

According to the procedure described in the working example No.693, the compounds of the working examples No.691 and No.692 were prepared.

Working Example No.691 mass:548(M+1)$^+$.

Working Example No.692 mass:474(M+1)$^+$.

Working Example No.693

(1) According to the procedure in working example No.409(1),the compound (54 mg) of the working example No.120, trans-1,4-diaminocyclohexane protected by mono Boc group (56 mg), which was prepared from the reaction of trans-1,4-diaminocyclohexane and (Boc)$_2$O in chloroform following the ordinary method, to afford the desired compound (61 mg).

(2) According to the procedure in working example No.548(2), the titled compound (37 mg) was obtained from the compound (61 mg) described above in (1).

$^1$H-NMR(DMSO-d$_6$) 0.98–1.20(1H,m), 1.48–1.53(4H, m), 1.88–2.09(4H,m), 2.26–2.43(2H,m), 2.63–2.71(1H,m), 2.90–3.08(1H,m), 3.23–3.83(3H,m), 4.74–4.85(1H,m), 6.71 (1H,s), 7.26(1H,d,J=7.4 Hz), 7.44(1H,dd,J=7.4, 7.9 Hz), 7.54(1H,dd,J=7.7, 8.3 Hz), 7.80(1H,d,J=8.3 Hz), 7.88(1H, d,J=7.7H z), 8.02–8.13(2H,br), 8.23(1H,s), 8.26(1H,d,J=6.6 Hz), 8.48(1H,d,J=7.9 Hz), 9.20–9.40(1H,br), 9.84(1H,s).

mass:514(M+1)$^+$.

Working Examples No.694–700

According to the procedure described in the working example No.693, the compounds of the working examples from No.694 to No.700 were prepared.

Working Example No.694 mass:490(M+1)$^+$.

Working Example No.695 mass:514(M+1)$^+$.

Working Example No.696 mass:514(M+1)$^+$.

Working Example No.697 mass:560(M+1)$^+$.

Working Example No.698 mass:527(M+1)$^+$.

Working Example No.699 mass:536(M+1)$^+$.

Working Example No.700 mass:528(M+1)$^+$.

Working Example No.701

According to the method described in working example No.118(4), the titled compound (69 mg) was obtained from the compound in working example No.703(100 mg).

mass:298(M+1)$^+$.

Working Example No.702

(1) According to the procedure in working example No.703, the desired compound was prepared from 3-amino-4-ethoxycarbonyl pyrazole.

(2) According to the procedure in working example No.118(4), the titled compound was obtained from the compound (300 mg) obtained above in (1).

mass:370(M+1)$^+$.

Working Example No.703

(1) A mixture of 3-aminopyrazole (3.00 g), benzylbromide (5.60 g), and sodium hydride (1.72 g) in dimethylformamide (30 ml) was stirred for 3 hours at room temperature. To the reaction mixture, was added saturated aqueous ammonium chloride and extracted with ethyl acetate. The organic layer was dried over magnesium sulfate. After filtration, the filtrate was concentrated to leave a residue, which was purified by column chromatography on silica gel (Wakogel C-200, hexane-ethyl acetate (3:1–1:1)) to afford the desired compound (2.87 g).

(2) According to the procedure in the working example No. 118(2), the compound (2.89 g) obtained above in (1) was used to afford the titled compound (989 mg).

mass:388(M+1)$^+$.

Working Example No.704

(1) A solution of the compound (300 mg) of the working example No.702(1) in tetrahydrofuran (20 ml) was cooled to 0° C. and lithium aluminum hydride (30 mg) was added. The mixture was stirred for 30 minutes and 1N hydrochloric acid was added. The whole was extracted with ethyl acetate. The organic layer was washed with brine and dried over magnesium sulfate. After filtration, the filtrate was concentrated to leave a residue, which was purified by column chromatography on silica gel (Wakogel C-200, hexane-ethyl acetate (1:1–1:2)) to afford the titled compound (248 mg).

mass:418(M+1)$^+$.

Working Example No.705

According to the procedure described in working example No.118(2), the titled compound (196 mg) was obtained from 3-amino-1-methylpyrazole (100 mg).

mass:312(M+1)$^4$.

Working Example No.706

(1) A solution of the compound (280 mg) of the reference example No.3 in chloroform (5 ml) was bubbled by chlorine gas to afford a crude product, which was collected by filtration. The crude product was dissolved in a mixture of aqueous sodium hydroxide and chloroform. The organic layer was separated and then concentrated to leave a residue, which was purified by TLC (Merck Art5744, chloroform-methanol (10:1)) to afford monochloride (A) (84 mg) and dichloride (B)(66 mg).

(2) According to the procedure in working example No.1, the titled compound was obtained as a white cystal from the compound obtained above in (1)-A(42 mg).

mass:343(M+1)$^+$.

Working Example No.707

(1) A solution of the compound (2.02 g) of the reference example No.3 in chloroform was cooled to −20° C. and bromine (1.16 ml) was added. The mixture was stirred for 10 minutes and warmed up to room temperature. The precipitation was collected by filtration, which was dissolve in a mixture of aqueous sodium hydroxide and chloroform. The organic layer was separated and then concentrated to leave a residue, which was purified by TLC (Wakogel C-200, chloroform-methanol (99:1)) to afford monobromide (A) (1.30 g) and dibromide (B)(1.14 g).

(2) According to the procedure in working example No.1, the titled compound (1.24 g) was obtained from the compound obtained above in (1)-A(1.03 g).

$^1$H-NMR(DMSO-d$_6$) 0.98–1.14(1H,m), 2.22–2.40(2H, m), 2.43–2.60(1H,m), 3.27–3.40(1H,m), 3.49–3.60(1H,m), 4.73–4.80(1H,m), 7.06(1H,dd,J=7.2, 12 Hz), 7.26(1H,d,J= 8.7 Hz), 7.59(1H,d,J=8.4 Hz), 7.79(1H,ddd,J=2.1,8.7,12 Hz), 8.30(1H,dd,J=2.1, 7.2 Hz), 8.26(1H,d,J=8.4 Hz), 10.0 (1H,s), 11.3(11H,s).

mass:387,389(M+1)$^+$.

Working Example No.708

According to the method described in the working example No.1, the titled compound was obtained from the compound obtained in working example No.707(1)-B.

mass:467,469(M+1)$^+$.

Working Example No.709

According to the method described in the working example No.1, the titled compound was obtained from the compound (37 mg) obtained in working example No.706 (1)-B.

mass:378(M+1)$^+$.

Working Example No.710

(1) According to the procedure in working example No.56, a light yellow solid (121 mg) as a mixture of two compounds was prepared from 4-nitro-1,2-benzoisothiazole-3-one-1,1-dioxide (100 mg) and 2-propanol (67 µl).

(2) The mixture obtained above in (1)(30 mg) was reacted in the same conditions as that in reference example No.3. The raw product was purified with TLC (Merck Art5744, chloroform-methanol, 80:1) to yield N-alkylcompound (A) (6 mg) and O-alkylcompound (B) (20 mg).

(3) According to the procedure in working example No.1, the titled compound was obtained from the compound (6 mg) obtained above in (2)-A.

$^1$H-NMR(CDCl$_3$) 1.65(6H,d,J=7.8 Hz), 4.55(1H,dq,J= 7.8, 7.8 Hz), 6.95(1H,d,J=7.8H z), 7.04(1H,t,J=6.3 Hz), 7.47(1H,d,J=7.5 Hz), 7.61(1H,br), 7.66–7.78(1H,m), 8.47 (1H,d,J=5.7 Hz), 9.00(1H,d,J=8.4 Hz), 13.1(1H,br mass:361(M+1)$^+$.

Working Example No.711

According to the method described in the working example No.1, the titled compound was obtained as a light yellow solid (93 mg) from the compound (75 mg) obtained above in working example No.710(2)-B.

$^1$H-NMR(CDCl$_3$) 1.45(6H,d,J=6 Hz), 5.49(1H,dq,J=6, 6 Hz), 6.85(1H,d,J=8.1 Hz), 7.03–7.07(1H,m), 7.59–7.75(3H, m), 8.27–8.30(1H,m), 8.36(1H,d,J=9.3 Hz), 11.8(1H,br).

mass:361(M+1)$^+$.

Working Examples No.712–713

Compounds of working examples No.712–713 were prepared according to the procedures described in working examples No.710 and No.711.

Working Example No.712 mass:387(M+1)$^+$.

Working Example No.713 mass:387(M+1)$^+$.

Working Example No.714

The compound (55 mg) of the working example No. 711 was dissolved in tetrahydrofuran (4 ml) and sodium borohydride (17 mg) was added. The mixture was stirred for 30 minutes at room temperature. To the reaction mixture was added aqueous sodium bicarbonate and extracted with chloroform. The organic layer was washed with saturated brine and then dried over magnesium sulfate. Ater filtration, the filtrate was concentrated to leave a residue, which was purified to TLC (Merck Art5744, chloroform-methanol (80:1)) to afford the titled compound (5 mg) as a white solid.

$^1$H-NMR(DMSO-d$_6$) 4.41(2H,br), 7.04(1H,t,J=6 Hz), 7.40(1H,d,J=7.2 Hz), 7.47(1H,d,J J=8.1 Hz), 7.56(1H,t,J=8.1 Hz), 7.75–7.87(2H,m), 8.25–8.33(2H,m), 9.84(1H,s), 10.9(1H,br).

mass:305(M+1)$^+$.

Working Example No.715

According to the procedure described working example No.56, the titled compound was obtained as a white solid (3 mg) from the compound obtained above in working example No.714(5 mg) and 2-propanol (7 μL).

$^1$H-NMR(CDCl$_3$) 1.46(3H,t,J=7.2 Hz), 4.47(2H,q,J=7.2 Hz), 4.94(2H,s), 6.83(1H,d. J=8.1 Hz), 7.04(1H,t,J=8.4 Hz), 7.54(1H,d,J=6.9 Hz), 7.61(1H,t,J=8.1 Hz), 7.73(1H,t,J=8.7 Hz), 7.97(1H,s), 8.33(1H,d,J=3.3 Hz), 8.46(1H,d,J=7.8 Hz), 12.5(1H,s).

mass:377(M+1)$^+$.

REFERENCE EXAMPLES OF THE INVENTION

Reference Example No.1

A mixture of 9-fluorenone-4-carboxylic acid (10.0 g, 44.6 mmol), and thionyl chloride (50 ml) in dimethylformamide (1 ml) was refluxed for 1 hour. The reaction mixture was concentrated to afford an acid chloride of the titled compound as a yellow solid, which was used for the next reaction without further purification.

Sodium azide (4.06 g. 62.5 mmol) was dissolved in water (50 ml) and cooled in an ice-bath. To the solution was added the suspension of the acid chloride obtained above in tetrahydrofuran (200 ml) in one portion. The reaction mixture was stirred for 1 hour at the same temperature and then extracted with tetrahydrofuran-ethyl acetate (10:1). The organic layer was separated and washed with brine and dried over magnesium sulfate. After filtration, the filtrate was concentrated to leave a crystal precipitated, from which the titled compound (10.3 g) was obtained by filtration.

$^1$H-NMR(CDCl$_3$)δ:7.29–7.43(2H,m), 7.56(1H,dt,J=7.7 Hz,1.3 Hz), 7.75(1H,d,J=7.5 Hz), 7.90(1H,dd,J=7.3 Hz.1.3 Hz), 8.02(1H,dd,J=7.9 Hz,1.2 Hz), 8.43(1H,d,J=7.9 Hz).

mass:250(M+1)$^+$.

Reference Example No.2

(1) 2-chloro-3-nitrobenzoic acid (2 g, 10.0 mmol) was mixed with thionyl chloride (30 ml) at room temperature. 4-Dimethylaminopyridine (122 mg, 1.00 mmol) was added. The reaction mixture was refluxed for 12 hours and then concentrated to afford a crude acid chloride. To a solution of pyrrole (3.5 ml, 50.0 mmol) and triethylamine (7.0 ml, 50.0 mmol) in methylenechloride (80 mL), was added above-mentioned acid chloride at room temperature. The reaction mixture was stirred for 6 hours at the same temperature and then diluted with ethyl acetate. The whole was washed with brine and dried over magnesium sulfate. After filtration, the filtrate was concentrated to leave a residue, which was purified by column chromatography on silica gel (hexane-ethyl acetate, 1:0–7:3) to afford a yellow oil (2.43 g).

(2) To a solution of the yellow oil (2.40 g, 9.60 mmol) obtained above in (1) in dimethylacetoamide (180 ml) was added potassium acetate (1.80 g, 19.2 mmol). The air in the reactor was replaced by nitrogen. To the mixture, was added tetrakistriphenylphosphine palladium (1.10 g, 0.960 mmol) at room temperature. The reaction mixture was stirred overnight at 130° C. and then diluted with ethyl acetate-ether (1:2). The whole was washed with water and brine in turn and dried over magnesium sulfate. After filtration, the filtrate was concentrated to leave a residue, which was purified by column chromatography on silica gel (hexane-chloroform, 1:0–1:1) to afford the titled compound (2.24 g) as a brown solid.

$^1$H-NMR(CDCl$_3$)δ:6.34(1H,t,J=3.2 Hz), 7.10(1H,dd,J=3.3 Hz,0.85 Hz), 7.21(1H,m), 7.35(1H,dd,J=8.3 Hz,7.3 Hz), 7.94(1H,dd,J=7.3 Hz,1.0 Hz), 8.28(1H,dd,J=8.5 Hz,1.0 Hz).

Reference Example No.3

To a solution of the compound (2.24 g) of the reference example No.2 in methanol-tetrahydrofuran (1:1) (80 ml) was added 10% palladium-carbon catalyst (0.200 g) at room temperature. The reaction mixture was stirred for 12 hours at room temperature under an atmosphere of hydrogen. The insoluble material was removed by filtration with celite and the filtrate was concentrated to leave a residue, which was purified by column chromatography on silica gel (chloroform-methanol, 1:0–98:2–95:5) to afford the titled compound (1.03 g) as a brown solid.

$^1$H-NMR(DMSO-d$_6$)δ:0.80–0.93(1H,m), 2.10–2.30(2H, m), 2.43–2.51(1H,m), 3.18–3.24(1H,m), 3.38–3.47(1H,m), 4.50(1H,dd,J=10 Hz,5.5 Hz), 5.34(2H,s), 6.72(1H,d,J=7.9 Hz), 6.76 (1H,d,J=7.4 Hz), 7.11(1H,t,J=7.6 Hz).

Reference Example No.4.

To a cooled ethanol (90 mL) was added sodium (500 mg, 22 mmol) under an atmosphere of nitrogen. The reaction mixture was stirred for 50 minutes at room temperature and then cooled in an ice-bath. To the cooled reaction mixture was added a solution of 4-[2-[[(1,1-dimethylethyl) diphenylsilyl] oxy]ethyl]-2-pyridinecarbonitrile (45 g, 120 mmol) in ethanol (150 mL) over a period of 15 minutes. The reaction mixture was warmed up to room temperature and stirred for 4 hours. Under an ice-bath, the reaction mixture was made acidic by adding 1N hydrochloric acid (120 ml, 120 mmol) and further to this, water (50 ml) was added at the same temperature. The whole was extracted with ethyl acetate. The organic layer was washed with water, 1N sodium hydroxide and brine in turn, and dried over magnesium sulfate. After filtration, the filtrate was concentrated to leave a brown oil, which was purified by column chromatography on silica gel (hexane-ethyl acetate, 2:1–1:1) to afford the titled compound (42 g) as a yellow oil.

$^1$H-NMR(CDCl$_3$)δ:1.00(9H,s), 1.45(3H,t,J=7.0 Hz), 2.89 (2H,t,J=6.3 Hz), 3.90(2H,t,J=6.3 Hz), 4.49(2H,q,J=7.0 Hz), 7.28(1H,d,J=4.9 Hz), 7.32–7.45(6H,m), 7.55(4H,dd), 7.99 (1H,s), 8.62(1H,d,J=5.6 Hz).

Reference Example No.5

(1) To a solution of the compound (13 g. 32 mmol) of the reference example No.4 in methanol (200 mL) was added hydrazine monohydrate (7.8 mL, 160 mmol) at room temperature. The reaction mixture was stirred for 19 hours in the same temperature and diluted with chloroform, and washed with brine. The organic layer was dried over magnesium sulfate. After filtration, the filtrate was concentrated to afford a yellow oil (14 g), which was used for the next reaction without further purification.

(2) A solution of the compound obtained above in (1) in chloroform (100 mL) was cooled in an ice-bath and 1N hydrochloric acid (97 mL, 97 mmol) and sodium sulfite (4.5 g, 65 mmol) were added. The reaction mixture was stirred for 40 minutes at the same temperature and then chloroform was added. The organic layer was separated and dried over magnesium sulfate. After filtration, the filtrate was concentrated to afford a yellow oil (14 g), which was used for the next reaction without further purification.

(3) To a solution of the compound (14 g, 32 mmol) obtained above in (2) in tetrahydrofuran (200 ml), was added the compound (2.00 g, 10.6 mmol) of the reference example No. 3 at room temperature. The reaction mixture was stirred for 2.5 hours at 95° C. The reaction mixture was concentrated to leave a residue, which was purified by column chromatography on silica gel (hexane-ethyl acetate, 1:1–1:2) to afford a light yellow crystal (8.0 g).

$^1$H-NMR(CDCl$_3$)δ:1.01(9H,s), 1.22–1.37(1H,m), 2.33–2.47(2H,m), 2.58–2.65(1H,m), 2.81(2H,t,J=6.3 Hz), 3.45(1H,t,J=10 Hz), 3.78(1H,dt), 3.90(2H,t,J=6.3 Hz), 4.80 (1H,dd), 6.53(1H,s), 6.82(1H,d,J=5.2 Hz), 7.30–7.47(8H, m), 7.53–7.58(5H,m), 8.07(1H,d,J=4.2 Hz), 8.32(1H,d,J= 7.3 Hz), 12.0(1H,s).

Reference Example No.6

The compound (8.0 g, 14 mmol) of the reference example No. 5 was dissolved in chloroform (50 mL). To this solution, were added an imine (50 mL) prepared by the method wherein p-formaldehyde (71.44 g, 2.38 mol) and tert-butylamine (250 mL, 2.38 mol) were stirred at room temperature and one drop of concentrated sulfuric acid. The reaction mixture was stirred for 3 days at 95° C. The reaction mixture was concentrated to leave a residue, which was purified by column chromatography on silica gel (hexane-ethyl acetate, 3:1–1:1–1:2) to afford a colorless powder (7.0 g).

$^1$H-NMR(CDCl$_3$)δ:0.98(9H,s), 0.98–1.02(1H,m), 1.28 (9H,s), 2.20–2.35(3H,m), 2.80(2H,t,J=6.0 Hz), 3.33–3.42 (1H,m), 3.64–3.73(1H,m), 3.86(2H,t,J=7.2 Hz), 4.67(1H,d, J=12 Hz), 4.73–4.80(1H,m), 4.85(1H,d,J=8.8 Hz), 5.05–5.15(1H,br), 5.43–5.52(1H,br), 6.86(1H,d,J=5.6 Hz), 7.30–7.41(6H,m), 7.49(1H,dd), 7.54–7.60(5H,m), 7.76(2H, d,J=12 Hz), 8.23(1H,d,J=4.8 Hz).

Reference Example No.7

The compound (2.00 g) of the reference example No. 6 was dissolved in tetrahydrofuran (20 mL). To the mixture, was added a solution of tetra-n-butylammonium fluoride in tetrehydrofuran (1.0 M, 3.50 mL. 3.50 mmol) at room temperature. The reaction mixture was stirred for 1 hour at the same temperature and then water was added. The reaction mixture was extracted with ethyl acetate. The organic layer was combined and washed with brine and then dried over magnesium sulfate. After filtration, the filtrate was concentrated to result in the formation of crystal, which was collected by filtration. The filtrate was concentrated again to leave a residue, which was purified by column chromatography on silica gel (hexane-ethyl acetate, 1:2–0:1-chloroform-methanol, 50:1) to afford a crystal, which was combined with the crystal collected above to provide the titled compound (700 mg).

$^1$H-NMR(CDCl$_3$)δ:1.2–1.35(1H,m), 1.30(9H,s), 2.20–2.40(3H,m), 2.83(2H,t,J=6.6 Hz), 3.33–3.45(1H,m), 3.61–3.74(1H,m), 3.78(2H,t,J=6.6 Hz), 4.64–4.89(3H,m), 5.07–5.20(1H,m), 5.42–5.55(1H,m), 6.91(1H,d,J=5.3 Hz), 7.45–7.59(2H,m), 7.74–7.81(2H,m), 8.28(1H,d,J=5.3 Hz).

Reference Example No.8

(1) The compound (190 mg) of the reference example No. 7 was dissolved in chloroform (2 mL). To the solution, were added triphenylphosphine (146 mg, 0.56 mmol), diphenylphosphoryl azide (0.12 mL, 0.56 mmol) and a solution of diethyl azodicarboxylate in toluene (40%, 0.24 mL, 0.55 mmol) at room temperature. The reaction mixture was stirred for 15 hours at the same temperature and water was added. The mixture was extracted with ethyl acetate. The organic layer was combined and washed with water and brine and then dried over magnesium sulfate. After filtration, the filtrate was concentrated to leave a residue, which was purified by thin layer chromatography (chloroform-methanol, 19:1) to afford a light yellow 1 amorphous (130 mg).

(2) The compound (130 mg) obtained above in (1) was dissolved in methanol-tetrahydrofuran (1:1) (2 mL). To the solution, was added 10% palladium-carbon catalyst (130 mg) at room temperature. The reaction mixture was stirred for 2 hours at the same temperature under an atomosphere of hydrogen. The insoluble material was filtered through a celite pad and the filtrate was concentrated to leave a residue, which was purified by thin layer chromatography (chloroform-methanol, 19:1) to afford the titled compound (32 mg) as a light yellow oil and the compound (80 mg) of the working example No.109.

$^1$H-NMR(DMSO-d$_6$)δ:1.23–1.35(1H,m), 1.29(9H,s), 2.21–2.41(3H,m), 2.89(2H,brt), 3.00(2H,brt), 3.34–3.41 (1H,m), 3.62–3.71(1H,m), 4.65(1H,d,J=12 Hz), 4.73–4.80 (1H,m), 4.83(1H,d,J=12 Hz), 5.00–5.20(1H,br), 5.40–5.50 (1H,br), 6.81(1H,d,J=5.6 Hz), 7.50(2H,t), 7.71(2H,d,J=8.8 Hz), 8.26(1H,d, J=5.6 Hz).

Reference Example No.9

The compound (800 mg) of the working example No. 81 was dissolved in pyridine (25 mL). To the solution, was added methanesulfonyl chloride (0.263 ml, 3.40 mmol) at room temperature. The reaction mixture was stirred for 1 hour at the same temperature. The insoluble material was filtrated and the filtrate was concentrated to leave a residue, which was dissolved in dimethylformamide. To the mixture, was added sodium azide (295 mg, 4.54 mmol) at room temperature. The reaction mixture was stirred for 30 minutes at 80° C. The reaction mixture was cooled to room temperature and water was added. The whole was extracted with ethyl acetate. The organic layer was washed with saturated brine and then dried over magnesium sulfate. After filtration, the filtrate was concentrated to leave a residue, which was purified by column chromatography on silica gel (hexane-ethyl acetate, 1:2–0:1) to afford the titled compound (265 mg).

$^1$H-NMR(CDCl$_3$)δ:1.23–1.37(1H,m), 2.33–2.51(2H,m), 2.57–2.67(1H,m), 2.90(2H,t,J=6.4 Hz), 3.46(1H,dt,J=10 Hz,3.2 Hz), 3.61 (2H,t,J=6.4 Hz), 3.77(1H,q), 4.77–4.84 (1H,m), 6.81(1H,s), 6.90(1H,d,J=6.4 Hz), 7.50(1H,t,J=8.0 Hz), 7.57(1H,d,J=4.8 Hz), 8.17(1H,d,J=4.8 Hz), 8.34(1H,d, J=7.2 Hz), 8.76(1H,s).

Reference Example No.10

(1) The solution of p-nitrobenzenesulfonyl chloride (5.00 g, 22.6 mmol) in chloroform (50 ml) was cooled in an ice-bath. To this, were added triethylamine (4.72 ml, 33.8 mmol) and 2,4-dimethoxybenzylamine (5.05 g, 30.1 mmol). The reaction mixture was stirred for 1 hour at room temperature and water was added. The whole was extracted with ethyl acetate. The organic layer was combined and washed with 1N hydrochloric acid, saturated aqueous sodium bicarbonate and brine in turn, and then dried over magnesium sulfate. After filtration, the filtrate was concentrated to leave a crude product, which was used for the next reaction without further purification.

(2) The compound (1.12 g) obtained above in (1) and the compound (1.00 g) of the reference example No.7 were dissolved in chloroform (10 mL). To the solution, were added triphenylphosphine (758 mg, 2.89 mmol) and a solution of diethylazodicarboxylate in toluene (40%, 1.26 mL, 2.89 mmol) at room temperature.

The reaction mixture was stirred for 15 hours at the same temperature. The mixture was concentrated to leave a residue, which was purified by column chromatography on silica gel (hexane-ethyl acetate, 1:2–1:4) to afford a yellow amorphous (1.54 g).

$^1$H-NMR(CDCl$_3$)δ:1.20–1.40(1H,m), 1.30(9H,s), 2.20–2.43(3H,m), 2.74(2H,t,J=7.6 Hz), 3.33–3.45(3H,m), 3.61(3H,s), 3.67–3.73(1H,m), 3.73(3H,s), 4.36(2H,s), 4.66 (1H,d,J=12 Hz), 4.71–4.80(1H,m), 4.84(1H,d,J=12 Hz), 6.29(1H,d,J=4.0 Hz), 6.40(1H,dd, J=8.0 Hz,4.0), 6.73(1H, d,J=4.0 Hz), 7.16(1H,d,J=8.0 Hz), 7.43–7.57(3H,m), 7.67 (2H,t), 7.77(1H,d,J=8.0 Hz), 7.80(2H,d,J=8.0 Hz), 8.19–8.22(3H,m).

Reference Example No.11

The compound (750 mg) of the reference example No.10 was dissolved in dimethylformamide (7.5 mL). To the solution, were added sodium carbonate (290 mg, 2.74 mmol) and thiophenol (0.120 ml, 1.17 mmol) at room temperature. The reaction mixture was stirred for 4 days at room temperature. The insoluble material was filtrated and the filtrate was concentrated to leave a residue, which was purified by column chromatography on silica gel (chloroform-methanol, 50:1–9:1–4:1) to afford a light yellow amorphous (350 mg).

$^1$H-NMR(CDCl$_3$)δ:1.30(10H,s), 2.10–2.37(3H,m), 2.75–2.90(4H,m), 3.34–3.43(1H,m), 3.73–3.77(9H,m), 4.67 (1H,d,J=9.6 Hz), 4.77(1H,dd), 4.85(1H,d,J=9.6 Hz), 5.05–5.15(1H,br), 5.40–5.50(1H,br), 6.39(2H,d,J=8.0 Hz), 6.87(1H,d,J=6.4 Hz), 7.09(1H,d d), 7.47–7.57(2H,m), 7.75 (2H,d,J=6.4 Hz), 8.25(1H,d,J=4.8 Hz).

FORMULATION EXAMPLES OF THE INVENTION

The compound of the present invention will be described in more detail hereinunder, with formulation examples, which, however, are to concretely demonstrate the invention but not to restrict the scope of the invention.

Formulation Example No.1

Compound of working example No.131 45 parts by weight, dimagnesium oxide 15 parts by weight and Lactose 75 parts by weight were mixed and homogenized to make a pulverulent or subtle granular powder under 350 μm. The powder was putted into capsules.

Formulation Example No.2

Compound of working example No.131 45 parts by weight, starch 15 parts by weight,
Lactose 16 parts by weight,
crystallinity cellulose 21 parts by weight,
polyvinylalcohol 3 parts by weight and
distilled water 30 parts by weight were mixed and homogenized, and made parvules by crushing and dried. It was then screened to make granules in size of 1410–177 μm.

Formulation Example No.3

Granules which were made by the same method described in the formation example No.2, were mixed with calcium stearate in ratio of 96:4(parts by weight). The mixture was pressed and mould to make tablets with a diameter of 10 mm.

Formulation Example No.4

Granules which were made by the method described in the formation example No.2 were mixed with crystallinity cellulose and calcium stearate in ratio of 90:10:3(parts by weight). The mixture was pressed and mould to make tablets with a diameter of 8 mm. A suspension of syrup gelatin and precipitated calcium carbonate was used to make sugar-coated tablets.

Formulation Example No.5

Compound of working example No.131 0.6 parts by weight, non-ionic surfactant 2.4 parts by weight and physiological salt solution 97 parts by weight were warmed for mixing and put into ampoules and sterilized to make injections.

INDUSTRIAL APPLICABILITY

According to the present invention, the compounds of the present invention have excellent activity of inhibiting the growth of the tumor cells, thus this invention is to provide Cdk4 and/or Cdk6 inhibitor for treating malignant tumor. According to the present invention, the compounds of the present invention have excellent activity of inhibiting the growth of the tumor cells, thus this invention is to provide novel Cdk4 and/or Cdk6 inhibitor for treating malignant tumor.

What is claimed is:

1. A compound of Formula (I) or a pharmaceutically acceptable salt thereof:

Formula (I)

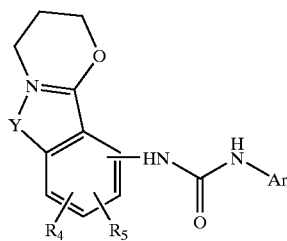

(I)

wherein Ar is a nitrogen-containing heteroaromatic ring group selected from the group consisting of a pyridyl group, a pyrimidinyl group, a pyrazinyl group, a pyridazinyl group, a thiazolyl group, an isothiazolyl group, an oxazolyl group, an isoxazolyl group, a pyrazolyl group, a pyrrolyl group, an imidazolyl group, an indolyl group, an isoindolyl group, a quinolyl group, an isoquinolyl group, a benzothiazolyl group, and a benzoxazolyl group, wherein:
(1) Ar is optionally substituted with one to three of the same or different substituent(s) selected from (1-1) and (1-2):
(1-1) a substituent selected from the group consisting of a lower alkyl group, a hydroxyl group, a cyano group, a halogen atom, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, a di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and (1-2) a substituent which is a group represented by the formula $Y_1$—$W_1$—$Y_2$—$R_p$, wherein:

$R_p$ is:
(i) a hydrogen atom;
(ii) a lower alkyl group, a lower alkenyl group or a lower alkynyl group, each of which is optionally substituted with one to three of said substituent(s) defined in (1-1) above; or
(iii) a cyclo lower alkyl group, an aryl group, a heteroaromatic ring group selected from the group consisting of an imidazolyl group, an isoxazolyl group, an isoquinolyl group, an isoindolyl group, an indazolyl group, an indolyl group, an indolizinyl group, an isothiazolyl group, an ethylenedioxyphenyl group, an oxazolyl group, a pyridyl group, a pyrazinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group selected from the group consisting of an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, a pyrrolinyl group, a morpholino group, a tetrahydroquinolinyl group and a tetrahydroisoquinolinyl group; each of which cyclic groups is optionally substituted with one to three of said substituent(s) as defined in (1-1) above, or furthermore, has optionally a bicyclic or tricyclic fused ring of a partial structure selected from the group consisting of:

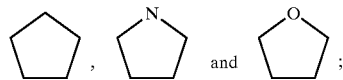

$W_1$ is a single bond, an oxygen atom, a sulfur atom, SO, $SO_2$, $NR_q$, $SO_2NR_q$, $N(R_q)SO_2NR_r$, $N(R_q)SO_2$, $CH(OR_q)$, $CONR_q$, $N(R_q)CO$, $N(R_q)CONR_r$, $N(R_q)COO$, $N(R_q)CSO$, $N(R_q)COS$, $C(R_q)=CR_r$, C≡C, CO, CS, OC(O), OC(O)$NR_q$, OC(S)$NR_q$, SC(O), SC(O)$N_q$ or C(O)O, wherein:

$R_q$ and $R_r$ are each independently:
(iv) a hydrogen atom, or
(v) a substituent selected from the group consisting of a lower alkyl group, a cyclo lower alkyl group, a hydroxyl group, a cyano group, a halogen atom, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, a di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, or (vi) a lower alkyl group, an aryl group or an aralkyl group which is optionally substituted with one to three of said substituent(s) as defined in (v);

$Y_1$ and $Y_2$ are each, the same or different, a single bond or a straight-chain or branched lower alkylene group which optionally has said bicyclic or tricyclic fused ring;
or, (2) Ar is optionally fused to a five- to seven-membered ring selected from the group consisting of:

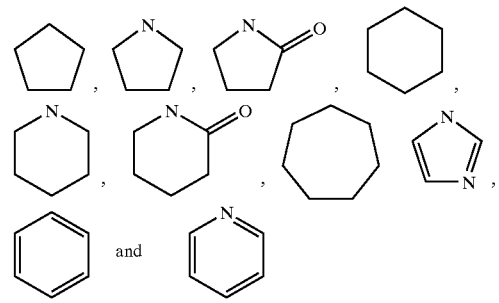

and which ring is formed by two adjacent carbon atoms of said nitrogen-containing heteroaromatic cyclic group, which carbon atoms are each bonded to a ring-substituent through a carbon atom, an oxygen atom and/or a nitrogen atom of said ring-substituent selected from the group consisting of a lower alkyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkylsulfinyl group, a lower alkylsulfonyl group, a lower alkylsulfonylamino group, and a lower alkanoylamidino lower alkyl group;
or, (3) Ar is optionally fused to a five- to seven-membered ring selected from the group consisting of:

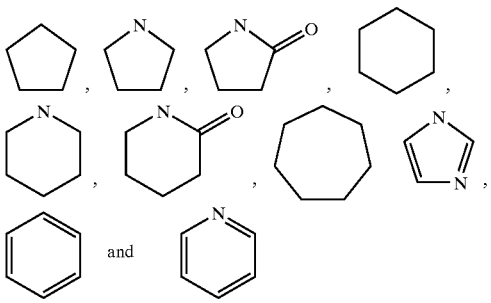

and which ring is formed by two adjacent carbon atoms of said nitrogen-containing heteroaromatic cyclic group, which carbon atoms are each bonded to a ring-substituent through a carbon atom, an oxygen atom and/or a nitrogen atom of said ring-substituent represented by the formula $Y_1-W_1-Y_2-R_p$, wherein $Y_1$, $W_1$, $Y_2$ and $R_p$ have the same meanings as stated above;

Y is CO, SO or $SO_2$;

wherein the 1,3-oxazine ring in the compound of Formula (1) is optionally further fused with any one of a cyclo lower alkyl group, an aryl group, a heteroaromatic ring group selected from the group consisting of an imidazolyl group, an isoxazolyl group, an isoquinolyl group, an isoindolyl group, an indazolyl group, an indolyl group, an indolydinyl group, an isothiazolyl group, an ethylenedioxyphenyl group, an oxazolyl group, a pyridyl group, a pyrazinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group, or an aliphatic heterocyclic group(s) selected from the group consisting of an isoxazolinyl group, an isoxazolidinyl group, a tetrahydropyridyl group, an imidazolidinyl group, a tetrahydrofuranyl group, a tetrahydropyranyl group, a piperazinyl group, a piperidinyl group, a pyrrolidinyl group, a pyrrolinyl group, a morpholino group, a tetrahydroquinolinyl group and a tetrahydroisoquinolinyl group, and wherein the 1,3-oxazine ring in the compound of the Formula (I) is optionally substituted with one to three of the same or different substituent(s) selected from the group consisting of a lower alkyl group, a spiro cyclo lower alkyl group which is optionally substituted, a hydroxyl group, a cyano group, a halogen atom, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, a di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group; or a substituent represented by the formula $Y_1-W_1-Y_2-R_p$, wherein $R_p$, $W_1$, $Y_1$ and $Y_2$ have the same meanings as stated above, $R_4$ and $R_5$ are each, the same or different, a hydrogen atom, a halogen atom, a hydroxy group, an amino group, or a substituent represented by the formula $Y_3-W_2-Y_4-R_s$, wherein:

$R_s$ is a hydrogen atom; a lower alkyl group, a lower alkenyl group, a lower alkynyl group, a cyclo lower alkyl group, an aryl group; a heteroaromatic ring group selected from the group consisting of an imidazolyl group, an isoxazolyl group, an isoquinolyl group, an isoindolyl group, an indazolyl group, an indolyl group, an indolizinyl group, an isothiazolyl group, an ethylenedioxyphenyl group, an oxazolyl group, a pyridyl group, a pyradinyl group, a pyrimidinyl group, a pyridazinyl group, a pyrazolyl group, a quinoxalinyl group, a quinolyl group, a dihydroisoindolyl group, a dihydroindolyl group, a thionaphthenyl group, a naphthyridinyl group, a phenazinyl group, a benzoimidazolyl group, a benzoxazolyl group, a benzothiazolyl group, a benzotriazolyl group, a benzofuranyl group, a thiazolyl group, a thiadiazolyl group, a thienyl group, a pyrrolyl group, a furyl group, a furazanyl group, a triazolyl group, a benzodioxanyl group and a methylenedioxyphenyl group; or an aliphatic heterocyclic group selected from the group consisting of an isoxazolinyl group, an isoxazolidinyl group, a tetrahydropyridyl group, an imidazolidinyl group, a tetrahydrofuranyl group, a piperazinyl group, a piperidinyl group, a pyrrolidinyl group, pyrrolinyl group, a morpholino group, a tetrahydroquinolinyl group and a tetrahydroisoquinolinyl group;

each of which is optionally substituted with one to three of said substituent(s) as defined in (1-1) above;

$W_2$ is a single bond, an oxygen atom, a sulfur atom, SO, $SO_2$, $NR_t$, $SO_2NR_t$, $N(R_t)SO_2NR_u$, $N(R_t)SO_2$, $CH(OR_t)$, $CONR_t$, $N(R_t)CO$, $N(R_t)CONR_u$, $N(R_t)$ COO, $N(R_t)CSO$, $N(R_t)COS$, $C(R_s)=CR_t$, $C\equiv C$, CO, CS, OC(O), OC(O)$N_t$, OC(S)$NR_t$, SC(O), SC(O)$NR_t$ and C(O)O, wherein:

$R_t$ and $R_u$ are each independently:

(vii) a hydrogen atom, or (viii) a substituent selected from the group consisting of a lower alkyl group, a hydroxy group, a cyano group, a halogen atom, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, a di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group;
or
(ix) a lower alkyl group, an aryl group or an aralkyl group which is optionally substituted with one to three of said substituent(s)) as defined in (1-1) above;
$Y_3$ and $Y_4$ are each, the same or different, a single bond or a straight-chain or branched lower alkylene group, or
a substituent selected from the group consisting of a lower alkyl group, an aryl group or an aralkyl group which is optionally substituted with one to three of the same or different substituent(s) selected from the groups consisting of a lower alkyl group, a cyano group, a nitro group, a carboxyl group, a carbamoyl group, a formyl group, a lower alkanoyl group, a lower alkanoyloxy group, a hydroxy lower alkyl group, a cyano lower alkyl group, a halo lower alkyl group, a carboxy lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a di-lower alkylcarbamoyl group, a carbamoyloxy group, a lower alkylcarbamoyloxy group, di-lower alkylcarbamoyloxy group, an amino group, a lower alkylamino group, a di-lower alkylamino group, a tri-lower alkylammonio group, an amino lower alkyl group, a lower alkylamino lower alkyl group, a di-lower alkylamino lower alkyl group, a tri-lower alkylammonio lower alkyl group, a lower alkanoylamino group, an aroylamino group, a lower alkanoylamidino lower alkyl group, a lower alkylsulfinyl group, a lower alkylsulfonyl group, a lower alkylsulfonylamino group, a hydroxyimino group and a lower alkoxyimino group, and the group represented by the formula $Y_3$—$W_2$—$Y_4$—$R_s$, wherein $R_s$, $W_2$, $Y_3$ and $Y_4$ have the same meanings as stated above.

2. The compound according to claim 1, having a structure of Formula (I-a), or a pharmaceutically acceptable salt thereof:

Formula (I-a)

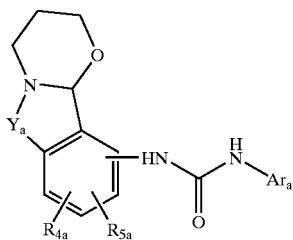

(I-a)

wherein $Ar_a$ is a nitrogen-containing heteroaromatic ring group selected from the group consisting of a pyridyl group, a pyrimidinyl group, a pyrazinyl group, a pyridazinyl group, a thiazolyl group, a pyrazolyl group, and an imidazolyl group;
wherein:
(1') $Ar_a$ is optionally substituted with one to three of the same or different substituent(s) selected from (1'-1) and (1'-2):

(1'-1) a substituent selected from the group consisting of a lower alkyl group, a hydroxyl group, a halogen atom, a formyl group, a lower alkanoyl group, a lower alkanoyloxy group, a hydroxy lower alkyl group, a halo lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a lower alkylcarbamoyloxy group, an amino group, a lower alkylamino group, a di-lower alkylamino group, an amino lower alkyl group, a lower alkylamino lower alkyl group, a di-lower alkylamino lower alkyl group, a lower alkanoylamino group, an aroylamino group, and a lower alkylsulfonylamino group, and
(1'-2) a substituent which is a group represented by the formula $Y_{1a}$—$W_{1a}$—$Y_{2a}$—$R_{pa}$, wherein:
$R_{pa}$ is:
(i) a hydrogen atom, or
(ii) a lower alkyl group, a lower alkenyl group or a lower alkynyl group, each of which is optionally substituted with one to three of said substituent(s) as defined in (1'-1) above; or
(iii) a cyclo lower alkyl group, an aryl group, a heteroaromatic ring group selected from the group consisting of an imidazolyl group, an isoxazolyl group, an isoquinolyl group, an indolyl group, an ethylenedioxyphenyl group, a pyridyl group, a pyrimidinyl group, a pyridazinyl group, a pyrazolyl group, a quinolyl group, a benzoimidazolyl group, a thiazolyl group, a thienyl group, and a triazolyl group, or an aliphatic heterocyclic group(s) selected from the group consisting of an isoxazolinyl group, an isoxazolidinyl group, a tetrahydropyridyl group, a tetrahydrofuranyl group, a tetrahydropyranyl group, a piperazinyl group, a piperidinyl group, a pyrrolidinyl group, a morpholino group, and a tetrahydroisoquinolinyl group; each of which cyclic groups is optionally substituted with one to three of said substituents as defined in (1'-1) above, or furthermore, optionally has a bicyclic or tricyclic fused ring which contains a partial structure selected from the group consisting of:

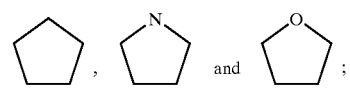

$W_{1a}$ is an oxygen atom, a sulfur atom, $NR_{qa}$, $SO_2NR_{qa}$, $N(R_{qa})SO_2$, $CONR_{qa}$, $N(R_{qa})CO$, $N(R_{qa})COO$, $C(R_{qa})=CR_{ra}$, $OC(O)$, $OC(O)NR_{qa}$, or $C(O)O$, wherein:
$R_{qa}$ and $R_{ra}$ are each independently:
(iv) a hydrogen atom, or
(v) a substituent selected from the group consisting of a lower alkyl group, a cyclo lower alkyl group, a hydroxyl group, a halogen atom, a formyl group, a lower alkanoyloxy group, a hydroxy lower alkyl group, a halo lower alkyl group, a carbamoyl lower alkyl group, lower alkoxy group, a lower alkoxycarbonyl group, a lower alkoxycarbonylamino group, a lower alkoxycarbonylamino lower alkyl group, a lower alkylcarbamoyl group, a lower alkylcarbamoyloxy group, an amino group, a lower alkylamino group, a di-lower alkylamino group, an amino lower alkyl group, a lower alkylamino lower alkyl group, a di-lower alkylamino lower alkyl group, a lower alkanoylamino group, an aroylamino group, and a lower alkylsulfonylamino group; or (vi) a lower alkyl group, an aryl group or an aralkyl group which is optionally substituted with one to three of said substituent(s) as defined in (v);

$Y_{1a}$ and $Y_{2a}$ are each, the same or different, a single bond or a straight-chain or branched lower alkylene group which is optionally a bicyclic or tricyclic fused ring;

or, (2') $Ar_a$ is optionally fused to a five- to six-membered ring selected from the group consisting of:

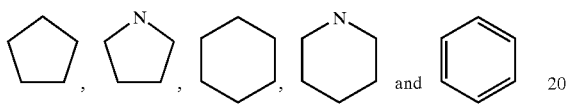

which ring is formed from two adjacent carbon atoms on said nitrogen-containing heteroaromatic ring group, which carbon atoms are each bonded to said ring-substituent through a carbon atom, an oxygen atom and/or a nitrogen atom of said ring-substituent selected from the group consisting of a lower alkyl group, a lower alkanoyloxy group, a hydroxy lower alkyl group, a halo lower alkyl group, a carbamoyl lower alkyl group, a lower alkoxy group, a lower alkoxycarbonyl group, a lower alkoxycarbonylamino group, a lower alkoxycarbonylamino lower alkyl group, a lower alkylcarbamoyl group, a lower alkylcarbamoyloxy group, a lower alkylamino group, a di-lower alkylamino group, an amino lower alkyl group, a lower alkylamino lower alkyl group, a di-lower alkylamino lower alkyl group, a lower alkanoylamino group, and an aroylamino group;

or, (3') $Ar_a$ is optionally fused to a five- to six-membered ring selected from the group consisting of:

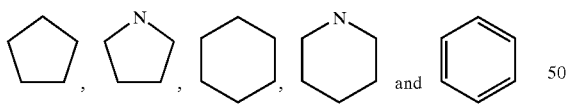

which ring is formed by two adjacent carbon atoms of said nitrogen-containing heteroaromatic ring group, which carbon atoms are each bonded to the ring-substituent through a carbon atom, an oxygen atom and/or a nitrogen atom of said ring-substituent represented by the formula $Y_{1a}$—$W_{1a}$—$Y_{2a}$—$R_{pa}$, wherein $Y_{1a}$, $W_{1a}$, $Y_{2a}$ and $R_{pa}$ have the same meanings as stated above;

$Y_a$ is a CO, SO or $SO_2$;

wherein the 1,3-oxazine ring of the compound of Formula (I-a) is optionally further fused with a cyclo lower alkyl group, an aryl group, a heteroaromatic ring group selected from the group consisting of a pyridyl group and a pyrazolyl group, and an aliphatic heterocyclic group selected from the group consisting of a piperidinyl group and a pyrrolidinyl group;

and wherein the 1,3-oxazine ring of the compound of Formula (I-a) is optionally substituted with one to three of the same or different substituent(s) selected both from the group consisting of a lower alkyl group, a spiro cyclo lower alkyl group which is optionally substituted, a hydroxy group, a hydroxy lower alkyl group, a lower alkoxy group, a lower alkoxycarbonyl group, a lower alkoxycarbonylamino group, a lower alkoxycarbonylamino lower alkyl group, a lower alkylcarbamoyl group, a lower alkylcarbamoyloxy group, a lower alkylamino group, a di-lower alkylamino group, an amino lower alkyl group, a lower alkylamino lower alkyl group, a di-lower alkylamino lower alkyl group, a lower alkanoylamino group and an aroylamino group, and the group represented by the formula $Y_{1a}$—$W_{1a}$—$Y_{2a}$—$R_{pa}$, wherein $R_{pa}$, $W_{1a}$, $Y_{1a}$ and $Y_{2a}$ have the same meanings as stated above, or furthermore, $R_{4a}$ and $R_{5a}$ are each, the same or different, a hydrogen atom or a substituent consisting of a halogen atom, a hydroxy group, an amino group, or a group represented by the formula $Y_{3a}$—$W_{2a}$—$Y_{4a}$—$R_{sa}$, wherein:

$R_{sa}$ is a hydrogen atom; a lower alkyl group, a lower alkenyl group, a cyclo lower alkyl group, an aryl group; or a heteroaromatic ring group selected from the group consisting of an indolyl group, or an aliphatic heterocyclic group selected from the group consisting of a tetrahydropyridyl group, a piperadinyl group, a piperidinyl group, a pyrrolidinyl group and a morpholino group; each of which groups is optionally substituted with one to three of the same or different said substituent(s) as defined in (1'-1) above;

$W_{2a}$ is a single bond, $NR_{ta}$, $CH(OR_{ta})$, $CONR_{ta}$, $N(R_{ta})CO$, $N(R_{ta})COO$, $OC(O)N_{ta}$ or $C(O)O$, wherein:

$R_{ta}$ is a hydrogen atom, a lower alkyl group, an aryl group or an aralkyl group which is optionally substituted with one to three of said substituent(s) as defined in (1'-1) above;

$Y_{3a}$ and $Y_{4a}$ are each, the same or different, a single bond, or a straight-chain or branched lower alkylene group; or a substituent selected from the group consisting of a lower alkyl group, an aryl group or an aralkyl group, each of which is optionally substituted with one to three of the same or different substituent(s) selected from the group consisting of a lower alkyl group, a hydroxy lower alkyl group, a halo lower alkyl group, a lower alkoxycarbonylamino group, a lower alkoxycarbonylamino lower alkyl group, a lower alkylcarbamoyl group, a lower alkylamino group, a lower alkylamino lower alkyl group, a lower alkanoylamino group, and an aroylamino group, and the group represented by the formula $Y_{3a}$—$W_{2a}$—$Y_{4a}$—$R_{sa}$, wherein $R_{sa}$, $W_{2a}$, $Y_{3a}$ and $Y_{4a}$ have the same meanings as stated above.

3. The compound according to claim 1, having a structure of Formula (I-b) or a pharmaceutically acceptable salt thereof,

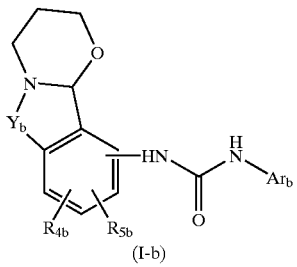

Formula (I-b)

(I-b)

wherein Arb is a nitrogen-containing heteroaromatic ring group selected from the group consisting of a pyridyl group and a pyrazolyl group;
wherein:
(1") Arb is optionally substituted with one to three substituent(s) selected from (1"-1) and (1"-2):
(1"-1) a substituent selected from the group consisting of a hydroxy group, a halogen atom, a lower alkanoyloxy group, a hydroxy lower alkyl group, a lower alkoxy group, a lower alkoxycarbonyl group, an amino group, and a lower alkylamino lower alkyl group, and
(1"-2) a substituent which is a group represented by the formula $Y_{1b}—W_{1b}—Y_{2b}—R_{pb}$, wherein:
$R_{pb}$ is:
(i) a hydrogen atom, or
(ii) a lower alkyl group, a lower alkenyl group or a lower alkynyl group which is optionally substituted with one to three of said substituent(s) as defined in (1"-1) above; or
(iii) a cyclo lower alkyl group, an aryl group, a heteroaromatic ring group selected from the group consisting of a pyridyl group and a pyrazolyl group, or an aliphatic heterocyclic group selected from the group consisting of an isoxazolinyl group, a tetrahydropyridyl group, a piperadinyl group, a piperidinyl group, a pyrrolidinyl group, a morpholino group and a tetrahydroisoquinolinyl group; each of which cyclic substituent groups is optionally substituted with one to three of said substituent(s) as defined in (1"-1) above, or furthermore, optionally has a bicyclic or tricyclic fused ring, which contains the partial structure of which is selected from the group consisting of:

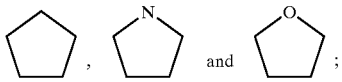

$W_{1b}$ is $NR_{qb}$, $N(R_{qb})SO_2$, $CON_{qb}$, $N(R_{qb})CO$, $N(R_{qb})COO$, $OC(O)$, or $C(O)O$, wherein:
$R_{qb}$ is:
(iv) a hydrogen atom, or
(v) a substituent selected from the group consisting of a hydroxy group, a halogen atom, a cyclo lower alkyl group, a lower alkanoyloxy group, a hydroxy lower alkyl group, a lower alkoxy group, a lower alkoxycarbonyl group, an amino group, and a lower alkylamino lower alkyl group; or a lower alkyl group, an aryl group or an aralkyl group, each of which is optionally substituted with one to three of said substituent(s);

$Y_{1b}$ and $Y_{2b}$ are each, the same or different, a single bond or a straight-chain or branched lower alkylene group which may have said bicyclic or tricyclic fused ring;
or
(2") Arb is optionally fused to a five- or six-membered ring selected from the group consisting of:

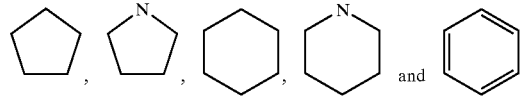

which ring is formed by two adjacent carbon atoms of said nitrogen-containing heteroaromatic ring group, which carbon atoms are each bonded to the ring-substituent through a carbon atom, an oxygen atom and/or a nitrogen atom of said ring-substituent selected from the group consisting of a lower alkanoyloxy group, a hydroxy lower alkyl group, a lower alkoxy group, a lower alkoxycarbonyl group and a lower alkylamino lower alkyl group;
or,
(3") Arb is optionally fused to a five- or six-membered ring selected from the group consisting of:

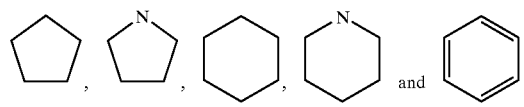

which ring is formed by two adjacent carbon atoms of said nitrogen-containing heteroaromatic ring group, which carbon atoms are each bonded to the ring-substituent through a carbon atom, an oxygen atom and/or a nitrogen atom of said ring-substituent represented by the formula $Y_{1b}—W_{1b}—Y_{2b}—R_{1b}$, wherein $Y_{1b}$, $W_{1b}$, $Y_{2b}$ and $R_{pb}$ have the same meanings as stated above;
$Y_b$ is a CO, SO or $SO_2$;
wherein the 1,3-oxazine ring of the compound of Formula (I-b) is optionally further fused with a cyclo lower alkyl group, an aryl group and an aliphatic heterocyclic group selected from the group consisting of a piperidinyl group and a pyrrolidinyl group, and the 1,3-oxazine ring of the compound of Formula (I-b) is optionally substituted with one to three of the same or different substituent(s) selected from the group consisting of a lower alkyl group, a Spiro cyclo lower alkyl group which is optionally substituted, a hydroxy lower alkyl group and a lower alkoxycarbonyl group, or a group represented by the formula $Y_{1b}—W_{1b}—Y_{2b}—R_{pb}$, wherein $R_{pb}$, $W_{1b}$, $Y_{1b}$ and $Y_{2b}$ have the same meanings as stated above;
$R_{4b}$ and $R_{5b}$ are each independently, the same or different, or a lower alkyl group, an aryl group or an aralkyl group which is optionally substituted with one to three of the same or different substituent(s) selected from the group consisting of a hydrogen atom, a halogen atom and a substituent represented by the formula $Y_{3b}—W_{2b}—Y_{4b}—R_{sb}$,
wherein:
$R_{sb}$ is a hydrogen atom or a lower alkyl group, a cyclo lower alkyl group, and an aryl group, which is optionally substituted with one to three of said substituent(s);

$W_{2b}$ is a single bond, $N(R_{tb})COO$ or $C(O)O$, wherein $R_{tb}$ is a hydrogen atom or a lower alkyl group, an aryl group or an aralkyl group which is optionally substituted with one to three of said substituent(s);

$Y_{3b}$ and $Y_{4b}$ are each, the same or different, a single bond, or a straight-chain or branched lower alkylene group, or a lower alkyl group which is optionally substituted with one to three of the same or different substituent(s) selected from the group consisting of a hydroxy lower alkyl group and a group represented by the formula $Y_{3b}$—$W_{2b}$—$Y_{4b}$—$R_{sb}$, wherein $R_{sb}$, $W_{2b}$, $Y_{3b}$ and $Y_{4b}$ have the same meanings as stated above, or a substituent selected from the group consisting of a lower alkyl group, a hydroxy lower alkyl group, a halo lower alkyl group, a lower alkoxycarbonylamino group, a lower alkoxycarbonylamino lower alkyl group, a lower alkylcarbamoyl group, a lower alkylamino group, a lower alkylamino lower alkyl group, a lower alkanoylamino group, and an aroylamino group.

4. A compound which has a structure of Formula (I-p) or a pharmaceutically acceptable salt thereof,

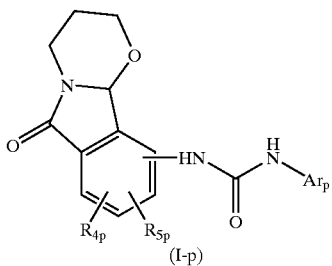

Formula (I-p)

wherein $Ar_p$ is a nitrogen-containing heteroaromatic ring group which is optionally substituted, wherein said nitrogen-containing heteroaromatic ring group does not include a quinolyl group, wherein the 1,3-oxazine ring of Formula (I-p) is optionally further fused with a cyclo lower alkyl group, and the 1,3-oxazine ring of Formula (I-p) is optionally substituted, $R_{4p}$ and $R_{5p}$ are each, the same or different, a hydrogen atom, halogen atom, a hydroxy group, an amino group or a lower alkyl group, an aryl group or an aralkyl group which is optionally substituted.

5. A compound which is:
N'-(isoindolino[2,3-b]perhydro-1,4-methano-6,11a-benzoxazin-11-on-7-yl)-N-(pyridin-2-yl)urea,
N'-(isoindolino[2,3-c]perhydro-5,10a-benzoxazin-10-on-6-yl)-N-(pyridin-2-yl)urea,
N'-(isoindolino[2,3-c]perhydro-5,10a-benzoxazin-10-on-6-yl)-N-(4-(N-benzylpyrrolidin-3-yl)pyridin-2-yl)urea,
N'-(isoindolino[2,3-b]perhydro-1,4-methano-6,11a-benzoxazin-11-on-7-yl)-N-(4-(N-benzylpyrrolidin-3-yl) urea,
N'-(4-phenylisoindolino[3,2-b]perhydro-1,3-oxazin-5-on-9-yl)-N-(pyridin-2-yl)urea,
N'-(isoindolino[3,2-b]perhydro-1,3-oxazin-5-on-9-yl)-N-(pyridin-2-yl) urea,
N'-(4-phenylisoindolino[3,2-b]perhydro-1,3-oxazin-5-on-9-yl)-N-(4-(N-benzylpyrrolidin-3-yl) pyrid in-2-yl)urea,
N'-(isoindolino[3,2-b]perhydro-1,3-oxazin-5-on-9-yl)-N-(4-(N-benzylpyrrolidin-3-yl)pyridin-2-yl)urea,
N'-(2-methylisoindolino[3,2-b]perhydro-1,3-oxazin-5-on-9-yl)-N-(pyridin-2-yl)urea,
N'-(2,3-dimethylisoindolino[3,2-b]perhydro-1,3-oxazin-5-on-9-yl)-N-(pyridin-2-yl)urea,
N'-(2-methylisoindolino[3,2-b]perhydro-1,3-oxazin-5-on-9-yl)-N-(4-(N-benzylpyrrolidin-3-yl)pyridin-2-yl)urea,
N'-(2,3-dimethylisoindolino[3,2-b]perhydro-1,3-oxazin-5-on-9-yl)-N-(4-(N-benzylpyrroidin-3]-yl)pyridin-2-yl) urea,
N'-(2,3-dimethylisoindolino[3,2-b]perhydro-1,3-oxazin-5-on-9-yl)-N-(4-bromoindan-2-yl-aminomethyl)urea,
N'-(2-methylisoindolino[3,2-b]perhydro-1,3-oxazin-5-on-9-yl)-N-(4-bromoindan-2-yl-aminomethyl)urea, or
N'-(10-propylisoindolino[3,2-b]perhydro-1,3-oxazin-5-on-9-yl)-N-(4-(N-benzylpyrrolidin-3-yl)pyridin-2-yl)urea, or
a pharmaceutically acceptable salt thereof.

6. A pharmaceutical composition comprising a therapeutically effective amount of the compound of claim 1 or a pharmaceutically acceptable salt thereof together with a pharmaceutically acceptable additive.

7. A method for inhibiting cyclin dependent kinase 4(Cdk4) and/or cyclic dependent kinase 6 (Cdk6)which comprises administering a therapeutically effective amount of the compound of claim 1 or a pharmaceutically acceptable salt thereof to a patient in need thereof.

8. A method for colon cancer treatment which comprises administering therapeutically effective amount of the compound of claim 1 or a pharmaceutically acceptable salt thereof to a patient in need thereof.

* * * * *